US006335324B1

(12) United States Patent     (10) Patent No.: US 6,335,324 B1
Bisacchi et al.     (45) Date of Patent: Jan. 1, 2002

(54) BETA LACTAM COMPOUNDS AND THEIR USE AS INHIBITORS OF TRYPTASE

(75) Inventors: Gregory S. Bisacchi, Ringoes; William A. Slusarchyk, Skillman, both of NJ (US); Uwe Treuner, Yardley, PA (US); James C. Sutton, Princeton Junction, NJ (US); Robert Zahler; Steven Seiler, both of Pennington, NJ (US); David R. Kronenthal, Yardley, PA (US); Michael E. Randazzo, East Windsor, NJ (US); Mark D. Schwinden, Holland, PA (US); Zhongmin Xu, Plainsboro; Zhongping Shi, West Windsor, both of NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/458,847

(22) Filed: Dec. 13, 1999

Related U.S. Application Data

(63) Continuation-in-part of application No. 09/336,253, filed on Jun. 18, 1999, now abandoned.
(60) Provisional application No. 60/090,636, filed on Jun. 25, 1998.

(51) Int. Cl.[7] ...................... C07D 40/14; C07D 403/14; C07D 403/06; C07D 205/08; A61P 11/06
(52) U.S. Cl. .................. 514/210.02; 514/210.15; 540/200; 540/354; 540/355; 540/359; 540/362
(58) Field of Search ................ 540/200, 354, 540/355, 359, 362; 514/210.02, 210.15

(56) References Cited

U.S. PATENT DOCUMENTS

| | | | |
|---|---|---|---|
| 4,775,670 A | 10/1988 | Sykes et al. | 514/210 |
| 5,037,819 A | 8/1991 | Han | 514/210 |
| 5,110,812 A | 5/1992 | Han | 514/210 |
| 5,175,283 A | 12/1992 | Han | 540/200 |
| 5,250,677 A | 10/1993 | Han | 540/200 |
| 5,326,863 A | 7/1994 | Han | 540/200 |
| 5,525,623 A | 6/1996 | Spear et al. | 514/423 |

FOREIGN PATENT DOCUMENTS

| | | |
|---|---|---|
| EP | 199630 B | 10/1986 |
| EP | 337549 B | 10/1989 |
| EP | 481671 A | 4/1992 |
| GB | 2266527 | 11/1993 |
| WO | 87/04429 | 7/1987 |
| WO | 94/22820 | 10/1994 |
| WO | 97/13750 | 4/1997 |
| WO | 97/49674 | 12/1997 |
| WO | 98/25895 | 6/1998 |
| WO | 99/12935 | 3/1999 |

OTHER PUBLICATIONS

Yoakin et al., Med. Chem., vol. 41, p. 2882–2891 (1998).
Zheng et al., Med. Chem. Res., vol. 4, p. 597–603 (1994).
Adlington et al., "Design And Synthesis Of Novel Monocyclic β–Lactam Inhibitors Of Prostate Specific Antigen" Bioorganic & Medicinal Chemistry Letters, vol. 7, No. 13, p. 1689–94 (1997).

(List continued on next page.)

Primary Examiner—Mark L. Berch
(74) Attorney, Agent, or Firm—Stephen B. Davis

(57) ABSTRACT

Compounds of the formulas:

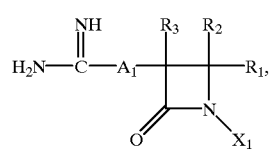

(I)

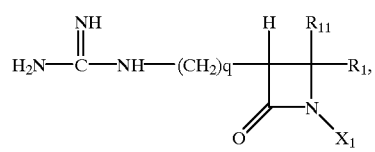

(II)

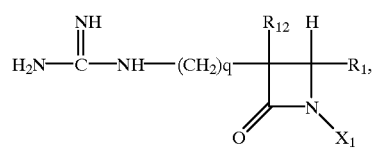

(III)

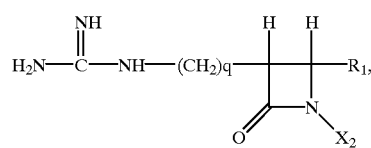

(IV)

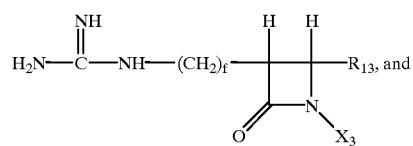

(V)

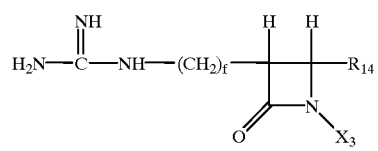

(VI)

are disclosed. These compounds inhibit tryptase as well as other enzyme systems or are selective tryptase inhibitors and are useful as antiinflammatory agents particularly in the treatment of chronic asthma.

39 Claims, No Drawings

OTHER PUBLICATIONS

Baldwin et al., "Stereospecific Synthesis Of Dealanylalahopcin", Tetrahedron, vol. 46, Nos. 13, 14, p. 4733–48 (1990).

Wu et al., "An Efficient Method For The Preparation of Bis–Urethane Protected Arginine Derivative", Synthetic Communications, vol. 23 (21), p. 3055–60 (1993).

Anderson et al., "Isoquinoline Derivatives as Local Anesthetics", Journal American Pharmaceutical Assoc., vol. 41, No. 12, p. 643–650 (1952).

Sakai et al., "A Novel Heparin–dependent Processing Pathway For Human Tryptase", Journal Clinical Invest., vol. 97, No. 4, p. 988–95 (1996).

Han et al., "Azetidine–2–one Derivatives as Inhibitors of Thromoin", Biorganic & Medicinal Chemistry, vol. 3, No. 8, p. 1123–43 (1995).

March, "Advanced Organic Chemistry", $4^{th}$ Ed., p. 94–164 (1991).

BETA LACTAM COMPOUNDS AND THEIR USE AS INHIBITORS OF TRYPTASE

RELATED APPLICATIONS

This application is a continuation-in-part of Ser. No. 09/336,253 filed Jun. 18, 1999 now abandoned which claimed priority from application Ser. No. 60/090,636 filed Jun. 25, 1998.

BACKGROUND OF THE INVENTION

Han in U.S. Pat. Nos. 5,037,819, 5,110,812, 5,175,283, 5,250,677 and 5,326,863 discloses 3-guanidinoalkyl-2-azetidinones of the formula:

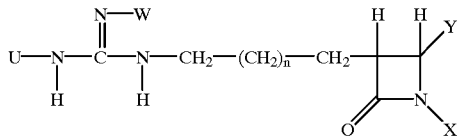

wherein:
U and W are independently selected from hydrogen and amino protecting groups;
n is an integer from 1 to 3;
X is hydrogen, trialkylsilyl, arylsulfonyl, amino substituted arylsulfonyl, alkylsulfonyl, arylaminocarbonyl, alkylcarbonyl or arylcarbonyl;
Y is hydrogen, arylalkenyl, arylalkyl, formyl, carboxy, alkoxycarbonyl, acyloxy, arylthio, arylsulfinyl, arylsulfonyl, alkythio, alkylsulfinyl, alkylsulfonyl, arylaminocarbonyl,

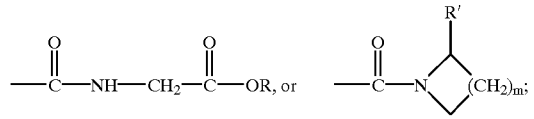

R is hydrogen, alkyl, or arylalkyl;
m is an integer from 1 to 3; and
R', is hydrogen or —CO$_2$R" wherein R" is hydrogen, alkyl, or arylalkyl.
Han further discloses that the above compounds wherein:
U and W are hydrogen;
X is arylsulfonyl, amino substituted arylsulfonyl, alkylsulfonyl, arylaminocarbonyl, alkylcarbonyl, or arylcarbonyl; and
Y is hydrogen, arylalkyl, carboxy, alkoxycarbonyl, acyloxy, arylsulfonyl, alkylthio, alkylsulfonyl, arylaminocarbonyl,

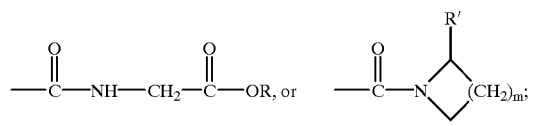

R is hydrogen, alkyl or arylalkyl;
R', is hydrogen or —CO$_2$R";
R", is hydrogen, alkyl, or arylalkyl and pharmaceutically acceptable salts thereof are inhibitors against serine proteases, particularly against thrombin and trypsin, and can be used to control blood coagulation or to treat pancreatitis.

Han defines "aryl" as a phenyl or naphthyl group which may be unsubstituted or substituted with one or more groups such as amino, nitro, or alkyl and defines "amino" as unsubstituted or substituted with one or two alkyl radicals.

SUMMARY OF THE INVENTION

This invention is directed to the novel beta lactam compounds of formulas I, II, III, IV, and V shown below and to the use of such compounds as inhibitors of various in vivo enzyme systems including tryptase, thrombin, trypsin, Factor Xa, Factor VIIa, and urokinase-type plasminogen activator. This invention is also directed to the use of the compounds of formula VI shown below as tryptase, Factor Xa, Factor VIIa, and urokinase-type plasminogen activator inhibitors.

Compounds of this invention include the formula:

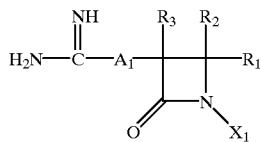

wherein:

R$_1$ is hydrogen, carboxy, alkoxycarbonyl, A$_2$-aryl,

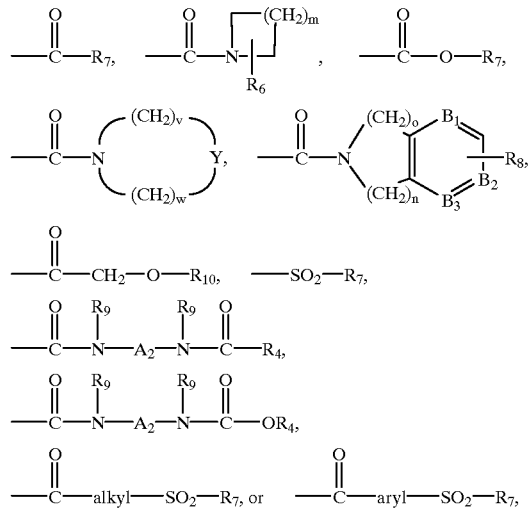

or R$_1$ is alkyl provided that R$_2$ is alkyl and R$_3$ is hydrogen.
R$_2$ and R$_3$ are both hydrogen, or R$_2$ is alkyl provided that R$_3$ is hydrogen, or R$_3$ is alkyl provided that R$_2$ is hydrogen.

X$_1$ is

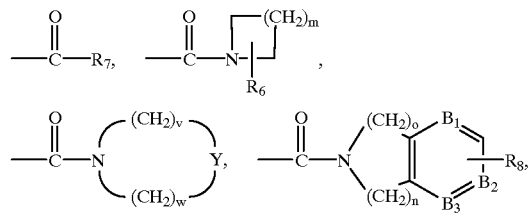

-continued $$-\overset{O}{\underset{\|}{C}}-alkyl-SO_2-R_7, \quad -\overset{O}{\underset{\|}{C}}-aryl-SO_2-R_7,$$

$$-\overset{O}{\underset{\|}{C}}-CH_2-O-R_{10}, \quad -SO_2-R_7,$$

$$-\overset{O}{\underset{\|}{C}}-NH-SO_2-R_7.$$

$$-\overset{O}{\underset{\|}{C}}-\overset{R_9}{\underset{|}{N}}-A_2-\overset{R_9}{\underset{|}{N}}-\overset{O}{\underset{\|}{C}}-R_4, \text{ or}$$

$$-\overset{O}{\underset{\|}{C}}-\overset{R_9}{\underset{|}{N}}-A_2-\overset{R_9}{\underset{|}{N}}-\overset{O}{\underset{\|}{C}}-OR_4.$$

$A_1$ is $-(CH_2)_p-$, $-(CH_2)_r-\underset{(CH_2)_s-}{\text{phenyl}}$, $-\underset{R_{20}}{N}-(CH_2)_q-$, $-NH-(CH_2)_r-\underset{(CH_2)_s-}{\text{phenyl}}$, or $-N\underset{(CH_2)_u-}{\overset{(CH_2)_t}{\diagup}}$.

$R_4$ and $R_5$ are independently selected from hydrogen, alkyl, substituted alkyl, cycloalkyl, substituted cycloalkyl, $A_2$-cycloalkyl, $A_2$-substituted cycloalkyl, aryl, substituted aryl, $A_2$-aryl, $A_2$-substituted aryl, heteroaryl, $A_2$-heteroaryl, heterocycloalkyl, $A_2$-heterocycloalkyl, aryl-$A_3$-aryl, $A_2$-aryl-$A_3$-aryl, aryl-$A_3$-cycloalkyl, $A_2$-aryl-$A_3$-cycloalkyl, aryl-$A_3$-heteroaryl, $A_2$-aryl-$A_3$-heteroaryl, aryl-$A_3$-heterocycloalkyl, $A_2$-aryl-$A_3$-heterocycloalkyl, aryl-$A_3$-substituted aryl, $A_2$-aryl-$A_3$-substitued aryl, aryl-$A_3$-substituted cycloalkyl, $A_2$-aryl-$A_3$-substituted cycloalkyl, cycloalkyl-$A_3$-cycloalkyl, $A_2$-cycloalkyl-$A_3$-cycloalkyl, cycloalkyl-$A_3$-aryl, $A_2$-cycloalkyl-$A_3$-aryl, cycloalkyl-$A_3$-heteroaryl, $A_2$-cycloalkyl-$A_3$-heteroaryl, cycloalkyl-$A_3$-heterocycloalkyl, $A_2$-cycloalkyl-$A_3$-heterocycloalkyl, cycloalkyl-$A_3$-substituted cycloalkyl, $A_2$-cycloalkyl-$A_3$-substituted cycloalkyl, cycloalkyl-$A_3$-substituted aryl, $A_2$-cycloalkyl-$A_3$-substituted aryl, substituted cycloalkyl-$A_3$-cycloalkyl, $A_2$-substituted cycloalkyl-$A_3$-cycloalkyl, substituted cycloalkyl-$A_3$-substituted cycloalkyl, $A_2$-substituted cycloalkyl-$A_3$-substituted cycloalkyl, substituted cycloalkyl-$A_3$-aryl, $A_2$-substituted cycloalkyl-$A_3$-aryl, substituted cycloalkyl-$A_3$-heteroaryl, $A_2$-substituted cycloalkyl-$A_3$-heteroaryl, substituted cycloalkyl-$A_3$-heterocycloalkyl, $A_2$-substituted cycloalkyl-$A_3$-heterocycloalkyl, substituted cycloalkyl-$A_3$-substituted aryl, $A_2$-substituted cycloalkyl-$A_3$-substituted aryl, heteroaryl-$A_3$-heteroaryl, $A_2$-heteroaryl-$A_3$-heteroaryl, heteroaryl-$A_3$-cycloalkyl, $A_2$-heteroaryl-$A_3$-cycloalkyl, heteroaryl-$A_3$-substituted cycloalkyl, $A_2$-heteroaryl-$A_3$-substituted cycloalkyl, heteroaryl-$A_3$-aryl, $A_2$-heteroaryl-$A_3$-aryl, heteroaryl-$A_3$-heterocycloalkyl, $A_2$-heteroaryl-$A_3$-heterocycloalkyl, heteroaryl-$A_3$-substituted aryl, $A_2$-heteroaryl-$A_3$-substituted aryl, heterocycloalkyl-$A_3$-heterocycloalkyl, $A_2$-heterocycloalkyl-$A_3$-heterocycloalkyl, heterocycloalkyl-$A_3$-cycloalkyl, $A_2$-heterocycloalkyl-$A_3$-cycloalkyl, heterocycloalkyl-$A_3$-substituted cycloalkyl, $A_2$-heterocycloalkyl-$A_3$-substituted cycloalkyl, heterocycloalkyl-$A_3$-aryl, $A_2$-heterocycloalkyl-$A_3$-aryl, heterocycloalkyl-$A_3$-substituted aryl, $A_2$-heterocycloalkyl-$A_3$-substituted aryl, heterocycloalkyl-$A_3$-heteroaryl, $A_2$-heterocycloalkyl-$A_3$-heteroaryl, substituted aryl-$A_3$-substituted aryl, $A_2$-substituted aryl-$A_3$-substituted aryl, substituted aryl-$A_3$-cycloalkyl, $A_2$-substituted aryl-$A_3$-cycloalkyl, substituted aryl-$A_3$-substituted cycloalkyl, $A_2$-substituted aryl-$A_3$-substituted cycloalkyl, substituted aryl-$A_3$-aryl, $A_2$-substituted aryl-$A_3$-aryl, substituted aryl-$A_3$-heteroaryl, $A_2$-substituted aryl-$A_3$-heteroaryl, substituted aryl-$A_3$-heterocycloalkyl, and $A_2$-substituted aryl-$A_3$-heterocycloalkyl.

$R_6$ is hydrogen, alkyl, substituted alkyl, cycloalkyl, substituted cycloalkyl, $A_2$-cycloalkyl, $A_2$-substituted cycloalkyl, aryl, substituted aryl, $A_2$-aryl, $A_2$-substituted aryl, aryl-$A_3$-aryl, $A_2$-aryl-$A_3$-aryl, heteroaryl, $A_2$-heteroaryl, heterocycloalkyl, $A_2$-heterocycloalkyl, aryl-$A_3$-cycloalkyl, $A_2$-aryl-$A_3$-cycloalkyl, aryl-$A_3$-heteroaryl, $A_2$-aryl-$A_3$-heteroaryl, aryl-$A_3$-heterocycloalkyl, $A_2$-aryl-$A_3$-heterocycloalkyl, carboxy, alkoxycarbonyl,

alkoxycarbonylamino, aryloxycarbonylamino, arylcarbonylamino, —N(alkyl)(alkoxycarbonyl), —N(alkyl)(aryloxycarbonyl), alkylcarbonylamino, —N(alkyl)(alkylcarbonyl), or —N(alkyl)(arylcarbonyl).

m is an integer from 1 to 5.

Y is O, S, N—$R_4$, N—$SO_2$—$R_7$, $$N-\overset{O}{\underset{\|}{C}}-A_3-R_7, \quad N-\overset{O}{\underset{\|}{C}}-A_3-O-R_7,$$

$$N-\overset{O}{\underset{\|}{C}}-O-A_3-R_7, \quad N-\overset{O}{\underset{\|}{C}}-N\underset{\diagdown}{\diagup}N-R_4,$$

$$N-\overset{O}{\underset{\|}{C}}-N\underset{\diagdown}{\diagup}N-\overset{O}{\underset{\|}{C}}-R_7, \quad N-\overset{O}{\underset{\|}{C}}-A_3-\overset{O}{\underset{\|}{C}}-R_7,$$

$$N-\overset{O}{\underset{\|}{C}}-N\underset{\diagdown}{\diagup}N-\overset{O}{\underset{\|}{C}}-CH_2-O-R_7,$$

$$-(CH_2)_d-\underset{R_{21}}{N}-\overset{O}{\underset{\|}{C}}-(CH_3)_e,$$

$$N-\overset{O}{\underset{\|}{C}}-N\underset{\diagdown}{\diagup}N-\overset{O}{\underset{\|}{C}}-O-R_7, \text{ or}$$

$$N-\overset{O}{\underset{\|}{C}}-N\underset{\diagdown}{\diagup}N-\overset{O}{\underset{\|}{C}}-\overset{O}{\underset{\|}{C}}-R_7.$$

$R_7$ is alkyl, substituted alkyl, cycloalkyl, substituted cycloalkyl, $A_2$-cycloalkyl, $A_2$-substituted cycloalkyl, aryl, substituted aryl, $A_2$-aryl, $A_2$-substituted aryl, heteroaryl, $A_2$-heteroaryl, heterocycloalkyl, $A_2$-heterocycloalkyl, aryl- $A_3$-aryl, $A_2$-aryl-$A_3$-aryl, aryl-$A_3$-cycloalkyl, $A_2$-aryl-$A_3$-cycloalkyl, aryl-$A_3$-heteroaryl, $A_2$-aryl-$A_3$-heteroaryl, aryl-$A_3$-heterocycloalkyl, $A_2$-aryl-$A_3$-heterocycloalkyl, aryl-$A_3$-substituted aryl, $A_2$-aryl-$A_3$-substitued aryl, aryl-$A_3$-substituted cycloalkyl, $A_2$-aryl-$A_3$-substituted cycloalkyl, cycloalkyl-$A_3$-cycloalkyl, $A_2$-cycloalkyl-$A_3$-cycloalkyl, cycloalkyl-$A_3$-aryl, $A_2$-cycloalkyl-$A_3$-aryl, cycloalkyl-$A_3$-heteroaryl, $A_2$-cycloalkyl-$A_3$-heteroaryl, cycloalkyl-$A_3$-heterocycloalkyl, $A_2$-cycloalkyl-$A_3$-heterocycloalkyl, cycloalkyl-$A_3$-substituted cycloalkyl, $A_2$-cycloalkyl-$A_3$-substituted cycloalkyl, cycloalkyl-$A_3$-substituted aryl, $A_2$-cycloalkyl-$A_3$-substituted aryl, substituted cycloalkyl-$A_3$-cycloalkyl, $A_2$-substituted cycloalkyl-$A_3$-cycloalkyl, substituted cycloalkyl-$A_3$-substituted cycloalkyl, $A_2$-substituted cycloalkyl-$A_3$-substituted cycloalkyl, substituted cycloalkyl-$A_3$-aryl, $A_2$-substituted cycloalkyl-$A_3$-aryl, substituted cycloalkyl-$A_3$-heteroaryl, $A_2$-substituted cycloalkyl-$A_3$-heteroaryl, substituted cycloalkyl-$A_3$-heterocycloalkyl, $A_2$-substituted cycloalkyl-$A_3$-heterocycloalkyl, substituted cycloalkyl-$A_3$-substituted aryl, $A_2$-substituted cycloalkyl-$A_3$-substituted aryl, heteroaryl-$A_3$-heteroaryl, $A_2$-heteroaryl-$A_3$-heteroaryl, heteroaryl-$A_3$-cycloalkyl, $A_2$-heteroaryl-$A_3$-cycloalkyl, heteroaryl-$A_3$-substituted cycloalkyl, $A_2$-heteroaryl-$A_3$-substituted cycloalkyl, heteroaryl-$A_3$-aryl, $A_2$-heteroaryl-$A_3$-aryl, heteroaryl-$A_3$-heterocycloalkyl, $A_2$-heteroaryl-$A_3$-heterocycloalkyl, heteroaryl-$A_3$-substituted aryl, $A_2$-heteroaryl-$A_3$-substituted aryl, heterocycloalkyl-$A_3$-heterocycloalkyl, $A_2$-heterocycloalkyl-$A_3$-heterocycloalkyl, heterocycloalkyl-$A_3$-cycloalkyl, $A_2$-heterocycloalkyl-$A_3$-cycloalkyl, heterocycloalkyl-$A_3$-substituted cycloalkyl, $A_2$-heterocycloalkyl-$A_3$-substituted cycloalkyl, heterocycloalkyl-$A_3$-aryl, $A_2$-heterocycloalkyl-$A_3$-aryl, heterocycloalkyl-$A_3$-substituted aryl, $A_2$-heterocycloalkyl-$A_3$-substituted aryl, heterocycloalkyl-$A_3$-heteroaryl, $A_2$-heterocycloalkyl-$A_3$-heteroaryl, substituted aryl-$A_3$-substituted aryl, $A_2$-substituted aryl-$A_3$-substituted aryl, substituted aryl-$A_3$-cycloalkyl, $A_2$-substituted aryl-$A_3$-cycloalkyl, substituted aryl-$A_3$-substituted cycloalkyl, $A_2$-substituted aryl-$A_3$-substituted cycloalkyl, substituted aryl-$A_3$-aryl, $A_2$-substituted aryl-$A_3$-aryl, substituted aryl-$A_3$-heteroaryl, $A_2$-substituted aryl-$A_3$-heteroaryl, substituted aryl-$A_3$-heterocycloalkyl, $A_2$-substituted aryl-$A_3$-heterocycloalkyl,

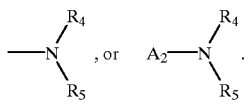

n and o are one or two provided that the sum of n plus o is two or three.

v and w are one, two, or three provided that the sum of v plus w is three, four, or five.

$R_8$ is hydrogen, halo, amino, —NH(lower alkyl), —N(lower alkyl)$_2$, nitro, alkyl, substituted alkyl, alkoxy, hydroxy, aryl, substituted aryl, $A_2$-aryl, $A_2$-substituted aryl, aryl-$A_3$-aryl, $A_2$-aryl-$A_3$-aryl, cycloalkyl, substituted cycloalkyl, $A_2$-cycloalkyl, $A_2$-substituted cycloalkyl, heteroaryl, $A_2$-heteroaryl, heterocycloalkyl, $A_2$-heterocycloalkyl, aryl-$A_3$-cycloalkyl, $A_2$-aryl-$A_3$-cycloalkyl, aryl-$A_3$-heteroaryl, $A_2$-aryl-$A_3$-heteroaryl, aryl-$A_3$-heterocycloalkyl, or $A_2$-aryl-$A_3$-heterocycloalkyl.

$B_1$, $B_2$ and $B_3$ are each CH, or two of $B_1$, $B_2$ and $B_3$ are CH and the other is N, or one of $B_1$, $B_2$ and $B_3$ is CH and the other two are N.

$R_9$ is hydrogen or lower alkyl.

$R_{10}$ is alkyl, substituted alkyl, alkyl-O-alkyl, alkyl-O-alkyl-O-alkyl, cycloalkyl, substituted cycloalkyl, $A_2$-cycloalkyl, $A_2$-substituted cycloalkyl, aryl, substituted aryl, $A_2$-aryl, $A_2$-substituted aryl, aryl-$A_3$-aryl, $A_2$-aryl-$A_3$-aryl, heteroaryl, $A_2$-heteroaryl, heterocycloalkyl, $A_2$-heterocycloalkyl, aryl-$A_3$-cycloalkyl, $A_2$-aryl-$A_3$-cycloalkyl, aryl-$A_3$-heteroaryl, $A_2$-aryl-$A_3$-heteroaryl, aryl-$A_3$-heterocycloalkyl or $A_2$-aryl-$A_3$-heterocyloalkyl.

$R_{20}$ is alkyl, substituted alkyl, cycloalkyl, substituted cycloalkyl, $A_2$-cycloalkyl, $A_2$-substituted cycloalkyl, $A_2$-aryl, or $A_2$-substituted aryl.

$R_{21}$ and $R_{22}$ are independently selected from hydrogen, alkyl, substituted alkyl, cycloalkyl, substituted cycloalkyl, $A_2$-cycloalkyl, $A_2$-substituted cycloalkyl, $A_2$-aryl, and $A_2$-substituted aryl.

p is an integer from 2 to 6.

q is an integer from 1 to 6.

r is zero, one or two.

s is one or two.

t is one, two, three or four.

u is one, two or three.

$A_2$ is an alkylene or a substituted alkylene bridge of 1 to 10 carbons, an alkenyl or substituted alkenyl bridge of 2 to 10 carbons having one or more double bonds, or an alkynyl or substituted alkynyl bridge of 2 to 10 carbons having one or more triple bonds.

$A_3$ is a bond, an alkylene or a substituted alkylene bridge of 1 to 10 carbons, an alkenyl or substituted alkenyl bridge of 2 to 10 carbons having one or more double bonds, an alkynyl or substituted alkynyl bridge of 2 to 10 carbons having one or more triple bonds,

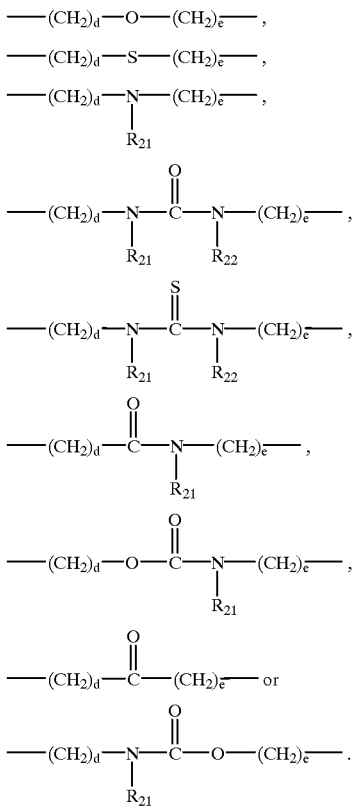

d and e are independently selected from zero and an integer from 1 to 10 provided that the sum of d plus e is no greater than 10.

Compounds of this invention include the formula:

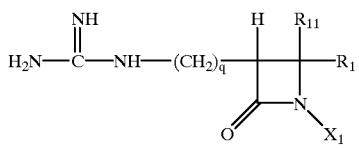
(II)

wherein:

$R_{11}$ is alkyl.

$R_1$, $X_1$ and q are as defined above.

Compounds of this invention include the formula:

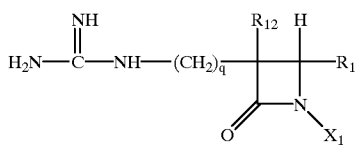
(III)

wherein:

$R_{12}$ is alkyl.

$R_1$, $X_1$, and q are as defined above.

Compounds of this invention include the formula:

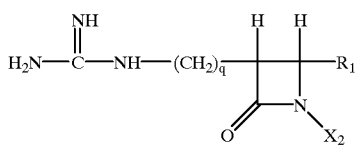
(IV)

wherein:

$R_1$ and q are as defined above.

$X_2$ is

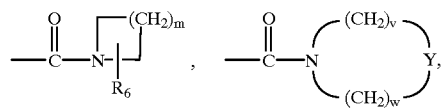

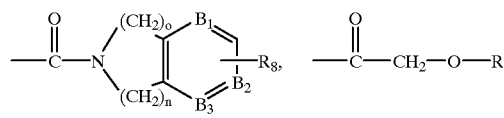

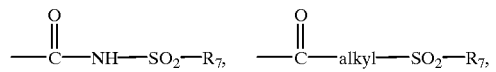

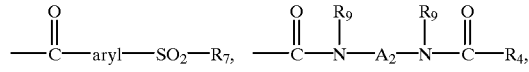

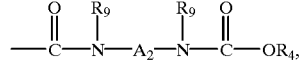

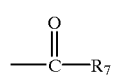

provided that

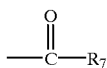

is other than alkylcarbonyl, phenylcarbonyl, substituted phenylcarbonyl, naphthylcarbonyl, substituted naphthylcarbonyl, phenylaminocarbonyl, substituted phenylaminocarbonyl, napthylaminocarbonyl, or substituted naphthylaminocarbonyl, or —SO$_2$—R$_7$ provided that —SO$_2$R$_7$ is other than alkylsulfonyl, phenylsulfonyl, substituted phenylsulfonyl, naphthylsulfonyl or substituted naphthylsulfonyl.

$R_4$, $R_5$, Y, $R_6$, m, n, o, $B_1$, $B_2$, $B_3$, $R_8$, $R_9$ and $R_{10}$ are as defined above.

Compounds of this invention include the formula:

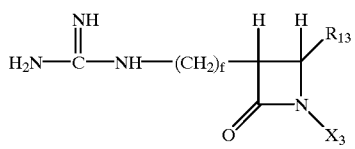
(V)

wherein:

f is an integer from 3 to 5.

$R_{13}$ is

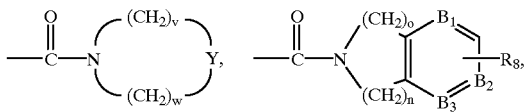

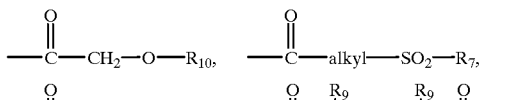

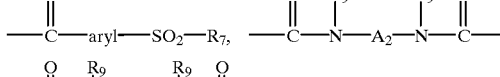

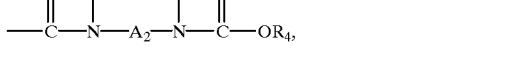

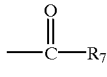

provided that

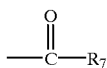

is other than phenylaminocarbonyl, substituted phenylaminocarbonyl, naphthylaminocarbonyl, substituted naphthylaminocarbonyl, carboxymethylaminocarbonyl, or alkoxycarbonylmethylaminocarbonyl, —SO$_2$—R$_7$ provided that —SO$_2$R$_7$ is other than alkylsulfonyl, phenylsulfonyl, substituted phenylsulfonyl, naphthylsulfonyl or substituted naphthylsulfonyl, or

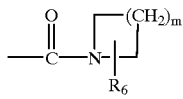

provided that if m is 1, 2 or 3 than $R_6$ is other than hydrogen, carboxy, alkoxycarbonyl or aryloxycarbonyl.

$X_3$ is phenylaminocarbonyl, substituted phenylaminocarbonyl, naphthylaminocarbonyl, substituted naphthylaminocarbonyl, alkylcarbonyl, phenylcarbonyl, substituted phenylcarbonyl, naphthylcarbonyl, substituted naphthylcarbonyl, alkylsulfonyl, phenylsulfonyl, substituted phenylsulfonyl, naphthylsulfonyl, or substituted naphthylsulfonyl.

$R_4$, $R_5$, Y, m, n, o, $B_1$, $B_2$, $B_3$, v, w, and $R_8$ are as defined above.

This invention is also directed to the use of the beta lactam compounds of formula VI shown below as inhibitors of tryptase, Factor Xa, Factor VIIa, and urokinase plaminogen activator.

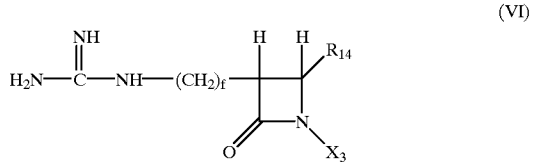
(VI)

wherein:

$R_{14}$ is hydrogen, carboxy, alkoxycarbonyl, alkylcarbonyl, phenylcarbonyl, substituted phenylcarbonyl, naphthylcarbonyl, substituted naphthylcarbonyl, alkylsulfonyl, phenylsulfonyl, substituted phenylsulfonyl, naphthylsulfonyl, substituted naphthylsulfonyl, phenylaminocarbonyl, substituted phenylaminocarbonyl, naphthylaminocarbonyl, substituted naphthylaminocarbonyl, $A_2$-aryl,

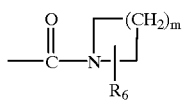

wherein m is 1, 2 or 3 and $R_6$ is hydrogen, carboxy, alkoxycarbonyl, or aryloxycarbonyl.

$X_3$ and f are as defined above.

DETAILED DESCRIPTION OF THE INVENTION

The term "alkyl" refers to straight or branched chain radicals having up to ten carbon atoms The term "lower alkyl" refers to straight or branched radicals having up to four carbon atoms and is a preferred subgrouping for the term alkyl.

The term "substituted alkyl" refers to such straight or branched chain radicals of 1 to 10 carbons wherein one or more, preferably one, two or three, hydrogens have been replaced by a hydroxy, amino, cyano, halo, trifluoromethyl, nitro, —NH(lower alkyl), —N(lower alkyl)$_2$, alkoxy, alkylthio, carboxy, alkoxycarbonyl, aminocarbonyl, or alkoxycarbonylamino.

The term "alkoxy" refers to such alkyl groups as defined above attached to an oxygen. The term "alkylthio" refers to such alkyl groups as defined above attached to a sulfur. The terms "lower alkoxy" and "lower alkylthio" refer to such lower alkyl groups as defined above attached to an oxygen or sulfur.

The term "cycloalkyl" refers to fully or partially saturated rings of 3 to 7 carbons.

The term "substituted cycloalkyl" refers to such rings of 3 to 7 carbons having one or more substituents selected from lower alkyl, lower alkoxy, lower alkylthio, halo, hydroxy, trifluoromethyl, nitro, cyano, amino, —NH(lower alkyl), —N(lower alkyl)$_2$, or carboxy as well as such rings fused to a phenyl ring such as tetrahydronaphthyl.

The term "aryl" refers to phenyl, 1-naphthyl and 2-naphthyl.

The term "substituted aryl" refers to phenyl, 1-naphthyl, and 2-naphthyl having a substituent selected from alkyl of 1 to 10 carbons, lower alkoxy, lower alkylthio, halo, hydroxy, trifluoromethyl, nitro, amino, —NH(loweralkyl), —N(lower alkyl)$_2$, or carboxy, and di and tri-substituted phenyl, 1-naphthyl, or 2-naphthyl wherein said substituents are selected from methyl, methoxy, methylthio, halo, hydroxy and amino.

The term "heteroaryl" refers to unsaturated and partially saturated rings of 4 to 7 atoms containing one or two O and S atoms and/or one to four N atoms, one to three N atoms when the ring is 4 atoms, provided that the total number of hetero atoms in the ring is 4 or less, 3 or less when the ring is 4 atoms. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, 2- and 3-furyl, and 2-(1,4,5,6-tetrahydropyrimidinyl). The term heteroaryl also includes bicyclic rings wherein the 4 to 7 membered ring containing O, S and N atoms as defined above is fused to a benzene, cycloalkyl, heteroaryl or heterocycloalkyl ring. Preferred bicyclic rings are 2- and 3-indolyl and 4-and 5-quinolinyl. The mono or bicyclic heteroaryl ring can also be additionally substituted at one or more available carbon atoms by a lower alkyl, halo, carboxy, hydroxy, $A_2$-lower alkoxy, $A_2$-guanido, benzyl or cyclohexylmethyl. Also, if the mono or bicyclic ring has an available N-atom such N atom can also be substituted by an N-protecting group such as benzyloxycarbonyl, tert-butoxycarbonyl, benzyl or benzhydryl.

The term "heterocycloalkyl" refers to fully saturated rings of 4 to 7 atoms containing one or two O and S atoms and/or one to four N atoms, one to three N atoms when the ring is 4 atoms, provided that the total number of hetero atoms in the ring is 4 or less, 3 or less when the ring is 4 atoms. The heterocycloalkyl is attached by way of an available carbon or nitrogen atom. Preferred heterocycloalkyl groups include pyrrolidinyl, tetrahydrofuranyl, tetrahydrothienyl, morpholinyl, tetrahydro-1,2-thiazinyl, piperazinyl, piperidinyl, homopiperizinyl and azetidinyl. The term heterocycloalkyl also includes bicyclic rings wherein the 4 to 7 membered saturated ring containing O, S and N atoms as defined above is fused to a cycloalkyl, benzene, heteroaryl, or heterocycloalkyl ring. The mono or bicyclic heterocycloalkyl ring can also be substituted at one or more available carbon atoms by a lower alkyl, halo, carboxy, hydroxy, keto, $A_2$-lower alkoxy, $A_2$-guanido, benzyl or cyclohexylmethyl. Also, if the mono or bicyclic heterocycloalky ring has an available N atom such N atom can also be substituted by an N-protecting group such as benzyloxycarbonyl, tert-butoxycarbonyl, benzyl or benzhydryl.

The term "halo" refers to chloro, bromo, fluoro and iodo.

The terms "alkylene" and "substitued alkylene" refer to a bridge of 1 to 10 carbons such as —CH$_2$—, —(CH$_2$)$_2$—, —(CH$_2$)$_9$—, etc. One or more hydrogens, preferably one, in the alkylene bridge can be replaced by an alkyl, substituted alkyl, carboxy, alkoxycarbonyl, amino, —NH(lower alkyl), —N(lower alkyl)$_2$, hydroxy, aminocarbonyl, alkoxycarbonylamino, halo, cycloalkyl, substituted cycloalkyl, aryl, substituted aryl, hetereoaryl, or heterocycloalkyl, e.g.

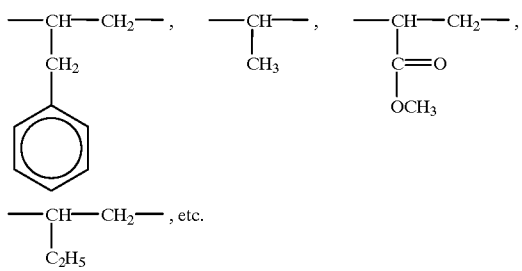

The terms "alkenyl" and "substituted alkenyl" refer to a bridge of 2 to 10 carbons having one or more double bonds, preferably 2 to 6 carbons with one double bond, such as —CH=CH—, —CH=CH—CH$_2$—, —CH$_2$—CH=CH—, etc. One or more hydrogens, preferably one, in the alkenyl bridge can be replaced by an alkyl, substituted alkyl, carboxy, alkoxycarbonyl, amino, —NH(lower alkyl), —N(lower alkyl)$_2$, hydroxy, aminocarbonyl, alkoxycarbonylamino, halo, cycloalkyl, substituted cycloalkyl, aryl, substituted aryl, heteroaryl, or heterocycloalkyl, e.g.

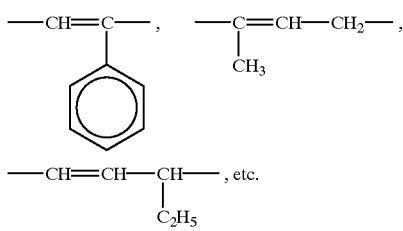

The term "alkynyl" and "substituted alkynyl" refer to a bridge of 2 to 10 carbons having one or more triple bonds, preferably 2 to 6 carbons with one triple bond, such as —C≡C—, —CH$_2$—C≡C—, —C≡C—CH$_2$—, etc. One or more hydrogens in the alkynyl bridge can be replaced by an alkyl, substituted alkyl, carboxy, alkoxycarbonyl, amino, carboxy, alkoxycarbonyl, amino, —NH(lower alkyl), —N(lower alkyl)$_2$, hydroxy, aminocarbonyl, alkoxycarbonylamino, halo, cycloalkyl, substituted cycloalkyl, aryl, substituted aryl, heteroaryl, or heterocycloalkyl, e.g.

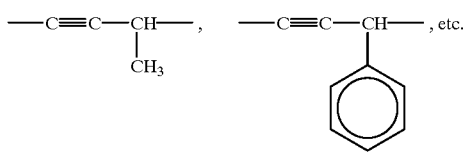

The compounds of formulas IV, V and VI can be prepared as follows.

The carboxy substituted azetidinone of the formula:

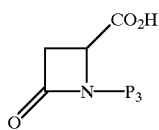

(VII)

wherein $P_3$ is a silyl protecting group such as tert-butyldimethylsilyl is treated with an alkyldihalide of the formula:

Cl—(CH$_2$)$_q$—I    (VIII)

in the presence of base to give the carboxy substituted azetidinone of the formula:

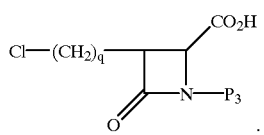

(IX)

The carboxy substituted azetidinone of formula IX is then treated with an azide such as sodium azide followed by a fluoride ion salt such as tetrabutylammonium fluoride to remove the silyl group and give

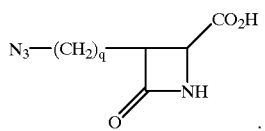

(X)

Hydrogenation of the compound of formula X by treating with hydrogen in the presence of palladium on carbon catalyst gives the alkylamino compound of the formula:

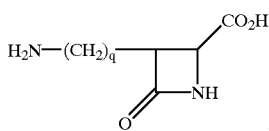

(XI)

The alkylamino compound of formula XI, preferably as an acid salt, is reacted with the diprotected guanylating agent of the formula:

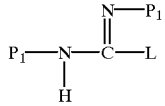

(XII)

wherein $P_1$ is an N-protecting group such as tert-butoxycarbonyl or benzyloxycarbonyl and L is a leaving group such as methylthio or pyrazolyl to give the azetidinone compound of the formula:

(XIII)

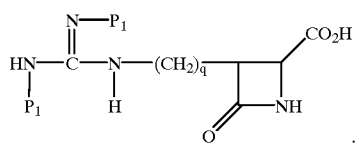

Coupling the intermediate of compound XIII with an amine selected from

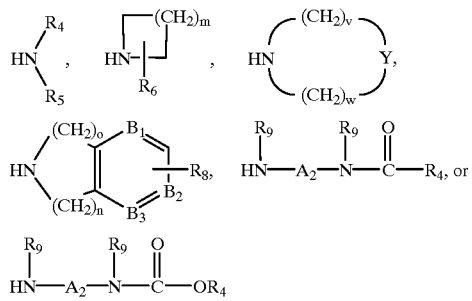

gives the compound of the formula:

(XIV)

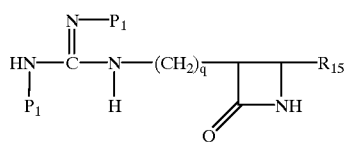

wherein $R_{15}$ is

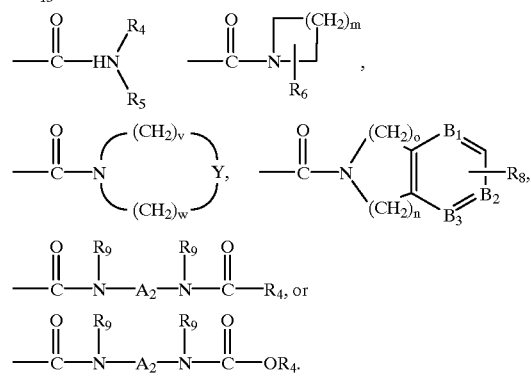

Reacting the intermediate of formula XIV with a chloro compound selected from

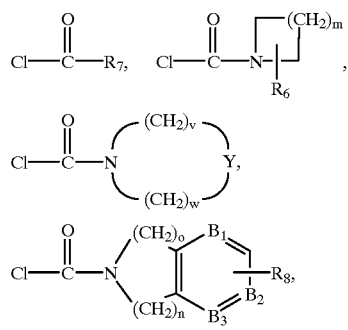

-continued

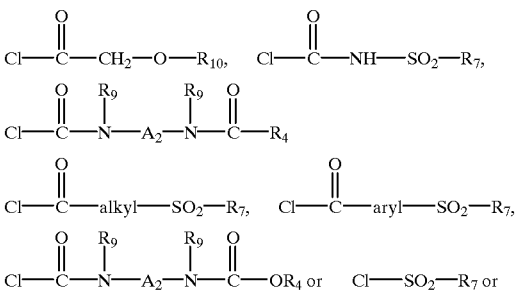

reacting with $OCN—SO_2—R_9$ gives the compound of the formula:

(XV)

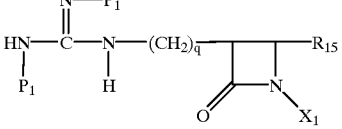

Removal of the N-protecting groups gives the compounds of formulas IV, V and VI.

The compounds of formula IV and VI wherein $R_1$ or $R_{14}$ is carboxy or alkoxy carbonyl can be prepared by reacting the intermediate of formula XIII with an alcohol, bromide, or iodide of the formula:

$$HO—Z, Br—Z, \text{ or } I—Z \quad \text{(XVI)}$$

wherein Z is alkyl, substituted alkyl, benzyl or benzhydryl. When XVI is HO—Z, the reaction is performed in the presence of a coupling reagent such as dicyclohexylcarbodiimide, 1-ethyl-3-(3-dimethylamino) propyl carbodiimide, benzotriazol-1-yloxytris (dimethylamino)phosphonium hexafluorophosphate, or carbonyldiimidazole. When XVI is Br—Z or I—Z, the reaction is performed in the presence of a base such as sodium carbonate or bicarbonate. The reaction gives the compound of the formula:

(XVII)

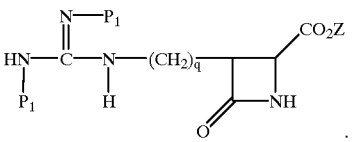

Reacting the intermediate of formula XVII with a chloro compound selected from

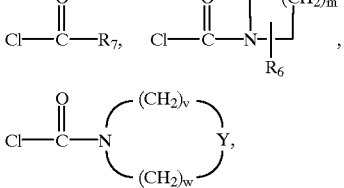

-continued

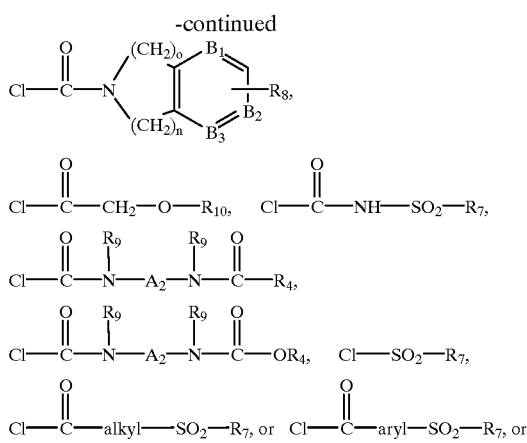

reacting with OCN—SO$_2$—R$_7$ gives the compound of the formula:

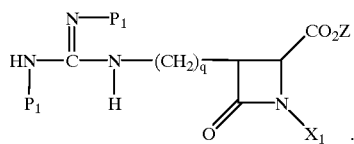
(XVIII)

When Z is a protecting group such as benzyl or benzhydryl, removal of this group and the N-protecting groups from the compound of formula XVIII gives the desired compounds of formulas IV and VI wherein R$_1$ or R$_{14}$ is carboxy.

Also, when Z is alkyl or substituted alkyl and X$_1$ is

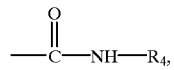

the compound of formula XVIII can be treated to remove the N-protectings groups followed by mild aqueous hydrolysis to give the desired compounds of formula IV and VI wherein R$_1$ or R$_{14}$ is carboxy.

In the above procedures when X$_1$ is a group such as

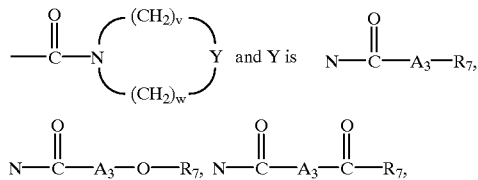

etc., the intermediate of formula XIV or XVII can be reacted with a carbamoyl chloride

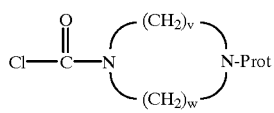

wherein Prot is an N-protecting group such as tert-butoxycarbonyl followed by removal of the N-protecting group and coupling with an acid such as

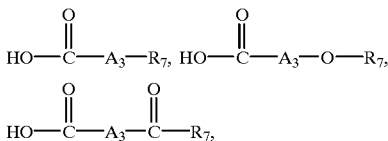

etc, in the presence of a coupling reagent.

The compounds of formula III can be prepared by treating the carboxy substituted azetidinone of formula IX with a haloalkyl of the formula:

halo—R$_{12}$ (XIX)

in the presence of base wherein halo is Cl, Br, or I to give the azetidinone

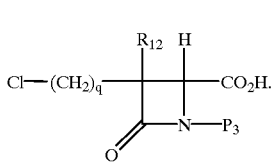
(XX)

The azetidinone of formula XX can also be prepared by reacting the azetidinone of formula VII with the haloalkyl of formula XIX in the presence of base to give the azetidinone of the formula:

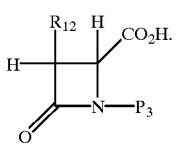
(XXI)

Treatment of the compound of formula XXI with an alkyldihalide of formula VIII in the presence of base gives the azetidinone of formula XX.

The azetidinone of formula XX is then reacted in the same manner as the azetidinone of formula IX described above to give the desired compounds of formula III.

The compounds of formula II wherein R$_1$ is other than alkyl can be prepared by treating the olefin of the formula:

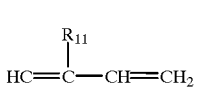
(XXII)

with chlorosulfonylisocyanate to give the azetidinone of the formula:

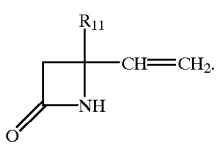
(XXIII)

Oxidation of compound XXIII such by treatment with, for example, potassium permanganate followed by silylation with a tri(lower alkyl) silyl chloride gives the azetidinone of the formula:

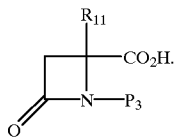

(XXIV)

The azetidinone of formula XXIV is then reacted in the same manner as the azetidinone of formula VII described above to give the desired compounds of formula II.

The compounds of formula II wherein $R_{11}$ and $R_1$ are both alkyl can be prepared by treating the azetidinone of the formula:

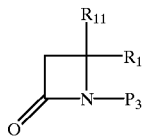

(XXV)

wherein $R_1$ and $R_{11}$, are both alkyl in the same manner as the azetidinone of formula VII described above. The dialkyl substituted azetidinones of formula XXV are known in the art, for example, see U.S. Pat. No. 4,775,670.

The compounds of formula IV and VI wherein $R_1$ or $R_{14}$ is —(CH$_2$)$_2$-aryl can be prepared by reacting an N-protected guanidine of the formula:

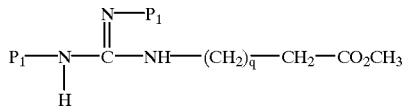

(XXVI)

with an N-protected compound of the formula:

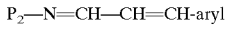

P$_2$—N=CH—CH=CH-aryl            (XXVII)

wherein P$_2$ is trimethylsilyl in the presence of lithium diisopropylamide to give the azetidinone of the formula:

(XXVIII)

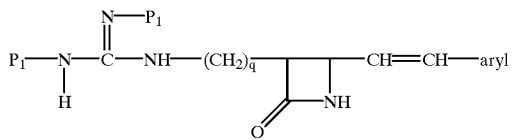

The azetidinone of formula XXVIII is then reacted with a chloro compound selected from

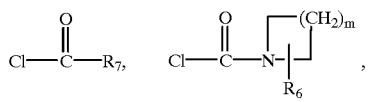

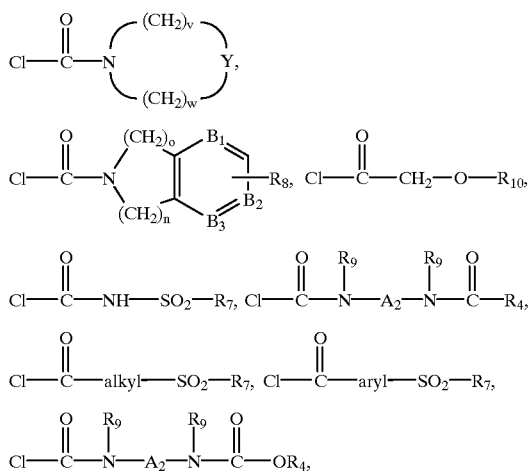

or Cl—SO$_2$—R$_7$, or with OCN—SO$_2$—R$_7$ to give, following the reduction of the alkene group and removal of the P$_1$ protecting groups, the desired compounds of formulas IV and VI.

Compounds of formula II, IV, and VI can also be prepared by reacting the chloro compound of the formula:

(XXIX)

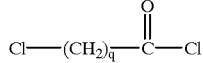

with the N-protected compound of the formula:

(XXX)

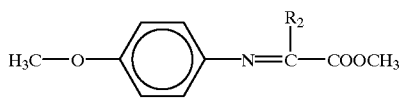

in the presence of base to give the azetidinone of the formula:

(XXXI)

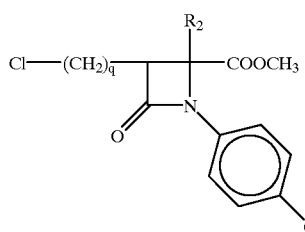

Treatment of the azetidinone of formula XXXI with an azide such as sodium azide gives the azetidinone (XXXII)

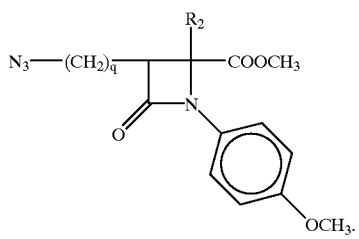

Treatment of the compound of formula XXXII with ceric ammonium nitrate removes the methoxyphenyl group and the resulting azetidinone can be reacted in the same manner as the azetidinone of formula X described above to give the desired compounds of formulas II, IV, and VI.

The compounds of formula I where $A_1$ is

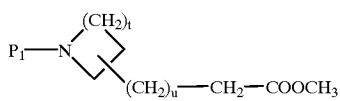

can be prepared by reacting the compound of the formula:

(XXXIII)

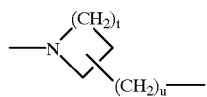

wherein $L_1$ is a leaving group such as bromo or iodo with the azetidinone of formula VII, XXI, XXIV or XXV in the presence of base to give the azetidinone of the formula:

(XXXIV)

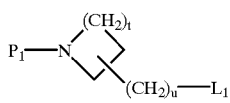

Removal of the $P_1$ protecting group and treatment of this azetidinone as 10 described above for the azetidinone of formula XI gives the desired compounds of formula I. Alternatively, the azetidinone of formula XXXIV can first be treated with a chloro compound to introduce the desired $X_1$ group, deprotected, and then reacted with the guanylating agent of formula XII.

Alternatively, the compounds of formula I wherein $A_1$ is

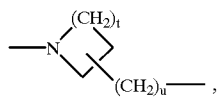

$R_1$ is —$(CH_2)_2$-aryl and $R_2$ and $R_3$ are hydrogen can be prepared by reacting a compound of the formula:

(XXXV)

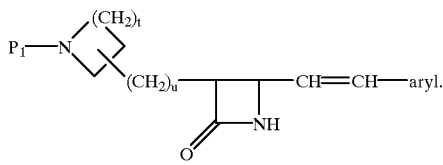

with the reagent of formula XXVII in the presence of lithium diisopropylamine to give the azetidinone of the formula:

(XXXVI)

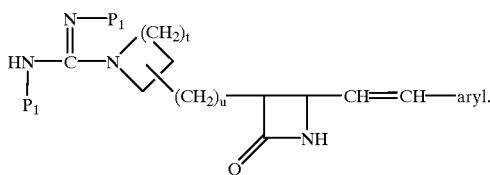

Removal of the $P_1$ protecting group and reaction with the guanylating agent compound of formula XII gives the azetidinone of the formula:

(XXXVII)

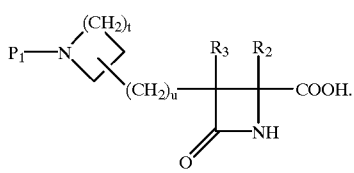

Reacting the intermediate of formula XXXVII with a chloro compound selected from

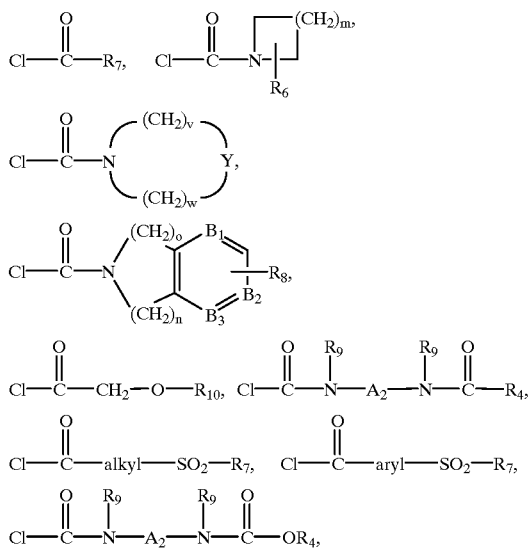

or CL—$SO_2$—$R_7$, or reacting with OCN—$SO_2$—$R_7$ followed by reduction of the alkene group and removal of the $P_1$ protecting groups gives the desired compounds of formula I.

As discussed above, when $X_1$ is a group such as

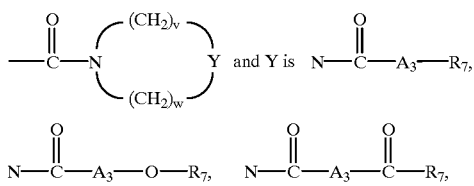

etc., the intermediate azetidinone can be reacted with a carbamoyl chloride

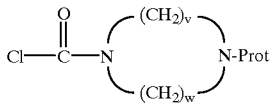

wherein Prot is as defined above followed by removal of the N-protecting group and coupling with an acid such as

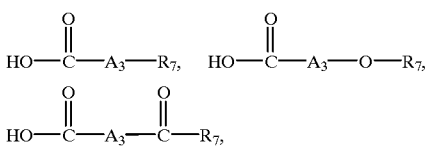

etc, in the presence of a coupling reagent to introduce the desired $X_1$ moiety.

Alternatively, the compounds of formula I wherein $A_1$ is

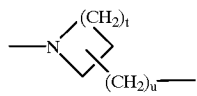

can be prepared from the azetidinone of formula XXXVII. According to this process, the ring nitrogen is protected by treating the azetidinone of formula XXXVII with, for example, tert-butyldimethylsilyl chloride. Treating with ozone reduces the moiety

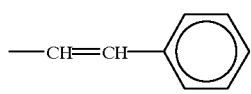

to an aldehyde which is then converted to a carboxylic acid by Jones oxidation or by treating with sodium chlorite and sulfamic acid. Removal of the silyl protecting group gives the azetidinone of the formula:

(XXXVIII)

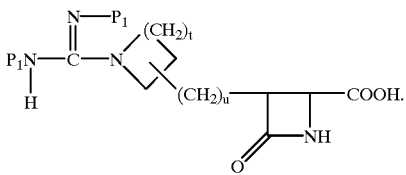

Treatment of this azetidinone as described above for the azetidinone of formula XIII gives the desired compounds of formula I.

The following is a preferred route to the intermediate of formula XIII. According to this procedure, the silyl protected azetidinone of formula VII is treated with the N-protected iodo compound of the formula:

(XXXIX)

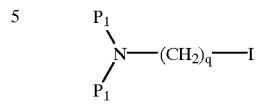

to give after removal of the silyl protecting group the azetidinone of the formula:

(XL)

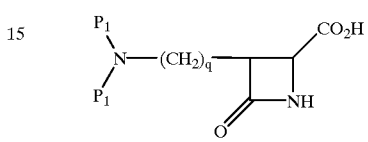

which may be isolated as an amine salt such as the tert-butylamine salt.

The $P_1$ protecting groups are removed from the azetidinone of formula XL and the resulting compound is reacted with the diprotected guanylating agent of formula XII to give the intermediate of formula XIII which again may be isolated as an amine salt such as the tert-butylamine salt.

The iodo compound of formula XXXIX can be prepared by reacting the diprotected amine of the formula:

(XLI)

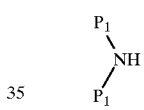

with the alkyldihalide of formula VIII to give the chloro compound of the formula:

(XLII)

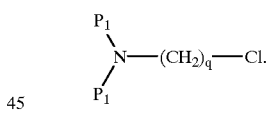

The chloro compound of formula XLII is then treated with sodium iodide in the presence of base to give the iodo compound of formula XXXIX.

The following alternate procedure can also be employed to prepare the compounds of formulas IV and VI.

The azetidinone of formula IX is reacted with benzylchloroformate in the presence of triethylamine and dimethylaminopyridine to give the benzyl ester of the formula:

(XLIII)

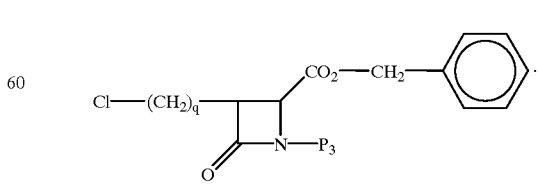

Treatment of the chloro compound of formula XLIII with sodium iodide gives the iodo compound of the formula:

(XLIV)

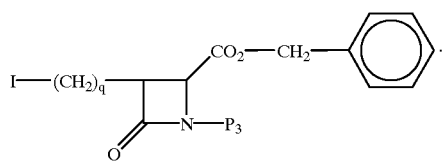

The iodo compound of formula XLIV is reacted with the diprotected guanidine of the formula:

(XLV)

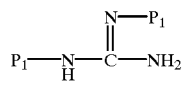

to give the azetidinone compound of the formula:

(XLVI)

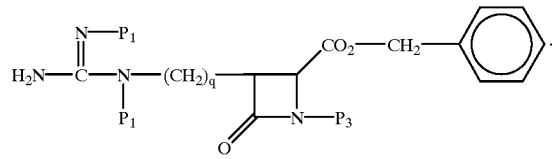

Removal of the silyl protecting group $P_3$ from the azetidinone of formula XLVI for example by reacting with ammonium fluoride gives the azetidinone compound of the formula:

(XLVII)

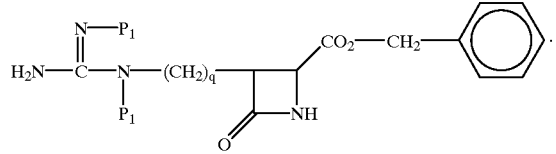

Reacting the intermediate of formula XLVII with a chloro compound

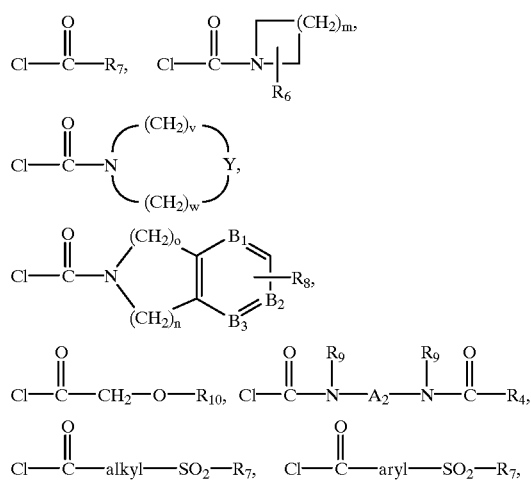

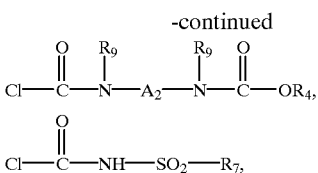

or $Cl-SO_2-R_7$, or reacting with $OCN-SO_2-R_7$ gives the compound of the formula:

(XLVIII)

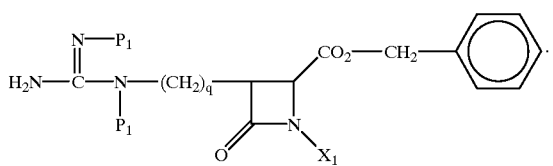

Removal of the benzyl protecting group and the $P_1$ N-protecting groups from the azetidinone of formula XLVIII gives the desired compounds of formulas IV and VI.

The compounds of formula I wherein $A_1$ is

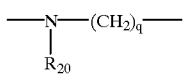

can be prepared by reacting the azetidinone of formula XL with an alcohol, bromide, or iodide of formula XVI to give the azetidinone of the formula:

(XLIX)

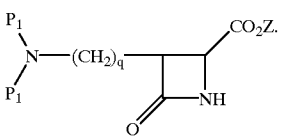

Reacting the intermediate of formula XLIX with a chloro compound selected from

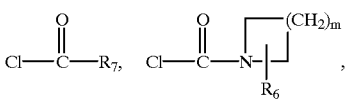

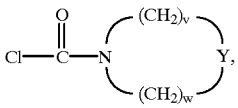

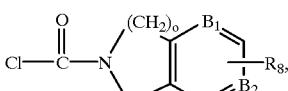

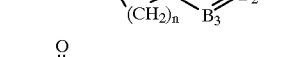

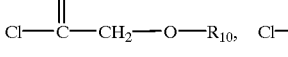

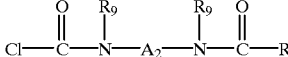

-continued

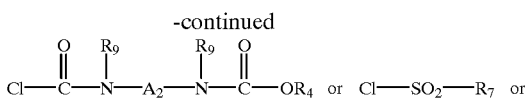

reacting with OCN—SO₂—R₉ gives the compound of the formula:

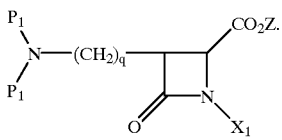
(L)

Removal of the P₁ protecting groups such as by treatment with trifluoroacetic acid when P₁ is tert-butoxycarbonyl gives the trifluoroacetic acid amine salt of the formula:

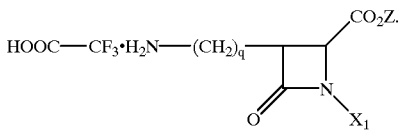
(LI)

Treatment of the trifluoroacetic acid amine salt of formula LI with the appropriate aldehyde in the presence of a reducing agent such as triacetoxy borohydride or sodium cyanoborohydride gives the compound of the formula:

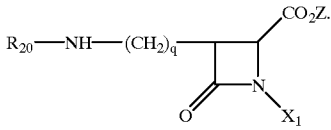
(LII)

The compound of formula LII is reacted with the diprotected guanylating agent of formula XII to give the azetidinone of the formula:

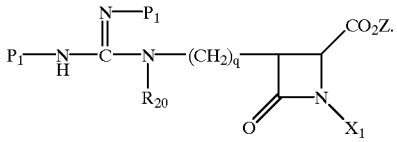
(LIII)

Removal of the P₁ and Z protecting groups gives the desired compounds of formula I.

The azetidinone compounds of formula I to VI and various intermediates and starting materials employed in their synthesis contain one or two asymmetric carbons as denoted below at ring positions 3 and 4

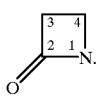

Of course, the compounds of formula II where $R_1$ and $R_{11}$ are the same and the compounds of formula VI where $R_{14}$ is hydrogen contain only one asymmetric ring carbon.

Additional asymmetric carbons may be present in the compounds of formula I to VI depending upon the definitions of the substituents $R_1$, $A_1$, $X_1$, $X_2$, $R_{13}$, $X_3$ and $R_{14}$. As is well known in the art, see for example J. March. Advanced Organic Chemistry, Fourth Edition, John Wiley & Sons, New York, N.Y. (1991), pages 94–164, such asymmetric carbon atoms give rise to enantiomers and diastereomers, and all such stereoisomers, either in pure form or in the form of mixtures, are included within the scope of this invention. In addition, when alkenes are present in the compounds of formula I to VI, they may, when appropriately substituted exist as cis or trans isomers, or as mixtures thereof. Again, all such forms are within the scope of this invention.

The compounds of formula I to VI can be obtained as a pharmaceutically acceptable salt, as a physiologically hydrolyzable ester, or as a solvate. The compounds of formulas I to IV and VI wherein $R_1$ or $R_{14}$ is carboxy can exist in the form of an inner salt or zwitterion. All such forms are within the scope of this invention. Pharmaceutically acceptable salts include salts with mineral acids such as hydrochloric, hydrobromic, phosphoric and sulfuric as well as salts with organic carboxylic acids or sulfonic acids such as acetic, trifluoroacetic, citric, maleic, oxalic, succinic, benzoic, tartaric, fumaric, mandelic, ascorbic, malic, methanesulfonic, p-toluensulfonic and the like. Preparation of these acid addition salts is carried out by conventional techniques.

The novel compounds of formulas I to V and the compounds of formula VI possess tryptase inhibition activity. This activity was confirmed using either isolated human skin tryptase or recombinant human tryptase; prepared from the human recombinant beta-protryptase expressed by baculovirus in insect cells. The expressed beta-protryptase was purified using sequential immobilized heparin affinity resin followed by an immunoaffinity column using an anti-tryptase monoclonoal antibody. The protryptase was activated by auto-catalytic removal of the N-terminal in the presence of dextran sulfate followed by dipeptidyl peptidase I (DPPI) removal of the two N-terminal amino acids to give the mature active enzyme (Sakai et al., J. Clin. Ivest., 97, pages 988–995, 1996). Essentially equivalent results were obtained using isolated native enzyme or the activated expressed enzyme. The tryptase enzyme was maintained in 2M sodium chloride, 10 nM 4-morpholinepropanesulfonic acid, pH 6.8.

The assay procedure employed a 96 well microplate. To each well of the microplate (Nunc MaxiSorp), 250 μl of assay buffer [containing low molecular weight heparin and tris (hydroxymethyl)aminomethane] was added followed by 2.0 μl of the test compound in dimethylsulfoxide. The substrate (10 μl) was then added to each well to give a final concentration of either 370 μM benzoyl-arginine-p-nitroaniline (BAPNA) or 100 μM benzyloxycarbonyl-glycine-proline-arginine-p-nitroaniline (CBz-Gly-Pro-Arg-pNA). Similar data was obtained using either substrate. The microplate was then shaken on a platform vortex mixer at a setting of 800 (Sarstedt TPM-2). After a total of three minutes incubation, 10 μl of the working stock solution of tryptase (6.1 mM final tryptase concentration for use with BAPNA or 0.74 nM for use with CBz-Gly-Pro-Arg-pNA) was added to each well. The microplate was vortexed again for one minute and then incubated without shaking at room temperature for an additional 2 minutes. After this time the microplate was read on a microplate reader (Molecular Devices UV max) in the kinetic mode (405 nm wavelength) over twenty minutes at room temperature. To determine the compound concentration that inhibited half of the enzyme activity ($IC_{50}$), the fraction of control activity (FCA) was plotted as a function of the inhibitor concentration (I) and curve to fit $FCA/(1+[I]/IC_{50})$. The $IC_{50}$ for each compound was determined 2–4 times and the obtained values were averaged.

As a result of this tryptase activity, the compounds of formula I to VI as well as an inner salt thereof, a pharmaceutically acceptable salt thereof, a hydrolyzable ester thereof, or a solvate thereof, are useful as antiinflammatory agents particularly in the treatment of chronic asthma and may also be useful in treating or preventing allergic rhinitis, inflammatory bowel disease, psoriasis, conjunctivitis, atopic dermatitis, rheumatoid arthritis, osteoarthritis, and other chronic inflammatory joint diseases, or diseases of joint cartilage destruction. Additionally, these compounds may be useful in treating or preventing myocardial infarction, stroke, angina and other consequences of atherosclerotic plaque rupture. Additionally, these compounds may be useful for treating or preventing diabetic retinopathy, tumor growth and other consequences of angiogenosis. Additionally, these compounds may be useful for treating or preventing fibrotic conditions, for example, fibrosis, scleroderma, pulmonary fibrosis, liver cirrhosis, myocardial fibrosis, neurofibromas and hypertrophic scars.

The compounds of formula I to VI are also inhibitors of Factor Xa and/or Factor VIIa. As a result, the compounds of formula I to VI as well as an inner salt or a pharmaceutically acceptable salt thereof, a hydrolyzable ester thereof, or a solvate thereof may also be useful in the treatment or prevention of thrombotic events associated with coronary artery and cerebrovascular disease which include the formation and/or rupture of atherosclerotic plaques, venous or arterial thrombosis, coagulation syndromes, ischemia and angina (stable and unstable), deep vein thrombosis (DVT), disseminated intravascular coagulopathy, Kasacach-Merritt syndrome, pulmonary embolism, myocardial infarction, cerebral infarction, cerebral thrombosis,transient ischemic attacks, atriala fibrillation, cerebral embolism, thromboembolic complications of surgery (such as hip or knee replacement, introduction of artificial heart valves and endarterectomy) and peripheral arterial occulsion and may also be useful in treating or preventing myocardial infarction, stroke, angina and other consequences of atherosclerotic plaque rupture. The compounds of formula I to VI possessing Factor Xa and/or Factor VIIa inhibtion activity may also be useful as inhibitors of blood coagulation such as during the preparation, storage and fractionation of whole blood.

The compounds of formula I to VI are also inhibitors of urokinase-type plasminogen activator. As a result, the compounds of formula I to VI as well as an inner salt or a pharmaceutically acceptable salt thereof, a hydrolyzable ester thereof, or a solvate thereof may be useful in the treatment or prevention of restenosis and aneurysms, in the treatment or prevention of myocardial infarction, stroke, angina and other consequences of atherosclerotic plaque rupture, and may also be useful in the treatment of malignancies, prevention of metastases, prevention of prothrombotic complications of cancer, and as an adjunct to chemotherapy.

The compounds of formulas I to V also possess thrombin and trypsin inhibitory activity similar to that reported by Han in the U.S. patents noted previously for the compounds of formula VI. As a result, the compounds of formula I to V as well as an inner salt or a pharmaceutically acceptable salt thereof, a hydrolyzable ester thereof, or a solvate thereof may be useful in treating or preventing pancreatitis, in the treatment or prevention of thrombotic events associated with coronary artery and cerebrovascular disease as described above, and may also be useful as inhibitors of blood coagulation such as during the preparation, storage, and fractionation of whole blood.

Certain compounds of formulas I to IV are also useful due to their selective tryptase inhibition activity. These compounds while having potent tryptase inhibition activity are much less active against other enzyme systems including trypsin, thrombin and Factor Xa. For example, this selective tryptase activity is seen with the compounds of formulas I to IV where $X_1$ or $X_2$ is the group

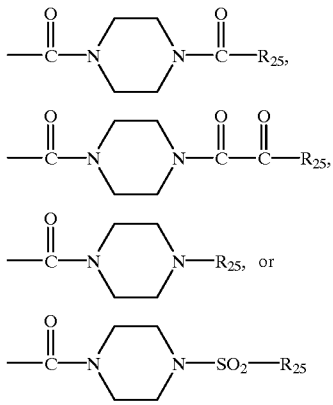

and $R_{25}$ is a spacer terminating in a lipophilic group. Suitable spacers include groups of 3 or more atoms such as

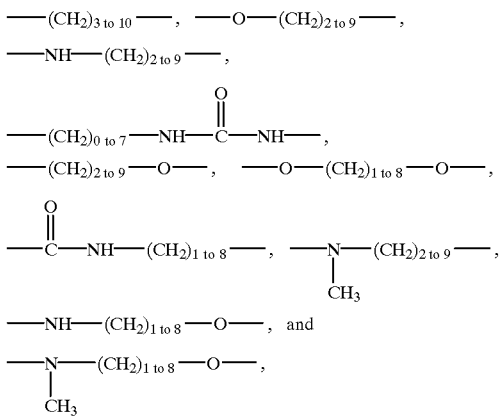

etc., as well as groups containing 2 or more atoms and a phenyl, substituted phenyl, cycloalkyl, heteroaryl, or heterocycloalkyl ring such as

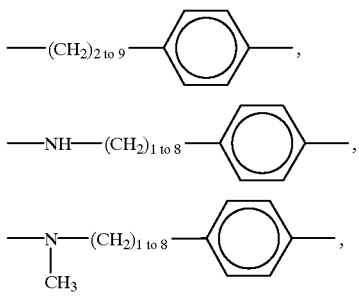

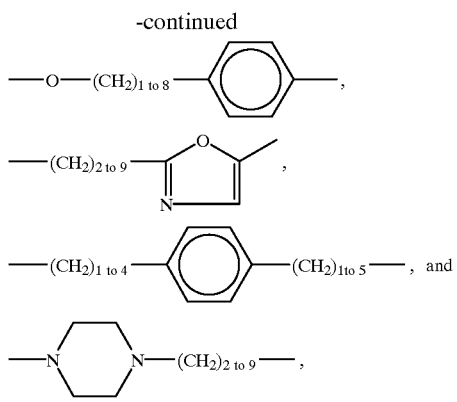

etc. Suitable lipophilic terminal groups include aryl, substituted aryl, cycloalkyl, heteroaryl, heterocycloalkyl, etc. These compounds of formulas I to IV as well as an inner salt, a pharmaceutically acceptable salt thereof, a hydrolyzable ester thereof, or a solvate thereof, are useful as antiinflammatory agents particularly in the treatment of chronic asthma and may also be useful in treating or preventing allergic rhinitis as well as some of the other diseases described above for the non-selective tryptase inhibitors. It is believed that as a result of their selective tryptase inhibition activity that these compounds will have less tendency to produce unwanted side-effects.

The compounds of formula I to VI as well as an inner salt or a pharmaceutically acceptable salt thereof, a hydrolyzable ester thereof, or a solvate thereof may be administered orally, topically, rectally or parenterally or may be administered by inhalation into the bronchioles or nasal passages. The method of administration will, or course, vary upon the type of disease being treated. The amount of active compound administered will also vary according to the method of administration and the disease being treated. An effective amount will be within the dosage range of about 0.1 to about 100 mg/kg, preferably about 0.2 to about 50 mg/kg and more preferably about 0.5 to about 25 mg/kg per day in a single or multiple doses administered at appropriate intervals throughout the day.

The composition used in these therapies can be in a variety of forms. These include, for example, solid, semisolid and liquid dosage forms such as tablets, pills, powders, liquid solutions or suspensions, liposomes, injectable and infusible solutions. Such compositions can include pharmaceutically acceptable carriers, preservatives, stabilizers, and other agents conventionally employed in the pharmaceutical industry.

When the compounds of formula I to VI as well as an inner salt or a pharmaceutically acceptable salt thereof, a hydrolyzable ester thereof, or a solvate thereof are employed to treat asthma or allergic rhinitis they will preferably be formulated as aerosols. The term "aerosol" includes any gas-borne suspended phase of the active compound which is capable of being inhaled into the bronchioles or nasal passage. Aerosol formulations include a gas-borne suspension of droplets of the active compound as produced in a metered dose inhaler or nebulizer or in a mist sprayer. Aerosol formulations also include a dry powder composition suspended in air or other carrier gas. The solutions of the active compounds of formulas I to VI used to make the aerosol formulation will be in a concentration of from about 0.1 to about 100 mg/ml, more preferably 0.1 to about 30 mg/ml, and most preferably from about 1 to about 10 mg/ml. The solution will usually include a pharmaceutically acceptable buffer such as a phosphate or bicarbonate to give a pH of from about 5 to 9, preferably 6.5 to 7.8, and more preferably 7.0 to 7.6. Preservatives and other agents can be included according to conventional pharmaceutical practice.

Other pharmaceutically active agents can be employed in combination with the compounds of formula I to VI depending upon the disease being treated. For example, in the treatment of asthma, β-adrenergic agonists such as albuterol, terbutaline, formoterol, fenoterol or prenaline can be included as can anticholinergics such as ipratropium bromide, anti-inflammatory cortiocosteroids such as beclomethasone, triamcinolone, flurisolide or dexamethasone, and anti-inflammatory agents such as cromolyn and nedocromil.

In addition to the novel compounds of formulas I to V and the methods of use for the compounds of formulas I to VI, this invention is also directed to novel intermediates and novel synthetic routes employed in the preparation of such compounds.

Preferred compounds of this invention are those of formula IV wherein:

q is 3;

$R_1$ is carboxy,

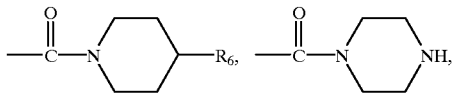

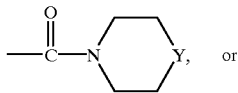

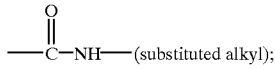

$X_2$ is 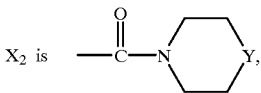

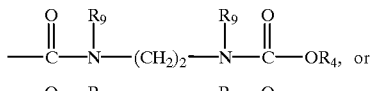

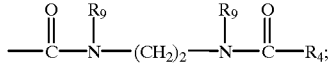

$R_6$ is aminocarbonyl,

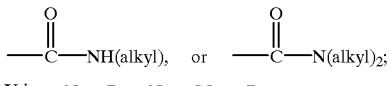

Y is   N—$R_4$,   N—$SO_2$—$R_7$,

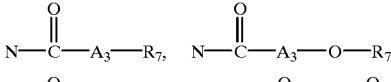

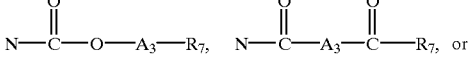

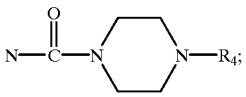

$R_4$ in the definition of Y and $X_2$ is alkyl, cycloalkyl, substituted alkyl, substituted cycloalkyl, —$(CH_2)_{1\ to\ 6}$-aryl, or heteroaryl;

$R_7$ is alkyl, cycloalkyl, substituted alkyl, substituted cycloalkyl, —$(CH_2)_{0\ to\ 4}$-aryl, —$(CH_2)_{0\ to\ 4}$-aryl-$A_3$- aryl, —(CH₂)₀ to ₄-heteroaryl, —(CH₂)₀ to ₄-heterocycloalkyl, —(CH₂)₀ to ₄-heteroaryl-A₃-aryl,

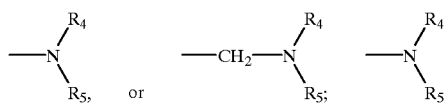

is amino, —NH(alkyl) —N(alkyl)₂ or —NH—(CH₂)₁ to ₄-aryl;

R₉ is lower alkyl;

A₃ is a bond, an alkylene bridge of 1 to 6 carbons,

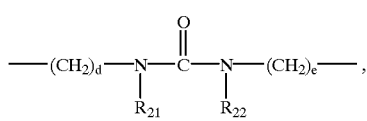

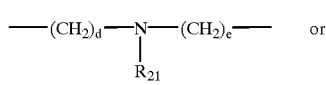   or

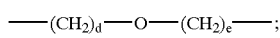;

d and e are independently selected from zero and an integer from 1 to 6 provided that the sum of d plus e is no greater than 10;

R₂₁ and R₂₂ are independently selected from hydrogen and lower alkyl; and an inner salt or pharmaceutically acceptable salt thereof.

Also preferred are the compounds of this invention of formula I wherein

A₁ is 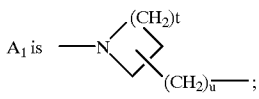;

R₂ and R₃ are both hydrogen;
R₁ is a defined above;

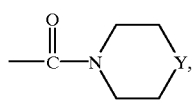

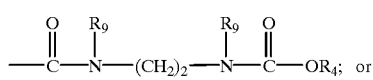

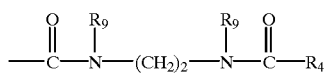

wherein Y, R₄ and R₉ are as preferably defined above;
t is two or three;
u is one; and an inner salt or a pharmaceutically acceptable salt thereof.

Most preferred are the following compounds of formula IV including an inner salt or a pharmaceutically acceptable salt thereof:

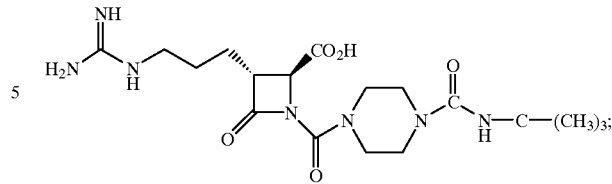

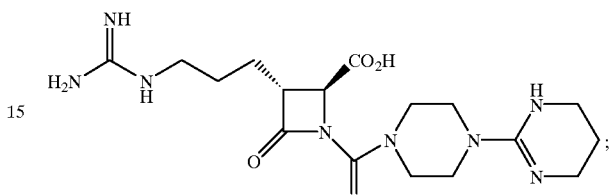

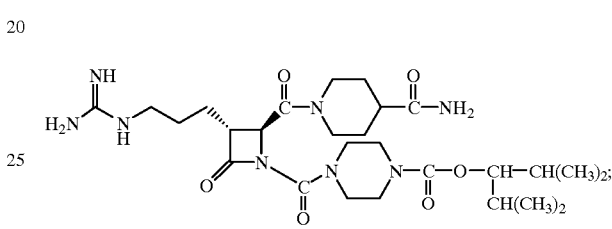

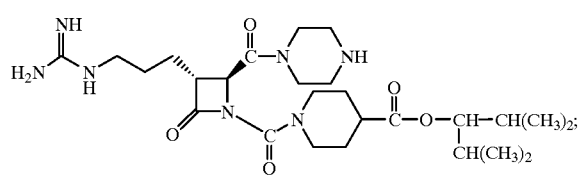

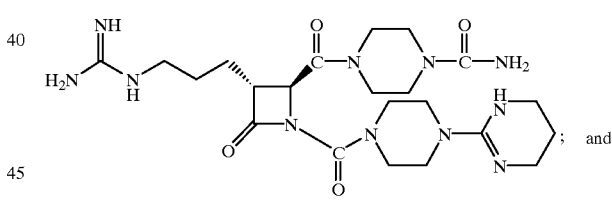; and

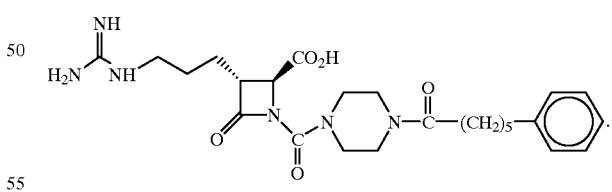

Also most preferred are the following compounds of formula I as diastereomeric mixtures including an inner salt or pharmaceutically acceptable salt thereof:

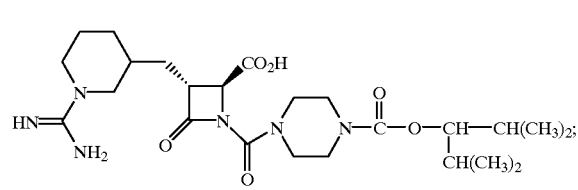

-continued
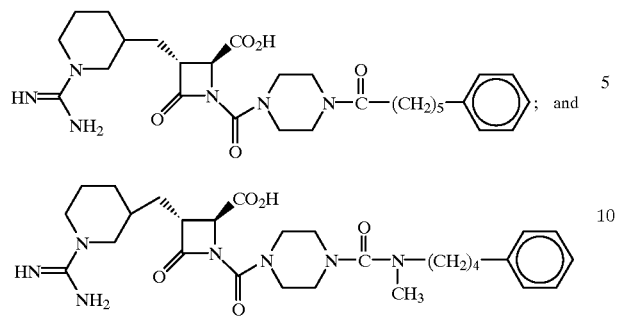
; and
and the individual homochiral compounds especially:
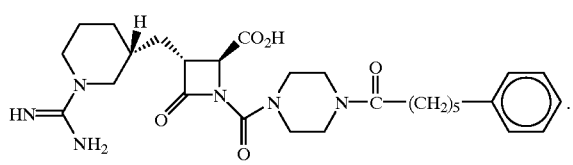
.
The following compounds of formula IV including an inner salt or a pharmaceutically acceptable salt thereof are also preferred:
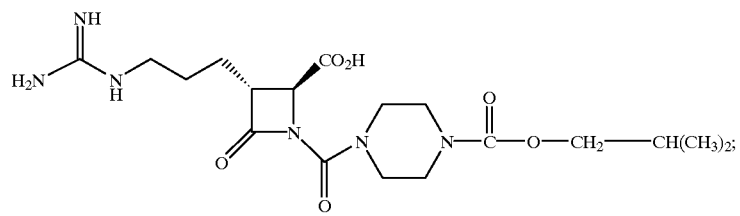
;
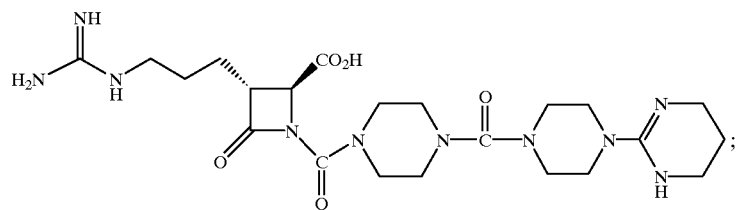
;
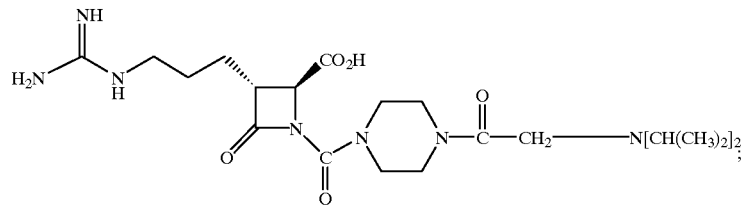
;

;
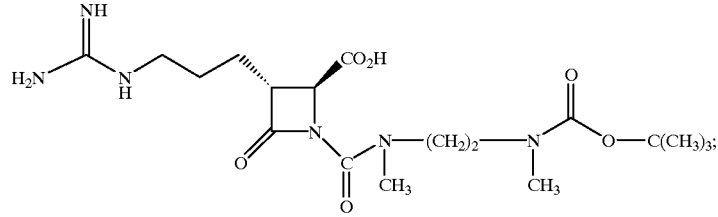
;

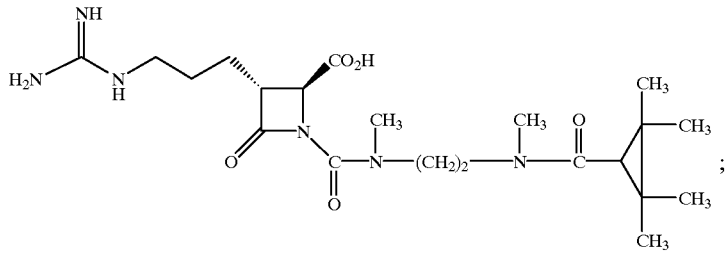
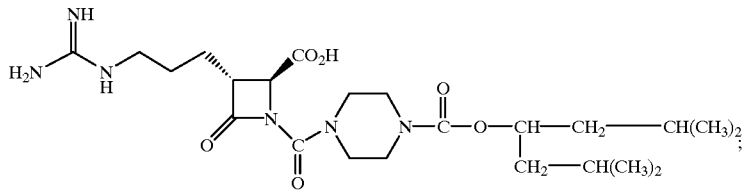
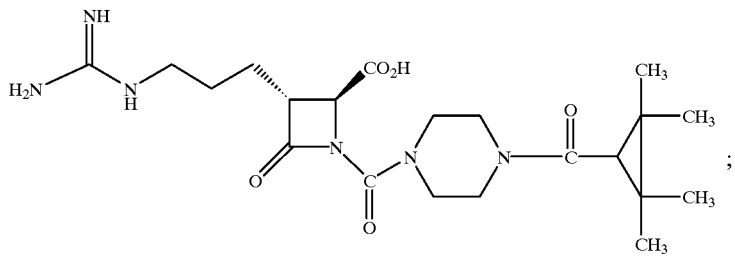
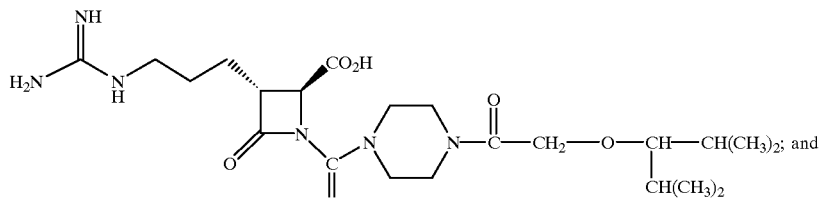
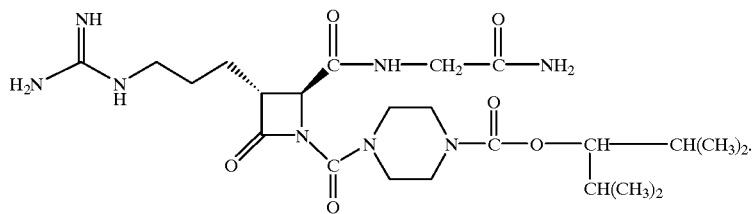
The following compounds of formula I including an inner salt or a pharmaceutically acceptable salt thereof are also preferred:
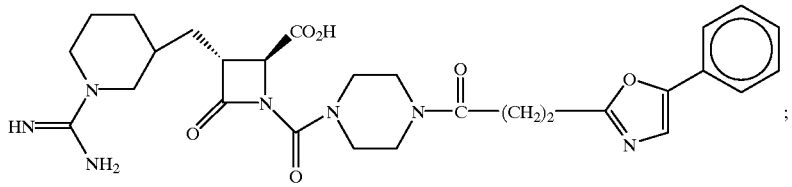
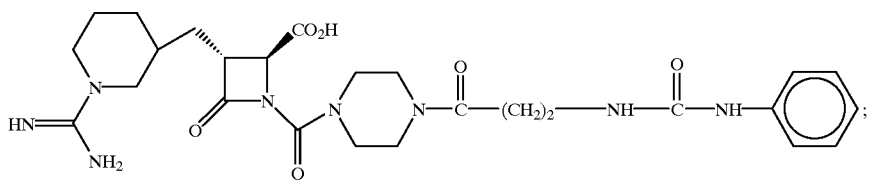

-continued
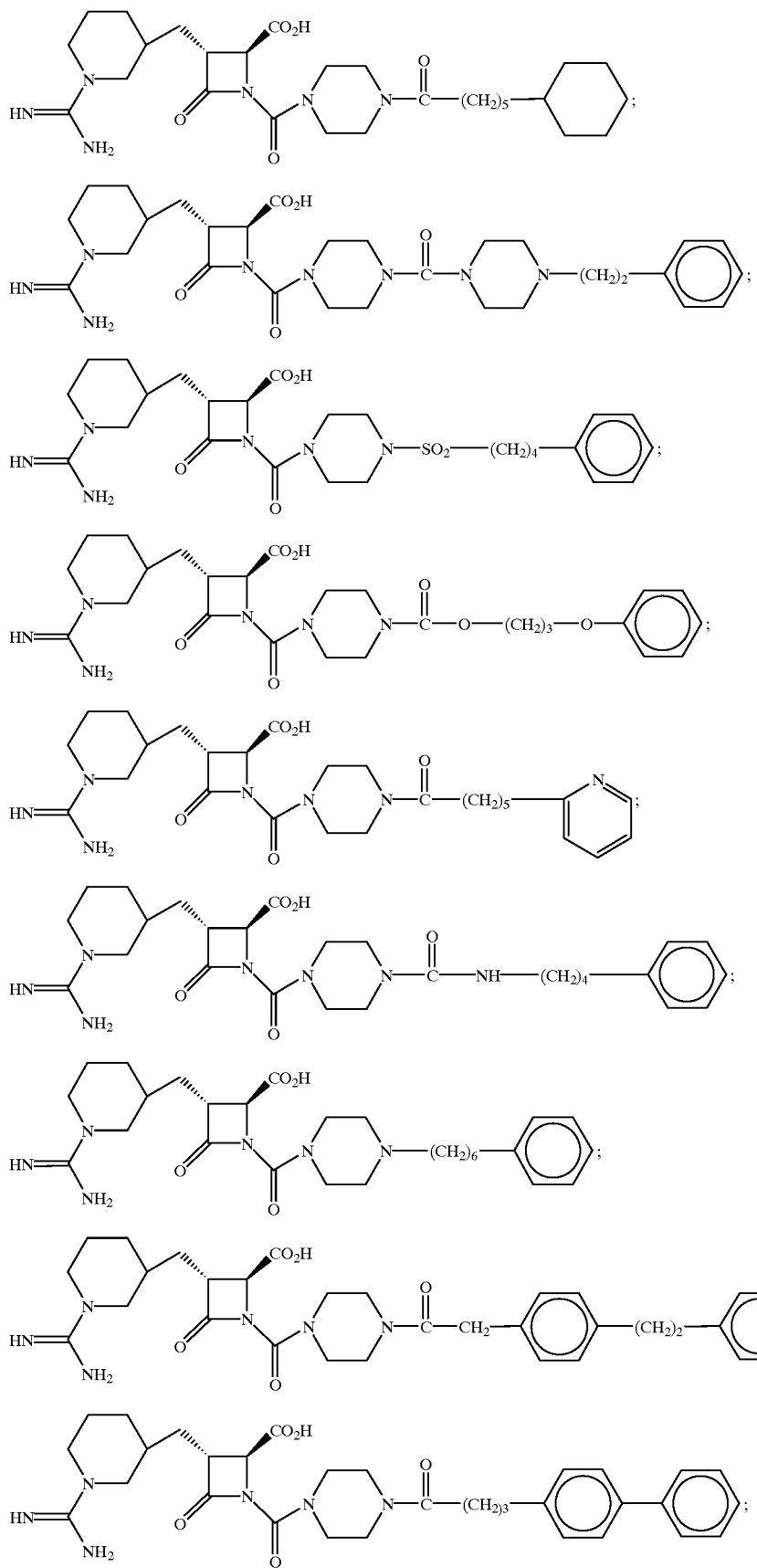

-continued

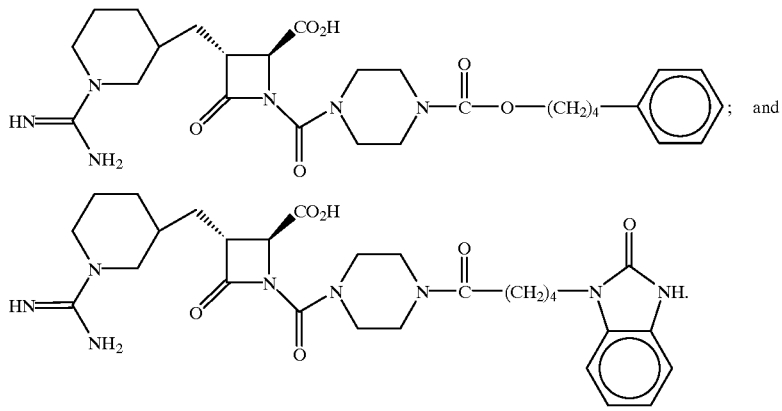

and

The following examples are illustrative of the invention.

EXAMPLE 1

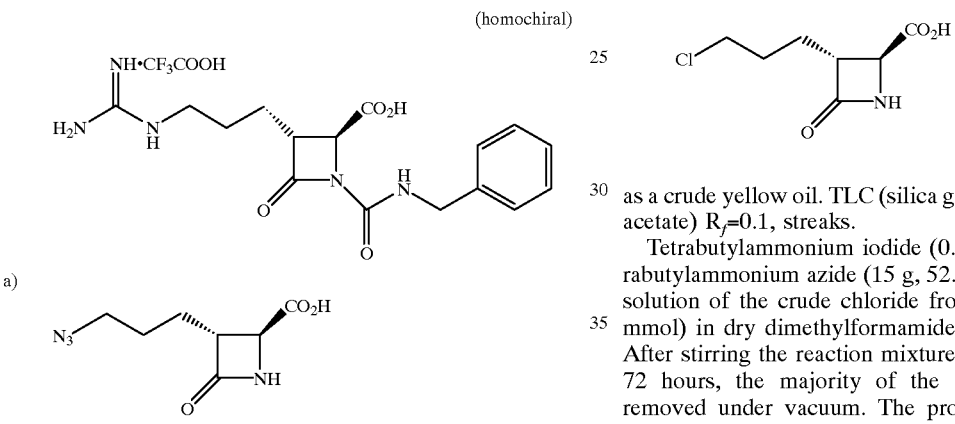

n-Butyl lithium in hexanes (2.5 M, 36.6 ml, 91.5 mmol) was added dropwise over 5 minutes to a solution of diisopropylamine (13.5 ml, 95.9 mmol) in dry tetrahydrofuran (40 ml) under nitrogen at −78° C. with mechanical stirring. After warming to 0° C. and stirring for 30 minutes, the solution was cooled to −78° C. and (4S)-N-(t-butyldimethylsilyl)-azetidine-2-one-4-carboxylic acid (10 g, 43.6 mmol) [Baldwin et al, Tetrahedron, Vol. 46, p. 4733–4748, 1990] was added in a single portion. After stirring the reaction mixture—gelatinous suspension at −78° C. for 5 minutes, the reaction was warmed to −20° C. to −10° C. and stirred at this temperature for 30 minutes. 1-Chloro-3-iodopropane (5.7 ml, 53.0 mmol) was added in a single portion and the reaction was stirred at −20° C. for 2 hours (gelatinous suspension disappears upon the addition of 1-chloro-3-iodopropane). The reaction mixture was then poured into 1N HCl saturated with sodium chloride (300 ml) and the aqueous phase was extracted with ethyl acetate (1×150 ml) which was then washed twice with saturated 1N HCl. The aqueous layers were then extracted twice, in order, with ethyl acetate (2×150 ml). The combined organics were then extracted twice with pH 7.5–8 water (2×100 ml, adjusted by the dropwise addition of 25% sodium hydroxide). The combined basic aqueous layers were then washed with ethyl acetate (2×150 ml). The basic aqueous layers were then acidified with concentrated HCl to pH 3, saturated with sodium chloride (solid) and extracted with ethyl acetate (2×150 ml), dried over sodium sulfate, filtered and concentrated. Evaporative drying with toluene then gave:

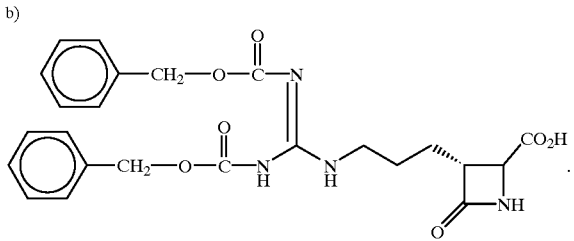

as a crude yellow oil. TLC (silica gel, 1% acetic acid in ethyl acetate) $R_f$=0.1, streaks.

Tetrabutylammonium iodide (0.5 g, 1.36 mmol) and tetrabutylammonium azide (15 g, 52.7 mmol) were added to a solution of the crude chloride from above (less than 43.6 mmol) in dry dimethylformamide (40 ml) under nitrogen. After stirring the reaction mixture at room temperature for 72 hours, the majority of the dimethylformamide was removed under vacuum. The product was extracted into ethyl acetate (150 ml) which was washed with 1N HCl saturated with sodium chloride (3×150 ml). The aqueous layers were extracted, in order, with ethyl acetate (2×150 ml). The combined organics were then extracted into pH 7.5–8 water (2×100 ml, adjusted by the dropwise addition of 25% sodium hydroxide). The combined basic aqueous layers were then washed with ethyl acetate (3×150 ml). The basic aqueous layers were then acidified with concentrated HCl to pH 3, saturated with sodium chloride (solid) and extracted with ethyl acetate, dried over sodium sulfate, filtered and concentrated. Evaporative drying with toluene gave the desired azide as a yellow-brown foam (6.56 g, 33.1 mmol). TLC (silica gel, 1% acetic acid in ethyl acetate) $R_f$=0.1 b)

Acetic acid (4 ml, 66 mmol) was added to a solution of the azide from step (a) (6.5 g, 32.8 mmol) in dimethylformamide (40 ml) followed by 10% palladium on carbon (1.3 g).

Hydrogen was bubbled through the reaction mixture for 25 minutes and then the reaction was stirred under hydrogen for 6 hours. After degassing the mixture with nitrogen for 25 minutes, triethylamine (15 ml, 108 mmol) and N,N'-bis(benzyl-oxycarbony)-1-guanylpyrazole (15 g, 39.7 mmol) [Wu et al., Synthetic Communications, 23(21), p. 3055–3060, (1993)] were added. The reaction was then stirred at room temperature for 18 hours. The reaction mixture was then filtered through Celite® which was then washed with ethyl acetate. Solvents were reduced under vacuum and the resulting residue was dissolved in ethyl acetate (150 ml) and washed with 1N HCl saturated with sodium chloride (3×150 ml). The aqueous washes were extracted, in order, with ethyl acetate (2×100 ml). The combined organics were then extracted with pH 7.5–8 water (2×150 ml, adjusted by the dropwise addition of 25% sodium hydroxide). The combined basic aqueous layers were then washed with ethyl acetate (3×150 ml) to remove excess N,N'-bis(benzyloxycarbonyl)-1-guanylprazole from the product. The basic aqueous layers were then acidified with concentrated HCl to pH 3, saturated with sodium chloride (solid), extracted with ethyl acetate (2×150 ml), dried over sodium sulfate, filtered and concentrated. Evaporative drying with toluene gave a light brown foam. Purification by flash chromatography (silica gel, 1–3% acetic acid in ethyl acetate) gave the desired product (8.5 g, 17.6 mmol) as an off-white solid. TLC (silica gel, 1% acetic acid in ethyl acetate) $R_f$=0.2.

c)

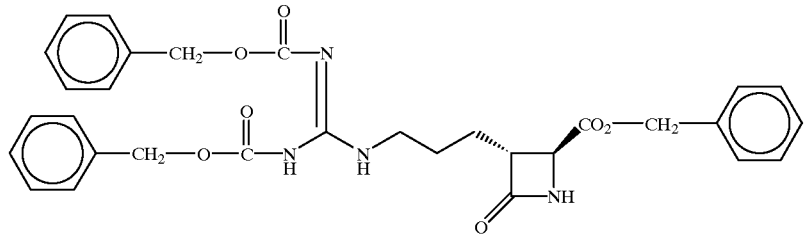

Solid sodium bicarbonate (1.5 g, 17.9 mmol), tetrabutylammonium iodide (200 mg, 0.54 mmol) and lastly benzyl bromide (2.5 ml, 21.0 mmol) were added to a solution of the product from step (b) (1.7 g, 3.52 mmol) in dimethylformamide (20 ml) under nitrogen at room temperature. The reaction mixture was stirred at room temperature for 48 hours. Dimethylformamide was removed under vacuum and the resulting residue was dissolved in ethyl acetate which was then washed twice with saturated aqueous sodium bicarbonate. The organic phase was separated, dried over magnesium sulfate, filtered and reduced to leave a brown oil. Purification by flash chromatography (silica gel, 0–10% methanol in methylene chloride) provided the desired product (1.84, 3.21 mmol) as a yellow oil.

d)

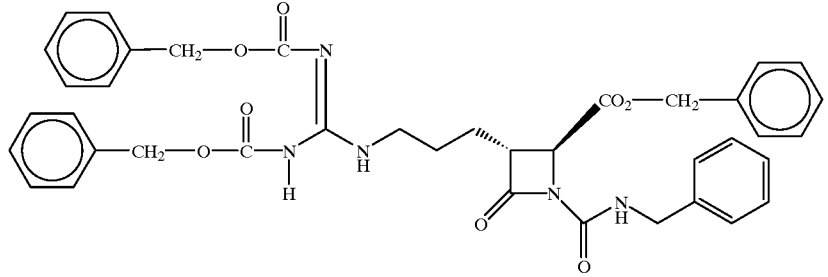

Sodium bis(trimethylsilyl)amide (1.0 M in tetrahydrofuran, 100 µl, 0.1 mmol) was added to a solution of the product from step (c) (46 mg, 0.08 mmol) in dry tetrahydrofuran (1.0 ml) under nitrogen at −78° C. The reaction mixture was stirred at −78° C. for 10 minutes and then at −20° C. for 10 minutes. After cooling the reaction mixture to −78° C., benzyl isocyanate (100 µl, 0.78 mmol) was added in a single portion. The reaction mixture was stirred at −78° C. for 5 minutes and then at −20° C. for 15 minutes. 1N HCl (1 ml) was added followed immediately by ethyl acetate (3 ml). The resulting biphasic solution was stirred vigorously while warming to room temperature. The organic phase was separated and washed once with saturated aqueous sodium bicarbonate, dried over magnesium sulfate, filtered and concentrated to leave a light yellow residue. Purification by flash chromatography (silica gel, 0–30% ethyl acetate in hexane) gave the desired product (33 mg, 0.047 mmol).

e)

(homochiral)

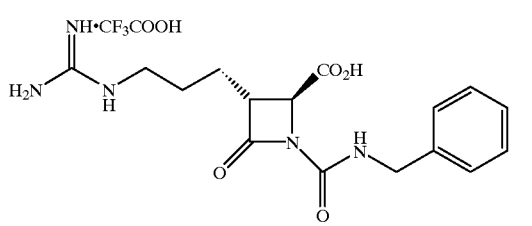

Concentrated HCl (4 µl, 0.048 mmol) was added to a solution of the product from step (d) (33 mg, 0.047 mmol) in dioxane (2 ml) followed by 10% palladium on carbon catalyst (15 mg). Hydrogen gas was bubbled through the reaction mixture for 1.5 hours. Water (0.5 ml) was added and the reaction was stirred under hydrogen for an additional 1 hour. The reaction mixture was then filtered through Celite® which was then washed with three portions of water. The combined eluent was lyophilized to give white powder. Purification by preparative HPLC (reverse phase, methanol, water, trifluoroacetic acid) provided after lyophilization the desired product (8.7 mg, 0.019 mmol). IR (film) 1773 cm$^{-1}$; MS 348.0 (M+H)$^+$, 346.3 (M−H)$^-$.

EXAMPLE 2

(homochiral)

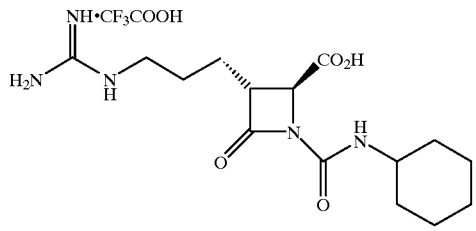

a)

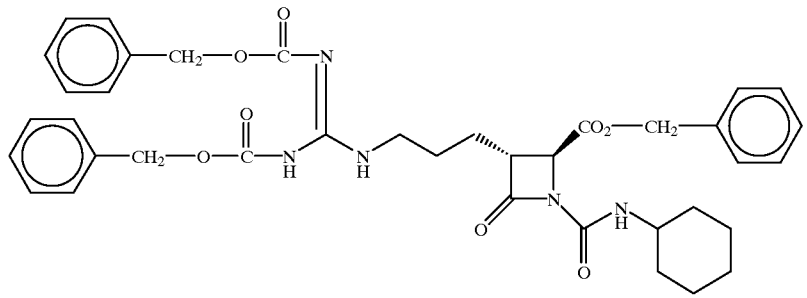

Sodium hydride (60% in mineral oil, 20 mg, 0.5 mmol) was added to a solution of the product from Example 1(c) (92 mg, 0.161 mmol) in dry tetrahydrofuran (1.5 ml) under nitrogen at room temperature. After stirring the reaction mixture for 10 minutes, cyclohexyl isocyanate (100 µl, 0.78 mmol) was added in a single portion. The reaction mixture was stirred at room temperature for 30 minutes. The reaction was then slowly poured over ice cold 1N HCl (2.5 ml). The resulting solution was extracted with ethyl acetate. The organic phase was washed twice with saturated aqueous sodium bicarbonate and once with brine. The organic layer was dried over sodium sulfate, filtered and concentrated. Purification by flash chromatography (silica gel, 0–10% methanol in methylene chloride) provided the desired product (91 mg, 0.13 mmol). MS 698.1 (M+H)$^+$, 696.4 (M−H)$^-$.

b)

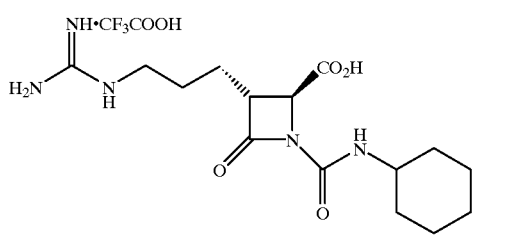
(homochiral)

Concentrated HCl (11 μl, 0.132 mmol) was added to a solution of the product from step (a) (91 mg, 0.13 mol) in dioxane (2 ml) followed by 10% palladium on carbon catalyst (45 mg). H$_2$ was bubbled through the reaction mixture for 45 minutes. Water (1 ml) was added and the reaction was stirred under hydrogen for an additional 45 minutes. The reaction mixture was then filtered through Celite® which was then washed with three portions of water. The combined eluent was lyophilized to give white powder. Purification by preparative HPLC (reverse phase, methanol water, trifluoroacetic acid) provided after lyophilization the desired product (28 mg, 0.062 mmol). IR (KBr) 1773 cm$^{-1}$; MS 340.1 (M+H)$^+$, 338.2 (M−H)$^−$.

EXAMPLE 3

(homochiral)

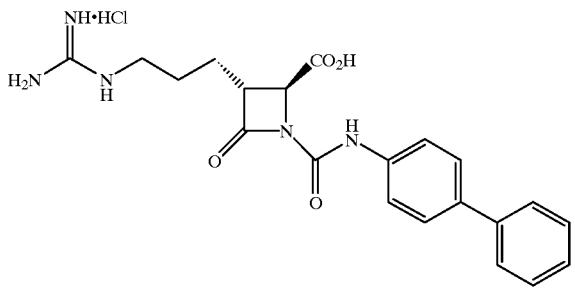

a)

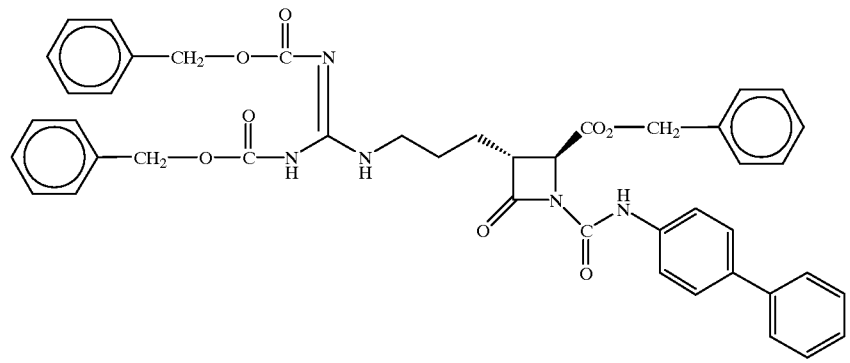

Following the procedure of Example 1(d) but substituting 4-biphenylisocyanate for the benzyl isocyanate, the desired product was obtained. IR (film) 1776 cm$^{-1}$; MS 768.1 (M+H)$^+$, 766.2 (M−H)$^−$.

b)

(homochiral)

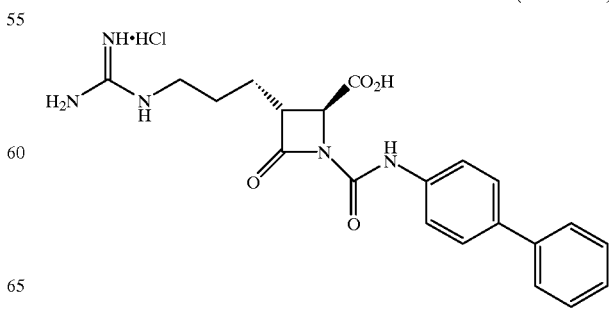

Concentrated HCl (10 μl, 0.12 mmol) was added to a solution of the product from step (a) (30 mg, 0.039 mmol) in dioxane (4 ml) followed by 10% palladium on carbon catalyst (30 mg). H$_2$ was bubbled through the reaction mixture for 5 minutes and then the reaction mixture was stirred under hydrogen gas for 1.5 hours. The reaction mixture was then filtered through Celite® which was then washed with two portions of water and one portion of dioxane. The combined eluent was lyophilized to give the desired product (16.3 mg, 0.036 mmol). IR (film) 1769 cm$^{-1}$; MS 410.1 (M+H)$^+$, 408.3 (M–H)$^-$.

EXAMPLE 4

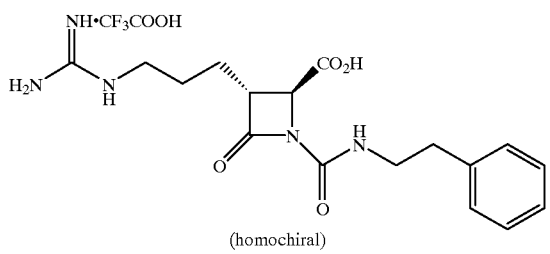

(homochiral)

Following the procedure of Example 1 but substituting phenethyl isocyanate for the benzyl isocyanate in step (d) followed by the deprotection work-up described in Example 1 step (e), the desired product was obtained. IR (film) 1775 cm$^{-1}$; MS 362.1 (M+H)$^+$, 360.3 (M–H)$^-$.

EXAMPLE 5

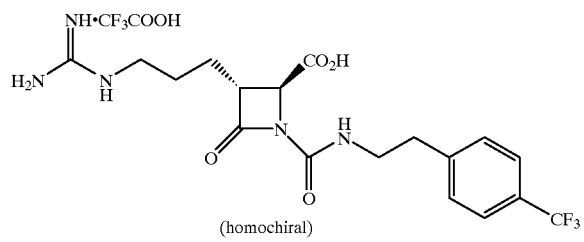

(homochiral)

Following the procedure of Example 1 but substituting 4-trifluoromethylphenyl isocyanate for the benzylisocyanate in step (d) followed by the work up described in Example 1 step (e), the desired product was obtained. IR (film) 1761 cm$^{-1}$; MS 402.1 (M+H)$^+$, 400.2 (M–H)$^-$.

EXAMPLE 6

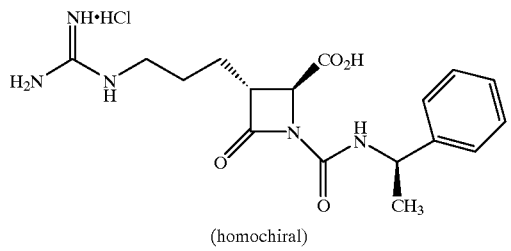

(homochiral)

Following the procedure of Example 1 but substituting (R)-α-methylbenzyl isocyanate for the benzyl isocyanate in step (d) followed by the deprotection and the work-up described in Example 3 (b), the desired product was obtained. IR (KBr) 1777 cm$^{-1}$; MS 362.1 (M+H)$^+$, 360.2 (M–H)$^-$.

EXAMPLE 7

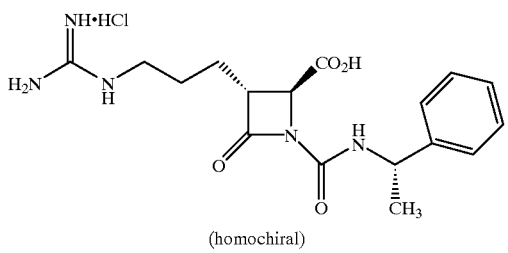

(homochiral)

Following the procedure of Example 1 but substituting (S)-α-methylbenzyl isocyanate for the benzyl isocyanate in step (d) followed by the deprotection and work-up described in Example 3(b), the desired product was obtained. IR (KBr) 1777 cm$^{-1}$; MS 362.1 (M+H)$^+$, 360.3 (M–H)$^-$.

EXAMPLE 8

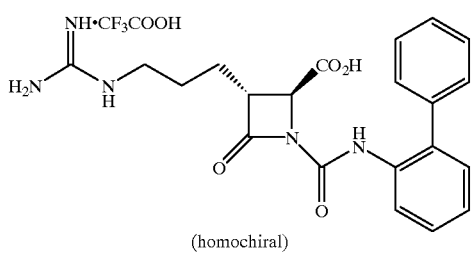

(homochiral)

Following the procedure of Example 1 but substituting 2-biphenyl isocyanate for the benzyl isocyanate in step (d) followed by the deprotection and work-up described in Example 1(e), the desired product was obtained. IR (KBr) 1780 cm$^{-1}$; MS 410.1 (M+H)$^+$, 408.2 (M–H)$^-$.

EXAMPLE 9

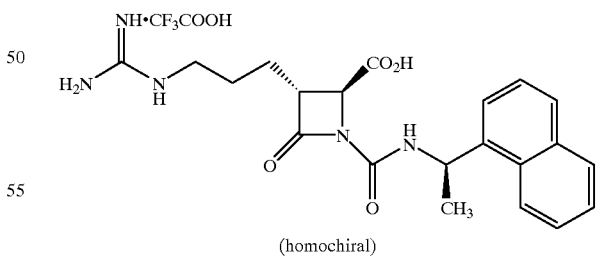

(homochiral)

Following the procedure of Example 1 but substituting (R)-(–)—(1-naphthyl)ethyl isocyanate for the benzyl isocyanate in step (d) followed by the deprotection and work-up described in Example 1(e), the desired product was obtained. IR (KBr) 1777 cm$^-$, MS 412.3 (M+H)$^+$, 410.2 (M–H)$^-$.

EXAMPLE 10

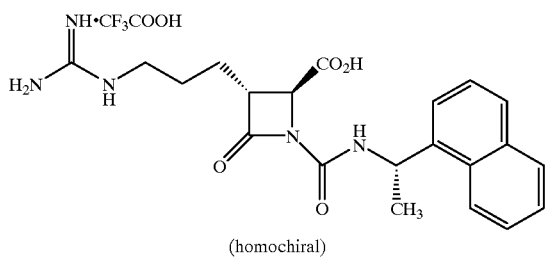

(homochiral)

Following the procedure of Example 1 but substituting (S)-(+)-(1-naphthyl)ethyl isocyanate for the benzyl isocyanate in step (d) followed by the work-up described in Example 1(e), the desired product was obtained. IR (KBr) 1777 cm$^{-1}$; MS 412.3 (M+H)$^+$, 410.2 (M-H)$^-$.

EXAMPLE 11

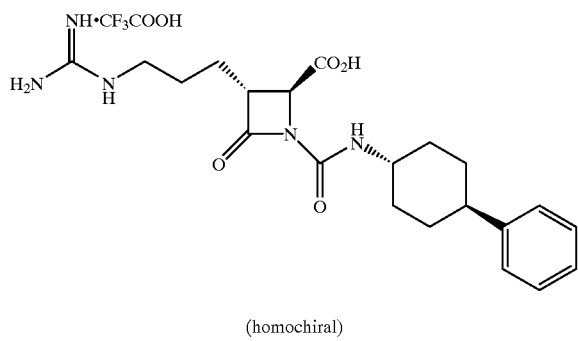

(homochiral)

a) trans-4-phenylcyclohexylisocyanate

Ammonium formate (18 g, 285 mmol) was added to a solution of 4-phenylcyclohexanone (5 g, 28.7 mmol) in methanol (150 ml) under nitrogen at room temperature followed by the portionwise addition of sodium cyanoborohydride (1.85 g, 29.4 mmol). After stirring the reaction mixture at room temperature for 24 hours, the methanol was removed under vacuum to leave an oily residue. The residue was dissolved in methylene chloride (100 ml) which was then washed with 1N sodium hydroxide (2×100 ml). The organic layer was separated, dried over sodium sulfate, filtered and concentrated to leave an off-white solid. Purification by flash chromatography (silica gel, 0–20% methanol/methylene chloride) provided 3.46 g of trans-4-phenyl-cyclohexylamine as a white solid.

Phosgene (20% in toluene, 5 ml) was added to a solution of trans-4-phenylcyclohexylamine (500 mg, 2.85 mmol) in toluene (5 ml) under nitrogen at room temperature. The resulting solution was heated at 80° C. for 24 hours. Solvents were then removed under vacuum to leave a solid residue. This residue was dispersed in ether and filtered. The eluent was collected and concentrated to give 379 mg of trans-4-phenylcyclohexylisocyanate as a light yellow oil. IR (film) 2259 cm$^{-1}$.

b)

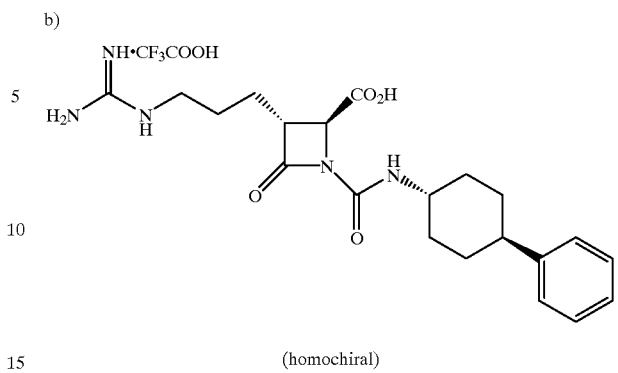

(homochiral)

Following the procedure of Example 1 but substituting trans-4-phenylcyclohexylisocyanate for the benzyl isocyanate in step (d) followed by the deprotection and work-up described in Example 1(e), the desired product was obtained. IR (KBr) 1778 cm$^{-1}$; MS 416.2 (M+H)$^+$, 414.4 (M-H)$^-$.

EXAMPLE 12

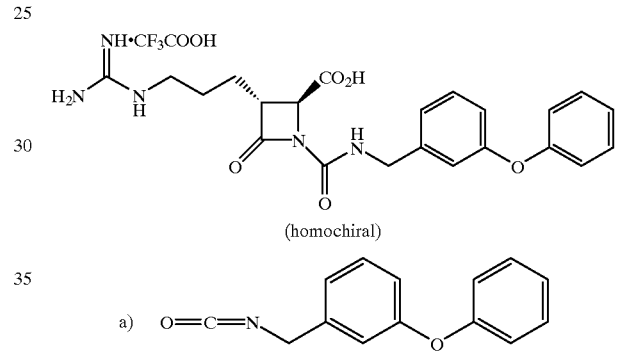

(homochiral)

a)  O=C=N 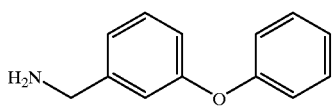

Ammonium formate (7.95 g, 126.12 mmol) and sodium cyanoborohydride (4.75 g, 75.66 mmol) were added to a solution of 3-phenoxybenzaldehyde (5g, 25.22 mmol) in methanol (125 ml) and the mixture was stirred at room temperature overnight. After 16 hours, the mixture was evaporated in vacuo and partitioned between 1N HCl and ethyl acetate. The aqueous layer was then basified using 6N sodium hydroxide solution to pH 12 and re-extracted with ethyl acetate. The organic phase was washed with brine, dried over sodium sulfate and concentrated to give 300 mg of as a colorless oil. MS 199.2 (M+H)$^+$.

This amino compound (300 mg, 1.51 mmol) in toluene (2 ml) was added to a mixture of phosgene (3 ml of a 20% phosgene in toluene solution) in toluene (2 ml). The mixture was heated at 80° C. for 2 hours, followed by stirring at 110° C. for 1 hour and stirring at 80° C. overnight. The mixture was then evaporated in vacuo and the residue was suspended in ether and filtered. The eluents were concentrated and co-evaporated with toluene to give the desired isocyanate as a brown oil (0.328 g). IR (film) 2263.5 cm$^{-1}$.

b)

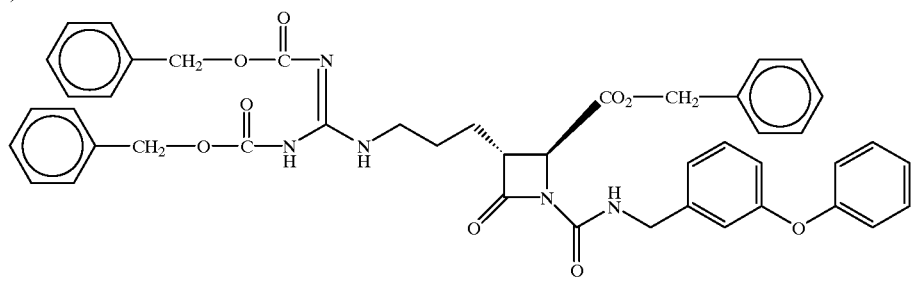

The benzyl ester product from Example 1(c) (69 mg, 0.121 mmol) was dissolved in tetrahydrofuran (1.5 ml) and cooled to −78° C. Sodium bis(trimethylsilyl)amide (0.15 ml, 0.145 mmol) was added over 2 minutes and the mixture was stirred at −78° C. for 1 hour. A solution of the isocyanate from step (a) (0.328 g, 0.145 mmol) in tetrahydrofuran (1.2 ml) was added over 1 minute and the reaction mixture was stirred at −78° C. After 30 minutes, the mixture was quenched with 0.5 N potassium bisulfate solution (10 ml) and extracted with ethyl acetate (2×10 ml). The organic phase was washed with brine (1×15 ml), dried over sodium sulfate, and condensed to give a yellow oil (150 mg). Purification by flash chromatography (silica gel, 0–25% ethyl acetate/hexane) gave the desired product as a pale yellow oil (50 mg). MS 798.1 (M +H)$^+$, 796.3 (M−H)$^-$; IR (film) 1776.6 cm$^{-1}$.

c)

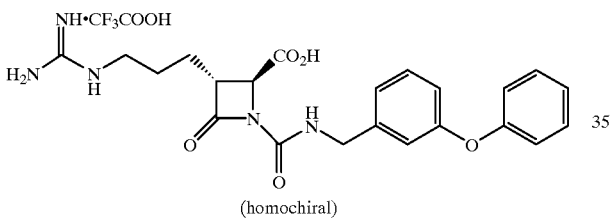

(homochiral)

10% Palladium on carbon catalyst (25 mg, wet type) was added to a solution of the product from step (b) (45 mg, 0.056 mmol) in 1,4-dioxane (7 ml) containing 1N HCl. Hydrogen gas was bubbled through the solution for 4 hours. The resulting mixture was filtered through Celite® which was then repeatedly washed with 1,4-dioxane. The combined eluents were evaporated in vacuo to give a pale yellow glue (40 mg). Purification by reverse phase preparative HPLC (YMC ODS 30×250 mm) using the solvent system described in Example 1(e) gave the desired product as a white solid (26 mg). MS 440.2 (M +H)$^+$, 438.3 (M−H)$^-$; IR (KBr) 1773 cm$^{-1}$.

EXAMPLE 13

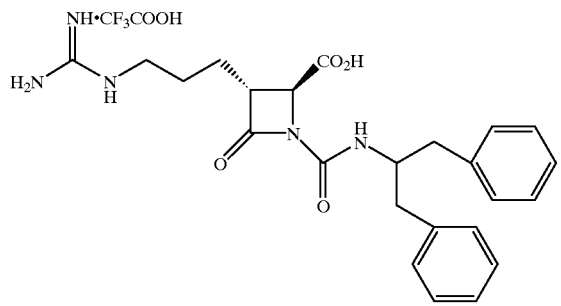

(homochiral)

a)

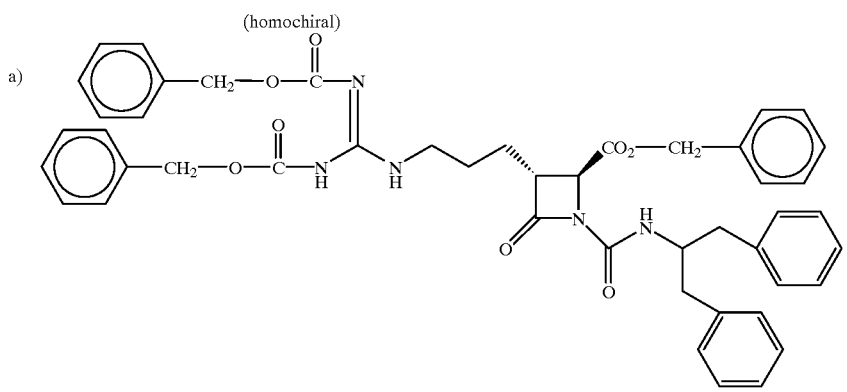

Sodium bis(trimethylsilyl)amide (1.0 M in tetrahydrofuran, 106 µl, 0.106 mmol) was added to a solution of the benzyl ester product from Example 1(c) (57.9 mg, 0.101 mmol) in dry tetrahydrofuran (2 ml) under nitrogen at −78° C. The reaction mixture was stirred at −78° C. for 1 hour and then 1-benzyl-2-phenethyl isocyanate (35 mg, 0.147 mmol) [prepared as described by Anderson et al., J. American Pharm. Assoc., Vol. 41, p. 643–650 (1952)] was added in a single portion. The reaction mixture was stirred at −78° C. for 20 minutes. The reaction was quenched by the addition of potassium bisulfate (3 ml) followed immediately by the addition of ethyl acetate (5 ml). The resulting biphasic solution was stirred vigorously while warming to room temperature. The organic phase was separated, dried over sodium sulfate, filtered and concentrated to leave a bright yellow residue. Purification by flash chromatography (silica gel, 0–20% ethyl acetate in hexane) gave the desired product (54.8 mg, 0.068 mmol). IR (film) 1776 cm$^{-1}$; MS 810.2 (M+H)$^{+}$, 808.4 (M−H)$^{-}$.

b)

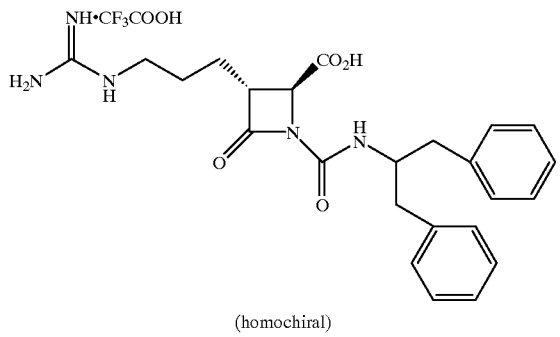

(homochiral)

Concentrated HCl (20 µl, 0.24 mmol) was added to a solution of the product from step (a) (54.8 mg, 0.068 mmol) in dioxane (3 ml) followed by 10% palladium on carbon catalyst (50 mg). Hydrogen gas was bubbled through the reaction mixture for 5 minutes and then the reaction mixture was stirred under hydrogen gas for 1.5 hours. The reaction mixture was then filtered through Celite® which was then washed with two portions of dioxane and three portions of water. The combined eluent was lyophilized to give a white powder. Purification by preparative HPLC (reverse phase, methanol, water trifluoroacetic acid) provided after lyophilization the desired product (21 mg). IR (KBr) 1776 cm$^{-1}$; MS 452.4 (M +H)$^{+}$, 450.4 (M−H)$^{-}$.

EXAMPLE 14

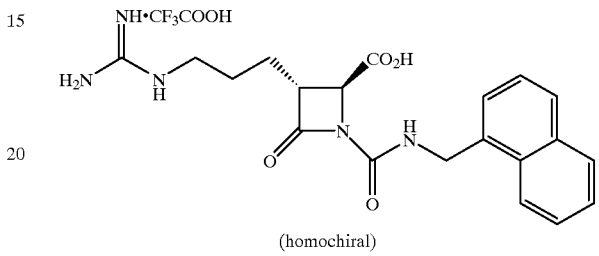

(homochiral)

a) 1-Naphthylmethylisocyanate

A solution of phosgene (20% in toluene, 5 ml) was diluted with toluene (10 ml). A mixture of 1-naphthalenemethylamine (500 µl, 3.41 mmol), triethylamine (0.95 ml, 6.82 mmol) in toluene (5 ml) was added dropwise. The reaction mixture was heated at reflux overnight. The mixture was cooled to room temperature, and the solvent was removed. The residue was stirred with ether (50 ml) for 10 minutes and filtered. The filtrate was concentrated to give the crude product which was purified by flash chromatography (silica gel, methylene chloride) to give the desired product (518 mg) as a colorless oil. IR 2260 cm$^{-1}$.

b)

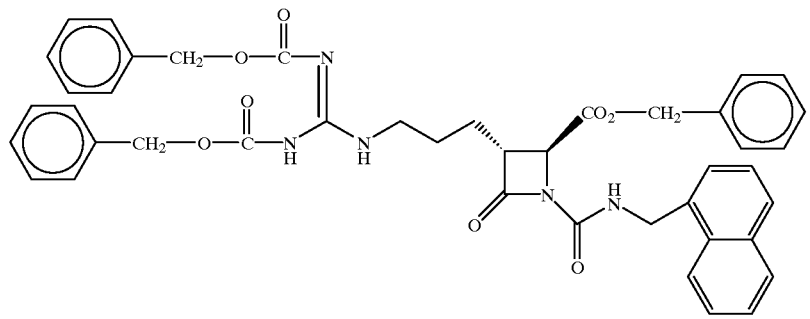

Sodium bis (trimethylsilyl)amide (1.0 M in tetrahydrofuran, 300 µl, 0.30 mmol) was added dropwise to a −78° C. solution of the benzyl ester product from Example 1(c) (144 mg, 0.25) in tetrahydrofuran (3 ml). The mixture was stirred at −78° C. for 1 hour. A solution of 1-naphthylmethyl-isocyanate (55 mg, 0.30 mmol) in tetrahydrofuran (1 ml) was added. The reaction mixture was stirred at −78° C. for an additional 40 minutes. The reaction was quenched by the addition of 1N potassium bisulfate (15 ml). The mixture was extracted with ethyl acetate (2×40 ml). The organic layers were combined and washed with brine (15 ml), dried over magnesium sulfate, filtered and concentrated to give 185 mg of crude product as a yellow oil. Purification by chromatography (silica, 30–50% ethyl acetate/hexane) gave the desired product as a colorless oil (122 mg). MS: (M+H)$^+$ 756.1; IR (KBr) 1776 cm$^{-1}$, 1732 cm$^{-1}$, 1639 cm$^{-1}$.

c)

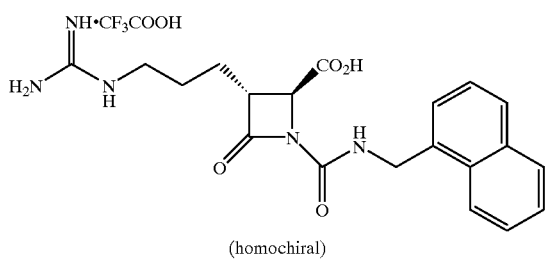

(homochiral)

A mixture of the product from step (b) (117 mg, 0.15 mmol), 1N HCl (170 μl, 0.17 mmol), palladium on carbon catalyst (10%, 50 mg) in dioxane (3 ml) was stirred under hydrogen atmosphere (hydrogen balloon) at room temperature for 1 hour. Analytical HPLC indicated the completion of the reaction. The reaction mixture was filtered through a Celite® cake and concentrated to give the crude product (68 mg) which was purified by reverse phase preparative HPLC as described in Example 1(e) to yield the desired product (37 mg) as a white powder. MS (M+H)$^+$ 398.2, (M−H)$^-$396.4; IR (KBr) 1780 cm$^{-1}$, 1670 cm$^{-1}$, 1541 cm$^{-1}$.

EXAMPLE 15

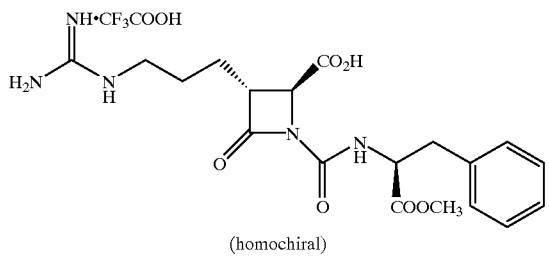

(homochiral)

Following the procedure of Example 1 but substituting methyl-(S)-(−)-2-isocyanato-3-phenylpropionate for the benzyl isocyanate in step (d) followed by the deprotection and work-up described in Example 3(b), the desired product was obtained. IR (KBr) 1769 cm$^{-1}$, 1674 cm$^{-1}$, and 1632 cm$^{-1}$; MS (M+H)$^+$420.1.

EXAMPLE 16

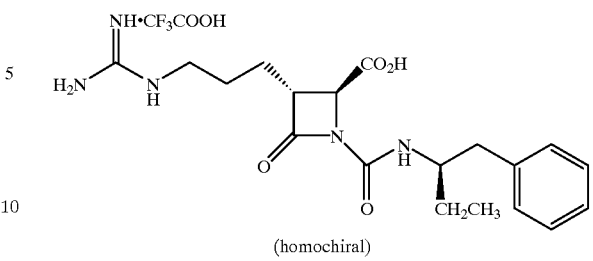

(homochiral)

a) R-(+)-1-Phenylpropylisocyanate

A solution of phosgene (20% in toluene, 5 ml) was diluted with toluene (10 ml). A mixture of R-(+)-1-phenylpropylamine (640 μl, 4.40 mmol), triethylamine (1.03 ml, 7.4 mmol) in toluene (5 ml) was added dropwise. Another 10 ml of toluene was added due to the difficulty of stirring. The reaction mixture was heated at reflux for 2 hours. TLC showed the completion of the reaction. The solvent was removed and the residue was stirred with ether (50 ml) for 10 minutes and filtered. The filtrate was concentrated to give the crude product which was purified by flash chromatography (silica, methylene chloride) to yield the desired product as a colorless oil (410 mg). IR 2262 cm$^{-1}$.

b)

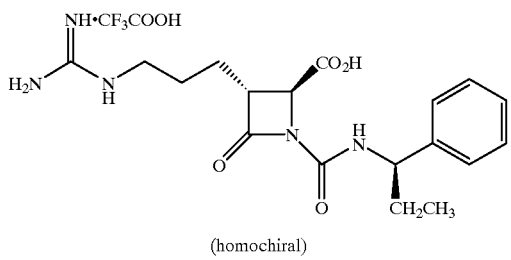

(homochiral)

Following the procedure of Example 1 but substituting R-(+)-1-phenylpropylisocyanate for the benzyl isocyanate in step (d) followed by the deprotection and work-up described in Example 1(e), the desired product was obtained. MS (M+H)$^+$ 376.1, (2M+H)$^+$ 751.2; IR (KBr) 1780 cm$^{-1}$, 1670 cm$^-$.

EXAMPLE 17

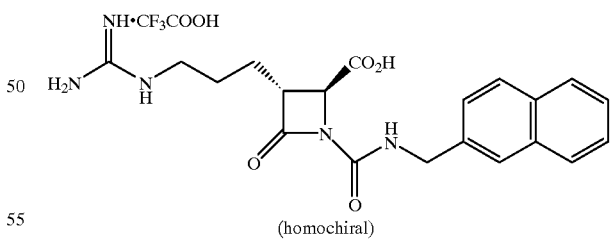

(homochiral)

a) 2-Naphthylmethylisocyanate

A drop of dimethylformamide and oxalyl chloride (1 ml) were added to a solution of 2-naphthylacetic acid (840 mg, 4.5 mmol) in methylene chloride (15 ml) at room temperature. This mixture was stirred at room temperature for 30 minutes. The solvent was removed and the residue was dissolved in acetone (15 ml) and cooled to 0° C. A solution of sodium azide (700 mg, 11 mmol) in water (10 ml) was added. The reaction mixture was stirred for 30 minutes at 5° C. and was then poured into a mixture of ice water (30 ml), ether (40 ml), and hexane (40 ml). The organic phase was separated, washed with brine, dried and concentrated to 5 ml. Chloroform (5 ml) was added to the residue. The resultant solution was added to chloroform (10 ml) at 80° C. dropwise. The mixture was heated at reflux for 1 hour. The solvent was evaporated to give 680 mg of crude product. Purification by chromatography (silica, methylene chloride) gave 342 mg of the desired product as a white solid. IR (neat) 2355 cm$^{-1}$, 2336 cm$^{-1}$, 2267 cm$^{-1}$.

b)

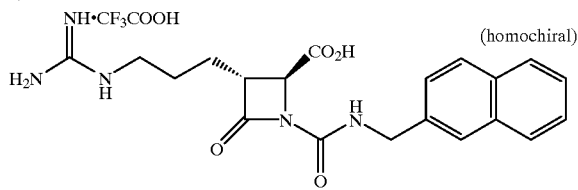

Following the procedure of Example 1 but substituting 2-naphthylmethylisocyanate for the benzyl isocyanate in step (d) followed by the deprotection and work-up described in Example 1(e), the desired product was obtained as a white fluffy powder. MS (M+H)$^+$ 398.1; IR (KBr) 1778 cm$^{-1}$, 1541 cm$^{-1}$.

EXAMPLE 18

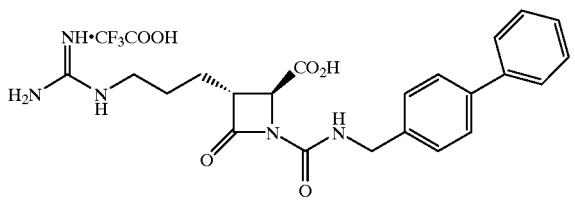

Following the procedure of Example 1, but substituting 4-isocyanatomethylbiphenyl for the benzyl isocyanate in step (d) followed by the deprotection and work-up described in Example 1(e), the desired product was obtained. IR (KBr) 1758 cm$^{-1}$; MS 424.1 (M+H)$^+$, 422.3 (M–H)$^-$.

EXAMPLE 19

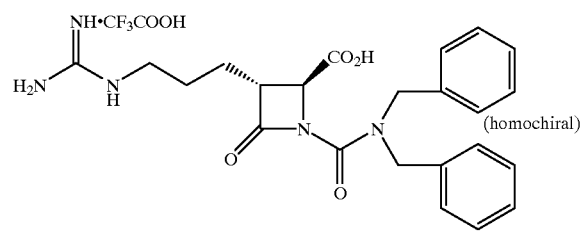

a)

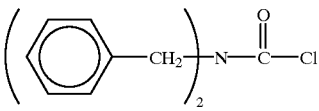

A solution of diphosgene (680 μl, 5.7 mmol) in toluene (5 ml) was added to a mixture of dibenzylamine (2.0 g, 9.8 mmol) and triethylamine (1.2 ml, 85 mmol) in toluene (15 ml). The resultant mixture was stirred at room temperature for 4 hours. The mixture was poured into 2N HCl aqueous solution (50 ml) and extracted with ethyl acetate (3×50 ml). The organic layers were combined, dried over magnesium sulfate and concentrated to give 2.60 g of the desired product as a white solid. IR (film) 1731 cm$^{-1}$.

b)

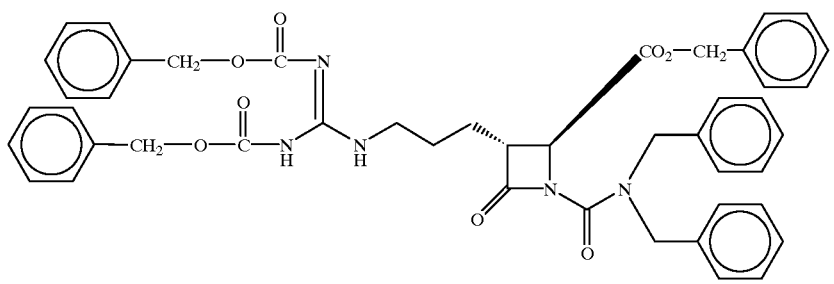

Triethylamine (42 μl), 4-dimethylaminopyridine (30 mg), and a solution of the carbamoyl chloride from step (a) (78 mg, 0.30 mmol) in methylene chloride (2 ml) were added to a solution of the benzyl ester product from Example 1(c) (116 mg, 0.20 mmol) in methylene chloride (2 ml). The mixture was stirred at room temperature for 3 days. Analytical HPLC indicated the reaction was complete. The reaction was quenched by the addition of 1N potassium bisulfate (15 ml). The mixture was extracted with ethyl acetate (100 ml). The organic layer was washed with brine (15 ml), dried over magnesium sulfate, and concentrated to give the crude product. Purification by flash chromatography (30% ethyl acetate/hexane) gave the desired product (95 mg). MS (M+H)$^+$ 796.1, (M–H)$^-$ 794.4; IR (film) 1785 cm$^{-1}$, 1732 cm$^{-1}$, 1671 cm$^{-1}$, 1639 cm$^{-1}$.

EXAMPLE 20 c)

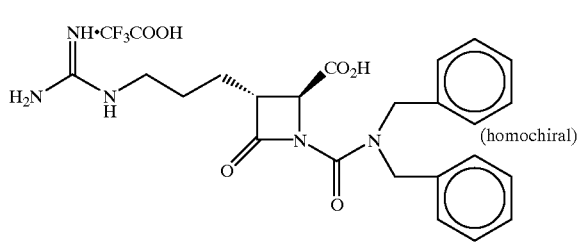
(homochiral)

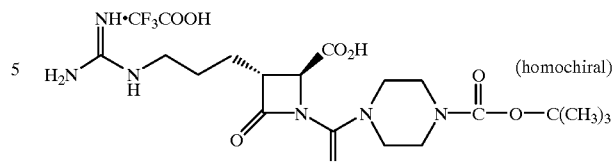
(homochiral)

a)

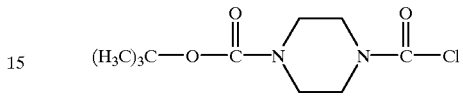

A mixture of tert-butylpiperizine carboxylate (1.0 g) and triethylamine (753 μl) in methylene chloride (5 ml) was added to a solution of diphosgene (326 μl, 20% in toluene) in methylene chloride at 0° C. The resultant mixture was stirred at 0° C. for 90 minutes. TLC showed completion of the reaction. The reaction was quenched by the addition of water (20 ml). The organic layer was separated. The aqueous layer was extracted with methylene chloride (2×20 ml. The organic layers were combined and washed with water (10 ml) and brine (2×10 ml), dried over magnesium sulfate, filtered and concentrated to give the crude product. Purification by flash chromatography (methylene chloride) provided 913 mg of the desired product as a white solid. IR (KBr) 1680 cm$^{-1}$, 1747 cm$^{-1}$.

A mixture of the product from step (b) (95 mg, 0.12 mmol), 1N HCl (145 μl), and 10% palladium on carbon catalyst (61 mg) in dioxane (3 ml) was stirred under hydrogen atmosphere (hydrogen balloon) at room temperature for 2 hours. Analytical HPLC indicated the reaction was complete. The reaction mixture was filtered through a Celite® cake and concentrated to give the crude product as a white powder. Purification by reverse phase HPLC using the solvent system described in Example 1(e) gives the desired product (36 mg) as a white powder. MS (M+H)$^+$ 438.1, (M−H)$^−$ 436.3; IR (KBr) 1786 cm$^{-1}$, 1672 cm$^{-1}$.

b)

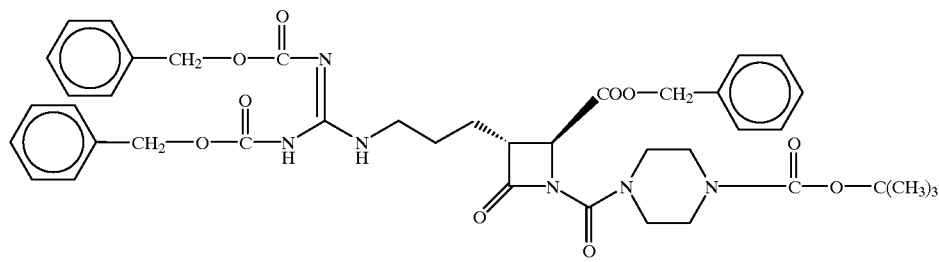

Sodium bis(trimethylsilyl)amide (1.0 M in tetrahydrofuran, 180 μl, 0.18 mmol) was added dropwise to a −78° C. solution of the benzyl ester product of Example 1(c) (85 mg, 0.15 mmol) in tetrahydrofuran (3 ml). The mixture was stirred at −78° C. for 90 minutes. A solution of the chloro product from part (a) (45 mg, 0.18 mmol) in tetrahydrofuran (1 ml) was added. The reaction mixture was stirred at −78° C. for 5 hours. The reaction was quenched by the addition of 1N potassium bisulfate (15 ml). The mixture was extracted with ethyl acetate (3×30 ml). The organic layers were combined and washed with brine (2×15 ml), dried over magnesium sulfate, filtered and concentrated to give the crude product. Purification by flash chromatography (30–50% ethyl acetate/hexane) provided 32 mg of the desired product as a colorless oil. MS (M+H)$^+$ 785.4, (M−H)$^−$ 783.7; IR (neat) 1786 cm$^{-1}$, 1732 cm$^{-1}$, 1681 cm$^{-1}$, 1640 cm$^{-1}$.

c)

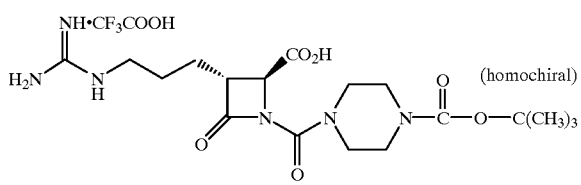

Deprotection and purification of the product from part (b) (32 mg) according to the procedure of Example 19(c) gives 17 mg of the desired product as a white fluffy powder. MS $(M+H)^+$ 427.1, $(M-H)^-$ 425.2; IR (KBr) 1792 cm$^{-1}$, 1670 cm$^{-1}$.

EXAMPLE 21 a)

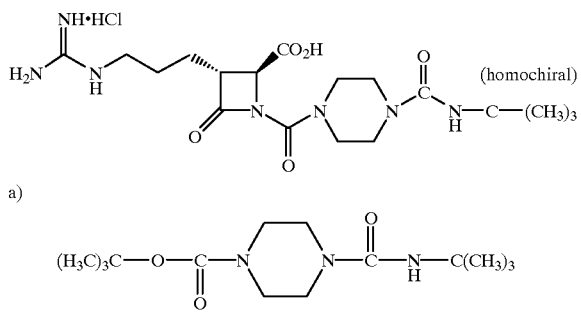

Tert-butyl isocyanate (0.28 g, 2.82 mmol) was added to a solution of a tert-butyl-1-piperazine carboxylate (0.5 g, 2.68 mmol) in methylene chloride (10 ml) and the mixture was stirred at room temperature. After 2 hours, the reaction mixture was evaporated in vacuo, suspended in water (50 ml) and extracted with ethyl acetate (2×50 ml). The organic phase was washed with saturated sodium chloride (1×50 ml) and filtered through a sintered glass funnel. The filtrate was dried over sodium sulfate and condensed to give 0.53 g of the desired product as a white solid.

b)

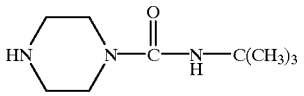

The product from part (a) (0.475 g, 1.67 mmol) was suspended in methylene chloride (4 ml) and trifluoroacetic acid (4 ml) was added over 1 minute. The mixture was stirred at room temperature. After 1 hour, the mixture was evaporated in vacuo. The residue was dissolved in water, the pH adjusted to 12–13 and extracted into ethyl acetate (2×25 ml). The organic phase was washed with saturated sodium chloride (1×50 ml), filtered, dried over sodium sulfate, and condensed to obtain 0.113 g of the desired product as a white solid.

c)

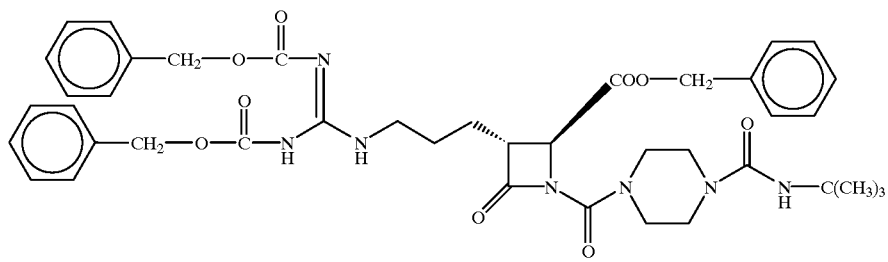

A solution of the benzyl ester product from Example 1(c) (65 mg, 0.114 mmol) in methylene chloride (1 ml) was cooled to −10° C. and triethylamine (24 μl, 0.17 mmol) was added, followed by the addition of 20% phosgene in toluene (0.15 ml, 0.285 mmol). After 90 minutes at −10° C., the mixture was evaporated in vacuo. The residue was taken up in methylene chloride (1 ml) and cooled to −10° C. Triethylamine (24 μl, 0.17 mmol) was added, followed by the addition of the piperazine product from part (b) (21 mg, 0.114 mmol). The mixture was stirred at −10° C. After 1 hour, the mixture was quenched with 10% monobasic potassium phosphate (15 ml) and extracted with ethyl acetate (2×20 ml). The organic phase was washed with saturated sodium chloride (1×30 ml), dried over sodium sulfate, and concentrated to obtain a pale yellow oil. Purification by preparative HPLC (reverse phase, methanol, water, trifluoroacetic acid) gave 27 mg of the desired product as a white foam. MS 784.2 $(M+H)^+$; IR (film): 1787.1, 1741.9, 1636.6 cm$^{-1}$.

d)

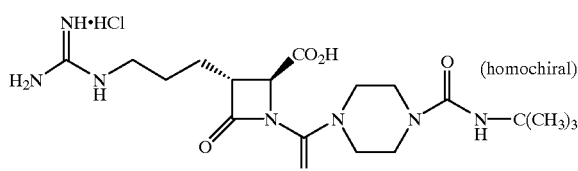

A solution of the product from part (c) (25 mg, 0.032 mmol) in 1,4-dioxane (7 ml) was treated with 1N HCl (40 μl, 0.038 mmol) and 10% palladium on carbon catalyst (15 mg). Hydrogen gas was bubbled through the mixture for 2 hours. The reaction mixture was filtered through a pad of Celite® which was then repeatedly washed with 1,4-dioxane. The combined eluents were lyophilized to give 15 mg of the desired product as a white lyophillate. MS 426.1 (M+H)$^+$, 424.3 (M–H)$^-$;IR (KBr) 1780 cm$^-$.

EXAMPLE 22

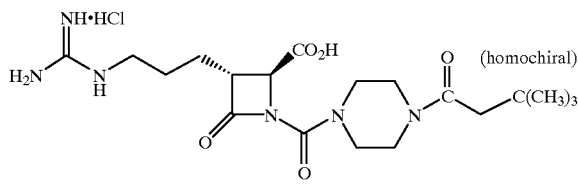

a)

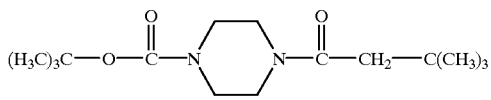

A solution of tert-butyl-1-piperazine carboxylate (0.5 g, 2.58 mmol) in methylene chloride (5 ml) was cooled to 0° C. N,N-Diisopropyl ethylamine (0.42 g, 3.22 mmol) and 4-dimethylaminopyridine (30 mg) were added, followed by the addition of tert-butyl acetyl chloride (0.36 g, 2.68 mmol) over 1 minute. The mixture was stirred at 0° C. for 2 hours.

After two hours, the mixture was partitioned between water (20 ml) and ethyl acetate (2×20 ml). The organic layer was washed with brine (1×75 ml), dried over sodium sulfate and condensed to give 0.763 g of the desired product as a white solid. MS 285.0 (M+H)$^+$.

b)

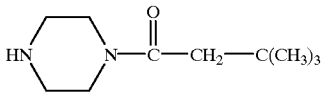

The product from part (a) (0.7 g, 2.46 mmol) was dissolved in methylene chloride (7 ml) and trifluoroacetic acid (4 ml) was added over 1 minute. The mixture was stirred at room temperature. After 1 hour, the mixture was evaporated in vacuo. The residue was dissolved in water, the pH was adjusted to 12–13 and extracted with ethyl acetate. The organic phase was washed with brine, dried over sodium sulfate and condensed to give 0.218 g of the desired product as a pale yellow oil. MS 184.9 (M +H)$^+$.

c)

A solution of the product from part (b) (109 mg, 0.59 mmole) in methylene chloride (0.5 ml) was added to a mixture of phosgene (0.79 ml of 20% phosgene in toluene solution, 1.48 mmol) in methylene chloride (2 ml) at 0° C. followed by the addition of triethylamine (82 μl, 0.59 mmol). The mixture was stirred at 0° C. for 1 hour. The reaction mixture was then partitioned between water (25 ml) and ethyl acetate (2×25 ml). The organic phase was washed with 1N HCl (40 ml), brine (50 ml), dried over sodium sulfate and condensed to give a brown oil. Purification by flash chromatography (silica gel, 0–30% ethyl acetate/Hexane) gave 70 mg of the desired product.

d)

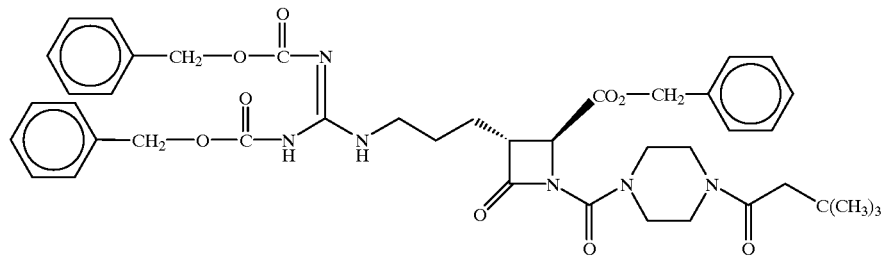

The product from part (c) (70 mg, 0.122 mmol) was dissolved in tetrahydrofuran (1 ml) and cooled to –78° C. Sodium bis (trimethylsilyl)amide (0.15 ml, 0.146 mmol) was added over one minute and the mixture was stirred at –78° C. for 1 hour. A solution of the benzyl ester product from Example 1(c) (36 mg, 0.146 mmol) in tetrahydrofuran (0.5 ml) was added and the reaction mixture was stirred at −78° C. After 2.5 hours, the reaction mixture was quenched with 0.5 N potassium bisulfate solution (25 ml) and extracted with ethyl acetate (2×25 ml). The organic phase was washed with brine (1×50 ml), dried over sodium sulfate and concentrated to a yellow oil. Purification by preparative HPLC (reverse phase, methanol, water, trifluoroacetic acid) gave 21 mg of the desired product as a colorless oil. MS 783.4 (M+H)$^+$, 781.3 (M−H)$^−$.

e)

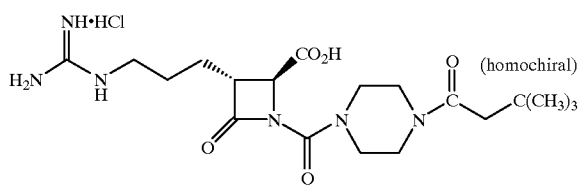

The product from part (d) was deprotected and worked-up as described in Example 21(d) to give 12 mg of the desired product as a white lyophillate. MS 425.1 (M+H)$^+$, 423.3 (M−H)$^−$; IR (KBr) 1786, 1736 cm$^{−1}$.

EXAMPLE 23

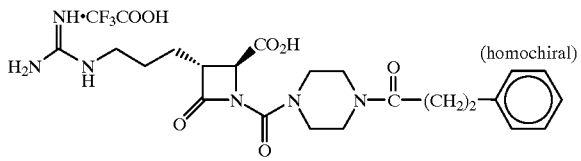

a)

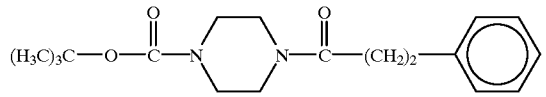

N,N-Diisopropylethylamine (560 µl), 4-dimethylaminopyridine (33 mg) and a solution of 3-phenylpropanoic acid chloride (400 µl, 2.69 mmol) in methylene chloride (2 ml) were added to a 0° C. solution of tert-butyl-1-piperazine carboxylate (500 mg, 2.68 mmol) in methylene chloride (4 ml). The mixture was stirred at 0° C. for 2 hours. The reaction was quenched with the addition of water (20 ml). The mixture was extracted with ethyl acetate (2×50 ml). The organic layers were combined and washed with brine (2×10 ml), dried over magnesium sulfate, and concentrated to give 872 mg of the desired product (crude) as a yellow solid. MS (M+H)$^+$ 319.1.

b)

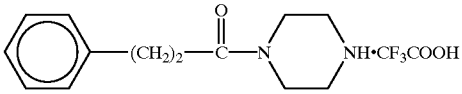

A mixture of the crude product from part (a) (860 mg, 2.68 mmol), trifluoroacetic acid (10 ml) and methylene chloride (10 ml) was stirred at room temperature for 1 hour. TLC showed the reaction was complete. The solvent was removed and 1N sodium hydroxide solution (15 ml) was added. The mixture was extracted with ethyl acetate (100 ml). The combined organic solution was washed with brine (10 ml), dried over magnesium sulfate, filtered and concentrated to give 238 mg of the desired product as a yellow oil which was used without further purification. IR(film) 1633 cm$^{−1}$.

c)

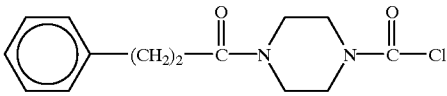

A mixture of the product from part (b) (200 mg, 0.92 mmol) and triethylamine (154 µl) in methylene chloride (4 ml) was added to a solution of phosgene in toluene (584 g, 20%) at 0° C. The resulting mixture was stirred at 0° C. for 20 minutes. TLC showed the completion of the reaction. The solvent was removed, and anhydrous ether (50 ml) was added. The mixture was filtered and the filtrate was concentrated to give the crude product as a yellow oil. Purification of the crude product by flash chromatography (50% ethyl acetate/hexanes) provided 235 mg of the desired product as a yellow oil. IR(film) 1741 cm$^{−1}$, 1703 cm$^{−1}$.

d)

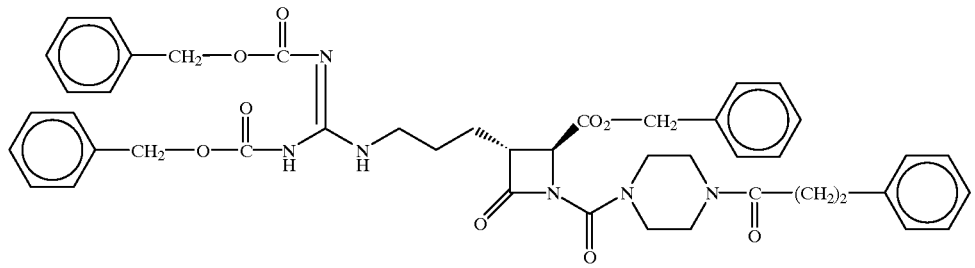

Sodium bis(trimethylsilyl)azide (1.0M in tetrahydrofuran, 210 µl, 0.21 mmol) was added dropwise to a −78° C. solution of the benzyl ester product from Example 1(c) (100 mg, 0.17 mmol) in tetrahydrofuran (2 ml). The mixture was stirred at −78° C. for 1 hour. A solution of the product from part (c) (58 mg, 0.21 mmol) in tetrahydrofuran (1 ml) was added. The reaction mixture was stirred at −78° C. for 2.5 hours. Analytical HPLC indicated that the starting material was not completely consumed. This was quenched with the addition of 1N potassium bisulfate (20 ml). The mixture was extracted with ethyl acetate (2×30 ml). The organic layers were combined and washed with brine (2×15 ml) dried (magnesium sulfate), filtered and concentrated to give the crude product. Purification of the crude product by reverse phase HPLC provided 32 mg of the desired product as a colorless oil. MS (M+H)$^+$ 817.1, (M−H)$^-$ 815.4.

e)

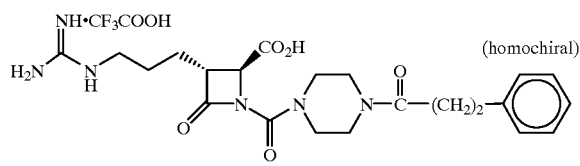 (homochiral)

Deprotection and purification of the product from part (d) according to the procedure of Example 19(c) gave 10 mg of the desired product as a white powder. MS (M+H)$^+$ 459.2, (M−H)$^-$ 457.4; IR (KBr) 1790 cm$^{-1}$, 1680 cm$^-$.

EXAMPLE 24

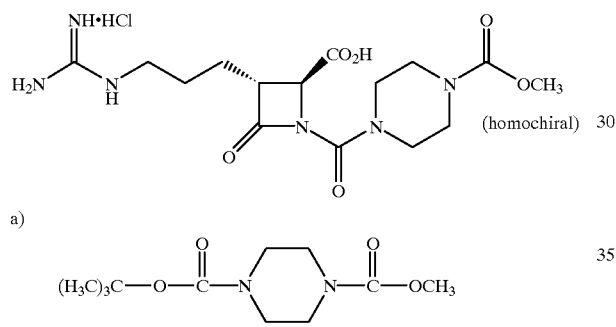 (homochiral)

a)

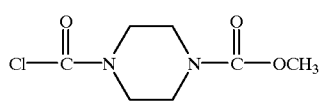

A solution of tert-butyl-1-piperazine carboxylate (0.5 g, 2.68 mmol) in methylene chloride (5 ml) was cooled to 0° C. N,N-Diisopropylethylamine (0.42 g, 3.22 mmol) and 4-dimethylaminopyridine (30 mg) were added, followed by addition of methyl chloroformate (0.25 g, 2.69 mmol) over 1 minute. The mixture was stirred at 0° C. for 1 hour. The mixture was partitioned between water (20 ml) and ethyl acetate (2×20 ml). The organic phase was washed with brine (1×75 ml), dried over sodium sulfate and condensed to give the desired product as a cream colored solid (0.636 g).

b)

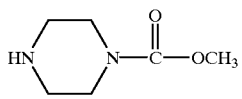

The product from part (a) (0.3 g, 1.23 mmol) was dissolved in methylene chloride (3 ml) and cooled to 0° C. Trifluoroacetic acid (3 ml) was added and the mixture was warmed to room temperature and stirred for 1 hour. The mixture was then evaporated in vacuo. The residue was dissolved in water, the pH adjusted to 12–13 with 6 N sodium hydroxide, and extracted with ethyl acetate. The organic phase was washed with brine, dried over sodium sulfate and condensed to give 91 mg of the desired free amine product. IR(film) 1696.2 cm$^-$; MS 144.9 (M+H)$^+$.

c)

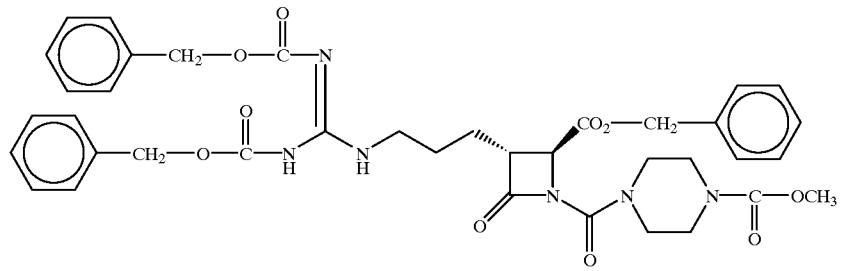

A mixture of the product from part (b) (89 mg, 0.617 mmol) and triethylamine (86 µl, 0.59 mmol) in methylene chloride (2 ml) was added to a mixture of phosgene (0.82 ml of a 20% phosgene in toluene solution, 1.54 mmol). The mixture was stirred at 0° C. for 1 hour. The reaction mixture was then partitioned between water (25 ml) and ethyl acetate (2×25 ml). The organic phase was washed with 1N HCl (40 ml), brine (50 ml), dried over sodium sulfate and concentrated to give 108 mg of the desired product as a brown oil. IR (film) 1738.8, 1704.7 cm$^{-1}$.

d)

The benzyl ester product from Example 1(c) (111 mg, 0.194 mmol) was dissolved in tetrahydrofuran (2 ml) and cooled to −78° C. Sodium bis(trimethylsilyl)amide (0.23 ml, 0.234 mmol) was added over 1 minute and the mixture was stirred at −78° C. for 1 hour. A solution of the product from part (c) (48 mg, 0.234 mmol) in tetrahydrofuran (1 ml) was added and the reaction mixture was stirred at −78° C. After 1 hour, the mixture was quenched with 0.5 N potassium bisulfate solution (25 ml) and extracted with ethyl acetate (2×25 ml). The organic phase was washed with brine (1×50 ml), dried over sodium sulfate and concentrated to give a pale yellow oil. Purification by preparative HPLC (reverse phase, methanol, water, trifluoroacetic acid) gave 25 mg of the desired product as a colorless oil/foam. MS 743.1 (M+H)$^+$, 741.4 (M−H)$^-$; IR(film) 1786.6 cm$^{-1}$.

e)

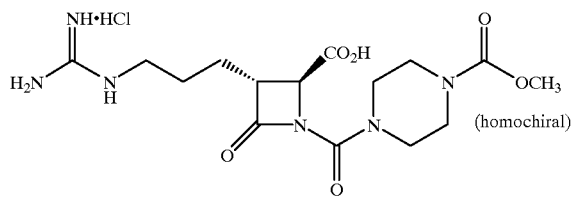
(homochiral)

Deprotection of the product from part (d) (22 mg, 0.027 mmol) and work-up as described in Example 21(d) gave 12 mg of the desired product as a white lyophilate. MS 385.1 (M+H)$^+$, 383.2 (M−H)$^-$; IR(film) 1786 cm$^{-1}$.

EXAMPLE 25 a)

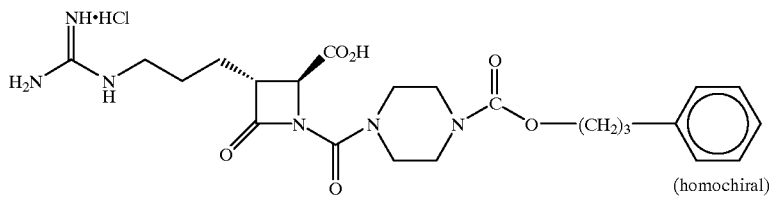
(homochiral)

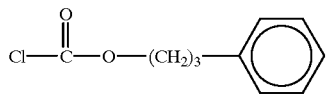

3-Phenyl-1-propanol (1.09 g, 7.34 mmol) was added to a mixture of phosgene (5.5 ml of 20% phosgene in toluene solution, 11.01 mmol) in methylene chloride (5 ml) at 0° C. The mixture was stirred at 0° C. for 5 hours. The reaction mixture was evaporated in vacuo to give a colorless oil. Purification by flash column chromatography (silica gel, 0–5% ethyl acetate/Hexane gave 1.33 g of the desired product.

b)

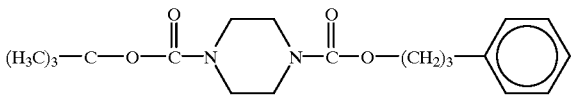

A solution of tert-butyl-1-piperazine carboxylate (0.2, 1.07 mmol) in methylene chloride (3 ml) was cooled to 0° C. N,N-Diisopropylethylamine (0.25 g, 1.93 mmol) and 4-dimethylaminopyridine (5–7 crystals) were added, followed by addition of a solution of the product from part (a) (0.2 g, 1.07 mmol) over 1 minute. The mixture was stirred at 0° C. for 1 hour. The mixture was then partitioned between water (20 ml) and ethyl acetate (2×20 ml). The organic layer was washed with brine (1×75 ml), dried over sodium sulfate and concentrated to give 0.35 g of the desired product as a yellow oil.

c)

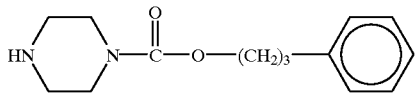

The product from part (b) (0.35 g, 1.03 mmol) was dissolved in methylene chloride (4 ml) and cooled to 0° C. Trifluoroacetic acid (4 ml) was added over 1 minute and the mixture was warmed to room temperature and stirred for 1 hour. The mixture was then evaporated in vacuo. The residue was dissolved in water, the pH was adjusted to 12–13 using 6 N sodium hydroxide and extracted with ethyl acetate. The organic phase was washed with brine, filtered over sodium sulfate and concentrated to give 0.23 g of the desired product as a white solid. MS 248.9 (M +H)

d)

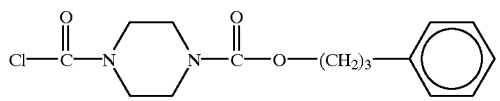

A solution of the product from part (c) (100 mg, 0.403 mmol) in methylene chloride (1 ml) was added to a mixture of phosgene (0.53 ml of a 20% phosgene in toluene solution, 1.01 mmol) followed by the addition of triethylamine (60 μl, 0.403 mmol). The mixture was stirred at 0° C. for 1 hour. The reaction mixture was then partitioned between water (25 ml) and ethyl acetate (2×25 ml). The organic phase was washed with 1N HCl (40 ml), brine (50 ml), dried over sodium sulfate and concentrated to give 115 mg of the desired product.

e)

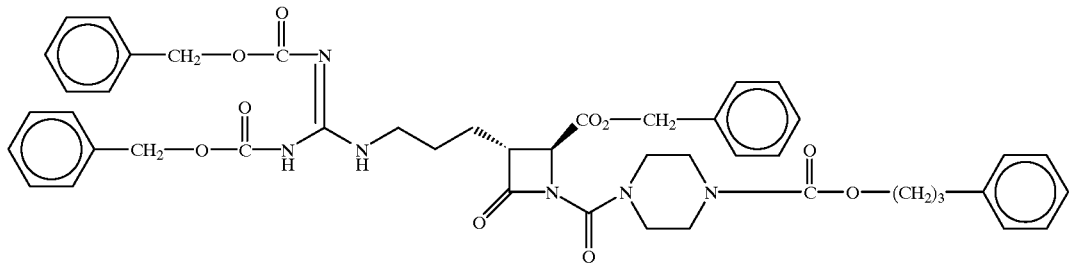

A solution of the benzyl ester product from Example 1(c) (43 mg, 0.075 mmol) in methylene chloride (1 ml) was cooled to 0° C. and triethylamine (11 mg, 0.113 mmol) and 4-dimethylaminopyridine (6–8 crystals) were added. A solution of the product from part (d) (58 mg) in methylene chloride (0.5 ml) was added and the mixture was stirred at 0° C. for 45 minutes followed by stirring at room temperature for 3 hours. The mixture was then evaporated in vacuo. Purification of the residue by flash column chromatography (silica gel, 30% ethyl acetate/hexane) gave 40 mg of the desired product as a pale yellow oil. MS 847.1 (M +H)$^+$, 845.4 (M–H)$^-$; IR (film) 1784 cm$^-$.

f)

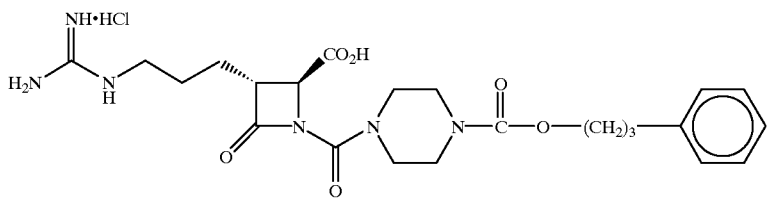

(homochiral)

Deprotection of the product from part (e) (40 mg, 0.027 mmol) and work-up as described in Example 21(d) gave 21 mg of the desired product as a white lyophilate. MS 489.1 (M +H)$^+$, 487.4 (M–H)$^-$; IR (KBr) 1784, 1667 cm$^{-1}$.

EXAMPLE 26

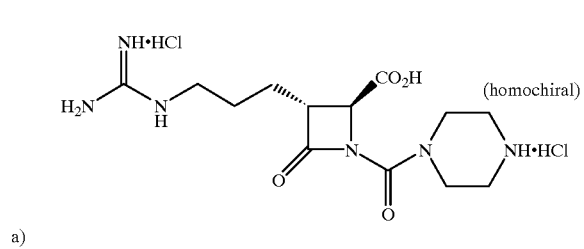

(homochiral)

a)

-continued

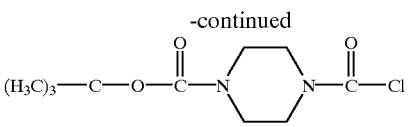

A solution of tert-butyl-1-piperazine carboxylate (0.5 g, 2.8 mmol) in methylene chloride (1 ml) was added to a mixture of phosgene (3.6 ml of 20% phosgene in toluene solution, 6.71 mmol) in methylene chloride (2 ml) at 0° C. Triethylamine (0.27 g, 6.71 mmol) was then added and the mixture was stirred at 0° C. for 1 hour. The mixture was then partitioned between water (30 ml) and ethyl acetate (2×30 ml). The organic layer was washed with brine (1×60 ml), dried over sodium sulfate and condensed to give crude product. Purification of the crude product by flash chromatography (silica gel, 40% ethyl acetate/hexane) gave 0.515 g of the desired product as a white solid. IR (film) 1737.6, 1697.0 cm$^{-1}$.

b)

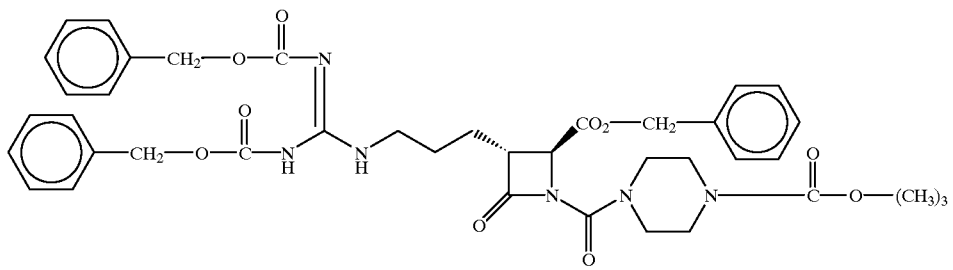

A solution of the benzyl ester product from Example 1(c) (47 mg, 0.082 mmol) in methylene chloride (1 ml) was cooled to 0° C. and triethylamine (12 mg, 0.123 mmol) and 4-dimethylaminopyridine (6–8 crystals) were added. A solution of the product from part (a) (51 mg) in methylene chloride (1 ml) was added and the mixture was stirred at 0° C. for 40 minutes followed by stirring at room temperature for 4–5 hours. The mixture was then evaporated in vacuo. Purification of the residue by flash chromatography (silica gel, 0–30% ethyl acetate/hexane) gave 48 mg of the desired product as a colorless oil. MS 785.1 (M +H)$^+$, 783.4 (M–H)$^-$.

c)

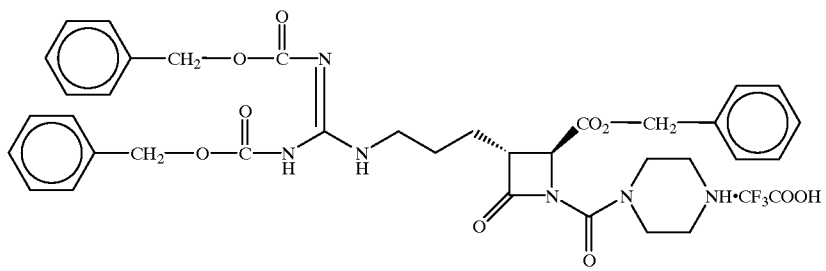

The product from part (b) (40 mg, 0.051 mmol) was dissolved in methylene chloride (1 ml) and cooled to 0° C. Trifluoroacetic acid (1 ml) was added over 1 minute and the mixture was warmed to room temperature and stirred for 1 hour. The mixture was then evaporated in vacuo to give the desired product as a yellow oil which was used in the next step without further purification. MS 685.1 (M +H)$^+$, 683.3 (M–H)$^-$.

d)

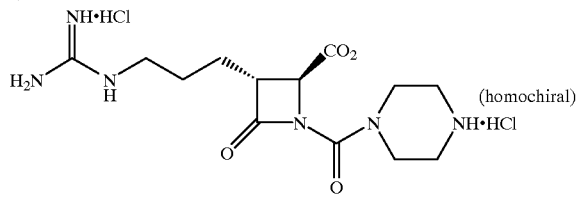

The product from part (c) (49 mg, 0.061 mmol) was deprotected and worked-up as described in Example 21(d) to give 15 mg of the desired product as a white lyophilate. MS 327.0 (M+H)$^+$, 325.0 (M–H)$^-$; IR (KBr) 1786, 1653 cm$^{-1}$.

EXAMPLE 27

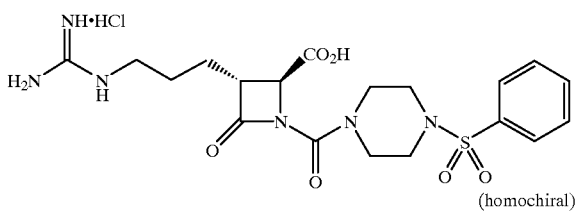

a)

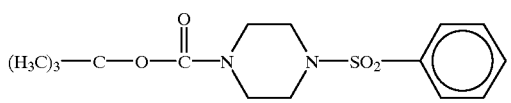

A solution of tert-butyl-1-piperazine carboxylate (0.2 g, 1.07 mmol) in methylene chloride (2 ml) was cooled to 0° C. N,N-diisopropylethylamine (0.167 g, 1.28 mmol) and 4-dimethylaminopyride (30 mg) were added, followed by addition of benzenesulfonyl chloride (0.19 g, 1.07 mmol) over 1 minute. The mixture was stirred at 0° C. for 2 hours. After two hours, water (20 ml) was added to the mixture and extracted with ethyl acetate (2×20 ml). The organic layer was washed with brine (1×75 ml), dried over sodium sulfate and concentrated to give 0.35 g of the desired product as a white solid.

b)

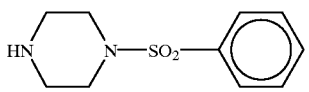

The product from part (a) (0.35 g, 1.07 mmol) was dissolved in methylene chloride (3 ml) and cooled to 0° C. Trifluoroacetic acid (3 ml) was added over 1 minute and the mixture was warmed to room temperature and stirred for 1 hour. The mixture was then evaporated in vacuo. The residue was dissolved in water, the pH adjusted to 12–13 using 6 N sodium hydroxide and extracted with ethyl acetate. The organic phase was washed with brine, dried over sodium sulfate and concentrated to give 0.208 g of the desired product as a pale yellow oil. MS 226.8 (M+H)$^+$.

c)

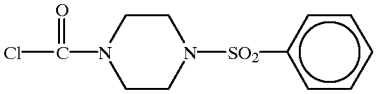

A mixture of the product from part (b) (100 mg, 0.442 mmol) and triethylamine (62 μl, 0.442 mmol) in methylene chloride (1 ml) was added to a mixture of phosgene (0.59 ml of a 20% phosgene in toluene solution, 1.1 mmol). The mixture was stirred at 0° C. for 1 hour. The mixture was then evaporated in vacuo. The residue was suspended in ether and filtered. The eluents were concentrated to give 100 mg of the desired product as a cream colored solid.

d)

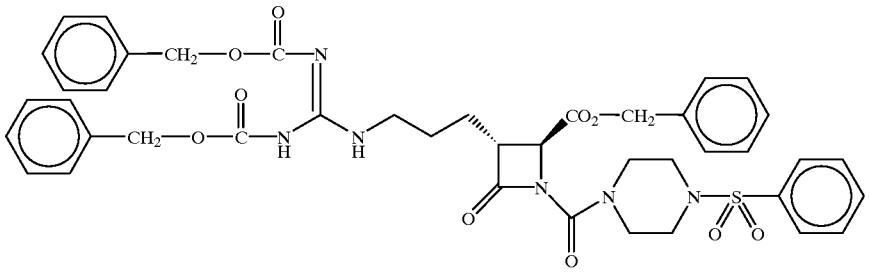

A solution of the benzyl ester product from Example 1(c) (64 mg, 0.112 mmol) in methylene chloride (1 ml) was cooled to 0° C. and triethylamine (17 mg, 0.168 mmol) and 4-dimethylaminopyridine (6–8 crystals) were added. The product from part (c) (58 mg, 0.168 mmol) was added and the mixture was stirred at 0° C. for 45 minutes followed by stirring at room temperature for 3 hours. The mixture was then evaporated in vacuo to give crude product. Purification of the crude product by preparative HPLC (reverse phase, methanol, water, trifluoroacetic acid) gave 28 mg of the desired product as a colorless oil. MS 825.1 (M+H)$^+$.

e)

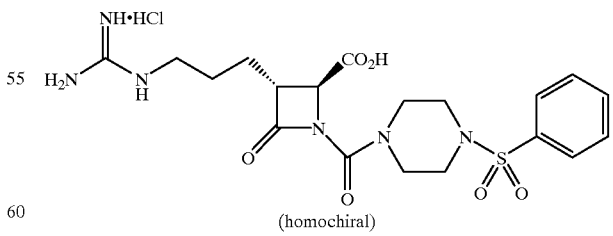

(homochiral)

The product from part (d) (25 mg, 0.03 mmol) was deprotected and worked-up as described in Example 21(d) to give 12 mg of the desired product as a white lyophilate. MS 467.0 (M+H)$^+$, 465.3 (M−H)$^-$; IR (film) 1787.25, 1662.13 cm$^{-1}$.

EXAMPLE 28

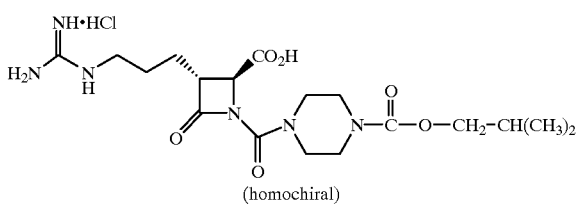
(homochiral)

a)

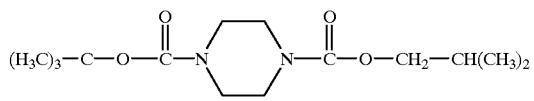

Diisopropylethylamine (30 mg), 4-dimethylaminopyridine (30 mg) and a solution of isobutyl chloroformate (366 µl, 268 mmol) in methylene chloride (2 ml) were added to a 0° C. solution of tert-butyl-1-piperazine carboxylate (500 mg, 2.68 mmol) in methylene chloride (2 ml). The mixture was stirred at 0° C. for 1 hour. The reaction was quenched with the addition of water (20 ml). The mixture was extracted with ethyl acetate (2×50 ml). The organic layers were combined and washed with brine (2×10 ml), dried over magnesium sulfate, and concentrated to give 819 mg of the desired product as a yellow solid; IR(film) 1701 cm$^{-1}$, 1688 cm$^{-1}$.

b)

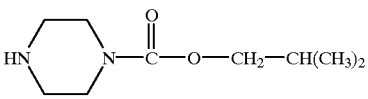

A mixture of the crude product from part (a) (800 mg, 2.79) mmol), trifluoroacetic acid (10 ml) and methylene chloride (10 ml) was stirred at room temperature for 1 hour. TLC showed the completion of the reaction. The solvent was removed and 1N sodium hydroxide solution (15 ml) was added. The mixture was extracted with ethyl acetate (100 ml). The combined organic solution was washed with brine (10 ml), dried over magnesium sulfate, filtered and concentrated to give 511 mg of the desired product as a yellow oil which was used without further purification. IR(film) 1692 cm$^{-1}$.

c)

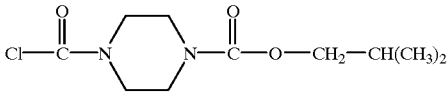

A mixture of the product from part (b) (477 mg, 2.56 mmol) and triethylamine (432 µL) in methylene chloride (5 ml) was added to a solution of phosgene in toluene (1.6 ml, 20%) at 0° C. The resultant mixture was stirred at 0° C. for 2 hours. TLC showed the completion of the reaction. The solvent was removed, and anhydrous ether (50 ml) was added. The mixture was filtered and the filtrate was concentrated to give the crude product (481 mg) as an orange oil. Purification of the crude product provided 453 mg of the desired product as a yellow oil. IR (film) 1741 cm$^{-1}$, 1703 cm$^{-1}$.

d)

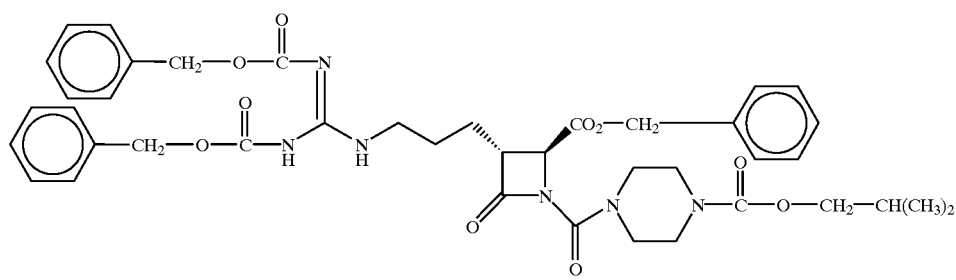

Triethylamine (36 µl), 4-dimethylaminopyridine (30 mg) and a solution of the product from step (c) (65 mg, 0.24) in methylene chloride (1 ml) were added to a solution of the benzyl ester product from Example 1(c) (100 mg, 0.17 mmol) in methylene chloride (1 ml). The mixture was stirred for 4 hours at room temperature. Analytical HPLC indicated that the reaction was complete. The reaction was quenched by the addition of 1N potassium bisulfate (15 ml). The mixture was extracted with ethyl acetate (100 ml). The organic layer was washed with brine (15 ml), dried over magnesium sulfate, and concentrated to give the crude product as a yellow oil. Purification by flash chromatography (50% ethyl acetate/hexane) gave 81 mg of the desired product. MS 785.2 (M+H)$^+$, 783.4 (M-H)$^-$.

e)

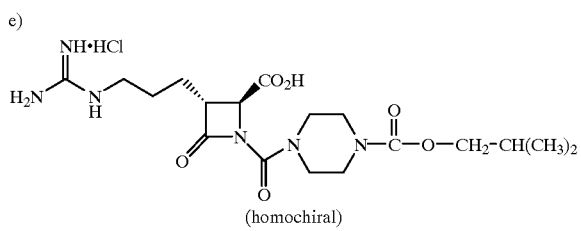

(homochiral)

The product from part (d) (80 mg, 0.10 mmol) was deprotected and worked-up as described in Example 21(d) to give 41 mg of the desired product as a white solid. MS (M+H)$^+$ 427.1, (M−H)$^−$ 425.3; IR (KBr) 1786 cm$^{-1}$, 1653 cm$^{-1}$.

b)

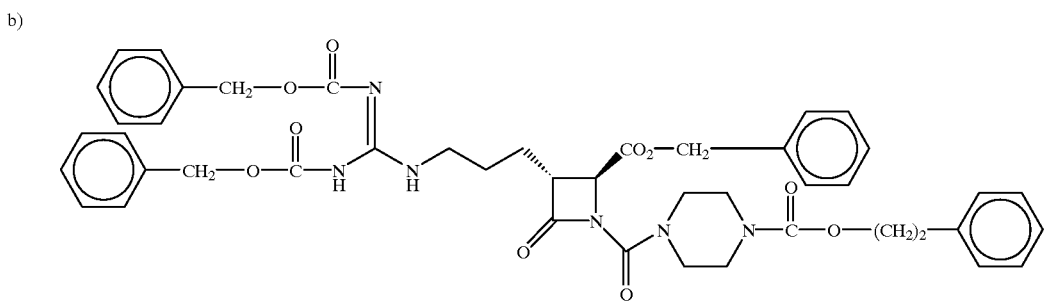

EXAMPLE 29

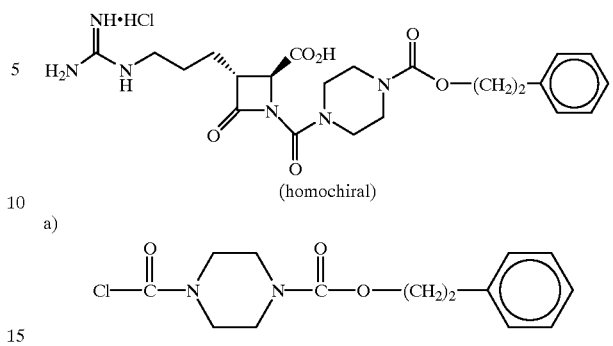

(homochiral)

a)

Following the procedure of Example 25(a) through (d) but substituting phenethyl alcohol for the 3-phenyl-1-propanol in (a), the desired product was obtained as an orange oil.

A solution of the benzyl ester product from Example 1(c) (69 mg, 0.121 mmol) in methylene chloride (1 ml) was cooled to 0° C. and triethylamine (18 mg, 0.181 mmol) and 4-dimethylaminopyridine (6–8 crystals) were added. A solution of the product from part (a) (54 mg) in methylene chloride (1 ml) was added and the mixture was stirred at 0° C. for 45 minutes followed by stirring at room temperature for 2.5 hours. The mixture was then evaporated in vacuo. Purification of the residue by flash chromatography (silica gel, 0–30% ethyl acetate/Hexane) gave 90 mg of the desired product as a colorless oil. MS 833.1 (M+H)$^+$, 831.4 (M−H)$^−$; IR (film) 1786, 1737.7 cm$^{-1}$.

c)

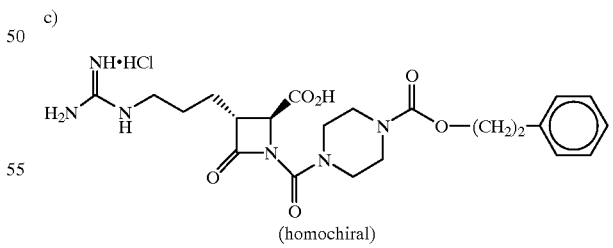

(homochiral)

The product from part (b) (85 mg, 0.108 mmol) was deprotected and worked-up as described in Example 21(d) to give 34 mg of the desired product as a white lyophilate. MS 475.1 (M+H)$^+$, 473.4 (M−H)$^−$; IR (film) 1783 cm$^{-1}$, 1665 cm$^{-1}$.

EXAMPLE 30

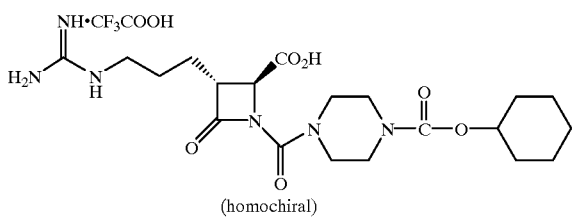

(homochiral)

a) Cyclohexyl chloroformate

A mixture of cyclohexanol (500 mg, 5.0 mmol) and triethylamine (836 μl) in methylene chloride (4 ml) was added to a 0° C. solution of phosgene in toluene (5.3 ml, 20%). The resultant mixture was stirred at 0° C. for 2.5 hours. TLC showed completion of the reaction. The solvent was removed and anhydrous ether (50 m l) was added. The mixture was filtered and the filtrate was concentrated to give 726 mg of the desired product as a colorless oil which was used without further purification. IR (film) 1776 cm$^{-1}$.

b)

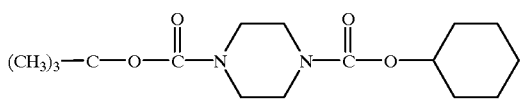

Disopropylethylamine (560 μl), 4-dimethylaminopyridine (30 mg) and a solution of cyclohexyl chloroformate (473 mg, 2.68 mmol) in methylene chloride (2 ml) were added to a 0° C. solution of tert-butyl-1-piperazine carboxylate (500 mg, 2.68 mmol) in methylene chloride (3 ml). The mixture was stirred at 0° C. and warmed to room temperature over 4 hours. The reaction was quenched with the addition of water (15 ml). The mixture was extracted with ethyl acetate (100 ml). The organic layer was washed with brine (2×10 ml), dried over magnesium sulfate, and concentrated to give 832 mg of the desired product as a white solid. IR(film) 1692 cm$^{-1}$.

c)

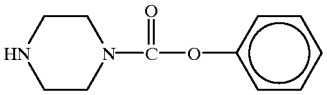

A mixture of the crude product from part (b) (832 mg, 2.68 mmol), trifluoroacetic acid (2 ml) and methylene chloride (2 ml) was stirred at room temperature for 3 hours. TLC showed completion of the reaction. The solvent was removed and 1N sodium hydroxide solution (15 ml) was added. The mixture was extracted with ethyl acetate (100 ml). The combined organic solution was washed with brine (10 ml), dried over magnesium sulfate, filtered and concentrated to give 535 mg of the desired product as a light yellow oil which was used without further purification.

d)

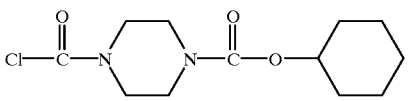

A mixture of the product from part (c) (459 mg) and triethylamine (448 μl) in methylene chloride (2 ml) was added to a solution of phosgene in toluene (2.1 ml, 20%) at 0° C. The resultant mixture was stirred at 0° C. for 1 hour. TLC showed the completion of the reaction. The solvent was removed and anhydrous ether (50 ml) was added. The mixture was filtered and the filtrate was concentrated to give the crude product (626 mg) as an orange oil. Purification of the crude product provided 626 mg of the desired product as a yellow solid. IR (film) 1740 cm$^{-1}$ 1697 cm$^{-1}$.

e)

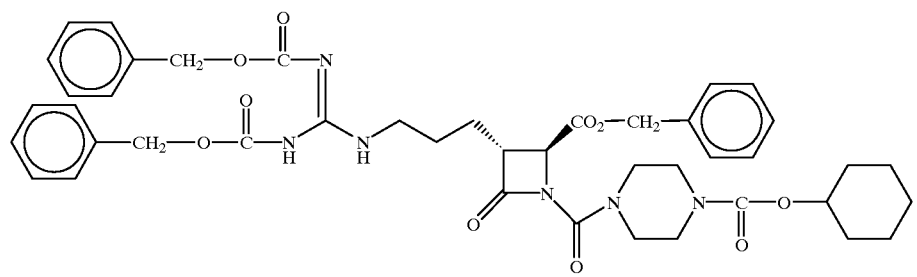

Triethylamine (34 μl), 4-dimethylaminopyridine (20 mg) and a solution of the product from part (d) (65 mg, 0.24 mmol) in methylene chloride (1 ml) was added to solution of the benzyl ester product from Example 1(c) (113 mg, 0.14 mmol) in methylene chloride (1 ml). The mixture was stirred at room temperature for 2 hours. Analytical HPLC showed the reaction was complete. The reaction was quenched with the addition of 1N potassium bisulfate (15 ml). The mixture was extracted with ethyl acetate (100 ml). The organic layer was washed with brine (15 ml), dried (magnesium sulfate) and concentrated to give the crude product as a colorless oil. Purification by flash chromatography (50% ethyl acetate/hexane) gave 113 mg of the desired product. IR (film) 1786 cm$^{-1}$, 1734 cm$^{-1}$, 1683 cm$^{-1}$, 1639 cm$^{-1}$.

f)

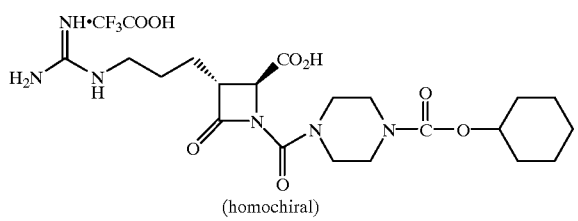

(homochiral)

Deprotection and purification of the product from part (e) (113 mg, 0.14 mmol) according to the procedure of Example 19(c) gives 33 mg of the desired product as a white solid. MS (M+H)$^+$ 453.3, (M−H)$^−$ 451.5; IR (KBr) 1790 cm$^{-1}$, 1674 cm$^{-1}$.

EXAMPLE 31

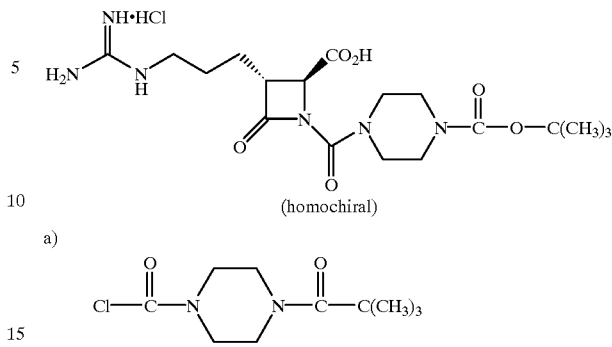

(homochiral)

a)

Following the procedure of Example 22(a) through (c) but substituting tert-butylcarbonyl chloride for the tert-butyl acetylchloride in part (a), the desired product was obtained as a pale brown solid. IR (film) 1733.2, 1616.4 cm$^{-1}$.

b)

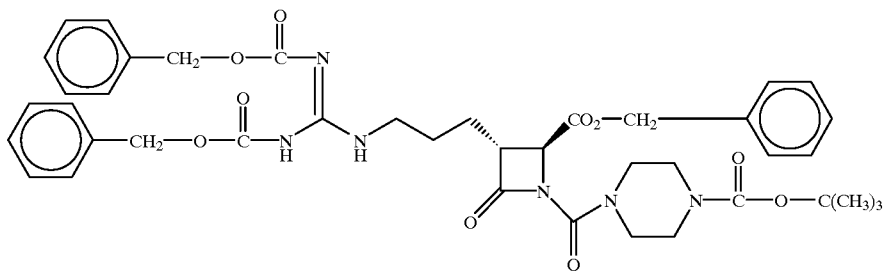

Triethylamine (24 mg, 0.236 mmol) and 4-dimethylaminopyridine (8–10 crystals) were added to a solution of the benzyl ester product from Example 1(c) (90 mg, 0.157 mmol) in methylene chloride (1 ml). A solution of the product from part (a) (59 mg, 0.236 mmol) in methylene chloride (1 ml) was added and the mixture was stirred at 0° C. for 30 minutes followed by stirring at room temperature for 6 hours. The mixture was then evaporated in vacuo. Purification of the residue by flash chromatography (silica gel, 0–30% ethyl acetate/Hexane) gave 89 mg of the desired product as a colorless. MS 769.4 (M+H)$^+$, 767.6 (M−H)$^−$; IR (film) 1785.4, 1733.4, 1679.4, 1635.9 cm$^{-1}$.

c)

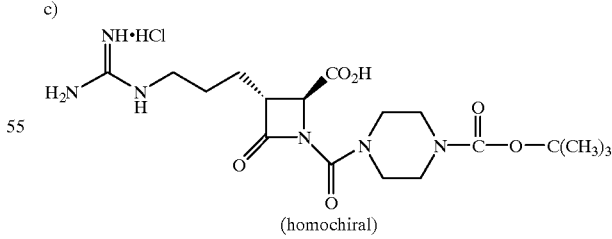

(homochiral)

The product from part (b) (87 mg, 0.11 mmol) was deprotected and worked-up as described in Example 21(d) to give 10 mg of the desired product as a white solid lyophilate. MS 411.2 (M+H)$^+$, 409.5 (M−H)$^−$; IR (KBr) 1788.0, 1742.0 cm$^{-1}$. QA206b

EXAMPLE 32

The product of Example 21 was also prepared as follows:

a)

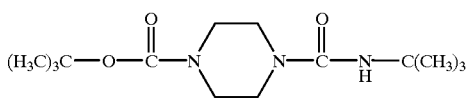

A solution of tert-butylisocyanate (10.28 g, 103 mmol) in methylene chloride (20 ml) was added over 2 minutes to a solution of tert-butyl-1-piperazine carboxylate (9.17 g, 49.2 mmol) in methylene chloride (40 ml) at 0° C. under nitrogen. After stirring the reaction mixture at room temperature for 2 hours, the reaction mixture was poured into hexane (60 ml). The resulting precipitate was collected by filtration and washed with hexane/methylene chloride (2:1) (2×50 ml). The combined eluent was concentrated to approximately a 20 ml volume and the precipitate that formed was collected by filtration, washed as above and combined with previously collected solid. The solid was dried under vacuum to give 14.1 g of the desired product. MS 286.2 (M+H)$^+$.

b)

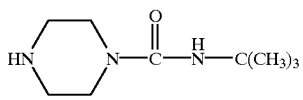

Trifluoroacetic acid (25 ml) was added dropwise over 5 minutes to a solution of the product from part (a) (14.1 g, 49 mmol) in methylene chloride (25 ml) at 0° C. under nitrogen. The reaction mixture was stirred at 0° C. for 20 minutes and then at room temperature for 2 hours. The reaction mixture was transferred to a beaker (100 ml) and diluted with ethyl acetate (200 ml) and water (200 ml). While vigorously stirring the biphasic mixture sodium hydroxide (25% aqueous) was added dropwise until the pH of the aqueous phase was about 12. The organic phase was separated with an additional portion of ethyl acetate (200 ml). The combined organics were dried over sodium sulfate, filtered and concentrated to give 11 g of the desired product as a white solid.

c)

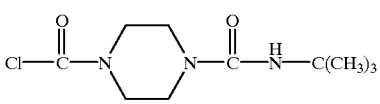

A solution of the product from part (b) (about 11 g) in methylene chloride: acetonitrile (1:1, 40 ml) was added dropwise over 10 minutes to a solution of phosgene (20% in toluene, 70 ml, 132 mmol) at 0° C. under nitrogen. Triethylamine (30 ml) was then added dropwise over 5 minutes. The reaction mixture was then stirred at room temperature for 2 hours. The reaction mixture was transferred to a separatory funnel, diluted with ethyl acetate (150 ml) and washed with 2N HCl (2×150 ml). The organics were dried over sodium sulfate, filtered and concentrated to a yellow oil. Purification by flash chromatrography (silica gel, 0 to 50% ethyl acetate in hexane) provided 7.8 g of the desired product.

d)

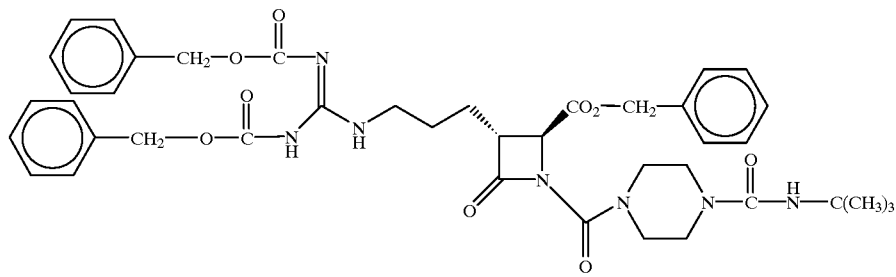

The carbamoyl chloride product from part (c) (4.5 g, 18.2 mmol), triethylamine (2.6 ml, 18.2 mmol) and dimethylaminopyridine (225 mg) were added to a solution of the benzyl ester product from Example 1(c) (6.94 g, 12.13 mmol) in methylene chloride (50 ml) at room temperature under nitrogen. After stirring the reaction mixture at room temperature for 4 hours, additional portions of the acid chloride product from part (c) (1 g, 4 mmol) and triethylamine (1 ml, 7 mmol) were added. The reaction was stirred for an additional 3 hours. The reaction was diluted with hexane (5 ml) and the crude reaction mixture was loaded onto a silica column (wetted with hexane) for purification by flash chromatography (0 to 60% ethyl acetate in hexane) to provide 7.46 g of the desired product. MS 784.4 (M+H)$^+$, 782.2 (M−H)$^−$.

e)

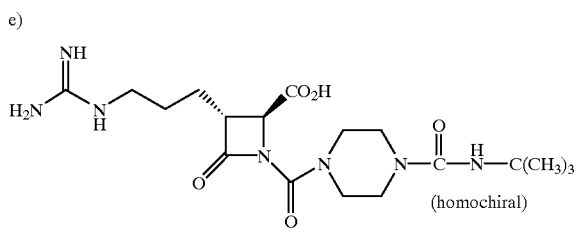

Water (50 ml), concentrated HCl (0.8 ml, 9.6 mmol) and 10% palladium on carbon catalyst (7.5 g, 50% water content) were added to a solution of the product from part (d) (7.46 g, 9.57 mmol) in dioxane (125 ml) at room temperature under nitrogen. Hydrogen was bubbled through the solution for 30 minutes and then the reaction was stirred under hydrogen (1 atmosphere) for 11 hours. The reaction was filtered through a Celite® pad which was washed with water (about 100 ml) until no product could be detected in the eluent. The solution was frozen and lyophilized to give 4.5 g of a white solid. Purification by HPLC (reverse phase, methanol, water, trifluoroacetic acid), subsequent lyophilization, filtration through polyvinylpyridine with a water mobile phase, and final lyophilization proved 3.3 g of the desired product as a voluminous white solid. MS 426.2 (M+H)$^+$, 424.4 (M−H)$^−$; IR (KBr) 1777 cm$^{-1}$.

Anal. calc'd for $C_{18}H_{31}N_7O_5 \cdot 1.56\ H_2O$: C, 47.66; H, 7.58; N, 21.62; O, 23.14. Found: C, 47.58, H, 7.37; N, 21.41.

EXAMPLE 33

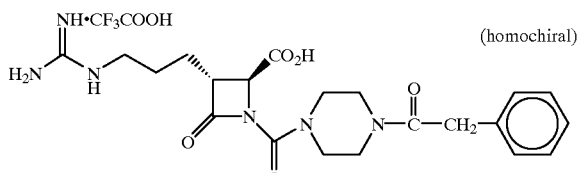

a)

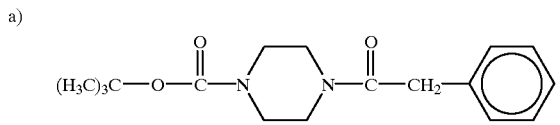

Following the procedure of Example 23(a) but substituting phenylacetyl chloride for the 3-phenylpropanoic acid chloride, the desired compound was obtained as a yellow solid.

b)

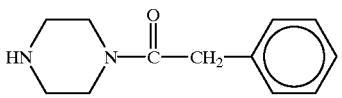

A mixture of the product from part (a) (2.68 mmol), trifluoroacetic acid (10 ml) and methylene chloride (10 ml) was stirred at room temperature for 90 minutes. TLC showed the completion of the reaction. The solvent was removed and 1N sodium hydroxide solution (10 ml) was added. The mixture was extracted with ethyl acetate (100 ml). The organic solution was washed with brine (20 ml), dried (magnesium sulfate), filtered and concentrated to give 536 mg of desired product as a colorless oil which was used without further purification. IR (film) 1630 cm$^{-1}$.

c)

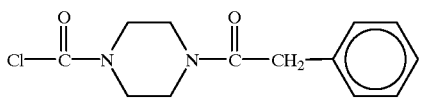

A mixture of the product from part(b) (113 mg, 0.55 mmol) and triethylamine (92 μl) in methylene chloride (1 ml) was added to a solution of phosgene (351 μl, 20% in toluene) in methylene chloride (1 ml) at 0° C. The resultant mixture was stirred at 0° C. for 2 hours and worked-up according to the procedure of Example 23(c) to give 74 mg of the desired product as a yellow solid. IR(film) 1735 cm$^{-1}$, 1645 cm$^{-1}$.

d)

Triethylamine (34 μl), 4-dimethylaminopyridine (30 mg) and a solution of the product from part (c) (74 mg, 0.28 mmol) in methylene chloride (2 ml) were added to a solution of the benzyl ester product from Example 1(c) (113 mg, 0.20 mmol) in methylene chloride (1 ml). The mixture was stirred at room temperature for 2 hours. Analytical HPLC indicated that the reaction was complete. The reaction was quenched with the addition of 1N potassium sulfate (10 ml). The mixture was extracted with ethyl acetate (100 ml). The organic layer was washed with brine (15 ml), dried (magnesium sulfate) and concentrated to give the crude product as a colorless oil. Purification using flash chromatography (30–50% ethyl acetate/hexane) gave 73 mg of the desired product. MS $(M+H)^+$ 803.4, $(M-H)^-$ 801.5; IR (film) 1785 $cm^{-1}$, 1733 $cm^{-1}$, 1733 $cm^{-1}$, 1677 $cm^{-1}$, 1640 $cm^{-1}$.

e)

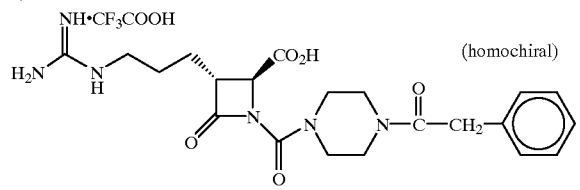

(homochiral)

The product from part (d) (67 mg, 0.83 mmol) was deprotected and worked-up according to the procedure of Example 19(c) to give 5 mg of the desired product as a white solid. MS $(M+H)^+$ +445.2, $(M-H)^-$ 443.4; IR (film) 1782 $cm^{-1}$, 1677 $cm^{-1}$.

EXAMPLE 34

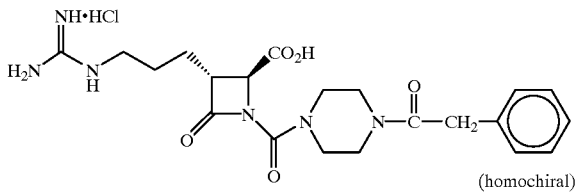

(homochiral)

a)

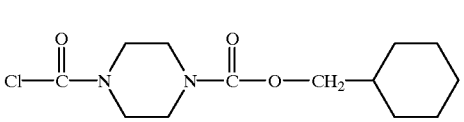

Following the procedure of Example 30 (a) through (d) but substituting cyclohexylmethanol for the cyclohexanol in step (a), the desired compound was obtained as a yellow oil. IR (film) 1743 $cm^{-1}$, 1702 $cm^{-1}$.

b)

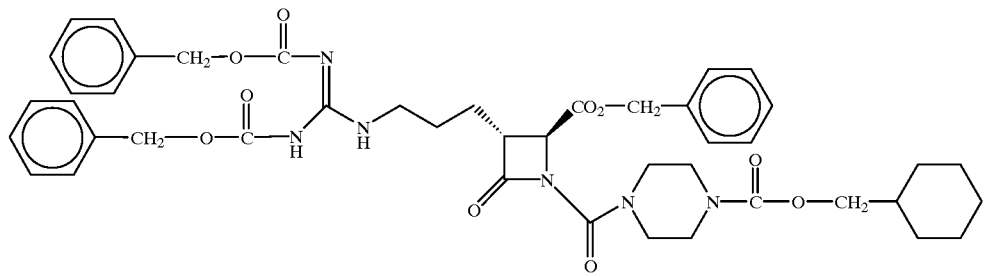

The product from part (a) is reacted with the benzyl ester product from Example 1(c) according to the procedure of Example 30 (e) to give the desired product as a colorless oil. IR (film) 1786 $cm^{-1}$, 1732 $cm^{-1}$, 1680 $cm^{-1}$, 1639 $cm^{-1}$.

c)

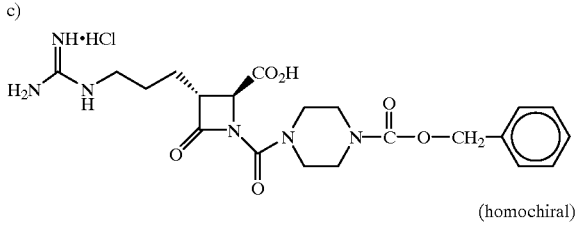

(homochiral)

The product from part (b) was deprotected and worked-up as described in Example 21(d) to give the desired product as a white solid. MS $(M+H)^+$ 467.3, $(M-H)^-$ 465.5; IR (KBr) 1778 $cm^{-1}$, 1541 $cm^{-1}$.

EXAMPLE 35

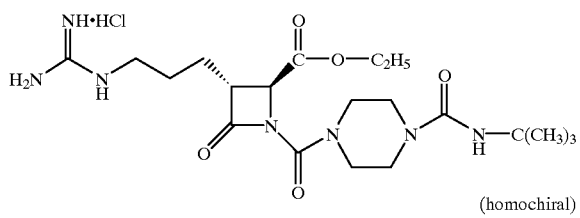
(homochiral)

a)

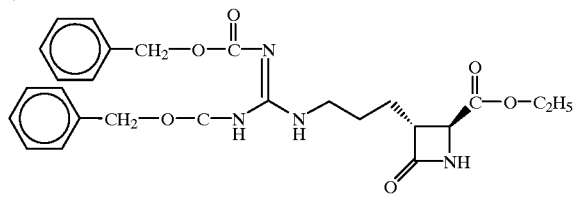

Cesium carbonate (14 mg, 0.042 mmol) was added to a stirred solution of the azetidinone product of Example 1(b) (40 mg, 0.083 mmol) and iodoethane (27 μl, 0.332 mmol) in dimethylformamide (200 μl) at room temperature. After 3 hours, the reaction mixture was partitioned between ethyl acetate and water containing a small amount of sodium thiosulfate. The organic phase was isolated, washed with saturated sodium chloride, dried over magnesium sulfate, and concentrated. The residue was purified by silica gel chromatography to afford 33 mg of the desired product.

b)

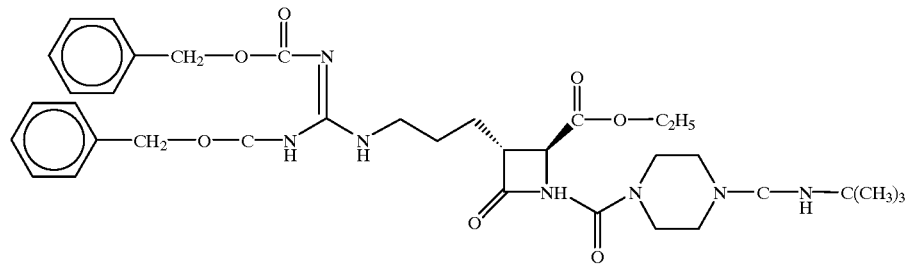

The product from part (a) (86 mg, 0.168 mmol) and the piperazinyl carbamoyl chloride of the formula:

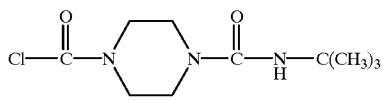

(56 mg, 0.227 mmol) [prepared as described in Example 32(c)] were dissolved in methylene chloride (1.80 ml) and tetrahydrofuran (0.20 ml). Triethylamine (35 μl, 0.252 mmol) was added followed by 4-dimethylaminopyridine (4.0 mg, 0.034 mmol). After 48 hours the reaction was concentrated and the crude product was purified by silica gel chromatography to give 71 mg of the desired product.

c)

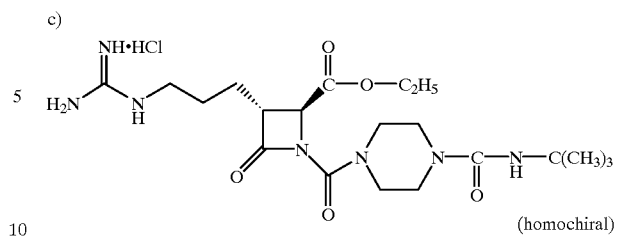
(homochiral)

The product from part (b) was deprotected and worked-up according to the procedure described in Example 21(d) to give the desired product as a lyophilate. IR(KBr) 1788 cm$^{-1}$.

EXAMPLE 36

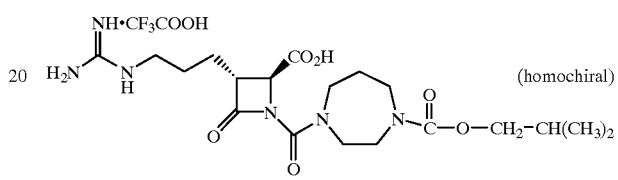
(homochiral)

a)

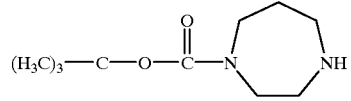

A solution of the di-tert-butyl dicarbonate (1.09, 4.99 mmol) and triethylamine (700 μl, 4.99 mmol) in tetrahydrofuran (15 ml) was added dropwise over 20 minutes to a solution of homopiperazine (400 mg, 4.99 mmol) in tetrahydrofuran (40 ml). The reaction mixture was stirred at room temperature for 2 hours. The mixture was then filtered and the filtrate was concentrated to give crude product as a colorless oil. Purification by flash chromatography (5% 2 N ammonia in methanol/methylene chloride) gave 410 mg of the desired product as a colorless oil. IR (film) 1691 cm$^{-1}$.

b)

(H$_3$C)$_3$—C—O—C(=O)—N⟨⟩NH—C(=O)—O—CH$_2$—CH(CH$_3$)$_2$

Diisopropylethylamine (380 μl), 4-dimethylaminopyridine (35 mg) and a solution of isobutyl chloroformate (242 μl, 1.87 mmol) in methylene chloride (2 ml) were added to a solution of the product from part (a)

(374 mg, 1.87 mmol) in methylene chloride (2 ml). The mixture was stirred at 0° C. and warmed to room temperature overnight. The reaction was quenched with the addition of water (15 ml) and worked-up according to the procedure described in Example 28 (a) to give 508 mg of the desired product. IR (film) 1696 cm$^{-1}$.

c)

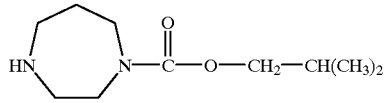

The product from part (b) (499 mg, 1.66 mmol) was treated with trifluoroacetic acid (2 ml) according to the procedure of Example 28(b) to give 324 mg of the desired product as a colorless oil which was used without further purification. IR(film) 1695 cm$^{-1}$.

d)

The product from part (c) (303 mg, 1.51 mmol) was reacted with phosgene in toluene (1.2 ml, 20%) at 0° C. according to the procedure of Example 28 (c) to give 298 mg of the desired product as a colorless oil. IR (film) 1737 cm$^{-1}$, 1697 cm$^{-1}$.

e)

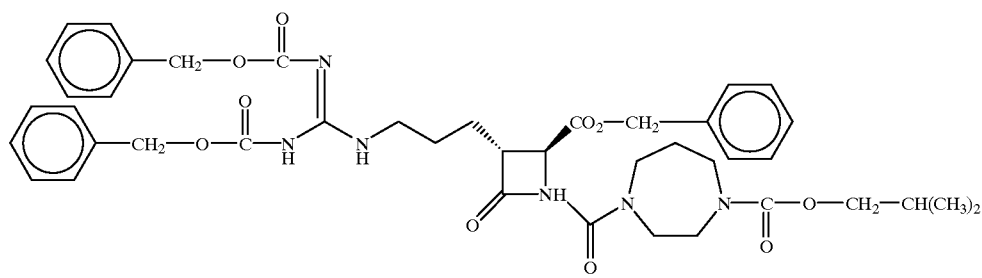

Triethylamine (34 μl), 4-dimethylaminopyridine (10 mg) and a solution of the product from part (d) (62 mg, 0.24 mmol) in methylene chloride (2 ml) were added to a solution of the benzyl ester product from Example 1(c) (113 mg, 0.20 mmol) in methylene chloride (1 ml). The mixture was stirred at room temperature overnight. Analytical HPLC indicated that the reaction was complete. The reaction was quenched with the addition of 1N potassium bisulfate (15 ml) and worked-up according to the procedure of Example 28(d) to give, following purification, 92 mg of the desired product as a colorless oil. MS (M+H)$^+$ 799.4, (M−H)$^−$ 797.6.

f)

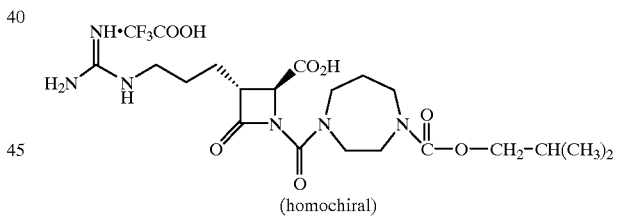

(homochiral)

The product from part (e) (81 mg, 0.10 mmol) was deprotected and worked-up according to the procedure of Example 19(c) to give 5 mg of the desired product as a colorless glass. MS (M+H)$^+$ 441.3, (M−H)$^{-1}$ 439.4; IR film) 1784 cm$^{-1}$, 1665 cm$^-$.

EXAMPLE 37

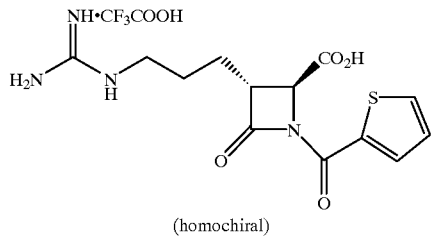

(homochiral)

a)

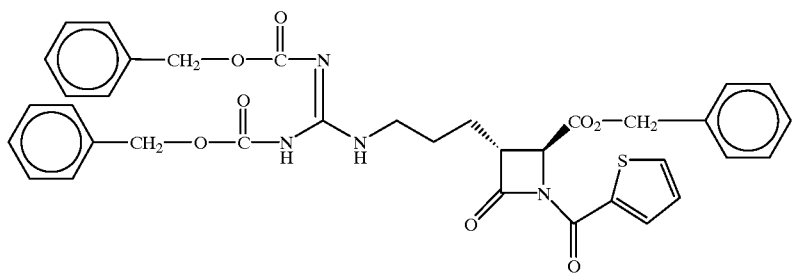

Sodium bis(trimethylsilyl)amide (1.0 M in tetrahydrofuran, 154 µl, 0.15 mmol) was added dropwise to a −78° C. solution of the benzyl ester product from Example 1(c) (80 mg, 0.14 mmol) in tetrahydrofuran (2 ml). The mixture was stirred at −78° C. for 40 minutes. A solution of 2-thiophenecarbonyl chloride (34 µl, 0.30 mmol) in tetrahydrofuran was added. The reaction was stirred at −78° C. for an additional 6 hours and was stored in a freezer (−50° C.) overnight. Analytical HPLC indicated the reaction was complete. The reaction mixture was quenched by the addition of saturated ammonium chloride solution (5 ml). The mixture was extracted with ethyl acetate (3×15 ml). The organic layers were combined and washed with brine (2×10 ml), dried (magnesium sulfate), filtered and concentrated to give the crude product which was purified by flash chromatography (silica, 20–30% ethyl acetate/hexane) to give 57 mg of the desired product as a white solid. MS (M+H)+ 683.7, (M−H)− 681.6; IR (KBr) 1796 cm−1, 1734 cm−1, 1640 cm−.

b)

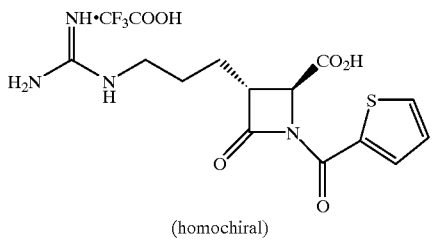
(homochiral)

The product from part (a) (53 mg, 0.078 mmol) was deprotected and worked-up according to the procedure of Example 19(c) to give 11 mg of the desired product as a white powder. MS (M+H)+ 324.9, (M−H)− 323.1.

EXAMPLE 38

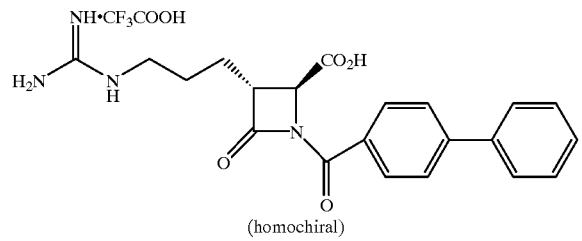
(homochiral)

a)

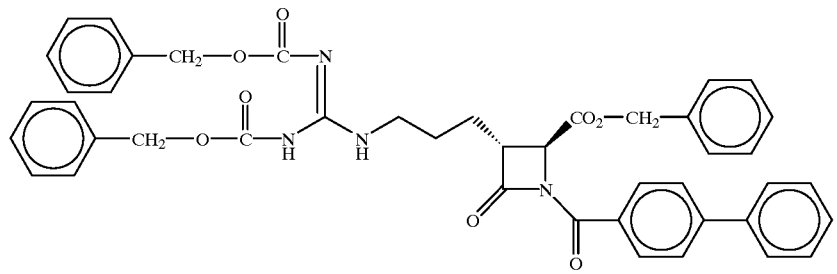

Sodium bis(trimethylsilyl)amide (1.0 M in tetrahydrofuran, 131 µl, 0.131 mmol) was added to a solution of the benzyl ester product from Example 1(c) (73.1 mg, 0.127 mmol) in dry tetrahydrofuran (2 ml) under nitrogen at −78° C. The reaction mixture was stirred at −78° C. for 30 minutes then 4-biphenylcarbonyl chloride (29 mg, 0.134 mmol) was added in a single portion. The reaction mixture was stirred at −78° C. for 5 minutes and then at −15° C. for 15 minutes. 1N HCl (1 ml) was added followed immediately by ethyl acetate (3 ml). The resulting biphasic solution was stirred vigorously while warming to room temperature. The organic phase was separated, dried over magnesium sulfate, filtered and concentrated to leave a light yellow residue. Purification by flash chromatography (silica gel, 0–30% ethyl acetate in hexane) gave 28 mg of the desired product. IR (film) 1797 cm$^{-1}$; MS 753.1 (M+H)$^+$.

b)

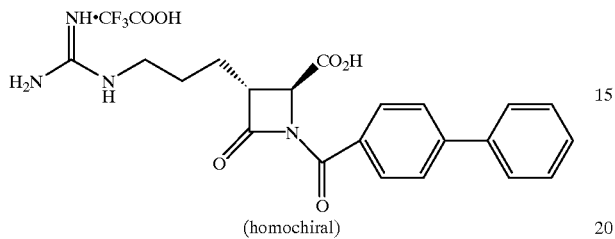

(homochiral)

The product from part (a) (28 mg, 0.037 mmol) was deprotected and worked-up according to the procedure of Example 19(c) to give 11.8 mg of the desired product as a lyophilate. IR (film) 1788 cm$^{-1}$; MS 395.1 (M+H)$^+$, 393.3 (M−H)$^−$.

EXAMPLE 39

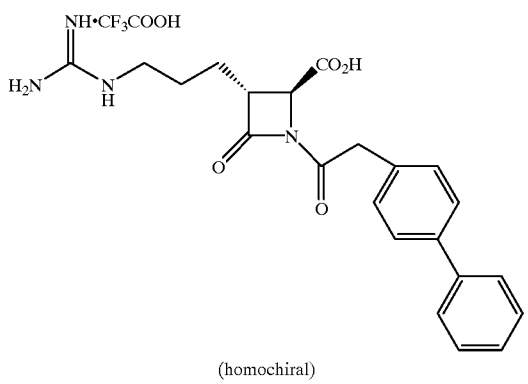

(homochiral)

a) Biphenylacetyl chloride

Oxalyl chloride (246 μl, 2.86 mmol) and one drop of dimethylformamide were added dropwise to a suspension of biphenylacetic acid (30 mg, 1.41 mmol) in methylene chloride (10 ml). The mixture was stirred at room temperature for 20 minutes. The solvent was evaporated and the residue was coevaporated with toluene twice to give 310 mg of the title product as a yellow solid.

b)

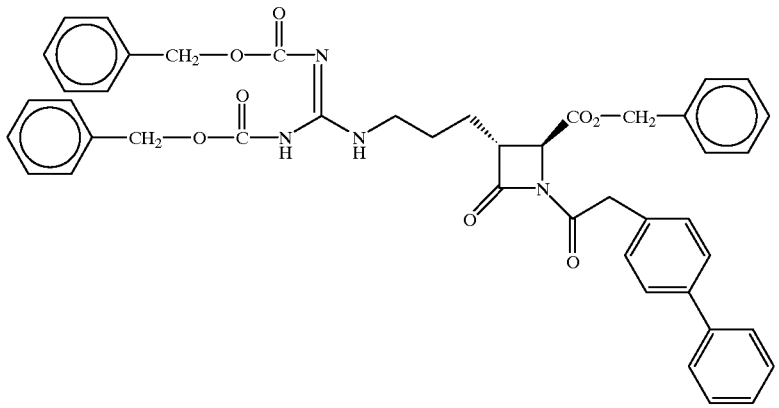

Sodium bis(trimethylsilyl)amide (1.0 M in tetrahydrofuran, 315 μl, 0.31 mmol) was added dropwise to a −78° C. solution of the benzyl ester product of Example 1(c) (120 mg, 0.21 mmol) in tetrahydrofuran (3 ml). The mixture was stirred at −78° C. for 2.5 hours. A solution of biphenylacetyl chloride (58 mg, 0.25 mmol) in tetrahydrofuran (1 ml) was added. The reaction mixture was stirred at −78° C. for an additional 2.5 hours and was stored in afreezer (−50° C.) overnight. The reaction mixture was partitioned between ethyl acetate (50 ml) and water (15 ml). The organic layer was separated and washed with brine (20 ml), dried (magnesium sulfate), filtered and concentrated to give the crude product which was purified by flash chromatography (silica, 20–30% ethyl acetate/hexane) to give 22 mg of the desired product as a yellow solid. MS (M+H)$^+$ 767.1; IR (KBr) 1796 cm$^{-1}$, 1730 cm$^{-1}$, 1640 cm$^{-1}$.

c)

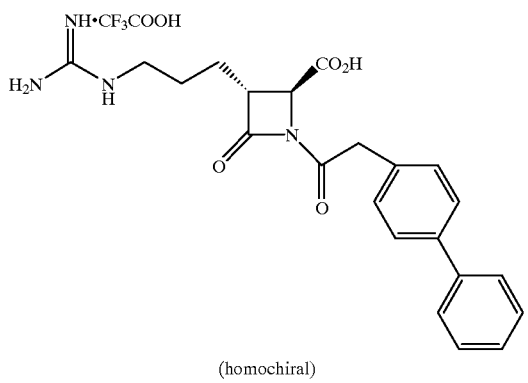

(homochiral)

The product from part (b) (40 mg, 0.052 mmol) was deprotected and worked-up according to the procedure of Example 19(c) to give 11 mg of the desired product as a white fluffy powder; MS:(M+H)$^+$ 409.2,(M−H)$^−$ 407.2; IR (KBr) 1782 cm$^{-1}$, 1684 cm$^{-1}$, 1645 cm$^{-1}$.

b)

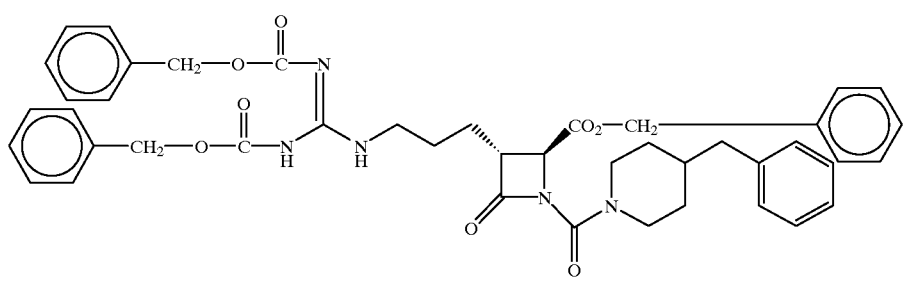

EXAMPLE 40

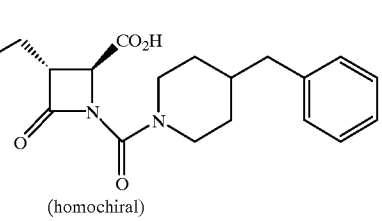

(homochiral)

a) 4-Benzylpiperidinylcarbonyl chloride

4-Benzylpiperidine (0.5 g, 2.86 mmol) was added to a mixture of phosgene (3.8 ml of 20% phosgene in toluene solution, 7.13 mmol). The mixture was stirred at 0° C. for 1 hour. The reaction mixture was partitioned between water (25 ml) and ethyl acetate (2×25 ml). The organic phase was washed with 1N HCl (1×40 ml), saturated sodium chloride (1×50 ml), dried over sodium sulfate and concentrated to give a yellow oil. Purification by flash column chromatography (silica gel, 0–10% ethyl acetate/hexane) gave 0.47 g of title product. IR (film) 1733.1 cm$^{-1}$.

Triethylamine (17 mg, 0.165 mmol) and 4-dimethylaminopyridine (6–8 crystals) were added to a cooled solution of the benzyl ester product from Example 1(c) (63 mg, 0.11 mmol) in methylene chloride (2 ml) at 0° C. 4-Benzylpiperidinylcarbonyl chloride (39 mg, 0.165 mmol) was added and the mixture was stirred at 0° C. for 45 minutes followed by stirring at room temperature for 2.5 hours. The mixture was then evaporated in vacuo. Purification of the residue by flash chromatography (silica gel, 0–30% ethyl acetate/hexane) gave 68 mg of the desired product as a colorless oil. MS 774.2 (M+H)$^+$, 772.4 (M−H)$^−$; IR (film) 1785.1, 1732.0, 1674.2, 1639.3 cm$^{-1}$.

c)

(homochiral)

The product from part (b) (65 mg, 0.084 mmol) was deprotected and worked-up as described in Example 21(d) to give 39 mg of the desired product as a white lyophilate. MS 416.2 (M+H)$^+$, 414 (M−H)$^−$; IR(KBr) 1784, 1657 cm$^{-1}$.

EXAMPLE 41

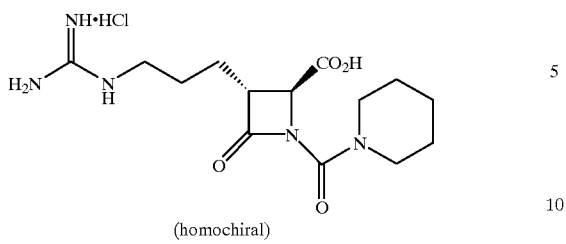
(homochiral)

a) N-Piperidinylcarbonyl chloride

Piperidine (0.3 g, 3.52 mmol) was added to a mixture of phosgene (4.7 ml of 20% phosgene in toluene solution, 8.81 mmol) in methylene chloride (5 ml) at 0° C. The mixture was stirred at 0° C. for 1 hour. The reaction mixture was evaporated in vacuo. The residue was suspended in ether, filtered and the eluents were condensed to obtain a yellow oil. Purification by flash column chromatography (silica gel, 0–20% ethyl acetate/hexane) gave 0.162 g of the title product. IR (film) 1738.9 cm$^{-1}$.

b)

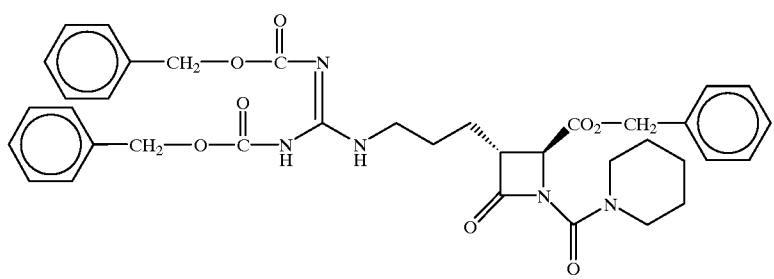

Triethylamine (32 mg, 0.314 mmol) and 4-dimethylaminopyridine (10–15 crystals) were added to a cooled solution of the benzyl ester product from Example 1(c) (120 mg, 0.21 mmol) in methylene chloride (1 ml) at 0° C. N-Piperidinylcarbonyl chloride (46 mg 0.314 mmol) was added and the mixture was stirred at room temperature for 16 hours. The mixture was then evaporated in vacuo. Purification of the residue by flash column chromatography (silica gel, 0–20% ethyl acetate/hexane) gave 95 mg of the desired product as a colorless gum. MS 684.3 (M+H)$^+$, 682.5 (M–H)$^-$; IR (film) 1783.9, 1731.0 cm$^{-1}$.

c)

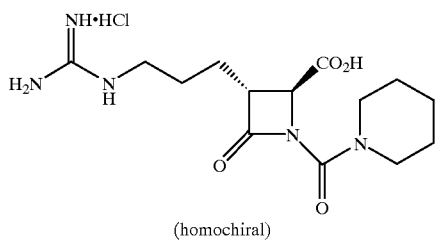
(homochiral)

The product from part (b) (65 mg, 0.089 mmol) was deprotected and worked-up as described in Example 21(d) to give 11 mg of the desired product as a colorless glass. MS 326.3 (M+H+), 324.3, (M–H)$^-$.

EXAMPLE 42

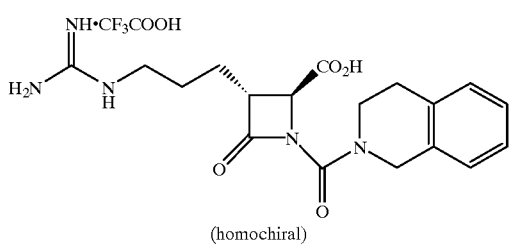
(homochiral)

a) 1,2,3,4-Tetrahydroisoquinolinylcarbonyl chloride 1,2,3,4-Tetrahydroisoquinoline (0.5 g, 3.76 mmol) was added to a cooled mixture of phosgene (5 ml of 20% phosgene in toluene solution, 9.4 mmol) in methylene chloride (5 ml) at 0° C. The mixture was stirred at 0° C. for 1 hour. The reaction mixture was evaporated in vacuo. The residue was suspended in ethyl ether, filtered and the eluents were condensed to give a pale pink oil. Purification by flash column chromatography (silica gel, 0–10% ethyl acetate/ hexane) gave 0.586 g of the desired product. IR (film) 1735.3 cm$^{-1}$.

b)

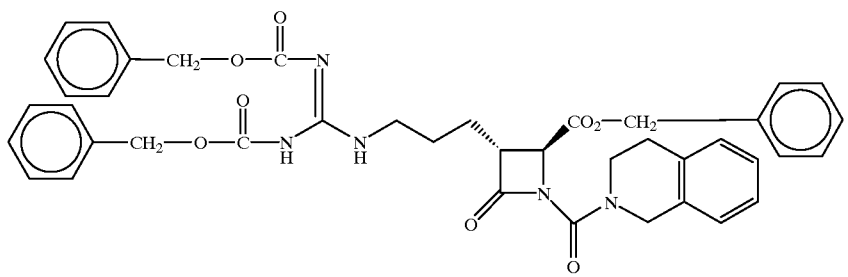

Triethylamine (20 mg, 0.2 mmol) and 4-dimethylaminopyridine (8–10 crystals) were added to a cooled solution of the benzyl ester product from Example 1(c) (77 mg, 0.135 mmol) in methylene chloride (2 ml) at 0°

C. 1,2,3,4-Tetrahydroisoquinolinylcarbonyl chloride (39 mg, 0.2 mmol) was added and the mixture was stirred at room temperature for 2.5 hours. The mixture was then evaporated in vacuo. Purification of the residue by flash column chromatography (silica gel, 0–30% ethyl acetate/hexane) have 66 mg of the desired product as a colorless oil. MS 732.3 (M+H+), 730.7, (M–H)$^-$; IR (film) 1790.2, 1732.0, 1673.8, 1638.9 cm$^{-1}$.

c)

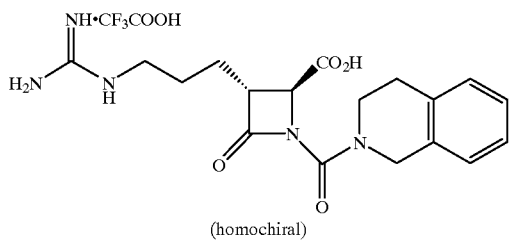

(homochiral)

The product from part(b) (65 mg, 0.089 mmol) was deprotected and worked-up as described in Example 19(c) to give 33 mg of the desired product as a white foam. MS 374.2 (M+H)$^+$, 372.4 (M–H)$^-$; (film) 1788.0, 1668.0 cm$^{-1}$.

EXAMPLE 43

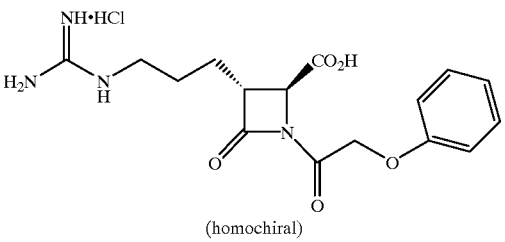

(homochiral)

a)

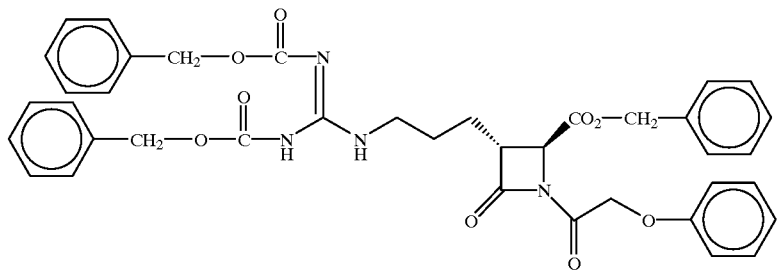

Sodium bis(trimethylsilyl)amide (1.0 M in tetrahydrofuran, 180 μl, 0.18 mmol) was added dropwise to a –78° C. solution of the benzyl ester product from Example 1(c) (92 mg, 0.16 mmol) in tetrahydrofuran (2 ml). The mixture was stirred at –78° C. for 1 hour. Phenoxyacetyl chloride (24 μl) was added. The reaction mixture was stirred at –78° C. for an additional 20 minutes and was stored in a freezer (–50° C.) overnight. Analytical HPLC indicated that the reaction was not completed. Another 24 μl of phenoxyacetyl chloride was added and the mixture was stirred at –78° C. for an additional 3.5 hours. The reaction mixture was quenched by the addition of water (10 ml). This was extracted with ethyl aceate (3×20 ml). The organic layers were combined and washed with brine (2×10 ml), dried (magnesium sulfate), filtered and concentrated to give the crude product which was purified by flash chromatography (silica, 30% ethyl acetate/hexane) to give 65 mg of the desired product as a colorless oil. MS (M+H)$^+$ 707.1, (M–H)$^-$ 705.4; IR (KBr) 1798 cm$^{-1}$, 1640 cm$^{-1}$.

b)

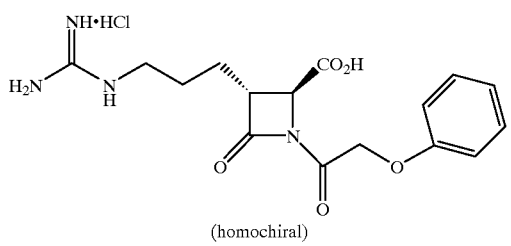

(homochiral)

The product from part (a) (63 mg, 0.089 mmol) was deprotected and worked-up as described in Example 21(d) to give 31 mg of the desired product as a white powder: MS: $(M+H)^+$ 349.0, $(M-H)^-$ 347.2; IR (KBr) 1800 $cm^{-1}$, 1723 $cm^{-1}$, 1649 $cm^{-1}$.

EXAMPLE 44

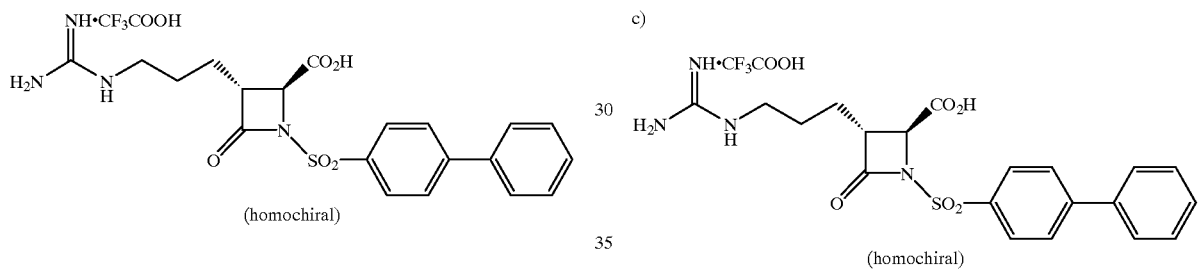

(homochiral)

(homochiral)

a) 4-Biphenylsulfonyl chloride

Sulfuryl chloride (392 µl, 4.74 mmol) was added dropwise to a 0° C. suspension of triphenylphosphine-resin (1.58 g) in methylene chloride (10 ml). A solution of 4-biphenylsulfonic acid (400 mg, 1.58 mmol) and triethylamine (220 µl) in methylene chloride (5 ml) was added. The mixture was stirred at room temperature for 6 hours and stored at 5° C. for 3 days. This was filtered and the filtrate was evaporated. The residue was coevaporated with toluene twice to give the crude product as a white solid. Purification of the crude product by chromatography (silica, methylene chloride) gave 180 mg of the title product as a white solid.

Sodium bis(trimethylsilyl)amide (1.0 M in tetrahydrofuran, 255 µl, 0.26 mmol) was added dropwise to a −78° C. solution of the benzyl ester product from Example 1(c) (95 mg, 0.17 mmol) in tetrahydrofuran (3 ml). The mixture was stirred at −78° C. for 40 minutes. A solution of 4-biphenylsulfonyl chloride (64 mg, 0.26 mmol) in tetrahydrofuran (1 ml) was added. The reaction was stirred at −78° C. for an additional 20 minutes and was stored in a freezer (−50° C.) overnight. Analytical HPLC indicated the reaction was completed. The reaction was quenched with the addition of 1N potassium bisulfate (20 ml). The mixture was extracted with ethyl acetate (2×50 ml). The organic layers were combined and washed with brine (20 ml), dried (magnesium sulfate), filtered and concentrated to give the crude product (158 mg) as a yellow oil. Purification of the crude product by flash chromatography (silica, 30% ethyl acetate/hexane) gave 76 mg of the desired product as a colorless oil. MS $(M+H)^+$ 789.0.

The product from part (b) (70 mg, 0.088 mmol) was deprotected and worked-up according to the procedure of Example 19(c) to give 17 mg of the desired product as a white fluffy powder. MS $(M+MeOH+H)^+$ 463.2, $M+MeOH-H)^-$ 461.5; IR (KBr) 1773 $cm^{-1}$, 1665 $cm^{-1}$, 1595 $cm^{-1}$.

b)

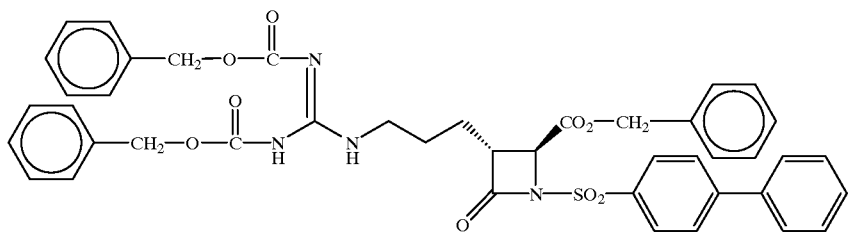

EXAMPLE 45 trans-3-[3-[(Aminoiminomethyl)amino]propyl]-2-oxo-4-(2-phenylethyl)-N-(phenylmethyl)-1-azetinecarboxamide, monohydrochloride

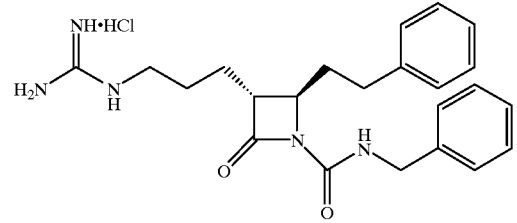

a)          (racemate)

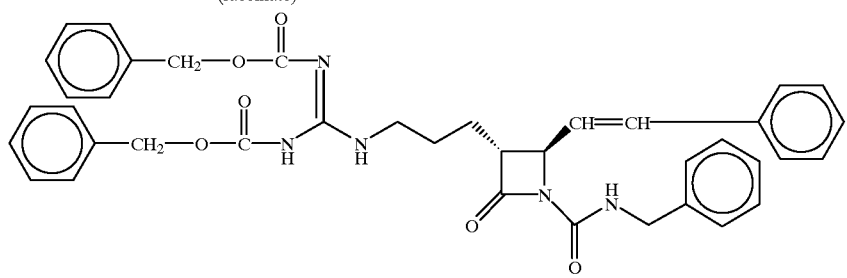

A solution of trans-4-(2-phenylethenyl)-3-[3-[N',N''-bis(carbobenzyloxy)guanidino]propyl]-2-azetidinone (130 mg, 0.2 mmol, prepared as described in Example 3 of Han U.S. Pat. No. 5,037,819) in tetrahydrofuran (1.5) was cooled to −78° C. under an argon atmosphere. A 1 M solution of sodium bis(trimethylsilyl)amide (0.21 ml) in tetrahydrofuran was added and the mixture stirred for 15 minutes. Benzylisocyanate (40 mg, 0.3 mmol) was added dropwise and the mixture was allowed to warm to room temperature and stirred for 1 hour. The reaction was diluted with aqueous 10% potassium hydrogen sulfate solution (10 ml) and extracted with ethyl acetate (3×10 ml); the combined organic phase was washed with water (25 ml), brine (25 ml) and dried over sodium sulfate. The solution was filtered and the solvent evaporated to give an oil. The residue was purified by flash column chromatography (silica, ethyl acetate:hexane, 2:3) yielding 69 mg of the desired product as a colorless oil. MS (M+H)$^+$ 674.

b) trans-3-[3-(Aminoiminomethyl)amino]propyl]-2-oxo-4-(2-phenylethyl)-N-(phenylmethyl)-1-azetinecarboxamide, monohydrochloride A solution of the product from part (a) (67 mg, 0.1 mmol) in dioxane (1.5 ml) containing aqueous 1N HCl (0.15 ml) and 10% palladium on carbon catalyst was stirred under a hydrogen atmosphere for 2 hours. The reaction was filtered and lyophilized to give 66 mg of the titled product as a colorless solid; m.p. 145–154° C.(dec). MS (M+H)$^+$ 408; IR (KBr) 1761 cm$^{-1}$.

EXAMPLE 46 trans-3-[3-[(Aminoiminomethyl)amino]propyl]-N-methyl-2-oxo-4-(2-phenylethyl)-1-azetinecarboxamide, monohydrochloride

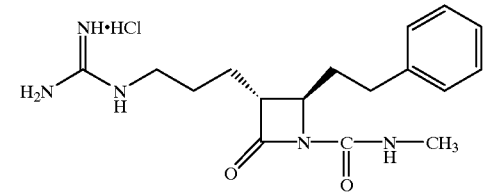

(racemate)

a)

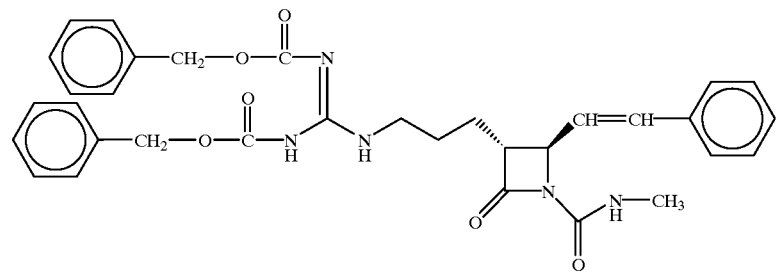

Following the procedure of Example 45(a) but substituting methylisocyanate (23 mg, 0.5 mmol) for the benzylisocyanate, the desired product (80 mg) was obtained as a colorless oil. MS (M+H)+ 598.

b) trans-3-[3-[(Aminoiminomethyl)amino]propyl]-N-methyl-2-oxo-4-(2-phenylethyl)-1-azetinecarboxamide, monohydrochloride b) The product from part (a) (77 mg, 0.13 mmol) was deprotected and worked-up as described in Example 45 (b) to give 42 mg of the titled 10 product as a colorless solid; m.p. 138–146° (dec). MS (M+H)+ 332; IR(KBr) 1761 cm$^{-1}$.

EXAMPLE 47

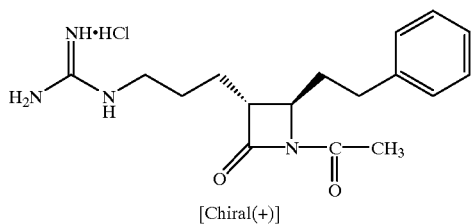

[Chiral(+)]

a)

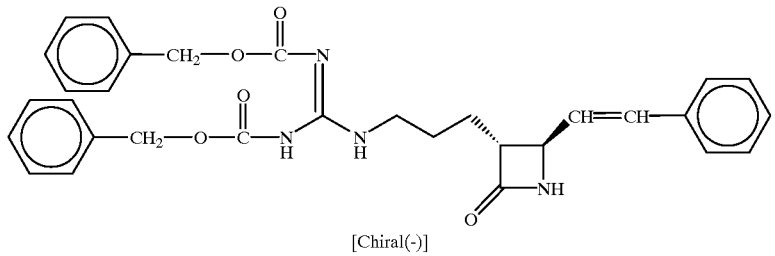

[Chiral(-)]

b) trans-4-(2-Phenylethenyl)-3-[3-[N,N"-bis(carbobenzyloxy)guanidino]propyl]-2-azetidinone was separated into enantiomerically pure (-) isomer and (+) isomer on a Chiralpak-AD® prep-column eluting with 30% 2-propanol/hexane.

b)

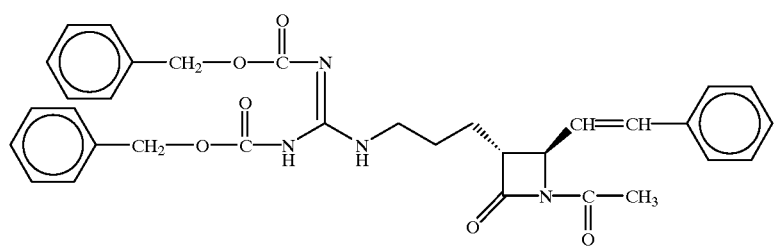

A solution of chiral(-)-trans-4-(2-phenylethenyl)-3-[3-[N',N"-bis(carbobenzyloxy)guanidino]propyl]-2-azetidinone (216 mg, 0.40 mmol) in tetrahydrofuran (2.0 ml) was cooled to −78° C. under an argon atmosphere. A 1M solution of sodium bis(trimethylsilyl)amide (0.44 ml) in tetrahydrofuran was added and the mixture was stirred for 15 minutes. Acetyl chloride (32.2 mg, 0.41 mmol) was added dropwise and the mixture was warmed to room temperature and stirred for 1 hour. The reaction was diluted with aqueous 10% potassium hydrogen sulfate solution (10 ml) and extracted with ethyl acetate (3×10 ml); the combined organic phase was washed with water (25 ml), brine (25 ml) and dried over sodium sulfate. The solution was filtered and the solvent evaporated to give an oil. The residue was purified by flash chromatography (silica, ethyl acetate:hexane, 1:3) to give 150 mg of the desired product as a colorless oil. MS (M+H)+ 583.

c)

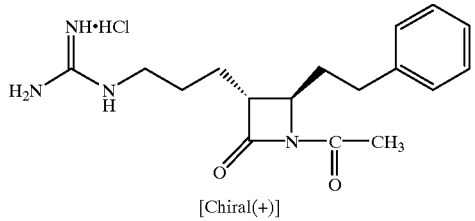

[Chiral(+)]

A solution of the product from part (b) (140 mg, 0.258 mmol) in dioxane (3.5 ml) containing 1N HCl (0.3 ml) and 10% palladium on carbon catalyst (60 mg) was stirred under a hydrogen atmosphere for 1 hour. The reaction was filtered and lyophilized to give 64 mg of the desired product as a colorless solid. MS (M+H)+ 317; IR(KBr) 1782 cm$^{-1}$; [α]$_D$=+18° (c=1, methanol).

EXAMPLE 48

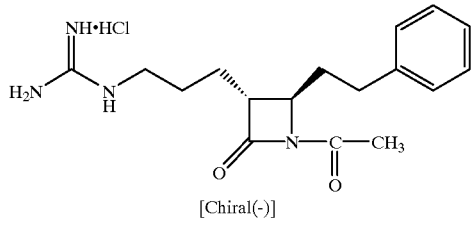

[Chiral(-)]

Following the procedure of Example 47(b) and (c) but employing chiral(+)-trans-4-(2-phenylethenyl)-3-[3-[N',N"-bis(carbobenzyloxy)-guanidino]propyl]-2-azetidinone, the desired product was obtained.

EXAMPLE 49

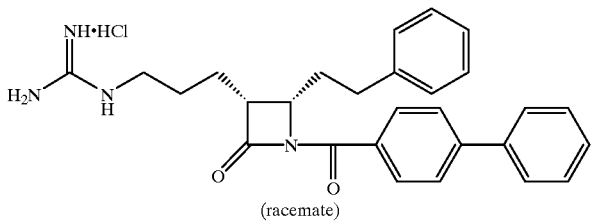

(racemate)

a)

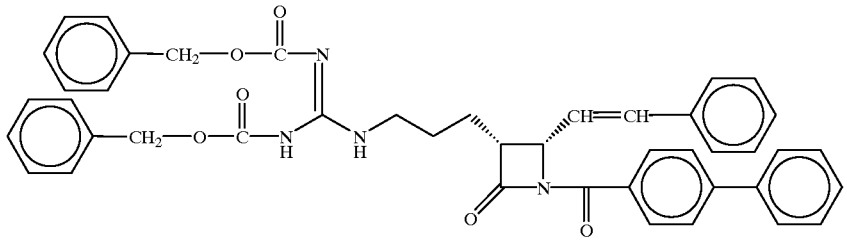

A solution of cis-4-(2-phenylethenyl)-3-[3-[N',N"-bis(carbobenzyloxy)guanidino]propyl]-2-azetidinone (300 mg, 0.555 mmol, prepared as described in Example 3 of Han U.S. Pat. No. 5,037,819) in tetrahydrofuran (2.5 ml) was cooled to −78° C. under an argon atmosphere. A 1 M solution of sodium bis(trimethylsilyl)amide in tetrahydrofuran (0.8 ml) was added and the mixture stirred for 15 minutes. 4-Biphenylcarbonyl chloride (180 mg, 0.832 mmol) was added dropwise and the mixture was allowed to warm to room temperature and stirred for 4 hours. The reaction was diluted with aqueous 10% potassium hydrogen sulfate solution (15 ml) and extracted with ethyl acetate (3×15 ml); the combined organic phase was washed with water (25 ml), brine (25 ml) and dried over sodium sulfate. The solution was filtered and the solvent evaporated to give an oil. The residue was purified by flash column chromatography (silica, ethyl acetate:hexane, 1:4) yielding 320 mg of the desired product as a colorless solid. MS (M+H)+=721.

b)

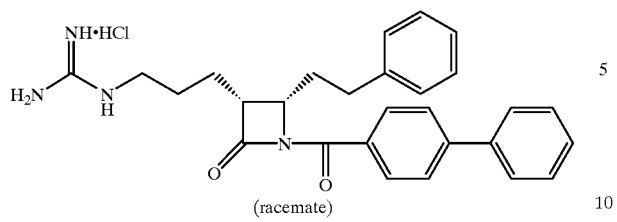
(racemate)

A solution of the product from part (a) (300 mg, 0.48 mmol) in dioxane (3 ml) containing aqueous 1N HCl (0.65 ml) and 10% palladium on carbon catalyst (150 mg) was stirred under a hydrogen atmosphere for 2 hours. The reaction was filtered and lyophilized to give 178 mg of the desired product as a colorless solid. MS $(M+H)^+$ 455; IR (KBr) 1782 cm$^{-1}$.

EXAMPLE 50

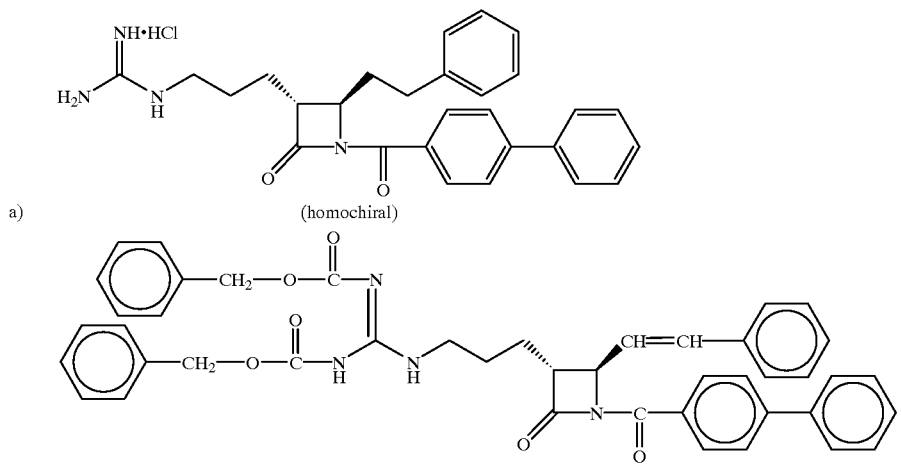
a)  (homochiral)

b)

A solution of chiral-(+)-trans-4-(2-phenylethenyl)-3-[3-[N',N"-bis(carbobenzyloxy)guanidino]propyl]-2-azetidinone (264 mg, 0.49 mmol) in tetrahydrofuran (2.5 ml) was cooled to −78° C. under an argon atmosphere. A 1M solution of sodium bis(trimethylsilyl)amide (0.74 ml) in tetrahydrofuran was added and the mixture stirred for 15 minutes. 4-Biphenylcarbonyl chloride (163 mg, 0.75 mmol) was added dropwise and the mixture was allowed to warm to room temperature and stirred for 4 hours. The reaction was diluted with aqueous 10% potassium hydrogen sulfate solution (15 ml) and extracted with ethyl acetate (3×15 ml); the combined organic phase was washed with water (25 ml), brine (25 ml) and dried over sodium sulfate. The solution was filtered and the solvent evaporated to give an oil. The residue was purified by flash column chromatography yielding 290 mg of the desired product as a colorless solid. MS $(M+H)^+$ 721.

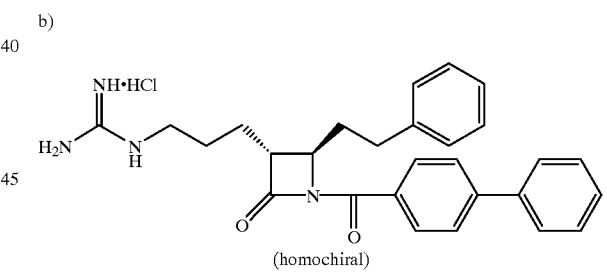
(homochiral)

The product from part (a) (280 mg, 0.4 mmol) was deprotected and worked up as described in Example 49(b) to give 172 mg of the desired product as a colorless solid. MS $(M+H)^+$ 455; IR(KBr) 1782 cm$^{-1}$; $[\alpha]_{22}$=+12° (c=1, methanol).

EXAMPLE 51

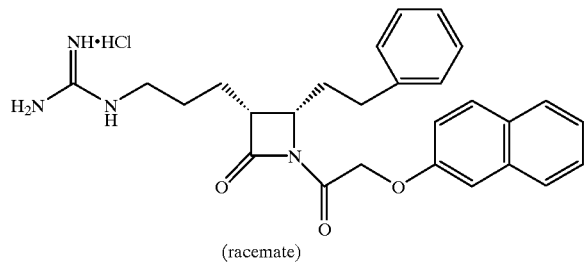
(racemate)

a)
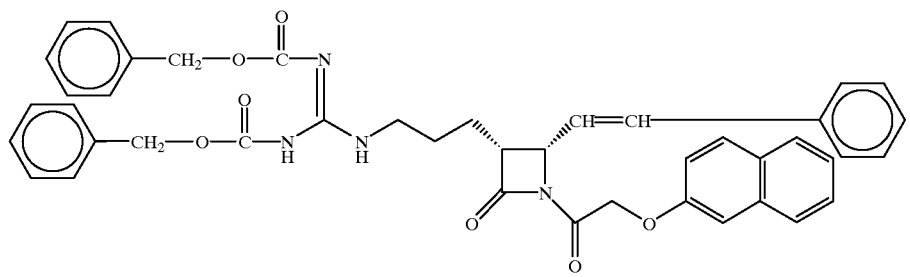

Following the procedure of Example 49(a) but substituting (2-naphthyloxy)acetyl chloride for the 4-biphenylcarbonyl chloride, the desired product (134 mg) was obtained as a colorless solid. MS (M+H)+ 725.

b)
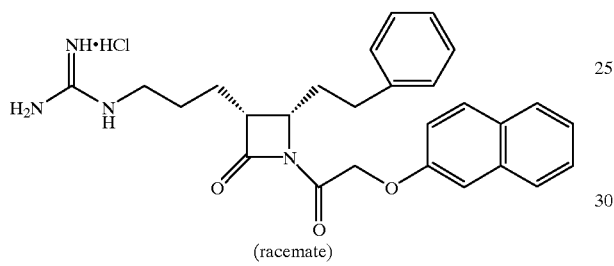
(racemate)

The product from part (a) (125 mg, 0.17 mmol) was deprotected and worked-up as described in Example 49(b) to give 76 mg of the desired product as a colorless solid. MS (M+H)+=459; IR(KBr) 1780 cm⁻¹.

EXAMPLE 52

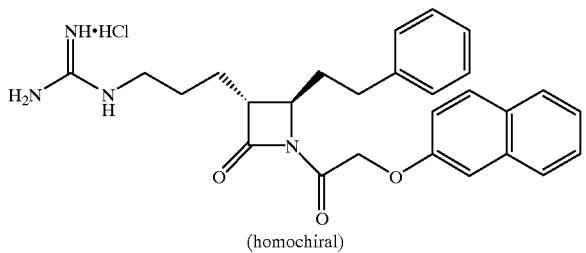
(homochiral)

a)
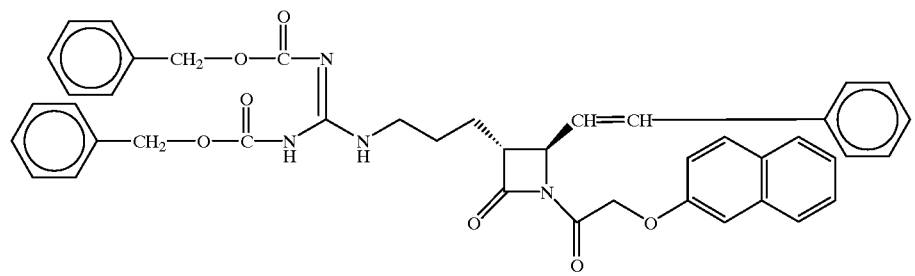

Following the procedure of Example 50(a) but substituting (2-naphthyloxy)acetyl chloride for the 4-biphenylcarbonyl chloride, the desired product (216 mg) was obtained as a colorless solid. MS (M+H)+ 725.

b)

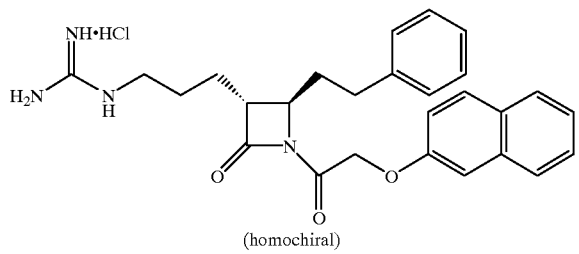

(homochiral)

The product from part (a) (200 mg, 0.276 mmol) was deprotected and worked-up as described in Example 49(b) to give 108 mg of the desired product as a colorless solid. MS (M+H)$^+$ 459; IR (KBr) 1780 cm$^{-1}$; $[\alpha]_{22}=+18°$ (c=1, methanol).

EXAMPLE 53

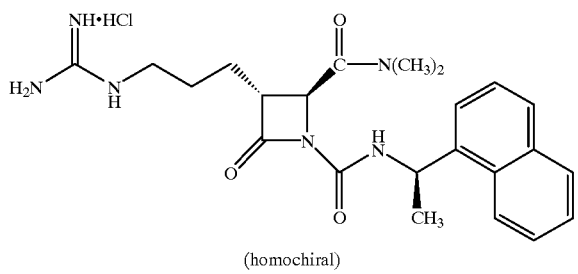

(homochiral)

-continued a)

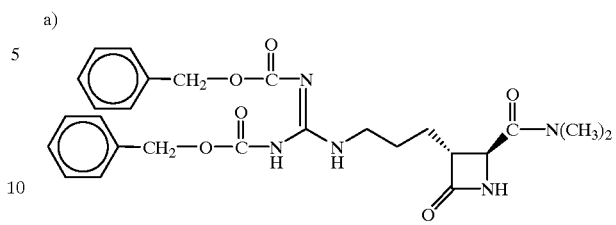

A solution of the carboxylic acid product from Example 1(b) (140 mg, 0.288 mmol) in tetrahydrofuran (2.5 ml) was cooled to −20° C. under an argon atmosphere and N-methylmorpholine (32.1 mg, 0.317 mmol) was added. A 2 M solution of dimethylamine (1.1 eq) in tetrahydrofuran was added followed by the addition of benzotriazol-1-yloxytris-(dimethylamino)phosphonium hexafluorophosphate (140 mg, 0.317 mmol). The reaction was stirred at −20° C. for 24 hours, poured into 5% potassium hydrogen sulfate solution and extracted with ethyl acetate. The ethyl acetate extract was washed with water, brine and dried over sodium sulfate. The solvents were evaporated and the crude residue was purified by silica chromatography eluting with ethyl acetate yielding 56 mg of the desired product as a colorless solid. MS (M+H)$^+$ 510.

b)

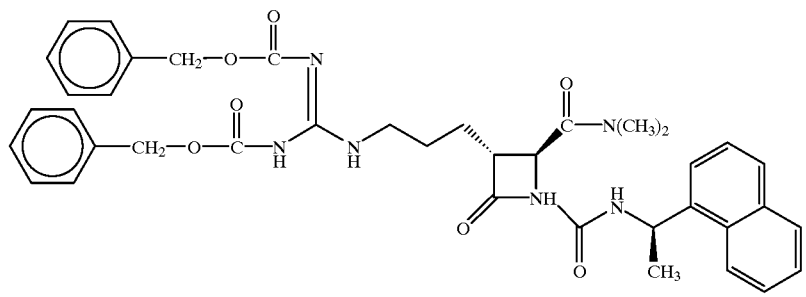

A solution of the product from part (a) (48 mg, 0.094 mmol) in tetrahydrofuran (0.4 ml) was cooled to −78° C. under an argon atmosphere. Sodium bis(trimethylsilyl) amide (1 M, 1.5 eq.) was added and the mixture was stirred for 30 minutes. (R)-(−)-1-(1-Naphthenyl)-ethyl isocyanate (27.2 mg, 0.141 mmol) was added. The mixture was stirred at −78° C. for 30 minutes and then allowed to warm to room temperature and stir for 4 hours. The reaction was poured into 5% potassium hydrogen sulfate solution and extracted with ethyl acetate. The ethyl acetate extract was washed with water, brine and dried over sodium sulfate. The solvents were evaporated and the crude residue purified on silica by chromatography eluting with ethyl acetate:hexane (3:2) yielding 25 mg of the desired product as a colorless glass-like residue. MS (M+H)$^+$ 707.

c)

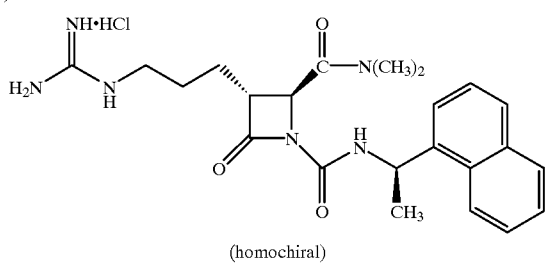

(homochiral)

A solution of the product from part (b) (24 mg, 0.03 mmol) in dioxane (1 ml) containing HCl (1.5 eq.) was stirred under a hydrogen atmosphere with 10% palladium on carbon catalyst (12 mg) for 2 hours. The reaction was filtered and the solvents lyophilized to yield 14 mg of the desired product as a colorless solid; MS (M+H)$^+$ 439; [α]$_D$=+12° (c=1, methanol).

EXAMPLE 54

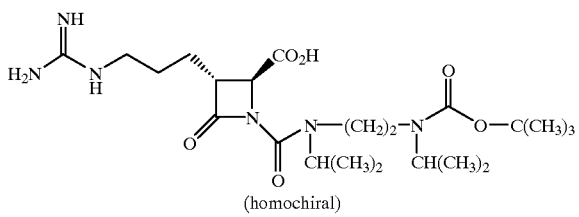

(homochiral)

a)

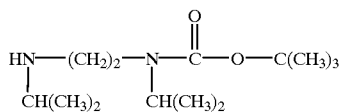

A mixture of di-tert-butyl dicarbonate (1.51 g, 6.9 mmol) and triethylamine (0.7 g, 6.9 mmol) in anhydrous tetrahydrofuran (3 ml) was added over 20 minutes to a solution of N,N'-diisopropylethylenediamine (1.0 g, 6.9 mmol) in anhydrous tetrahydrofuran (2 ml). The mixture was stirred at room temperature for 2 hours. The mixture was then filtered and washed with methylene chloride. The filtrate and washings were condensed to obtain a colorless oil. Purification by flash column chromatography (silica gel, 1–5% 2M ammonia in methanol/methylene chloride) gave 50 mg of the desired product as a colorless oil. MS 245.2 (M+H)$^+$.

b)

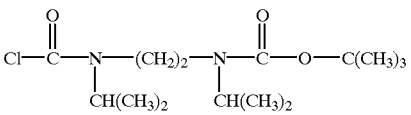

The product from part (a) (44 mg, 0.18 mmol) was added to a mixture of phosgene (0.24 ml of a 20% phosgene in toluene solution, 0.45 mol) in methylene chloride (1 ml) at 0° C. followed by the addition of triethylamine (25 μl, 0.18 mmol). The mixture was stirred at 0° C. for 1 hour. The reaction mixture was evaporated in vacuo. The residue was purified by flash chromatography (silica gel, 0–10% ethyl acetate/hexane) to give about 30 mg of the desired product as a colorless oil. IR(neat) 1732.0, 1694.5 cm$^{-1}$.

c)

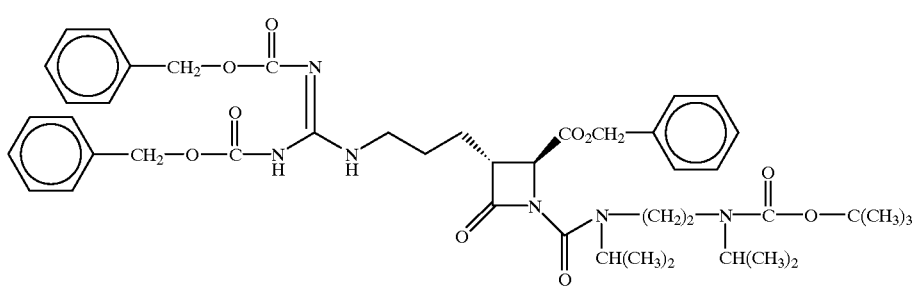

Triethylamine (15 μl, 0.104 mmol) and dimethylaminopyridine (10–12 crystals) were added to a solution of the benzyl ester product from Example 1(c) (40 mg, 0.07 mmol) in methylene chloride (1 ml) followed by the addition of the chloro product from part (b) (25 mg, 0.084 mmol). The mixture was stirred for 48 hours and then evaporated in vacuo and purified by flash chromatography (silica gel, 0–30% ethyl acetate/hexane) to give 21 mg of the desired product as a colorless oil.

MS 843.5 (M+H)$^+$, 841.8 (M−H)$^-$; IR (film) 1785.1, 1733.1, 1681.7, 1640.9 cm$^{-1}$.

d)

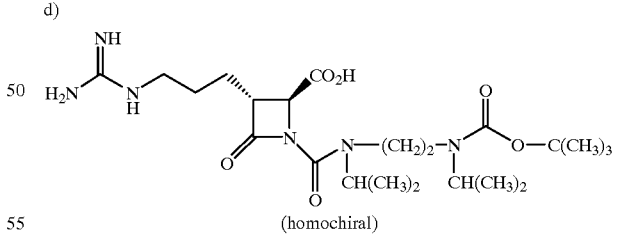

(homochiral)

10% Palladium on carbon catalyst (20 mg, wet type) was added to a solution of the product from part (c) (21 mg, 0.025 mmol) in 1,4-dioxane (5 ml) containing 1N HCl (25 μl, 0.025 mmol). Hydrogen gas was bubbled through the solution for 4 hours. The reaction mixture was filtered through a pad of Celite® which was then repeatedly washed with 1,4-dioxane (10 ml) and water (15 ml). The combined eluents were lyophilized. The white lyophilate was dissolved in water and passed through a plug of polyvinylpyrrolidone eluting with water. The eluents were lyophilized to give 12 mg of the desired product as a white lyophilate. MS 485.3 (M+H)+, 483.5 (M−H)−. IR (KBr) 1778.0, 1665.0 cm−1.

EXAMPLE 55

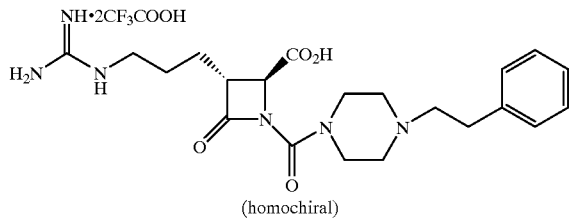

(homochiral)

a)

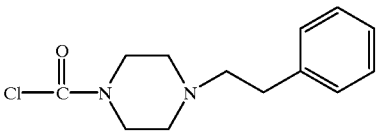

1-Phenethylpiperazine (0.5 g, 2.63 mmol) was added to a mixture of phosgene (3.5 ml of 20% phosgene in toluene solution, 6.6 mmol) in methylene chloride (2 ml) at 0° C., followed by the addition of triethylamine (0.37 ml, 2.63 mmol). The mixture was stirred at 0° C. for 2 hours and then evaporated in vacuo. The residue was suspended in ether, filtered and the eluents were condensed to give a cream solid. Purification by flash chromatography (silica gel, 0–10% ethyl acetate/hexane) gave 32.2 mg of the desired product as a crystalline, white solid. IR (film) 1729.3 cm−1.

b)

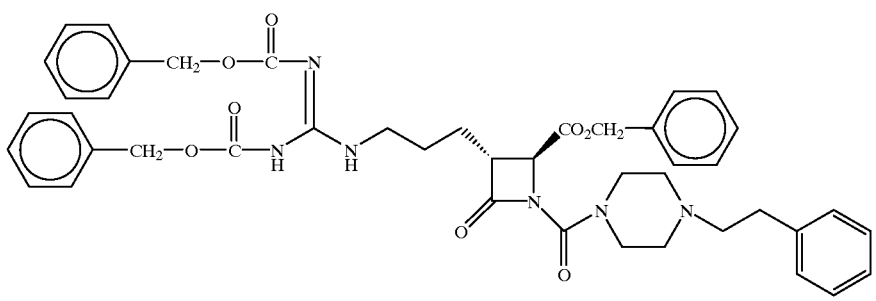

Triethylamine (47 μl, 0.34 mmol) and dimethylaminopyridine (10–12 crystals) were added to a solution of the benzyl ester product from Example 1(c) (129 mg, 0.23 mmol) in methylene chloride (3 ml) followed by the addition of the chloro product from part (a) (86 mg, 0.34 mmol). The mixture was stirred at room temperature for 5 hours and was then evaporated in vacuo giving a pale yellow paste. Purification by flash chromatography (silica gel, 0–35% ethyl acetate/hexane) gave 120 mg of the desired product as a colorless oil. MS 789.4 (M+H)+, 787.7 (M−H)−; IR (film) 1785.5, 1732.1, 1679.1, 1639.4cm−1.

c)

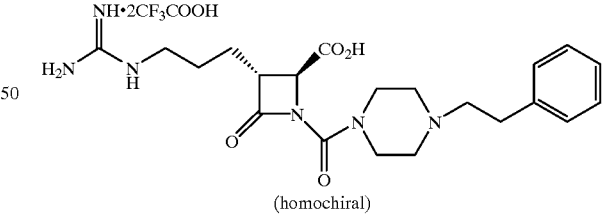

(homochiral)

10% Palladium on carbon catalyst (60 mg, wet added) was added to a solution of the product from part (b) (118 mg, 0.15 mmol) in 1,4-dioxane (8 ml) containing 1N HCl (0.18 ml, 0.18 mmol). Hydrogen gas was bubbled through the solution for 1 to 1.5 hours. The reaction mixture was filtered through a pad of Celite® which was repeatedly washed with 1,4-dioxane (10 ml) and water (15 ml). The combined eluents were lyophilized to obtain 77 mg of a white lyophilate. Purification by HPLC (reverse phase, methanol, water, trifluoroacetic acid) gave 52 mg of the desired product as a white lyophilate. MS 431.2 (M+H)+, 429.3 (M−H)−; IR (KBr) 1790.0, 1678.0 cm−1.

EXAMPLE 56 a)

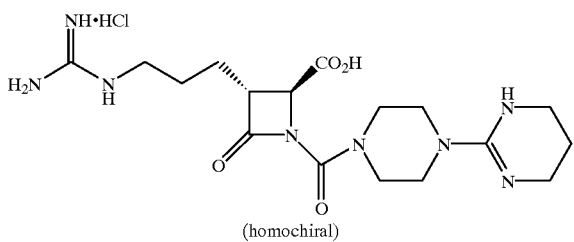
(homochiral)

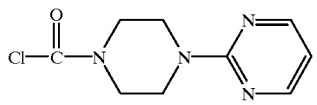

A solution of 1-(2-pyrimidyl)piperazine dihydrochloride (4.0 g, 16.9 mmol) in 1N sodium hydroxide saturated with sodium chloride (40 ml) was extracted with ethyl acetate (2×30 ml). The organic layer was dried over sodium sulfate, filtered and concentrated to give 2.6 g of 1-(2-pyrimidyl) piperazine.

A solution of 1-(2-pyrimidyl)piperazine (2.6 g) in methylene chloride (5 ml) was added dropwise over 3 minutes to a solution of phosgene (25 ml, 20% in toluene, 47.3 mmol) in methylene chloride (15 ml) over solid sodium bicarbonate (3 g) under nitrogen at room temperature. The resulting solution was stirred vigorously for 10 minutes, filtered through a fritted funnel, and the remaining solids were washed with methylene chloride (2×5 ml). The combined eluent was concentrated under vacuum to give a white solid. The solid was then recrystallized from methylene chloride/hexane to give 3g of the desired product as a white solid. IR(film) 1735 cm$^{-1}$.

b)

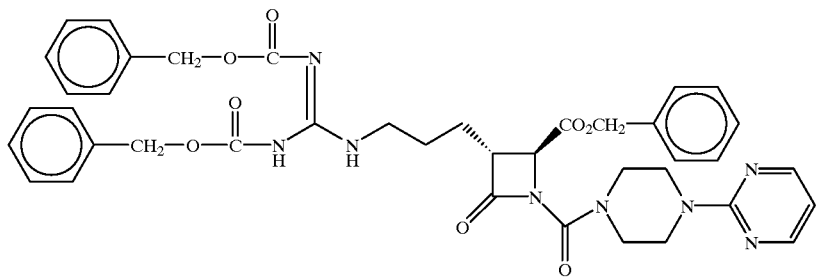

The chloro product from part (a) (1.11 g, 4.8 mmol), triethylamine (700 μl, 5.0 mmol), dimethylaminopyridine (200 mg, 1.64 mmol) were added to a solution of the benzyl ester product from Example 1(c) (1.56 g, 3.23 mmol) in methylene chloride (15 ml) under nitrogen at room temperature. After stirring at room temperature for 7 hours, the reaction mixture was diluted with hexane (5 ml) and was then added to the top of a silica gel column (wetted with methylene chloride) for purification by flash chromatography (0 to 30% ethyl acetate/methylene chloride) to give 1.6 g of the derived product as a white foam. MS 763.2 (M+H)$^+$, 761.7 (M−H)$^-$; IR (KBr) 1788 cm$^{-1}$.

c)

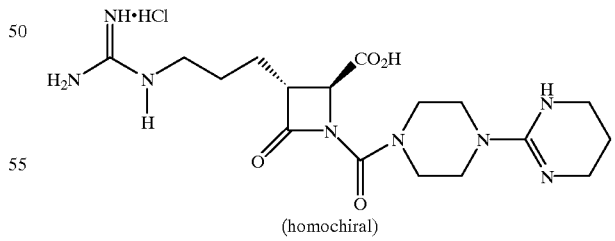
(homochiral)

The product from part (b) (1.6 g, 2.1 mmol) was deprotected and worked-up as described in Example 21(d) to give 854 mg of the desired product as white solid lyophilate. MS 409.2 (M+H)$^+$, 407.5 (M−H)$^-$; IR (KBr) 1777 cm$^{-1}$.

Anal. calc'd for $C_{17}H_{28}N_8O_4 \cdot 1.0$ HCl$\cdot 1.54$ H$_2$O: C, 43.20; H, 6.84; N, 23.71; O, 18.75; Cl, 7.50 Found: C, 43.31; H, 6.59; N, 23.09; O (not calculated); Cl, 7.06.

EXAMPLE 57

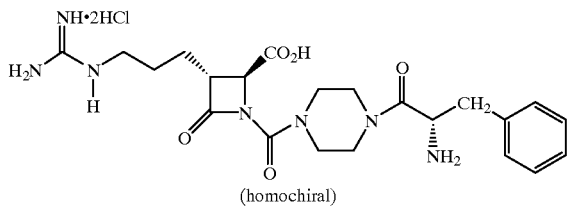
(homochiral)

a)

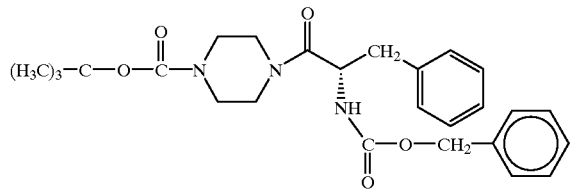

Triethylamine (0.22 ml, 1.6 mmol) and pyridine benzotriazol-1-yloxytris (dimethylamino)phosphonium hexafluorophosphate (0.83 g, 1.6 mmol) were added to a solution of N-carbobenzyloxy-L-phenylalanine (0.5 g, 1.6 mmol) in anhydrous methylene chloride (5 ml) followed by the addition of tert-butyl-1-piperazine carboxylate (0.3 g, 1.6 mmol). The mixture was stirred at room temperature for 2 hours. The mixture was then diluted with methylene chloride (30 ml) and washed with 1N HCl (1×25 ml), saturated sodium bicarbonate (1×25 ml), and saturated sodium chloride (1×25 ml). The organic phase was dried over sodium sulfate and concentrated to obtain a pale yellow oil. Purification by flash chromatography (silica gel, 0–20% ethyl acetate/hexanes) gave 554 mg of the desired product as a white foam. IR(film) 1698.2, 1649.6 cm$^{-1}$.

b)

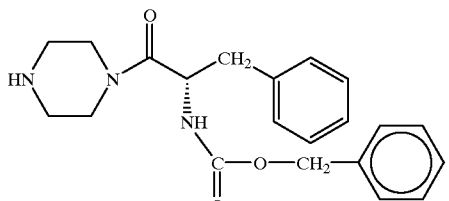

Trifluroacetic acid (3 ml) was added to a solution of the product from part (a) (550 mg, 1.14 mmol) in anhydrous methylene chloride (3 ml) at 0° C. The mixture was warmed to room temperature and stirred for 1.5 hours. The mixture was then condensed to give a colorless oil. The oil was dissolved in water, the pH was adjusted to 12–13 with sodium hydroxide (50% solution) and extracted with ethyl acetate (3×50 ml). The organic phase was dried over sodium sulfate and condensed to give 0.48 g of the desired product as a pale yellow oil. MS 368.2 (M+H)$^+$.

c)

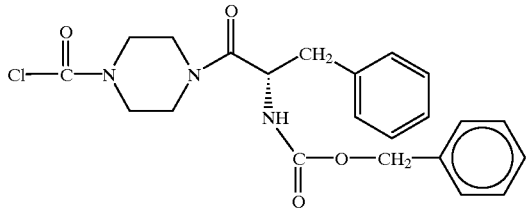

The product from part (b) (0.322 g, 0.84 mmol) in methylene chloride (3 ml) was added to a mixture of phosgene (1.11 ml of a 20% phosgene in toluene solution, 2.1 mmol) in methylene chloride (3 ml) at 0° C., followed by the addition of triethylamine (0.12 ml, 0.84 mmol). The mixture was stirred at 0° C. for 1 hour. The reaction mixture was evaporated in vacuo. The residue was suspended in ether, filtered, and the eluents were concentrated to give a yellow oil. Purification by flash column chromatography (silica gel, 0–20% ethyl acetate/hexane) gave 0.243 g of the desired product as a colorless oil.

d)

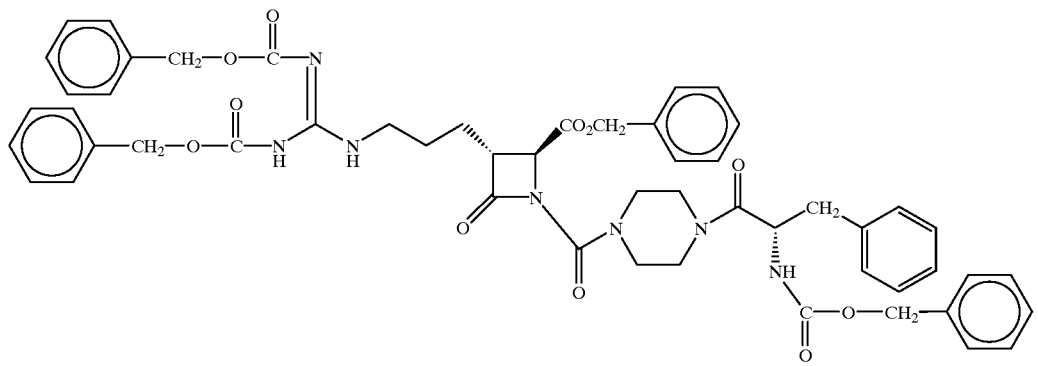

Triethylamine (37 μl, 0.262 mmol) and dimethylaminopyridine (10–12 crystals) were added to a solution of the benzyl ester product from Example 1(c) (100 mg, 0.175- mmol) in methylene chloride (3 ml), followed by the addition of the chloro product from part (c) (120 mg, 0.262 mmol). The mixture was stirred at room temperature for 4 hours and then evaporated in vacuo. Purification of the crude product by flash column chromatography (silica gel, 0–35%, ethyl acetate/hexane) gave 131 mg of the desired product as a colorless oil. MS 966.4 (M+H)$^+$, 964.6 (M−H)$^-$; IR (film) 1788.0, 1738.3, 1677.1, 1637.0 cm$^{-1}$.

e)

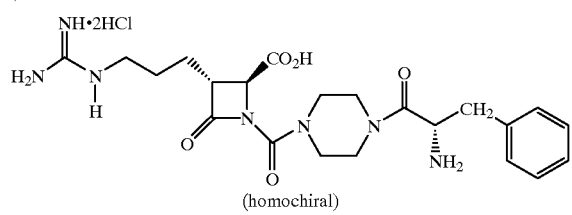

(homochiral)

10% Palladium on carbon catalyst (65 mg, wet type) was added to a solution of the product from part (d) (127 mg, 0.132 mmol) in 1,4-dioxane (8 ml) containing 1N HCl (0.26 ml, 0.264 mmol). Hydrogen gas was bubbled through the solution for 1 to 1.5 hours. The reaction mixture was filtered through a pad of Celite® which was repeatedly washed with 1,4-dioxane (10 ml) and water (15 ml). The combined eluents were lyophilized to give 64 mg of the desired product as a pale yellow lyophilate. MS 474.2 (M+H)$^+$, 472.4 (M−H)$^-$; IR (KBr) 1786.0, 1730.0, 1647.0 cm$^{-1}$.

EXAMPLE 58

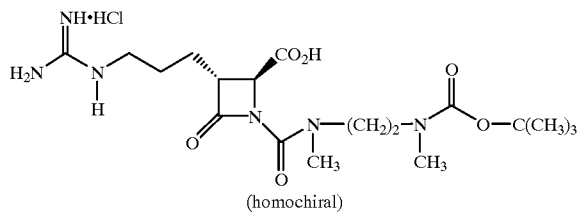

(homochiral)

c)

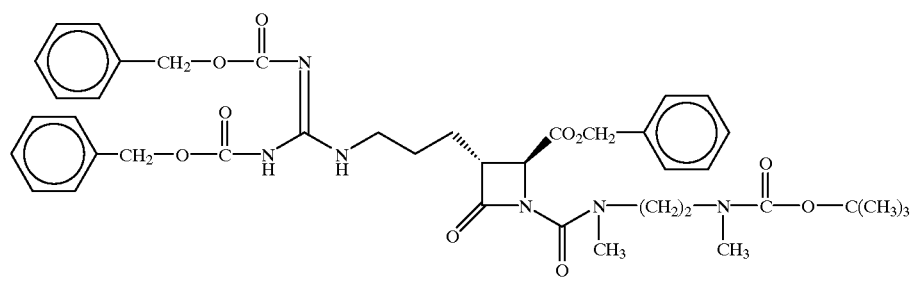

a)

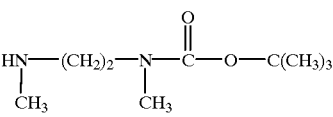

A solution of di-tert-butyl dicarbonate (1.24 g, 5.67 mmol) and triethylamine (790 µl, 5.67 mmol) in tetrahydrofuran (15 ml) was added dropwise to a solution of N, N'-dimethylethylene diamine (500 mg, 5.67 mmol) in tetrahydrofuran (35 ml). The reaction mixture was stirred at room temperature for 4 days. The mixture was then filtered and the filtrate was concentrated to give the crude product as a colorless oil. Purification by flash chromatography (10% 2N ammonia in methanol/methylene chloride) provided 362 mg of the desired product as a colorless oil. IR(film) 1694 cm$^{-1}$.

b)

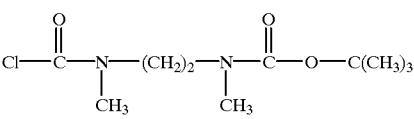

A mixture of the product from part (a) (250 mg) and triethylamine (278 µl) in methylene chloride (3 ml) was added to a solution of phosgene in toluene (1.4 ml, 20%) at 0° C. The resultant mixture was stirred at 0° C. for 5 hours. Anhydrous ether (10 ml) was added and the solid was filtered off. The filtrate was evaporated to give the crude product as an orange oil which was purified by flash chromatography (20–30% ethyl acetate/hexane) to give 313 mg of the desired product as a colorless oil. IR (film) 1740 cm$^{-1}$, 1694 cm$^{-1}$.

Triethylamine (25 µl), dimethylaminopyridine (15 mg) and a solution of the chloro product from part (b) (45 mg, 0.18 mmol) in methylene chloride (1 ml) were added to a solution of the benzyl ester product from Example 1(c) (70 mg) in methylene chloride (2 ml). The mixture was stirred overnight at room temperature. The reaction was quenched with the addition of 1N potassium bisulfate (15 ml). The mixture was extracted with ethyl acetate (2×30 ml). The organic layers were combined and washed with brine (10 ml), dried over magnesium sulfate and concentrated to give 101 mg of the crude product as a yellow oil. Purification using flash chromatography (30–50% ethyl acetate/hexane) gave 77 mg of the desired product as a colorless oil. IR (film) 1786 cm$^{-1}$, 1733 cm$^{-1}$, 1681 cm$^{-1}$, 1639 cm$^{-1}$.

d)

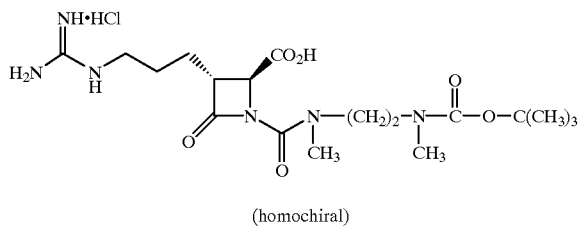

(homochiral)

A mixture of the product from part (c) (74 mg, 0.094 mmol), 1N HCl (94 μl), and palladium on carbon catalyst (10%, 19 mg) in dioxane (2 ml) was stirred under hydrogen atmosphere (hydrogen balloon) at room temperature for 1 hour. The reaction mixture was filtered through a Celite® cake and lyophilized to give 44 mg of the desired product as a white solid. MS 429.2 (M+H)$^+$, 427.5 (M–H)$^-$; IR (KBr) 1784, 1663 cm$^{-1}$.

b)

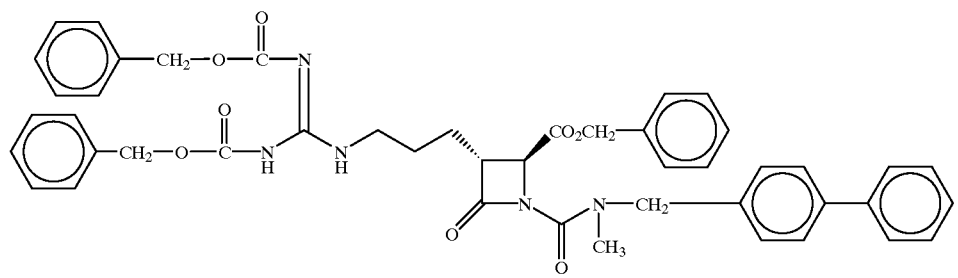

EXAMPLE 59

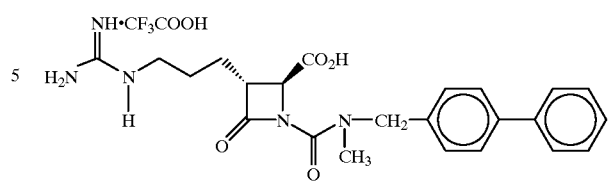

(homochiral)

a)

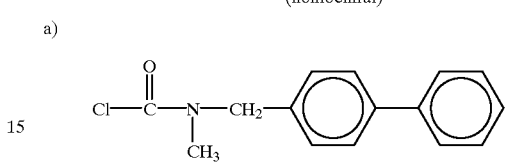

A solution of N-methyl-4-phenylbenzylamine [158 mg, 0.8 mmol, prepared as described by Dahn et al., Helv. Chim. Acta., 35, 1348–1358, (1952)] in toluene (3 ml) was added to a solution of phosgene (3 ml, 20% in toluene, 5.6 mmol) in toluene (3 ml) under nitrogen at room temperature followed by triethylamine (200 μl, 1.43 mmol). After stirring the reaction mixture at room temperature for 30 minutes, the solvents were removed under vacuum and the residue was purified by flash chromatography (silica gel, 100% methylene chloride) to give 136 mg of the desired product as an oily residue. IR(film) 1745 cm$^{-1}$.

The chloro product from part (a) (100 mg, 0.38 mmol), triethylamine (53 μl, 0.38 mmol) and dimethylaminopyridine (10 mg, 0.08 mmol) were added to a solution of the benzyl ester product of Example 1(c) (145 mg, 0.25 mmol) in methylene chloride (3 ml) under nitrogen at room temperature. After stirring the reaction for 6 hours at room temperature, the reaction was diluted with hexane (1 ml) and added to the top of a silica gel column (wetted with hexane) for purification by flash chromatography (0 to 20% ethyl acetate in hexane) to give 148 mg of the desired product as a light brown wax. MS 796.5 (M+H)$^+$, 794.7 (M–H)$^-$; IR (film) 1786 cm$^{-1}$.

c)

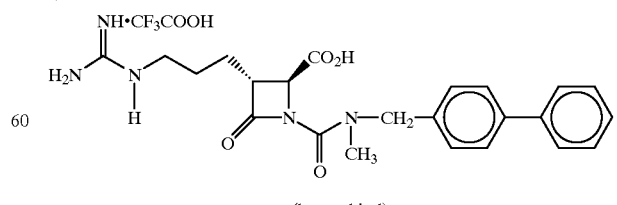

(homochiral)

Deprotection and purification of the product from part (b) (148 mg, 0.186 mmol) according to the procedure of Example 19(c) gave 33 mg of the desired product as a white foam. MS 438.2 (M+H)$^+$, 436.4 (M–H)$^-$; IR (KBr) 1788.0, 1699.0 cm$^{-1}$.

EXAMPLE 60

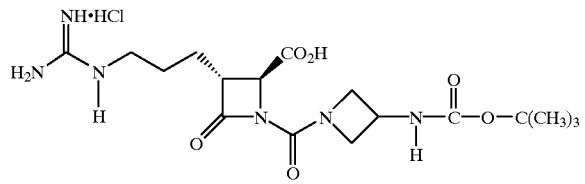

a)

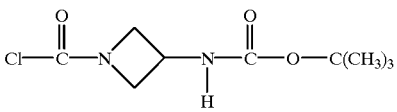

-continued

Phosgene (20% in toluene) (1.54 ml, 2.90 mmol) was added to a stirred solution of 3-tert-butoxycarbonylaminoazetidine [250 mg, 1.45 mmol, prepared as described by Arimoto et al., J. Antibiot., 39(9), 1243–56, (1986)] and triethylamine (222 µl, 1.6 mmol) in methylene chloride (5 ml) at 0° C. After 1 hour the reaction mixture was concentrated and the crude product was purified by silica gel chromatography to give 90 mg of the desired product.

b)

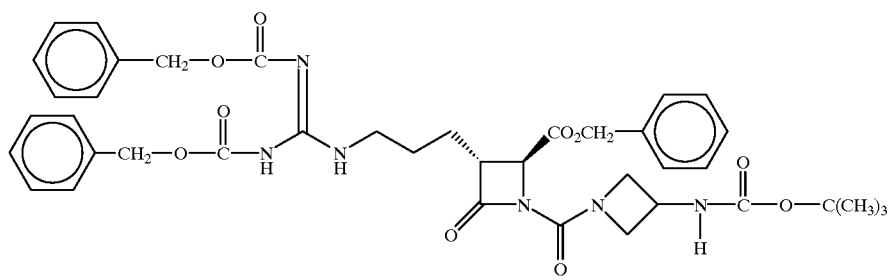

The chloro product from part (a) (119 mg, 0.506 mmol) and the benzyl ester product from Example 1(c) (193 mg, 0.337 mmol) were dissolved in methylene chloride (2.5 ml). Triethylamine (71 µl, 0.506 mmol) was added followed by dimethylaminopyridine (8 mg, 0.067 mmole). After 12 hours the reaction mixture was concentrated and the crude product was purified by silica gel chromatography to give 180 mg of the desired product.

c)

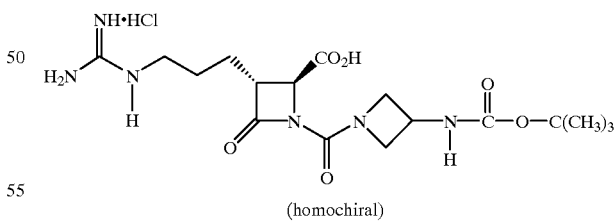

(homochiral)

The product from part (b) (80 mg, 0.104 mmol) was dissolved in 1,4-dioxane (1.0 ml) and water (0.10 ml). 1N HCl (104 µl, 0.104 mmol) was added followed by 10% palladium on carbon catalyst (16 mg). A hydrogen atmosphere was introduced via balloon. After 40 minutes of stirring at room temperature, the reaction mixture was diluted with water: 1,4-dioxane (1:1) and filtered. The filtrate was lyophilized to give 47 mg of the desired product. IR (KBr) 1792 cm$^{-1}$.

EXAMPLE 61 a) (homochiral)

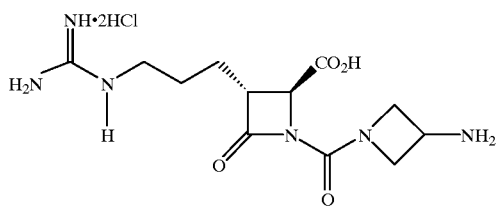

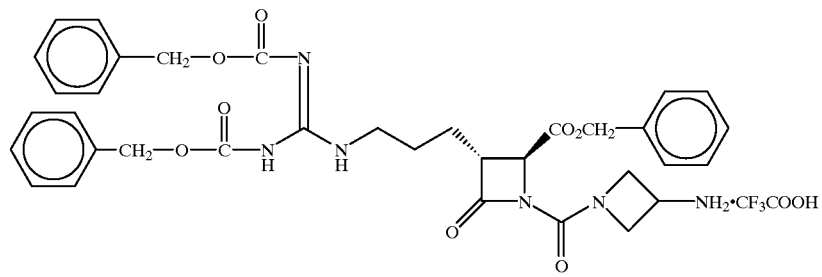

Trifluoroacetic acid (0.20 ml) was added drowise to a stirred solution of the product from Example 60 (b) (100 mg, 0.13 mmol) in methylene chloride at 0° C. The reaction mixture was then stirred at room temperature. After 40 minutes, the reaction mixture was concentrated in vacuo to give 120 mg of the desired product.

b)

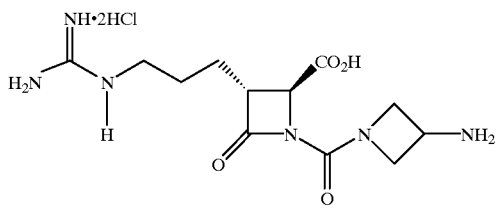

The product from part (a) (120 mg, 0.153 mmol) was deprotected and worked-up as described in Example 60(c) to give 51 mg of the desired product. IR(KBr) 1788 cm$^{-1}$.

EXAMPLE 62

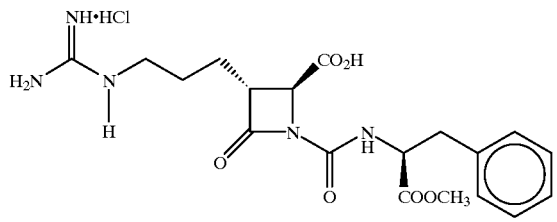

a)

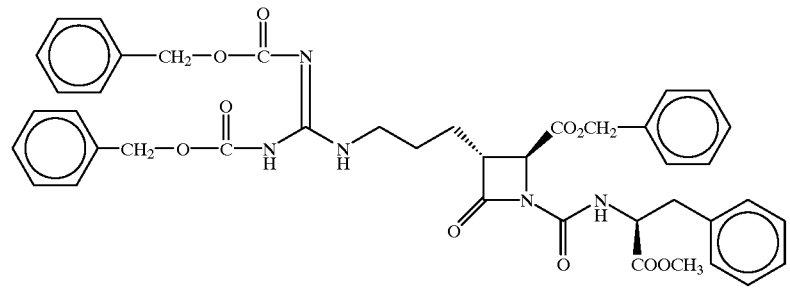

1N Sodium 1,1,1,3,3,3-hexamethyldisilazane in tetrahydrofuran (143 μl, 0.14 mmol) was added dropwise over 5 minutes to a solution of the benzyl ester product from Example 1(c) (81.5 mg, 0.142 mmol) in dry tetrahydrofuran (5 ml) under nitrogen at −78° C. After warming to −20° C. and stirring for 30 minutes, methyl-(S)-(−)-2-isocyanato-3-phenylpropionate (29.2 mg, 0.14 mmol) dissolved in tetrahydrofuran (5 ml) was added dropwise. After one more hour of stirring, the reaction solution was allowed to warm to 0° C. and was then poured into potassium bisulfate solution (30 ml, pH adjusted to 3.5) containing crushed ice, followed by extraction with ethyl acetate (3×15 ml). The combined organic phase was washed with water and brine and finally dried over sodium sulfate. The filtrate was concentrated it vacuo to give 102 mg of crude product as a light yellow oil. Purification by flash chromatography on silica gel using ethyl acetate/hexane (1:1) as eluent gave 90.8 mg of the desired product as a colorless oil. IR(film) 1780 cm$^{-1}$, 1743 cm$^{-1}$, and 1639 cm$^{-1}$; MS 788.8 (M+H)$^+$.

b)

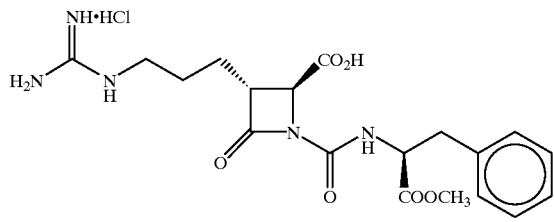

The product from part (a) (0.12 mmol) was dissolved in dioxane (5 ml). After addition of 10% palladium on carbon catalyst (40 mg) and 1N HCl in ether (120 μl), hydrogen was bubbled in the form of a constant slow stream over 90 minutes through the reaction suspension. After completion of the reaction as confirmed by TLC, a stream of nitrogen was used to remove excess hydrogen from the reaction material before filtering off the catalyst. Filtration through a layer of HyfloSuper Cel®, which was washed first with dioxane followed by dioxane/water yielded a clean filtrate. This was concentrated in vacuo and the remaining material lyophilized to give 45 mg of desired product as a white powder. IR (KBr) 1769 cm$^{-1}$, 1674 cm$^{-1}$ and 1632 cm$^{-1}$; MS 420.1 (M+H)$^+$.

EXAMPLE 63

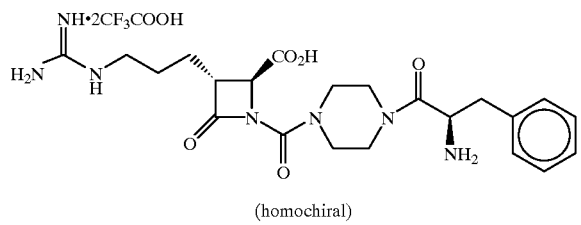

(homochiral)

a)

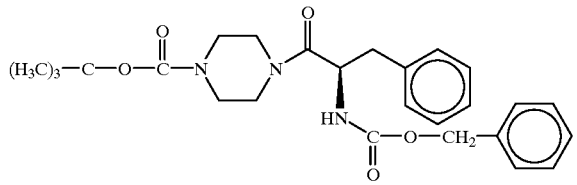

Triethylamine (0.37 ml, 2.68 mmol) and pyridine benzotriazol-1-loxytris(dimethylamino)phosphonium hexafluorophosphate (0.84 g, 2.68 mmol) were added to a solution of N-carbobenzyloxy-D-phenylalanine (0.84 g, 2.68 mmol) in anhydrous methylene chloride (10 ml), followed by the addition of tert-butyl-1-piperazine carboxylate (0.5 g, 2.68 mmol). After stirring the mixture for 5 hours at room temperature, methylene chloride (20 ml) was added and the mixture was washed with 1N HCl (1×25 ml), saturated sodium bicarbonate (1×25 ml), and saturated sodium chloride (1×25 ml). The organic phase was dried over sodium sulfate and condensed to give the crude product as a pale yellow oil. Purification by flash chromatography (silica gel, 0–30% ethyl acetate/hexane) gave 1.14 g of the desired product as a white foam.

b)

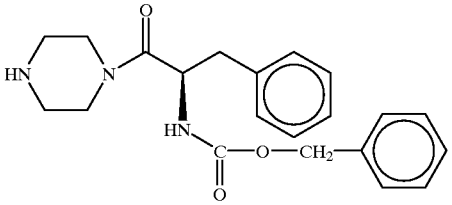

Trifluoroacetic acid (2 ml) was added to a solution of the product from part (a) (220 mg, 0.48 mmol) in anhydrous methylene chloride (2 ml) at 0° C. The mixture was warmed to room temperature and stirred for 1.5 hours. The mixture was condensed to give a colorless oil which was taken up in a solution of 1N HCl in ether (0.48 ml) and stirred vigorously. The resulting suspension was concentrated to give 230 mg of the hydrochloride salt of the desired product. MS 368.2 (M+H)$^+$.

c)

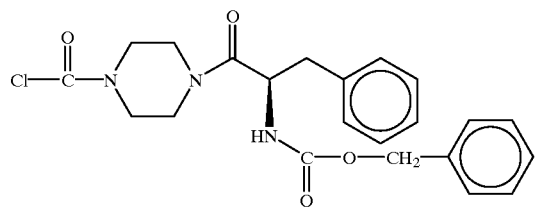

The product from part (b) (110 mg, 0.27 mmol) was added to a mixture of phosgene (0.36 ml of 20% phosgene in toluene solution, 0.68 mmol) and sodium bicarbonate (300 mg) in methylene chloride (4 ml). After stirring for 3 hours at room temperature, the mixture was filtered and the eluents were concentrated to give 165 mg of the desired product as a clear gel. IR (film) 1707.4, 1645.6 cm$^{-1}$.

d)

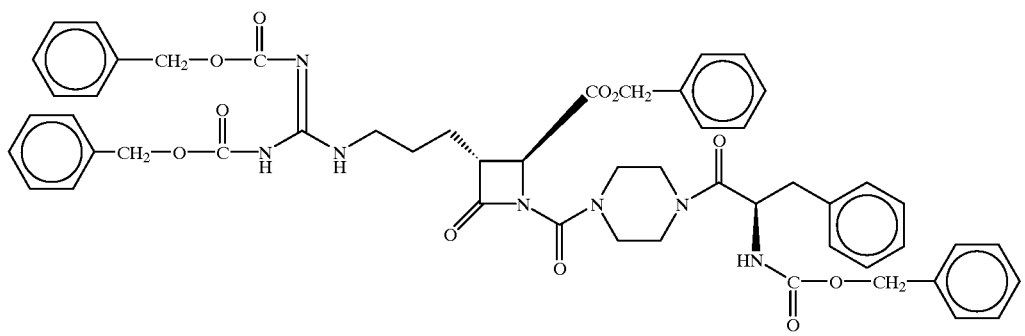

Triethylamine (31 μl, 0.23 mmol) and dimethylaminopyridine (10–12 crystals) were added to a solution of the benzyl ester product of Example 1(c) (86 mg, 0.15 mmol) in methylene chloride (3 ml), followed by the addition of the chloro product from part (c) (99 mg, 0.23 mmol). After stirring at room temperature for 1 hour, the mixture was concentrated and purified by flash column chromatography (silica gel, 0–50% ethyl acetate/hexane) to give 90 mg of the desired product as a colorless oil. MS 66.5 (M+H)$^+$, 964.7 (M–H)$^-$; IR(film) 1786.4, 1727.5, 1639.5 cm$^{-1}$.

e)

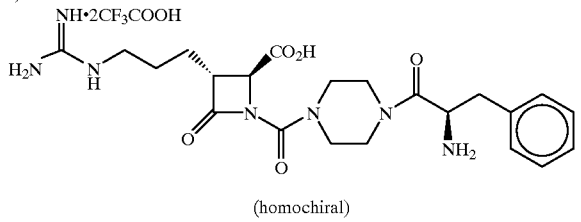

(homochiral)

The product from part (d) (89 mg, 0.092 mmol) was deprotected and worked-up according to the procedure of Example 55(c) to give 68 mg of the desired product as a white lyophilate. MS 474.3 (M+H)$^+$, 472.6 (M–H)$^-$; IR (KBr) 1790.0, 1670.0 cm$^{-1}$.

EXAMPLE 64

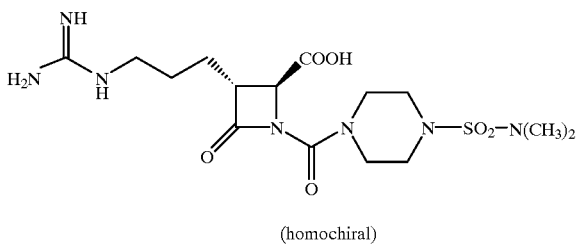

(homochiral)

a)

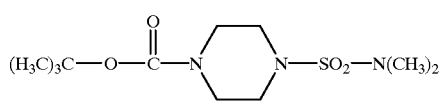

Diisopropylethylamine (560 μl), dimethylaminopyridine (33 mg) and dimethylsulfamoyl chloride (462 mg, 3.22 mmol) were added to a solution of N-(tert-butoxycarbonyl) piperizine (600 mg, 3.22 mmol) in methylene chloride (15 ml). The mixture was stirred overnight at room temperature. The reaction was quenched with the addition of 1N HCl solution (20 ml). The mixture was extracted with ethyl acetate (2×100 ml). The extracts were combined and washed with brine (2×20 ml), dried over magnesium sulfate and concentrated to give 0.93 g of the crude product as a white solid which was used without purification.

b)

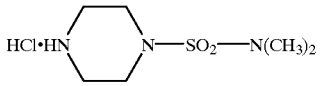

A mixture of the product from part (a) (0.60 g, 2.0 mmol), trifluoroacetic acid (15 ml) and methylene chloride (30 ml) was stirred at room temperature for 2 hours. TLC showed completion of the reaction. The solvent and excess trifluoroacetic acid were removed. The residue was dissolved in a minimum amount of methylene chloride followed by the addition of 1N HCl/ether (2.0 ml) and anhydrous ether (20 ml). The product was collected by filtration to give 430 mg of the desired product as a white powder. MS (M+H)$^+$ 194.1.

c)

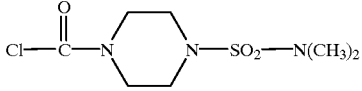

Sodium bicarbonate (3.0 g) was added to a solution of phosgene (2.1 ml, 20% in toluene) in methylene chloride (20 ml) followed by the addition of the product from part (b) (300 mg, 1.3 mmol). The resultant reaction mixture was stirred at room temperature for 40 minutes. TLC showed completion of the reaction. The reaction was quenched by filtering off the sodium bicarbonate. The residue was evaporated to give 330 mg of the desired product. IR (film) 1738 cm$^{-1}$.

d)

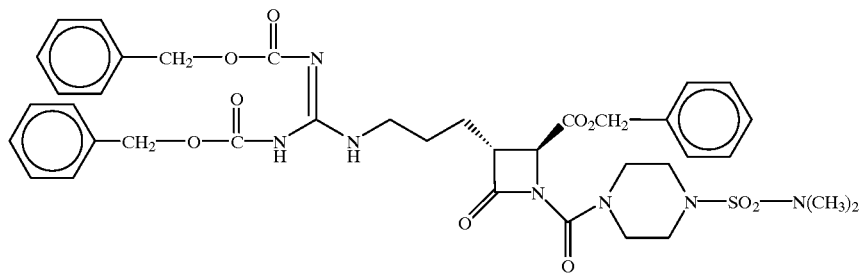

Diisopropylethylamine (35 μl, 0.20 mmol), dimethylaminopyridine (23 mg) and a solution of the chloro product from part (c) (51 mg, 0.20 mmol) in methylene chloride (2 ml) were added to a solution of the benzyl ester product of Example 1(c) (100 mg) in methylene chloride (1 ml). The mixture was stirred at room temperature overnight. Analytical HPLC indicated the reaction was complete. The reaction was quenched with the addition of 1N potassium sulfate. The mixture was extracted with ethyl acetate. The extracts were combined and washed with brine, dried over magnesium sulfate, and concentrated. The resulting crude product was purified by flash chromatography (3% methanol/methylene chloride) to give 101 mg of the desired product as a white foam. MS (M+H)$^+$ 792.4, (M-H)$^-$ 790.7; IR (film) 1786 cm$^{-1}$, 1736 cm$^{-1}$, 1680 cm$^{-1}$, 1640 cm$^{-1}$.

A mixture of the product from part (d) (95 mg, 0.12 mmol), 1N HCl (120 μl, 0.12 mmol), and 10% palladium on carbon catalyst (49 mg) in dioxane (3 ml) was stirred under hydrogen atmosphere (hydrogen balloon) at room temperature for 2 hours. Analytical HPLC indicated completion of the reaction. The reaction mixture was filtered through a Celite® cake and concentrated to give the crude product (HCl salt). Purification by preparative HPLC (reverse phase, methanol, water, trifluoroacetic acid) followed by passing through a polyvinylpyrrolidone column gave 32 mg of the desired product as a white fluffy powder. MS 434.3 (M+H)$^+$, 432.3 (M-H)$^-$; IR (KBr) 1778, 1663 cm$^{-1}$.

e)

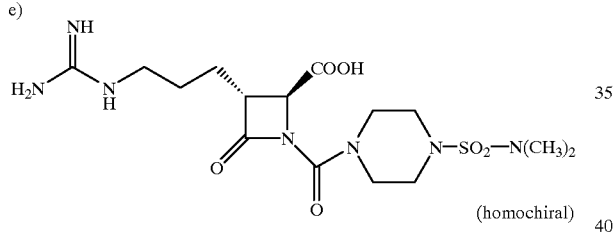

(homochiral)

EXAMPLE 65

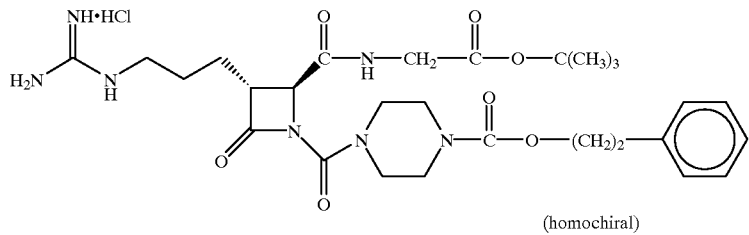

(homochiral)

a)

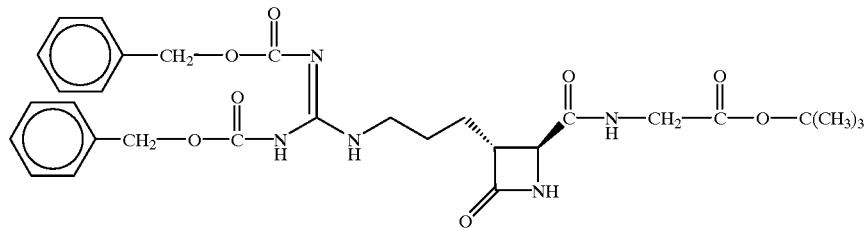

A solution of the carboxylic acid azetidinone product of Example 1(b) (482 mg, 1.0 mmol) in tetrahydrofuran (5 ml) was cooled to -20° C. under an argon atmosphere and N-methylmorpholine (223 mg, 2.2 mmol) was added. 1.1 Equivalents of a 0.5 M solution of tert-butylglycine ester, hydrochloride (184 mg, 1.1 mmol) was added followed by the addition of benzotriazol-1-yloxytris(dimethylamino)phosphonium hexafluorophosphate (486 mg, 1.1 mmol). The reaction was stirred at −20° C. for 24 hours, poured into 5% potassium bisulfate solution and extracted with ethyl acetate. The ethyl acetate extract was washed with water and brine, and dried over sodium sulfate. The solvents were evaporated and the crude residue was purified by silica gel chromatography eluting with ethyl acetate to give 396 mg of the desired product as a colorless solid. MS 596 (M+H)$^+$.

b)

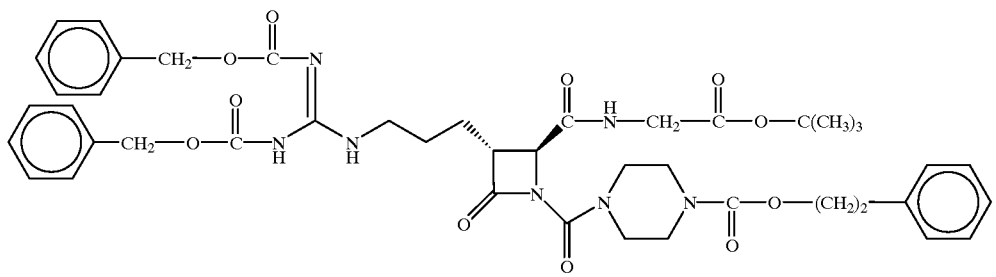

A solution of the product from part (a) (200 mg, 0.336 mmol) and triethylamine (38 mg, 0.37 mmol) in methylene chloride (4 ml) was stirred at room temperature and 1.1 equivalents of 1-phenethyloxypiperazine-4-carbonylchloride (110 mg, 0.37 mmol) was added. Dimethylaminopyridine (10 mg) was added and the reaction mixture was stirred for 30 hours. The reaction was diluted with methylene chloride, washed with brine, and dried over anhydrous sodium sulfate. The crude product was purified by flash chromatography on silica gel eluting with ethyl acetate yielding 210 mg of the desired product as a colorless glass-like residue. MS 856 (M+H)$^+$.

c)

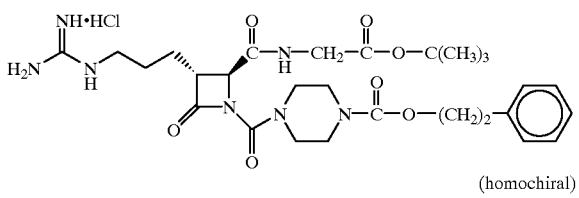

(homochiral)

A solution of the product from part (b) (200 mg, 0.234 mmol) in dioxane (5 ml) containing 1.1 equivalents of HCl was stirred under a hydrogen atmosphere with 10% palladium on carbon catalyst (75 mg) for 2 hours. The reaction was filtered and the solvents lyophilized to yield 122 mg of the desired product as a colorless solid. MS 588 (M+H)$^+$.

EXAMPLE 66

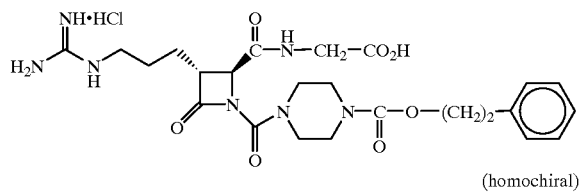

(homochiral)

The product of Example 65 (30 mg, 0.05 mmol) was added to trifluoroacetic acid (1 ml) at 0° C. and the mixture was stirred for 30 minutes. The trifluoroacetic acid was evaporated and the residue was dissolved in water/dioxane (1:1) (1 ml) and lyophilized to give 22 mg of the desired product as a colorless solid. MS 532 (M+H)$^+$.

EXAMPLE 67

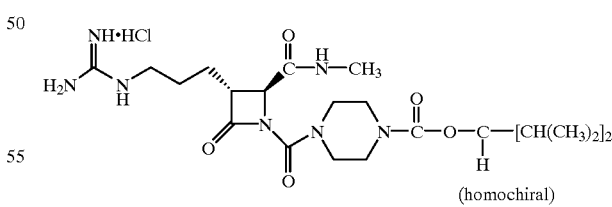

(homochiral)

a)

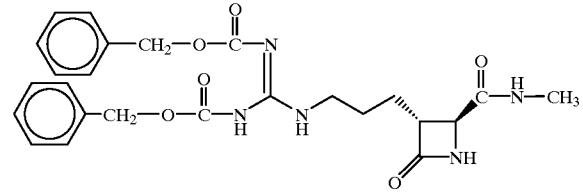

A solution of the carboxylic acid azetidinone product of Example 1(b) (150 mg, 0.311 mmol) in tetrahydrofuran (3 ml) was cooled to −20° C. under an argon atmosphere and N-methylmorpholine (34.6 mg, 0.342 mmol) was added. 1.1 Equivalents of a 2 M solution on monomethylamine in tetrahydrofuran was added followed by the addition of benzotriazol-1-yloxytris(dimethylamino)phosphonium hexafluorophosphate (151 mg, 0.341 mmol). The reaction was stirred at −20° C. for 48 hours, poured into 5% potassium bisulfate solution, and extracted with ethyl acetate. The ethyl acetate extract was washed with water and brine, and dried over sodium sulfate. The solvents were evaporated and the crude residue was purified by silica chromatography eluting with ethyl acetate to give 124 mg of the desired product as a colorless solid. MS 496 (M+H)$^+$.

b)

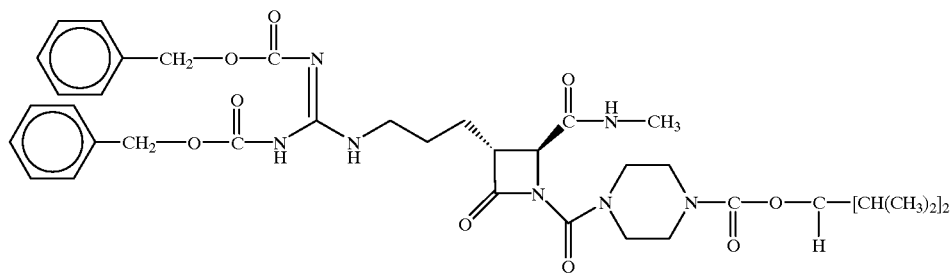

A solution of the product from part (a) (100 mg, 0.2 mmol) and triethylamine (23 mg, 0.225 mmol) in methylene chloride (2 ml) was stirred at room temperature and 1.1 equivalents of 1-diisopropylmethoxy-carbonylpiperazine-4-carbonylchloride (65 mg, 0.225 mmol) was added. Dimethylaminopyridine (8 mg) was added and the reaction mixture was stirred for 16 hours. The reaction was diluted with methylene chloride, washed with brine, and dried over anhydrous sodium sulfate. The crude product was purified by flash chromatography on silica eluting with ethyl acetate to give 58 mg of the desired product as a colorless glass-like residue. MS 750 (M+H)$^+$.

A solution of the product from part (b) (53 mg, 0.07 mmol) in dioxane (3 ml) containing 1.1 equivalents of 1N HCl was stirred under a hydrogen atmosphere with 10% palladium on carbon catalyst (20 mg) for 2 hours. The reaction was filtered and the solvents lyophilized to yield 32 mg of the desired product as a colorless solid. MS 482 (M+H)$^+$.

c)

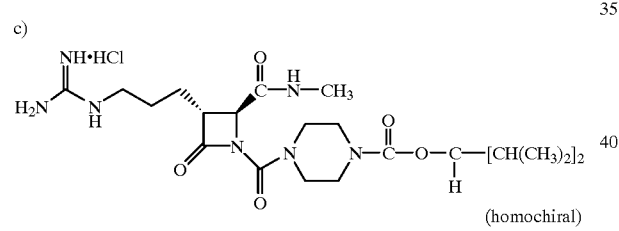

(homochiral)

EXAMPLE 68

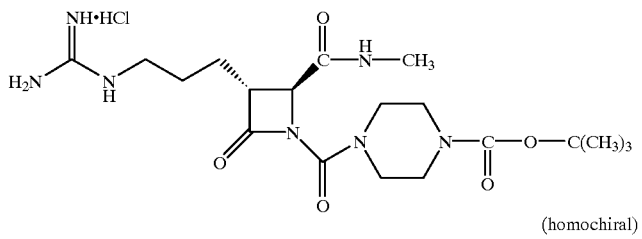

(homochiral)

a)

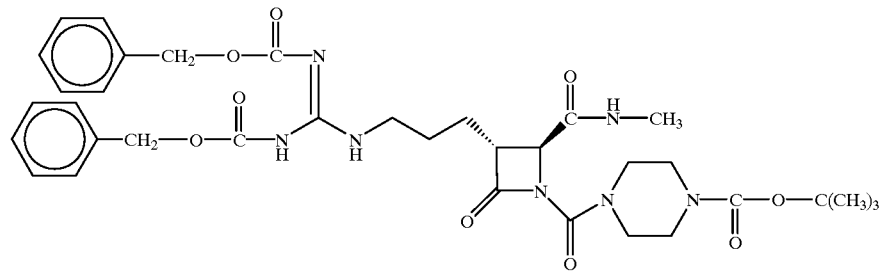

A solution of the product from Example 67(a) (120 mg, 0.242 mmol) and triethylamine (37 mg, 0.363 mmol) in methylene chloride (3.5 ml) was stirred at room temperature and 1.1 equivalents of 1-tert-butoxycarbonylpiperazine-4-carbonylchloride (90 mg, 0.363 mmol) was added. Dimethylaminopyridine (6 mg) was added and the reaction mixture was stirred for 2 hours. The reaction was diluted with methylene chloride, washed with brine, and dried over anhydrous sodium sulfate. The crude product was purified by flash chromatography on silica eluting with ethyl acetate to give 100 mg of the desired product as a colorless glass-like residue. MS 708 (M+H)$^+$.

b)

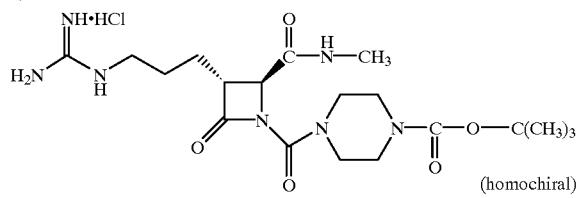

(homochiral)

A solution of the product from part (a) (90 mg, 0.127 mmol) in dioxane (3 ml) containing 1.5 equivalents of HCl was stirred under a hydrogen atmosphere with 10% palladium on carbon catalyst (35 mg) for 2 hours. The reaction was filtered and the solvents lyophilized to give 38 mg of the desired product as a colorless solid. MS 439 (M+H)$^+$; $[\alpha]=14°$ (c=1, methanol).

EXAMPLE 69

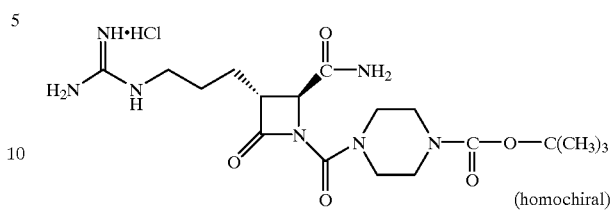

(homochiral)

a)

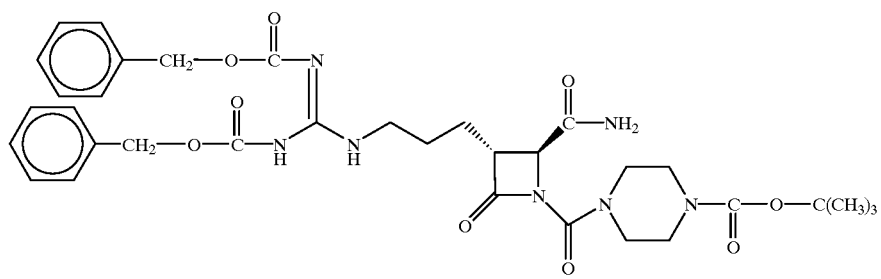

Following the procedure of Example 67(a) but substituting a 0.5 M solution of ammonia in dioxane for the 2M solution of monomethylamine, the desired product was obtained as a colorless solid. MS 482 (M+H)$^+$.

b)

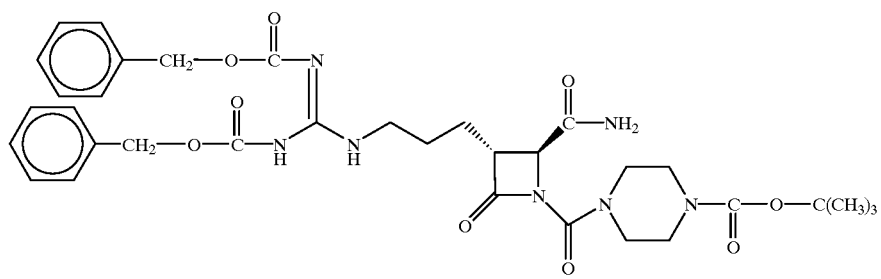

Reacting the product from part (a) with 1-tert-butoxycarbonylpiperazine-4-carbonylchloride according to the procedure of Example 68(a), the desired product was obtained as a colorless glass-like residue. MS 694 (M+H)$^+$.

c)

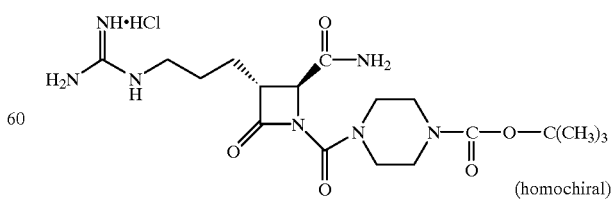

(homochiral)

Deprotection and work-up of the product from part (b) according to the procedure of Example 68(b) gives the desired product as a colorless solid. MS 426 (M+H)$^+$.

EXAMPLE 70 a)

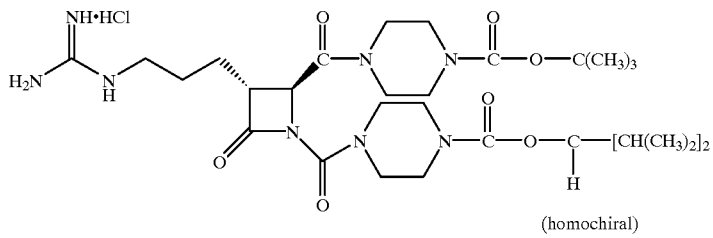

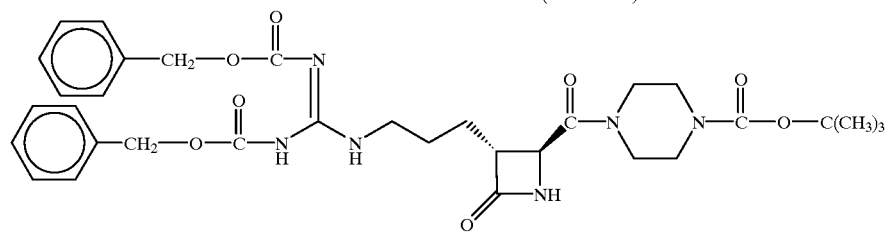
(homochiral)

Following the procedure of Example 67(a) but substituting 1-tert-butoxycarbonylpiperazine for the monomethylamine, the desired product was obtained as a colorless solid. MS 651 (M+H)+.

b)

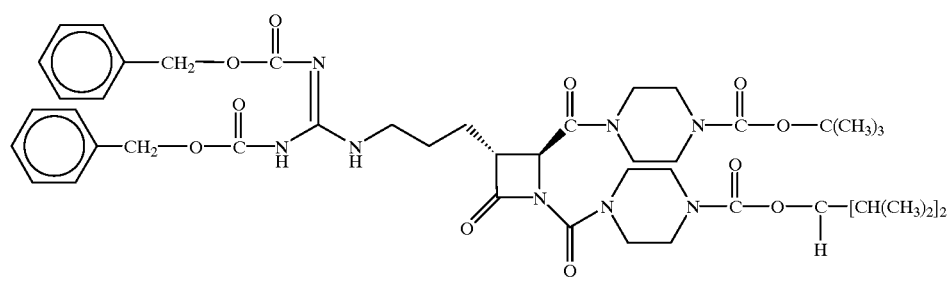

A solution of the product from part (a) (100 mg, 0.2 mmol) and triethylamine (23 mg, 0.225 mmol) in methylene chloride (2 ml) was stirred at room temperature and 1.1 equivalents of 1-diisopropyl-methyloxycarbonylpiperazine-4-carbonylchloride (65 mg, 0.225 mmol) was added. Dimethylaminopyridine (8 mg) was added and the reaction mixture was stirred for 48 hours. The reaction was diluted with methylene chloride, washed with brine, and dried over anhydrous sodium sulfate. The crude product was purified by flash chromatography on silica eluting with ethyl acetate to give 68 mg of the desired product as a colorless glass-like residue. MS 906 (M+H)+.

c)

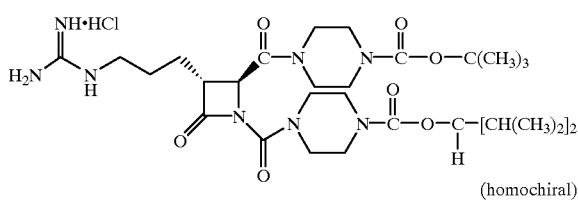
(homochiral)

A solution of the product from part (b) (60 mg, 0.07 mmol) in dioxane (2 ml) containing 1.1 equivalents of 1.0 N HCl was stirred under a hydrogen atmosphere with 10% palladium on carbon catalyst (25 mg) for 2 hours. The reaction was filtered and the solvents lyophilized to yield 42 mg of the desired product as a colorless solid. MS 637 (M+H)+.

EXAMPLE 71

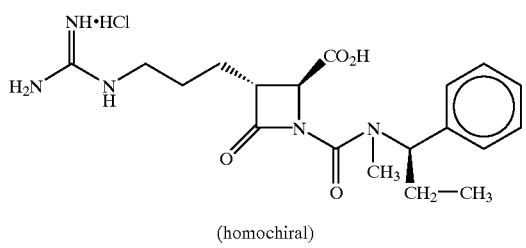
(homochiral)

a)

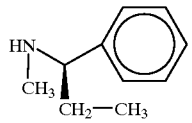

Methyliodide (200 mg, 1.41 mmol) was added to a solution of (R)1-phenylaminopropane (420 mg, 2.82 mmol) and potassium carbonate (292 mg, 2.12 mmol) in tetrahydrofuran (5 ml). The reaction mixture was stirred at room temperature for 4 hours and then heated at 40–45° C. for 14 hours. The reaction mixture was filtered. The filtrate was concentrated and purified by flash column chromatography [elute with 5–10% ammonia (2M in methanol) in methylene chloride] to yield 43 mg of the desired product as a light yellow oil.

b)

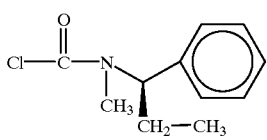

A solution of the product from part (a) (40 mg, 0.268 mmol) and triethylamine (27 mg, 0.268 mmol) in methylene chloride (1 ml) was added dropwise to a solution of phosgene (0.265 ml, 0.536 mmol, 20 % in toluene) in methylene chloride (1 ml) at 0° C. over 10 minutes. The reaction mixture was stirred at 0° C. for 1 hour. The reaction mixture was concentrated and the residue was added to anhydrous ether (20 ml). The formed white solid was filtered out. The resulting filtrate was concentrated to yield 51 mg of the desired product as a yellow oil.

c)

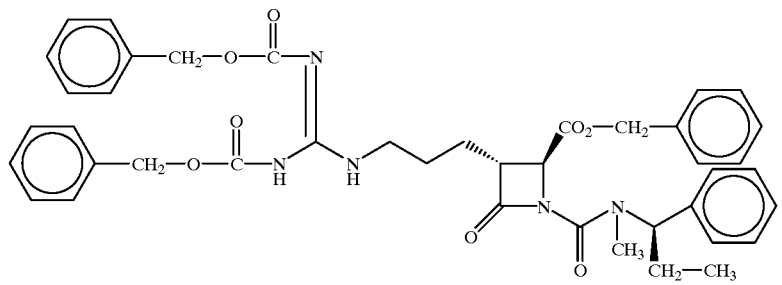

A mixture of the benzyl ester product from Example 1(c) (80 mg, 0.14 mmol), the chloro product from part (b) (44 mg, 0.21 mmol), dimethylaminopyridine (17.1 mg, 0.14 mmol) and triethylamine (21 mg, 0.21 mmol) in methylene chloride (3 ml) was stirred at room temperature for 7 hours. The reaction mixture was purified by flash column chromatography (eluting with 25% ethyl acetate in hexane) to yield 62 mg of the desired product as a colorless oil.

d)

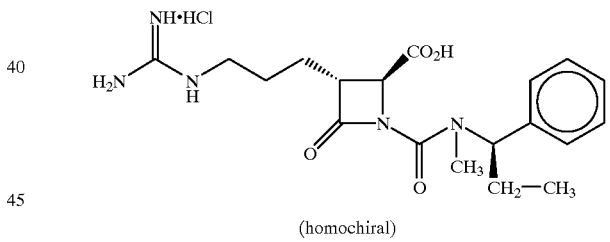

(homochiral)

A mixture of the product from part (c) (60 mg, 0.08 mmol), 10% palladium on carbon catalyst (8.48 mg, 0.0008 mmol), and 1N HCl (0.08 ml, 0.08 mmol) in dioxane (3 ml) was stirred under hydrogen atmosphere (hydrogen balloon) at room temperature for 1 hour. The reaction mixture was filtered through a Celite® cake. The resulting filtrate was lyophilized to yield 31 mg of the desired product as a white solid. MS 390.1 (M+H)$^+$; IR(film) 1780 cm$^{-1}$.

EXAMPLE 72

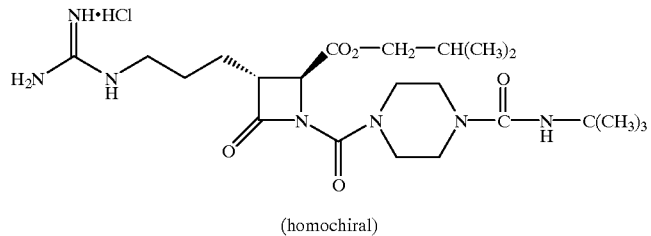

(homochiral)

a)

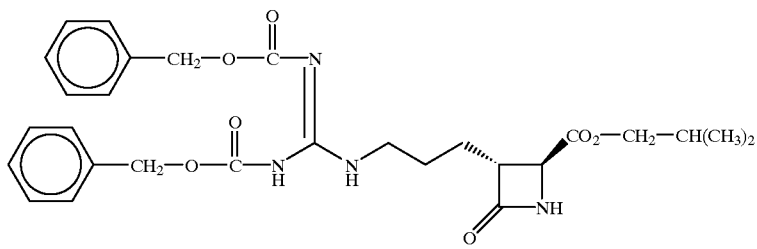

Cesium carbonate (29 mg, 0.088 mmol) was added to a stirred solution of the carboxylic acid azetidinone product of Example 1(b) (85 mg, 0.176 mmol) and 1-iodo-2-methylpropane (81 µl, 0.705 mmol) in dimethylformamide (500 µl) at room temperature. After 24 hours, the reaction was partitioned between ethyl acetate and water containing a small amount of sodium thiosulfate. The organic phase was isolated, washed with saturated sodium chloride, dried over magnesium sulfate, and concentrated. The residue was purified by silica gel chromatography to afford 62 mg of the desired product.

b)

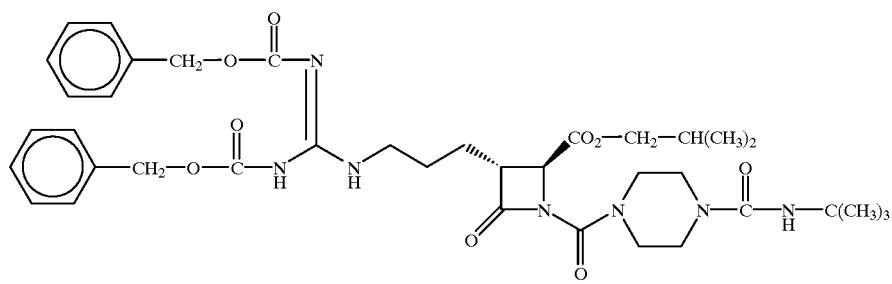

The product from part (a) (62 mg, 0.115 mmol) and the carbamoyl chloride product from Example 32 (c) were dissolved in methylene chloride (1.2 ml). Triethylamine (24 µl, 0.173 mmol) was added followed by dimethylaminopyridine (3 mg, 0.023 mmol). After 12 hours, the reaction mixture was concentrated and the crude product was purified by silica gel chromatography to give 65 mg of the desired product. After 30 minutes of stirring at room temperature, the reaction mixture was diluted with water: 1,4-dioxane (1:1, 4 ml) and filtered. The filtrate was lyophilized to afford 47 mg of the desired product. IR(KBr) 1788 cm$^{-1}$.

EXAMPLE 73

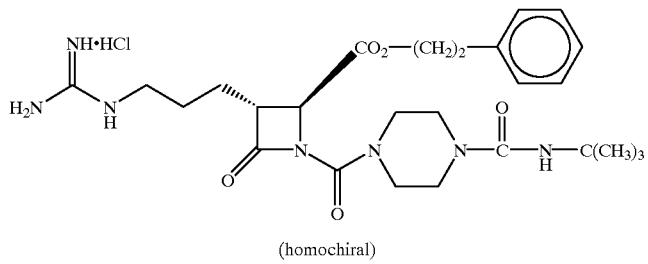

(homochiral)

a)
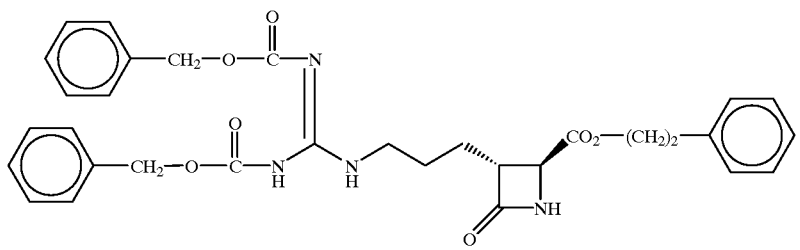

Following the procedure of Example 72 part (a) but substituting (2-iodoethyl)benzene for the 1-iodo-2-methylpropane, the desired compound was obtained.

b)
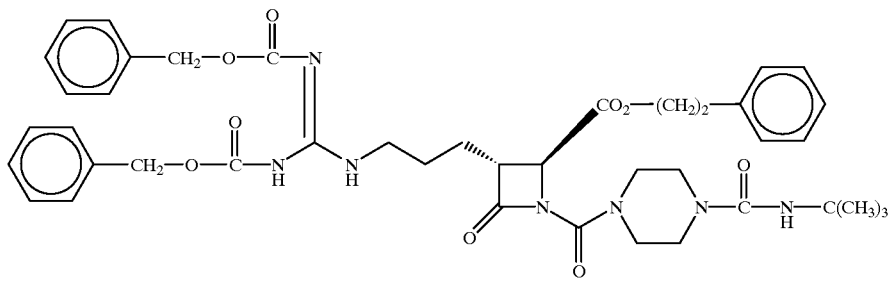

The product from part (a) (86 mg, 0.0147 mmol) and the carbamoyl chloride product from Example 32(c) (51 mg, 0.206 mmol) were reacted according to the procedure of Example 72 part (b) to give 98 mg of the desired product.

c)
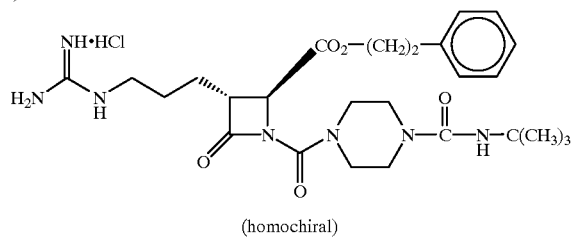
(homochiral)

The product from part (b) (97 mg, 0.122 mmol) was deprotected and worked-up according to the procedure of Example 72(c) to give 67 mg of the desired product. IR (KBr) 1790 cm$^{-1}$.

EXAMPLE 74

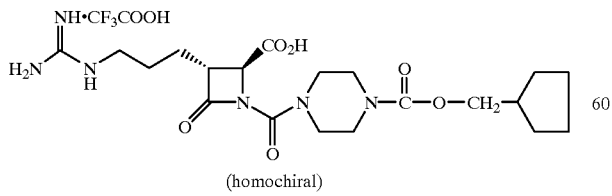
(homochiral)

Following the procedure of Example 34 but employing yclopentylmethanol in place of the cyclohexylmethanol, the desired product was obtained as a colorless glass. MS 453.3 (M+H)$^+$, 451.4 (M−H)$^-$; IR(KBr) 1788 cm$^-$, 1665 cm$^{-1}$.

EXAMPLE 75

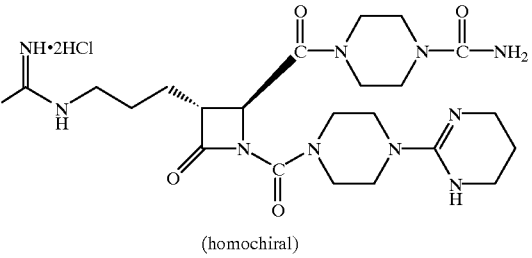
(homochiral)

a)
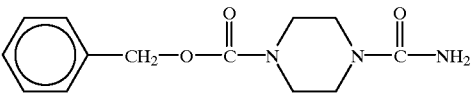

Trimethylsilyl isocyanate (3.8 ml, 3.22 g, 28 mmol) was added dropwise over 15 minutes to a solution of N-carbobenzyloxypiperazine (5.5 g, 25 mmol) and diisopropylethylamine (9.6 ml, 7.1 g, 55 mmol) in tetrahydrofuran (100 ml) at room temperature under an argon atmosphere. The reaction was stirred overnight at room temperature. The reaction was poured into water and extracted with ethyl acetate, washed with water and brine, and dried over sodium sulfate. The crude product was purified by column chromatography eluting with 20% ethyl acetate/hexane to give 5.1 g of the desired product. MS (M+H)$^+$ 264.

b)

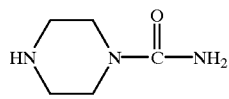

A mixture of the product from step (a) (3.96 g, 15 mmol) and palladium on carbon catalyst (10%, 2 g) in methanol (100 ml) was stirred under hydrogen atmosphere (hydrogen balloon) at room temperature for 1.25 hours. Filtration and concentration of the reaction gave 2.0 of the desired product.

c)

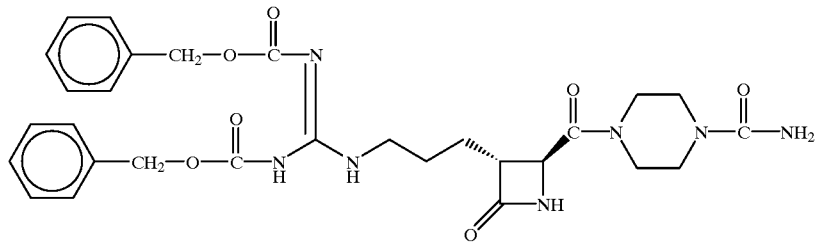

A mixture of the carboxylic acid azetidinone product of Example 1(b) (180 mg., 0.37 mmol), the product from step (b) (62 mg, 0.48 mmol), diisopropylethylamine (84 μl, 0.48 mmol), ethyl-3-(dimethylamino)propyl carbodiimide, hydrochloride salt (92 mg, 0.48 mmol) and 1-hydroxy-7-azabenzotriazole (65 mg, 0.48 mmol) in tetrahydrofuran (10 ml) was heated at 60° C. overnight. The mixture was diluted with methylene chloride, washed with water, dried over magnesium sulfate, and concentrated to give the crude product. Purification of the crude product by flash column chromatography (silica, 5–10% methanol/methylene chloride) gave 128 mg of the desired product as a white solid. MS 594.3 (M+H)$^+$, 592.3 (M−H)$^-$.

d)

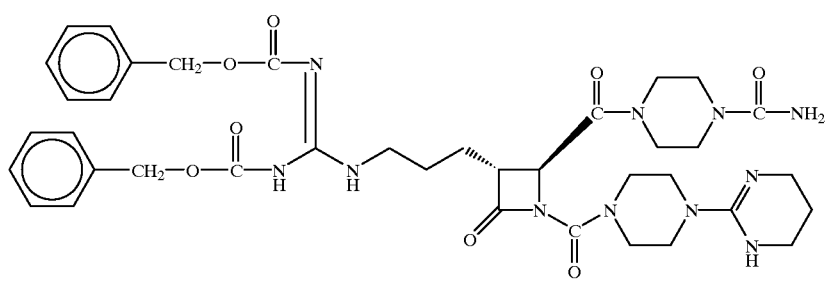

A mixture of the product from step (c) (110 mg, 0.185 mmol), the chloro product from Example 56(a) (63 mg, 0.28 mmol), diisopropylethylamine (96 μl), and 4-dimethylaminopyridine (18 mg) in methylene chloride (4 ml) was stirred at room temperature for 18 hours. The reaction was quenched by the addition of saturated sodium chloride solution and extracted with ethyl acetate (3×50 ml). The extracts were combined, dried over magnesium sulfate, and concentrated. The crude product was purified by flash chromatography (0–15% methanol/methylene chloride) to give 114 mg of the desired product as a white solid. MS 784.5 (M+H)$^+$, 782.5 (M−H)$^-$; IR (KBr) 1782 cm$^{-1}$, 1732 cm$^{-1}$, 1643 cm$^{-1}$, 1586 cm$^{-1}$.

e)

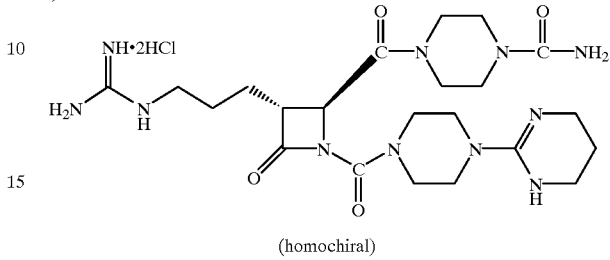

(homochiral)

A mixture of the product from step (d) (1.39 g, 1.77 mmol), 1N HCl (3.54 ml, 3.54 mmol) and palladium on carbon catalyst (10%, 750 mg) in dioxane (30 ml) was stirred under a hydrogen atmosphere (hydrogen balloon) at room temperature for 3.5 hours. Analytical HPLC indicated completion of the reaction. The reaction mixture was filtered through a Celite® cake and lyophilized to give 1.01 g as a white solid. MS 260.6 (M+2H)$^{2+}$; 1R 1780 cm$^{-1}$, 1632 cm$^{-1}$.

The following additional compounds of formula IV were also prepared:

| Ex | X$_2$ | R$_1$ | salt | stereochemistry | (M + H)$^+$ |
|---|---|---|---|---|---|
| 76 | ![structure] piperidine-N-C(O)-NH-C(CH$_3$)$_3$ | piperidine-N-C(O)-NH$_2$ (4-carboxamide) | 1.0 HCl | homochiral | 536 |
| 77 | -C(O)-N(CH$_3$)-(CH$_2$)$_2$-N(CH$_3$)-C(O)-cyclopropyl(CH$_3$)$_4$ | —CO$_2$H | — | homochiral | 453 |
| 78 | -C(O)-N(CH$_3$)-(CH$_2$)$_2$-N(CH$_3$)-C(O)-O-CH(CH(CH$_3$)$_2$)CH(CH$_3$)$_2$ | —CO$_2$H | — | homochiral | 471 |
| 79 | -C(O)-piperidine-N-C(O)-O-CH(CH(CH$_3$)$_2$)CH(CH$_3$)$_2$ | -C(O)-NH-(CH$_2$)$_2$-C(O)-NH$_2$ | 1.0 HCl | homochiral | 539 |
| 80 | -C(O)-piperidine-N-C(O)-O-CH(CH(CH$_3$)$_2$)CH(CH$_3$)$_2$ | -C(O)-NH-(CH$_2$)$_2$-N-[CH(CH$_3$)$_2$]$_2$ | 2.0 CF$_3$CO$_2$H | homochiral | 595 |

-continued
| Ex | X₂ | R₁ | salt | stereochemistry | (M + H)⁺ |
|----|----|----|----|----|----|
| 81 | 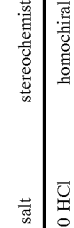 |  | 1.0 HCl | homochiral | 579 |
| 82 |  |  | 1.0 HCl | homochiral | 615 |
| 83 |  |  | 1.0 CF₃CO₂H | homochiral | 627 |
| 84 |  |  | 2.0 CF₃CO₂H | homochiral | 537 |
| 85 |  |  | 1.0 CF₃CO₂H | homochiral | 626 |

-continued
| Ex | X₂ | R₁ | salt | stereochemistry | (M + H)⁺ |
|---|---|---|---|---|---|
| 86 | 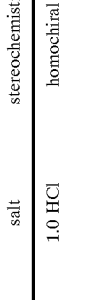 |  | 1.0 HCl | homochiral | 615 |
| 87 |  |  | 1.0 HCl | homochiral | 525 |
| 88 |  | —CO₂H | — | homochiral | 616 |
| 89 |  | —CO₂H | — | homochiral | 426 |
| 90 |  | —CO₂H | — | homochiral | 468 |

-continued
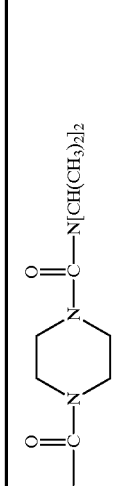
| Ex | X$_2$ | R$_1$ | salt | stereochemistry | (M + H)$^+$ |
|---|---|---|---|---|---|
| 91 | 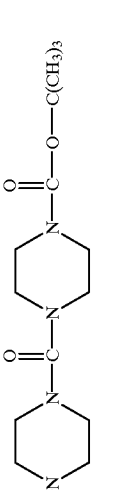 | —CO$_2$H | — | homochiral | 454 |
| 92 | 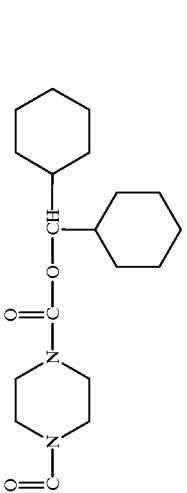 | —CO$_2$H | — | homochiral | 539 |
| 93 | 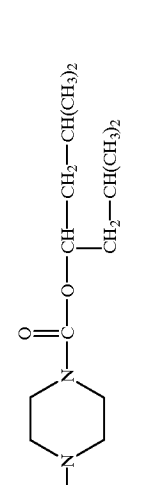 | —CO$_2$H | 1.0 HCl | homochiral | 549 |
| 94 | 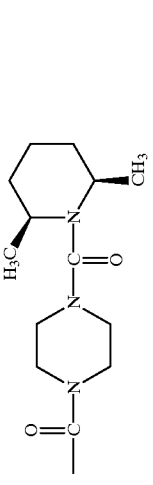 | —CO$_2$H | 1.0 CF$_3$CO$_2$H | homochiral | 497 |
| 95 |  | —CO$_2$H | — | homochiral | 466 |

-continued

| Ex | X₂ | R₁ | salt | stereochemistry | (M + H)⁺ |
|---|---|---|---|---|---|
| 96 | piperidine-acetyl-CH(CH₂-CH(CH₃)₂)-NH-C(O)-O-C(CH₃)₃ | —CO₂H | — | homochiral | 540 |
| 97 | piperidine-acetyl-CH(CH₂-CH(CH₃)₂)-NH-C(O)-O-C(CH₃)₃ | —CO₂H | — | homochiral | 540 |
| 98 | piperidine-acetyl-CH(CH₂-Ph)-NH-C(O)-O-CH(CH(CH₃)₂)CH(CH₃)₂ | —CO₂H | — | homochiral | 616 |
| 99 | N-acetyl-piperidine-C(O)-cyclohexyl | —CO₂H | 1.0 HCl | homochiral | 437 |
| 100 | N-acetyl-piperidine-C(O)-Ph | —CO₂H | 1.0 HCl | homochiral | 431 |

-continued

| Ex | X₂ | R₁ | salt | stereochemistry | (M + H)⁺ |
|---|---|---|---|---|---|
| 101 | (piperidine carbamate with CH—CH(CH₃)₂ / CH(CH₃)₂, N-acetyl) | —CO₂H | 0.02 CF₃CO₂H | homochiral | 469 |
| 102 | (2,2,3,3-tetramethylcyclopropyl carbonyl piperidine, N-acetyl) | —CO₂H | 1.0 CF₃CO₂H | homochiral | 451 |
| 103 | (piperidine acyl with CH—CH(CH₃)₂ / CH(CH₃)₂, N-acetyl) | —CO₂H | — | homochiral | 453 |
| 104 | (tetrahydropyrimidinyl-piperidine, N-acetyl) | (piperidine-1-carboxamide, N-acetyl) | 2.0 HCl | homochiral | 519 |

-continued

| Ex | X₂ | R₁ | salt | stereochemistry | (M + H)⁺ |
|---|---|---|---|---|---|
| 105 | | | 2.0 CF₃CO₂H | homochiral | 649 |
| 106 | | —CO₂H | 1.0 HCl | homochiral | 341 |
| 107 | | —CO₂H | — | homochiral | 441 |
| 108 | | —CO₂H | 1.0 HCl | homochiral | 521 |
| 109 | | —CO₂H | — | homochiral | 447 |

| Ex | X₂ | R₁ | salt | stereochemistry | (M + H)⁺ |
|---|---|---|---|---|---|
| 110 | ![X2 structure] | ![R1 structure with piperidine carboxamide] | 1.0 HCl | homochiral | 563 |
| 111 | ![N-acetyl piperidine carboxylic acid] | —CO₂H | 1.0 HCl | homochiral | 370 |
| 112 | ![bis-methoxymethyl pyrrolidine piperidine] | —CO₂H | — | homochiral | 512 |

-continued

| Ex | X₂ | R₁ | salt | stereochemistry | (M + H)⁺ |
|---|---|---|---|---|---|
| 113 | pyrrolidine with two CH₂-O-CH₃ groups, N-C(=O)-piperidine-N-C(=O)-CH₃ | —CO₂H | — | homochiral | 512 |
| 114 | (CH₃)₂CH-N[CH(CH₃)₂]-CH₂-C(=O)-piperidine-N-C(=O)-CH₃ | —CO₂H | 2.0 CF₃CO₂H | homochiral | 468 |
| 115 | CH(CH₃)₂-CH(CH(CH₃)₂)-NH-C(=O)-piperidine-N-C(=O)-CH₃ | —CO₂H | — | homochiral | 496 |
| 116 | (CH₃)₃C-C(=O)-O-pyrrolidine-NH-C(=O)- | —CO₂H | — | homochiral | 427 |
| 117 | (CH₃)₂CH-CH(CH(CH₃)₂)-O-CH₂-C(=O)-piperidine-N-C(=O)-CH₃ | —CO₂H | — | homochiral | 483 |

-continued

| Ex | X₂ | R₁ | salt | stereochemistry | (M + H)⁺ |
|---|---|---|---|---|---|
| 118 | [structure: acetylpiperazine-C(O)-C(CH₃)(NH₂)-] | —CO₂H | 2.0 CF₃CO₂H | homochiral | 434 |
| 119 | [structure: acetylpiperazine-C(O)-piperidine-NH] | —CO₂H | 2.0 CF₃CO₂H | homochiral | 439 |
| 120 | [structure: acetylpiperazine-C(O)-CH₂-N(CH(CH₃)₂)₂] | [structure: acetylpiperazine-C(O)-NH₂] | 2.0 CF₃CO₂H | homochiral | 579 |
| 121 | [structure: acetylpiperazine-C(O)-CH(CH₃)-NH-C(O)-OC(CH₃)₃] | —CO₂H | — | homochiral | 512 |
| 122 | [structure: acetylpyrrolidine-NH-C(O)-OC(CH₃)₃] | —CO₂H | — | homochiral | 427 |
| 123 | [structure: acetylpiperazine-C(O)-CH(OH)-Ph] | —CO₂H | 1.0 HCl | mixture of homochiral diastereomers | 461 |

| Ex | X₂ | R₁ | salt | stereochemistry | (M + H)⁺ |
|---|---|---|---|---|---|
| 124 | | | 1.0 HCl | homochiral | 479 |
| 125 | | | 1.0 HCl | homochiral | 494 |
| 126 | | | 2.0 CF₃COOH | homochiral | 551 |
| 127 | | | 2.0 CF₃COOH | homochiral | 594 |

-continued
| Ex | X₂ | R₁ | salt | stereochemistry | (M + H)⁺ |
|---|---|---|---|---|---|
| 128 | 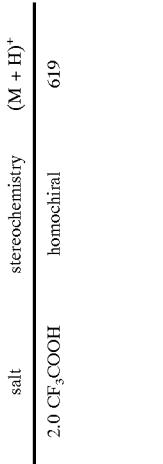 |  | 2.0 CF₃COOH | homochiral | 619 |
| 129 | 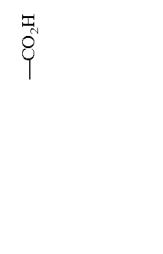 | —CO₂H | 2.0 CF₃COOH | homochiral | 567 |
| 130 | 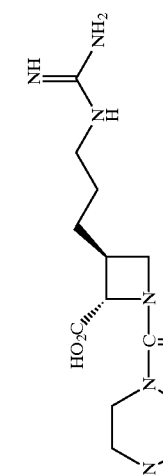 | 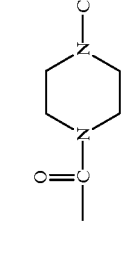 | 2.0 CF₃COOH | homochiral | 594 |

The following additional compounds of formula IV were also prepared:

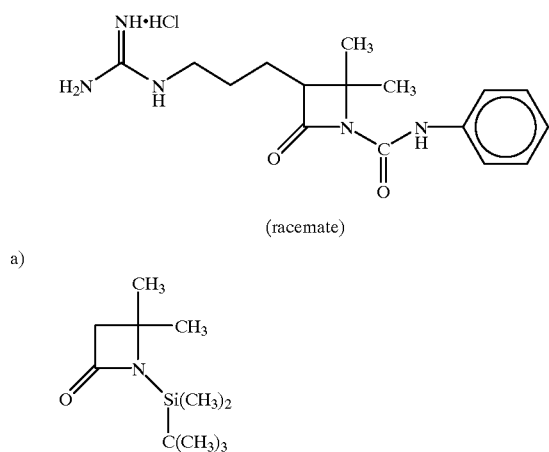

| Ex | X₂ | R₁ | salt | stereochemistry | (M + H)⁺ |
|---|---|---|---|---|---|
| 131 | —C(O)—N(piperazine)—C(O)—N—C(CH₃)₃ | —CO₂H | | homochiral | 426 |
| 132 | —C(O)—N(piperazine)—N=tetrahydropyrimidine-NH | —C(O)—N(piperazine)—C(O)—NH₂ | 2.0 HCl | homochiral | 520 |
| 133 | —C(O)—N(piperazine)—N=tetrahydropyrimidine-NH | —CO₂H | 1.0 HCl | homochiral | 409 |
| 134 | —C(O)—N(piperazine)—C(O)—CH(CH(CH₃)₂)—CH(CH₃)₂ | —C(O)—N(piperazine)—C(O)—NH₂ | 1.0 HCl | homochiral | 579 |

EXAMPLE 135

[Structure showing guanidinium·HCl group connected to azetidinone with CH₃, CH₃ substituents, N-C(O)-NH-phenyl] (racemate)

a)

[Structure of 4,4-dimethyl-2-azetidinone with N-Si(CH₃)₂C(CH₃)₃]

4,4-Dimethyl-2-azetidinone (17g, 0.171 mol) and tert-butyldimethylsilyl chloride (28.43 g, 0.188 mol) were dissolved in methylene chloride (270 ml). A solution of diisopropylethylamine (44.80 ml, 0.257 mol) in methylene chloride (130 ml) was added dropwise. The reaction mixture was stirred at room temperature for 24 hours and then concentrated. The residue was partitioned between ethyl acetate and water. The organic phase was washed with 1N potassium bisulfate, saturated sodium carbonate, saturated sodium chloride, dried over magnesium sulfate, and concentrated. The residue was purified by silica gel chromatography to give 34.55 g of the desired product.

b)

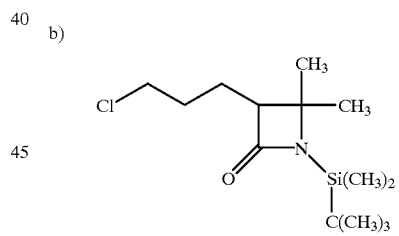

A 1.6 M hexane solution of n-butyl lithium (4.83 ml, 7.73 mmol) was added dropwise to a stirred solution of isopropylamine (1.08 ml, 7.73 mmol) in tetrahydrofuran (5.0 ml) at 0° C. After 30 minutes, the solution was cooled to −78° C. and a solution of the product from step (a) (1.50 g, 7.03 mmol) in tetrahydrofuran (2.5 ml) was added dropwise. After 40 minutes a solution of 1-chloro-3-iodopropane (1.72 g, 8.43 mmol) in tetrahydrofuran (2.5 ml) was added dropwise. The temperature was slowly raised to 0° C. After 1 hour the reaction mixture was quenched by the addition of 1N potassium bisulfate. The solution was partitioned between ethyl acetate and water. The organic phase was washed with 1N potassium bisulfate and saturated sodium chloride, dried over magnesium sulfate, and concentrated. The residue was purified by silica gel chromatography to give 1.46 g of the desired product.

c)

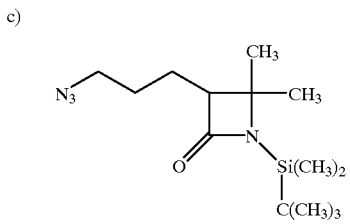

Sodium azide (0.91 g, 14.07 mmol) was added to a stirred solution of the product from step (b) (1.36 g, 4.69 mmol) and tetrabutylammonium iodide (0.35 g, 0.94 mmol) in dimethylformamide (10 ml). After 9 hours of heating at 45° C., the solution was cooled to room temperature and partitioned between ethyl acetate and water. The organic phase was washed with saturated sodium chloride, dried over magnesium sulfate, and concentrated to afford 1.34 g of the desired product.

d)

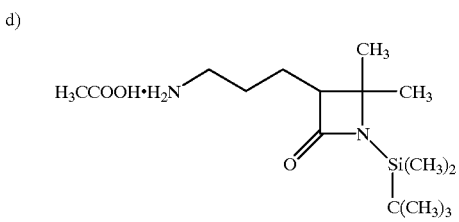

The product from step (c) (0.57g, 1.92 mmol) was dissolved in 1,4-dioxane. Acetic acid (0.11 ml, 1,92 mmol) was added followed by 10% palladium on carbon catalyst (0.15 mole%). A hydrogen atmosphere was introduced via balloon. After 1 hour of stirring at room temperature the solution was filtered and concentrated to give 0.59 g of the desired product.

e)

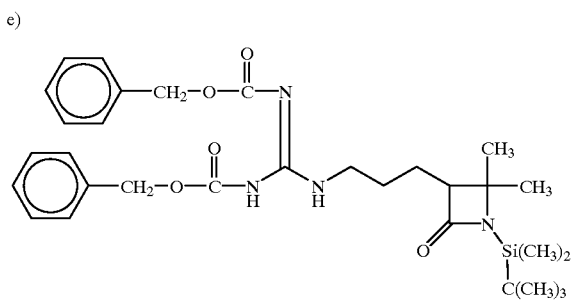

The product from step (d) (0.59 g, 1.78 mmol) was dissolved in acetonitrile (8.0 ml). Triethylamine (0.26 ml, 1.87 mmol) was added followed by N,N'-dicarbobenzyloxy—S-methylisothiourea (0.64 g, 1.78 mmol). After 12 hours of stirring at room temperature the solution was partitioned between ethyl acetate and water, the organic phase was washed with saturated sodium chloride, dried over magnesium sulfate and concentrated. The residue was purified by silica gel chromatography to give 0.37 g of the desired product.

f)

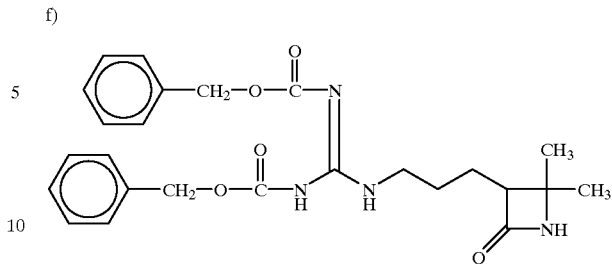

A 1.0 M tetrahydrofuran solution tetrabutylammonium fluoride (0.69 ml, 0.69 mmol) was added dropwise to a stirred soultion of the product from step (e) (0.36 g, 0.62 mmol) in tetrahydrofuran (5 ml) at 0° C. The reaction mixture was then stirred at room temperature. After 1 hour the solution was partitioned between ethyl acetate and water. The organic phase was washed with saturated sodium chloride, dried over magnesium sulfate, and concentrated. The residue was purified by silica gel chromatography to give 276 mg of the desired product.

g)

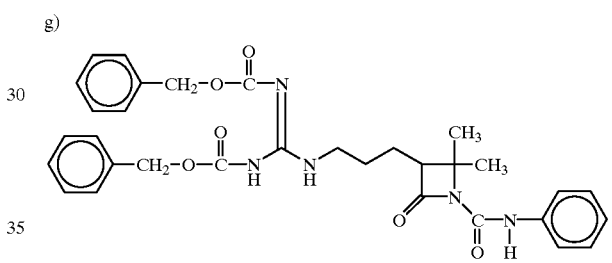

A 1.0 M tetrahydrofuran solution of sodium bis (trimethylsilyl) amide (0.28 ml, 0.28 mmol) was added dropwise to a stirred solution of the product from step (f) (0.12 g, 0.26 mmol) in tetrahydrofuran (1.5 ml) at −78° C. After 30 minutes of stirring, phenyl isocyanate (42 µl, 0.39 mmol) was added dropwise. The temperature was slowly raised to 0° C. After 30 minutes the reaction mixture was quenched by the addition of a 4.0 pH buffer solution. The mixture was partitioned between ethyl acetate and water. The organic phase was washed with saturated sodium chloride, dried over magnesium sulfate and concentrated. The residue was purified by silica gel chromatography to give 0.16 g of the desired product.

h)

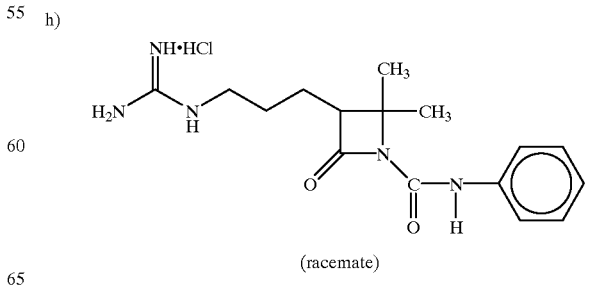

(racemate)

The product from part (g) (0.16 g, 0.27 mmol) was dissolved in 1,4-dioxane. 10% Palladium on carbon catalyst (0.15 mol %) was added followed by 4N HCl in 1,4-dioxane (68 μl, 0.27 mmol). A hydrogen atmosphere was introduced via balloon. After 30 minutes of stirring, water (0.20 ml) was added to keep the product in solution. After 30 more minutes, the reaction mixture was diluted with 50% acetonitrile in water (2.0 ml) and filtered. The solution was concentrated to remove organics and then lyophilized to give 84 mg of the desired product; IR (KBr) 1753, 1707 cm$^{-1}$; (M+H)$^+$=318.

The following additional compounds of formula II were also prepared

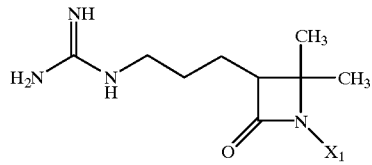

| Ex | X$_1$ | salt | stereochemistry | (M + H)$^+$ |
|---|---|---|---|---|
| 136 | —C(=O)—CH$_3$ | 1.0 CF$_3$CO$_2$H | racemate | 241 |
| 137 | —C(=O)—C$_6$H$_5$ | 1.0 HCl | racemate | 303 |
| 138 | —C(=O)—C$_6$H$_4$—C$_6$H$_5$ | 1.0 HCl | racemate | 379 |
| 139 | —C(=O)—C$_6$H$_4$—CF$_3$ | 1.0 HCl | racemate | 371 |
| 140 | —C(=O)—CH$_2$—O—C$_6$H$_5$ | 1.0 HCl | racemate | 333 |
| 141 | —C(=O)—NH—SO$_2$—C$_6$H$_5$ | 1.0 HCl | racemate | 382 |
| 142 | —C(=O)—N(CH$_3$)—C$_6$H$_5$ | 1.0 HCl | racemate | 332 |
| 143 | —C(=O)—NH—C$_6$H$_4$—F | 1.0 CF$_3$CO$_2$H | racemate | 336 |
| 144 | —SO$_2$—C$_6$H$_4$—C(CH$_3$)$_3$ | 1.0 HCl | racemate | 395 |
| 145 | —SO$_2$—C$_6$H$_5$ | 1.0 CF$_3$CO$_2$H | racemate | 339 |

EXAMPLE 146

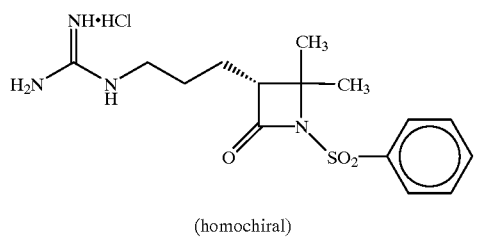
(homochiral)

a)

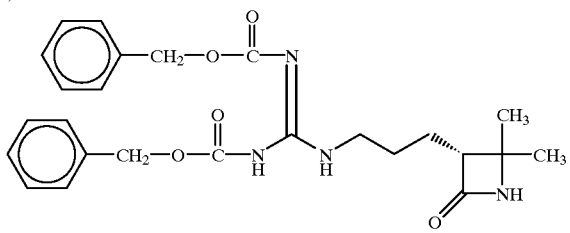

The racemic product from Example 135 step (f) was separated into pure enantiomers (−) isomer and (+) isomer on Chiralpak-AD prep-column eluting with 30% 2-propanol/hexane.

b)

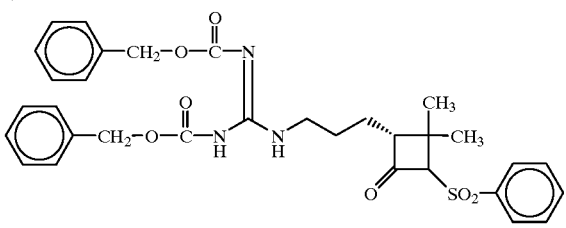

A solution of the (+) isomer from step (a) (125 mg, 0.268 mmol) in tetrahydrofuran (2 ml) was cooled to −78° C. under an argon atmosphere. A 1M solution of sodium bis(trimethylsilyl)amide (0.536 ml) in tetrahydrofuran was added dropwise and the mixture was stirred for 20 minutes. Benzene sulfonylchloride (95 mg, 0.536 mmol) was added dropwise and the mixture was stirred at −78° C. for 4 hours. The reaction was diluted with aqueous 10% potassium bisulfate solution (10 ml) and extracted with ethyl acetate (3×10 ml). The combined organic phase was washed with water (25 ml) and brine (25 ml), and dried over sodium sulfate. The solution was filtered and the solvent evaporated to give an oil. The residue was purified by flash column chromatography (silica, ethyl acetate: hexane, 1:3) to give 149 mg of the desired product as a colorless oil; (M+H)+= 607.

c)

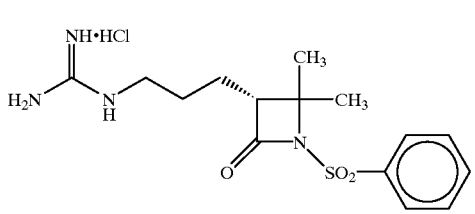
(homochiral)

A solution of the product from step (b) (140 mg, 0.23 mmol) in dioxane (4 ml) containing aqueous 1N HCl (0.46 ml) and 10% palladium on carbon catalyst (70 mg) was stirred under a hydrogen atmoshpere for 1 hour. The reaction was filtered and lyophilized to give 78 mg of the desired product as a colorless solid; IR(KBr) 1778 cm$^{-1}$; (M+H)+= 339; $[\alpha]_D$=+12° (methanol, c=1).

The following additional compounds of formula II were also prepared

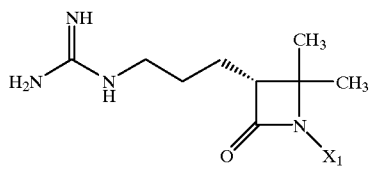

| Ex | $X_1$ | salt | stereochemistry | (M + H)+ |
|---|---|---|---|---|
| 147 | —CH$_2$—O—C$_6$H$_4$—C$_6$H$_5$) | 1.0 CF$_3$CO$_2$H | homochiral | 409 |
| 148 | —SO$_2$—C$_6$H$_4$—C$_6$H$_5$ | 1.0 HCl | homochiral | 415 |

-continued
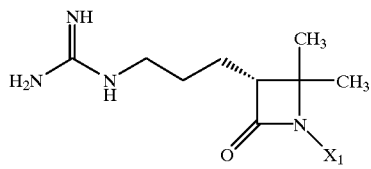
| Ex | X₁ | salt | stereochemistry | (M + H)⁺ |
|---|---|---|---|---|
| 149 | —SO₂—C₆H₄—C(O)—N(piperidine) | 1.0 HCl | homochiral | 450 |
| 150 | —C(O)—CH₂—O—C₆H₅ | 1.0 HCl | homochiral | 333 |
| 151 | —C(O)—CH₂—O—C₆H₄—OH | 1.0 HCl | homochiral | 349 |
| 152 | —C(O)—CH₂—O—(1-naphthyl) | 1.0 HCl | homochiral | 383 |
| 153 | —C(O)—CH₂—O—C₆H₄—O—C₆H₅ | 1.0 HCl | homochiral | 425 |
| 154 | —C(O)—CH₂—O—(2-naphthyl) | — | homochiral | 353 |
| 155 | —C(O)—CH₂—O—CH₃ | 1.0 HCl | homochiral | 270 |
| 156 | —C(O)—CH₂—O—(CH₂)₂—O—(CH₂)₂—O—CH₃ | 1.0 HCl | homochiral | 359 |
| 157 | —C(O)—CH₂—O—C₆H₄—C₆H₅ | 1.0 HCl | homochiral | 409 |

-continued

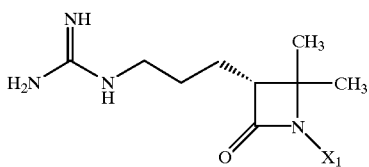

| Ex | X₁ | salt | stereochemistry | (M + H)⁺ |
|---|---|---|---|---|
| 158 | —C(O)—CH₂—O—(biphenyl) | 1.0 CF₃CO₂H | homochiral | 409 |
| 159 | —C(O)—(C₆H₄)—SO₂—N(C₃H₇)₂ | 1.0 HCl | homochiral | 466 |

EXAMPLE 160

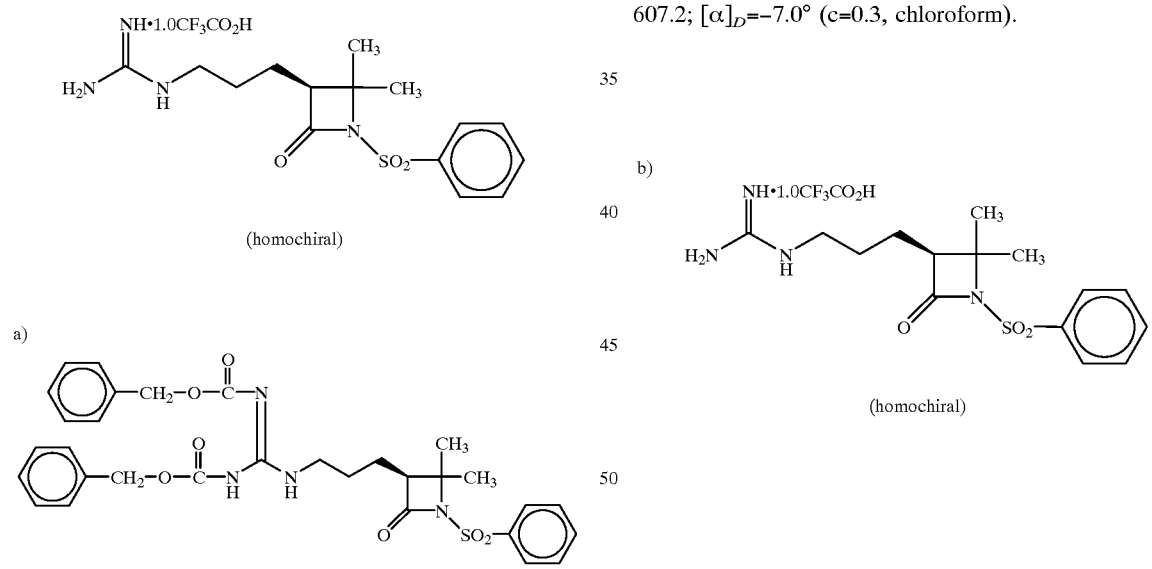

The (−) isomer from Example 146 step (a) (0.163, 0.349 mmol) was dissolved in tetrahydrofuran (2 ml) and cooled to −78° C. Sodium bis (trimethylsilyl) amide (0.52 ml, 0.524 mmol) was added dropwise. The mixture was stirred for 20 minutes. Benzenesulfonyl chloride (93 mg, 0.524 mmol) was added and the reaction mixture was stirred at −78° C. for 1.5 hours followed by stirring at room temperature overnight. The reaction was quenched with 0.5 N potassium bisulfate solution (25 ml) and extracted with ethyl acetate (2×20 ml). The organic phase was washed with brine (1×40 ml) and filtered over sodium sulfate. The filtrate was evaporated to a colorless oil. This was purified by reverse phase preparative HPLC (YMC ODS A 30×250 mm, 5 g column) to give 108 mg of the desired product as an oil; (M+H)⁺= 607.2; $[\alpha]_D$=−7.0° (c=0.3, chloroform).

10% Palladium on carbon catalyst (50 mg) was added to a solution of the product from step (a) (105 mg, 0.173 mmol) in 1,4-dioxane (15 ml) containing 1N HCl (0.21 ml). Hydrogen gas was bubbled through the solution for 1 hour. The reaction mixture was filtered over a pad of Celite® and was washed repeatedly with 1,4-dioxane. The filtrate and washings were combined and evaporated to give a colorless oil (53 mg). This was further purified by reverse phase preparative HPLC (YMC ODS A 20×100 mm, 5 µl, fast elution column) to give 23 mg of the desired product as an oil; (M+H)⁺=339; $[\alpha]_D$=−9.3° (c=0.42, methanol).

The following additional compounds of formula II were also prepared

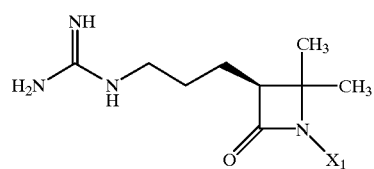

| Ex | $X_1$ | salt | stereochemistry | $(M + H)^+$ |
|---|---|---|---|---|
| 161 | —C(O)—CH$_2$—O—Ph | 1.0 CF$_3$CO$_2$H | homochiral | 333 |

The following additional compounds of formula II were also prepared

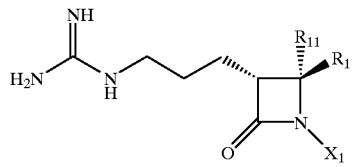

| Ex | $X_1$ | $R_1$ | $R_{11}$ | salt | stereochemistry | $(M + H)^+$ |
|---|---|---|---|---|---|---|
| 162 | —C(O)—NH—Ph | —CO$_2$H | CH$_3$ | — | racemate | 348 |
| 163 | —C(O)—NH—Ph | —CO$_2$CH$_3$ | CH$_3$ | 1.0 HCl | racemate | 362 |

The following additional compounds of formula II were also prepared

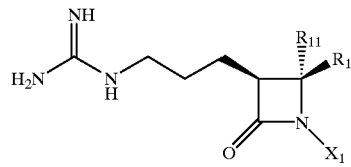

| Ex | $X_1$ | $R_1$ | $R_{11}$ | salt | stereochemistry | $(M + H)^+$ |
|---|---|---|---|---|---|---|
| 164 | —C(O)—NH—Ph | —CO$_2$H | CH$_3$ | 1.0 CF$_3$CO$_2$H | racemate | 348 |

-continued

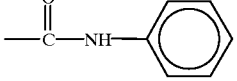

| Ex | X₁ | R₁ | R₁₁ | salt | stereochemistry | (M + H)⁺ |
|---|---|---|---|---|---|---|
| 165 | ![structure: -C(=O)-NH-phenyl] | —CO₂CH₃ | CH₃ | 1.0 HCl | racemate | 362 |

EXAMPLE 166

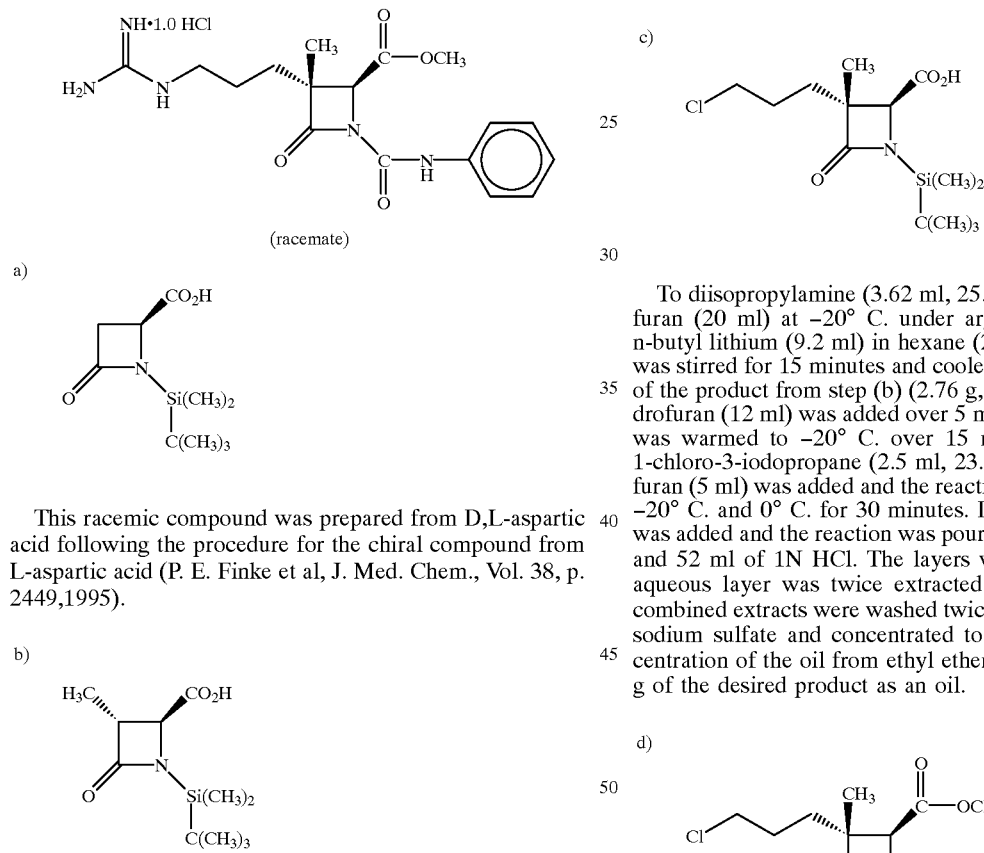

This racemic compound was prepared from D,L-aspartic acid following the procedure for the chiral compound from L-aspartic acid (P. E. Finke et al, J. Med. Chem., Vol. 38, p. 2449,1995).

b)

To diisopropylamine (5.6 ml, 40 mmol) in tetrahydrofuran (30 ml) at −20° C. under argon was added 2.5 M n-butyl lithium (14 ml) in hexane (35 mmol). The mixture was stirred for 15 minutes and cooled to −70° C. A solution of the racemic product from step (a) (4.00 g, 17.4 mmol) in tetrahydrofuran (16 ml) was added over 5 minutes and the reaction was warmed to −20° C. over 15 minutes. A solution of methyl iodide (2.72 ml, 43.7 mmol) in tetrahydrofuran (4 ml) was added and the reaction was stirred between −20° C. and 0° C. for 30 minutes. Dry ethyl ether (50 ml) was added and the reaction was poured into a mixture of ice and 80 ml. of 1N HCl. The layers were separated and the aqueous layer was extracted twice with brine, dried over sodium sulfate and concentrated to an amorphous solid. Treatment with hexane and ethyl acetate gave 2.86 g of the desired product as crystalline material.

c)

To diisopropylamine (3.62 ml, 25.8 mmol) in tetrahydrofuran (20 ml) at −20° C. under argon was added 2.5 M n-butyl lithium (9.2 ml) in hexane (23 mmol). The mixture was stirred for 15 minutes and cooled to −70° C. A solution of the product from step (b) (2.76 g, 11.3 mmol) in tetrahydrofuran (12 ml) was added over 5 minutes and the reaction was warmed to −20° C. over 15 minutes. A solution of 1-chloro-3-iodopropane (2.5 ml, 23.3 mmol) in tetrahydrofuran (5 ml) was added and the reaction was stirred between −20° C. and 0° C. for 30 minutes. Dry ethyl ether (50 ml) was added and the reaction was poured into a mixture of ice and 52 ml of 1N HCl. The layers were separated and the aqueous layer was twice extracted with ethyl ether. The combined extracts were washed twice with brine, dried over sodium sulfate and concentrated to an oil. Repeated concentration of the oil from ethyl ether and hexane gave 3.35 g of the desired product as an oil.

d)

The product from step (c) (1.92 g, 6 mmol) in ethyl ether (30 ml) was reated in an ice-water bath with excess etheral diazomethane until a yellow color persisted. Nitrogen was bubbled through the mixture for 10 minutes and the solution was concentrated. The residual oil was taken up in ethyl ether and the solution was washed with cold dilute potassium bisulfate and then brine (twice), dried over sodium sulfate and concentrated to give 2.046 g of the desired product as an oil.

e)

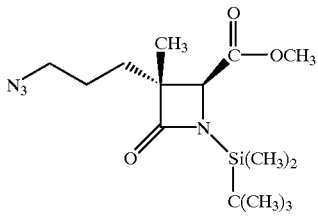

A mixture of the product from step (d) (2.95 g, 8.83 mmol), sodium azide (2.44 g, 35.3 mmol) and tetrabutylammonium iodide (2.45 g, 6.64 mmol) in dimethylformamide (12 ml) was stirred at 60° C. under argon for 16 hours. This material was combined with a second reaction mixture obtained from the product from step (d) (334 mg, 1 mmol). The dimethylformamide was removed in vacuo and the residue was taken up in ethyl acetate and dilute aqeuous lithium chloride. The ethyl acetate layer was washed again with dilute lithium chloride and then brine (twice), dried over sodium sulfate, and concentrated to give 3.53 g of the desired product as a crude viscous oil.

f)

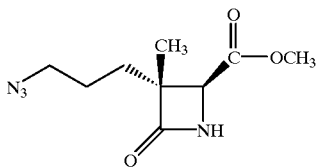

A solution of the product from step (e) (3.53 g) in tetrahydrofuran (30 ml), acetic acid (1.2 ml), and 1.0M tetrabutylammonium fluoride (20 ml) in tetrahydrofuran was stirred at room temperature for 2 hours and then concentrated to a residue which was taken up in ethyl acetate and brine. After extracting, the ethyl acetate layer was washed with brine (twice), dried and sodium sulfate, and concentrated to an oil (9.33 g). Chromatography of this oil over 200 g of silica gel using ethyl acetate:hexanes (7:3) gave 2.1 g of the desired product as an oil.

g)

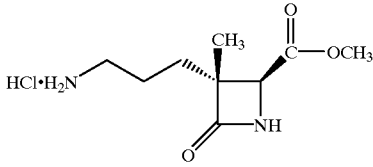

The product from step (f) (678 mg, 3 mmol) was hydrogenated in 20 ml of dioxane and 3.0 ml of aqueous 1M HCl in the presence of 10% palladium on carbon catalyst (237 mg) for 2 hours. After filtration using aqueous dioxane and concentration of the filtrate, the residue was concentrated from dioxane repeatedly to give 974 mg of the desired product as a crude thick gum.

h)

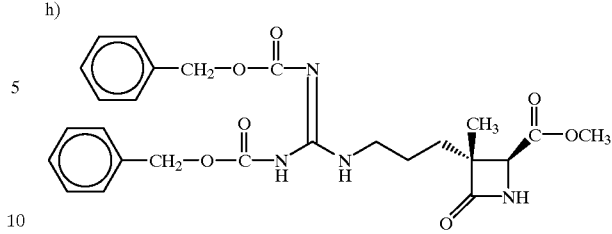

To a solution of the product from step (g) (945 mg) in dry methanol (7 ml) and dry dimethyl ether (7 ml) under argon was added sequentially N,N'-dicarbobenzyloxy—S-methylisothiourea (1.61, 4.5 mmol), triethylamine (1.5 ml, 10.7 mmol) and mercuric chloride (1.22 g, 4.5 mmol). The reaction was stirred at room temperature for 2 hours and the filtered through Celite® using ethyl acetate. Concentration of the filtrate gave a residue which was taken up in ethyl acetate and dilute potassium bisulfate. After two extractions with ethyl acetate, the combined ethyl acetate extracts were washed with brine (twice), dried over sodium sulfate, and concentrated to an oil (2.25 g). Purification by chromatography over silica gel (150 g) using ethyl acetate:hexanes (6:4) gave 1.03 g of the desired product as an oily residue.

i)

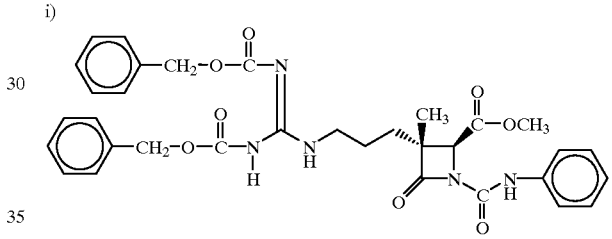

To the product from step (h) (582 mg, 1.14 mmol), previously dried by azetroping from tetrahydrofuran and toluene, in tetrahydrofuran (8 ml) at −78° C. under argon was added 1.0 M sodium bis(trimethylsilyl)amide (1.5 ml, 1.5 mmol). The mixture was stirred for 15 minutes and then phenylisocyanate (150 µl, 1.38 mmol) was added. The reaction was warmed to 0° C. over 30 minutes and poured into 8 ml of 10% potassium bisulfate and water. After extraction with ethyl acetate (3 times), the combined ethyl acetate extract was washed with water (twice), dried over sodium sulfate, and concentrated to a viscous oil (0.78 g). Purification by chromatography (silica gel, 60 g) using ethyl acetate:hexanes (35:65) gave 656 mg of the desired product as an oily residue.

j)

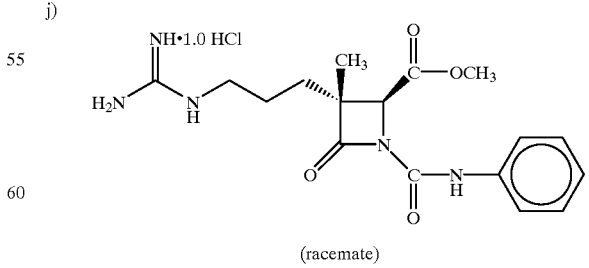

(racemate)

The product from step (i) (636 mg, 1.01 mmol) was hydrogenated in 12 ml of dioxane and 1.0 ml of 1N HCl (1 mmol) in the presence of 10% palladium on carbon catalyst (223 mg) at 1 atmosphere of hydrogen for 2 hours. After filtration using aqueous dioxane, the filtrate was concentrated to a residue which was lyophilized from aqueous acetonitrile to give 336 mg of the desired product as a white hydroscopic solid; IR(KBr) 1775 cm$^{-1}$; (M+H)+=362.

The following additional compounds of formula II were also prepared

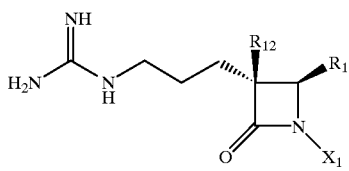

| Ex | $X_1$ | $R_1$ | $R_{12}$ | salt | stereochemistry | $(M + H)^+$ |
|---|---|---|---|---|---|---|
| 167 | —C(O)—NH—Ph | —C(O)—N(piperidine) | $CH_3$ | 1.0 HCl | racemate | 415 |

EXAMPLE 168

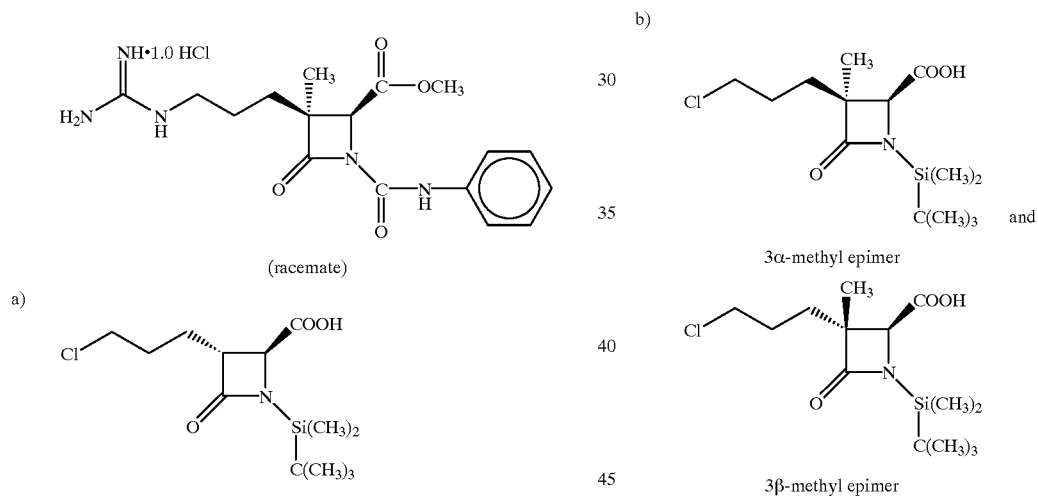

a) To diisopropylamine (8.9 ml, 63.5 mmol) in tetrahydrofuran (50 ml) at −20° C. under argon was added 22.6 ml of 2.5 M n-butyl lithium in hexane (56.6 mmol). The mixture was stirred for 15 minutes and cooled to −70° C. A solution of the racemic compound from Example 166 part (a) (6.49 g, 28.3 mmol) in tetrahydrofuran (30 ml) was added over 5 minutes and the reaction was warmed to −20° C. over 15 minutes. A solution of 1-chloro-3-iodopropane (6.3 ml, 58.7 mmol) in tetrahydrofuran (10 ml) was added and the reaction was stirred between −20° C. and 0° C. for 30 minutes. Dry ethyl ether (125 ml) was added and the reaction was poured into a mixture of ice, 1N HCl (130 ml), and ethyl ether. After separation, the aqueous layer was extracted with ethyl ether (twice). The combined ethyl ether extract was washed with brine (twice), dried over sodium sulfate, and concentrated to an oil, which was concentrated from hexanes (5×) to give 7.61 g of the desired product as an oil.

b) To diisopropylamine (4.7 ml, 33.5 mmol) in tetrahydrofuran (25 ml) at −20° C. under argon was added 12 ml of 2.5 M n-butyl lithium in hexane (30 mmol). The mixture was stirred for 15 minutes and cooled to −70° C. A solution of the product from step (a) (4.50 g, 14.7 mmol), previously dried by azetroping from toluene and tetrahydrofuran, in tetrahydrofuran (20 ml) was added over 5 minutes and the reaction was warmed to −20° C. over 15 minutes. A solution of methyl iodide (1.90 ml, 30.5 mmol) in tetrahydrofuran (6 ml) was added and the reaction was stirred between −20° C. and 0° C. for 30 minutes. Dry ethyl ether (70 ml) was added and the reaction was poured into a mixture of ice, 1N HCl (66 ml), and ethyl ether. After separation, the aqueous layer was extracted with ethyl ether (twice). The extracts were combined, washed with brine (twice), dried over sodium sulfate, and concentrated to an oil, which was concentrated from hexanes (5×) to give 4.60 g of an oil consisting of the 3α-methyl epimer and the corresponding 3β-methyl epimer in a ratio of 4:1.

c)

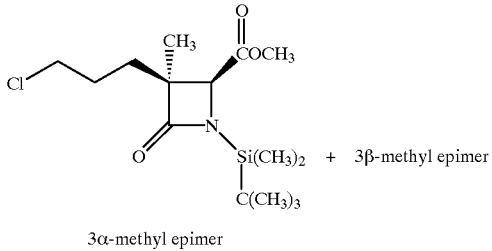

3α-methyl epimer

Treatment of the product mixture from part (b) (1.24 g) with diazomethane according to the procedure of Example 166 step (d) gave 1.36 g of an oil consisting of the 3α-methyl epimer and the corresponding 3β-methyl epimer in a ratio of 4:1.

d)

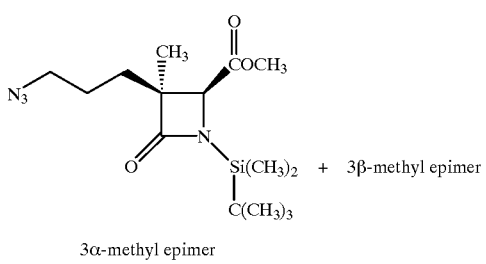

3α-methyl epimer

Treatment of the product mixture from part (c) (1.35 g) with sodium azide and tetrabutylammonium iodide in dimethylformamide according to the procedure of Example 166 step (e) gave 1.21 g of a crude oil containing the 3α-methyl and 3β-methyl epimers.

e)

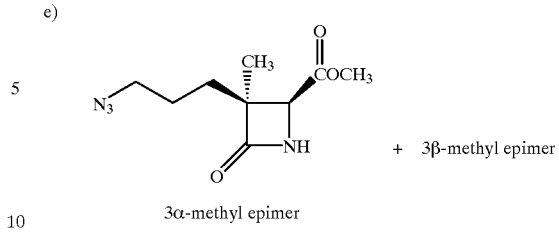

3α-methyl epimer

Treatment of the crude product mixture from part (d) (1.21 g) in tetrahydrofuran (10 ml) with 5.0 ml of 1.0 M tetrabutylammonium fluoride in tetrahydrofuran and acetic acid (0.3 ml) according to the procedure of Example 166 step (f) gave, after chromatography on 100 g of silica gel using ethyl acetate:hexanes (1:1), 343 mg of an oil consisting of the 3α-methyl epimer and the corresponding 3β-methyl epimer in a ratio of (86:14). An additional 256 mg of the mixture was obtained in the chromatography.

f)

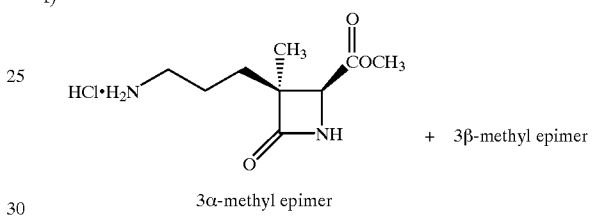

3α-methyl epimer

Hydrogenation of the product mixture from part (e) (335 mg) as described in Example 166 step (g) and concentration of the product from dioxane gave 469 mg of the crude product mixture as a gummy residue.

g)

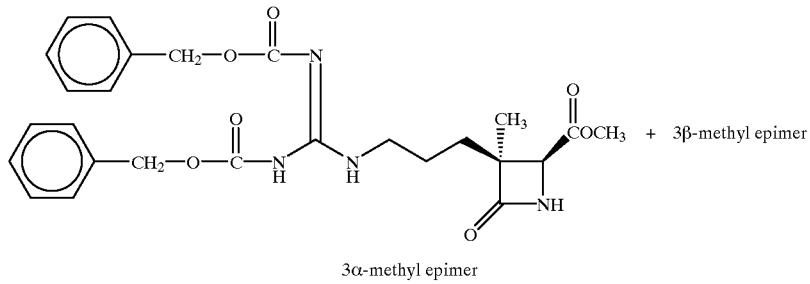

3α-methyl epimer

Treatment of the crude product mixture from part (f) (460 mg) with N,N'-dicarbobenzyloxy—S-methylisothiourea and mercuric chloride as described in Example 166 step (h) gave, after chromatography over 75 g of silica gel using ethyl acetate:hexanes (6:4), 541 mg of a gummy residue consisting of the 3α-methyl epimer and the corresponding 3β-methyl epimer in a ratio of (86:14).

h)

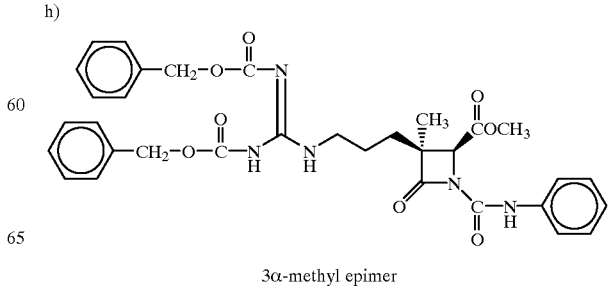

3α-methyl epimer and the 3β-methyl epimer

Treatment of the product mixture from part (g) (500 mg) with sodium bis(trimethylsilyl) azide and phenylisocyanate as described in Example 166 step (i) gave, after chromatography over 50 g of silica gel using ethyl acetate:hexanes (35:65), 525 mg of gummy residue consisting of 3α-methyl epimer and the corresponding 3β-methyl epimer in a ratio of (86:14).

i)

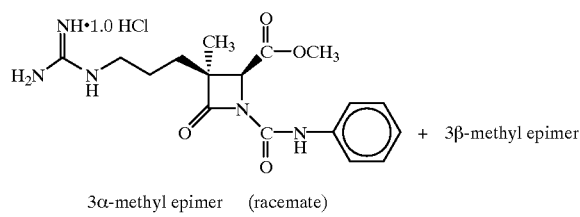

3α-methyl epimer    (racemate)    + 3β-methyl epimer

The product mixture from part (h) (457 mg) was hydrogenated in 9 ml of dioxane and 0.73 ml of 1.0N HCl in the presence of 10% palladium on carbon catalyst (160 mg) at 1 atmosphere for 2 hours. After filtration using aqueous dioxane, the filtrate was concentrated to a residue which was lyophilized from aqueous acetonitrile to give 249 mg of a white hydroscopic solid consisting of 3α-methyl epimer and the corresponding 3β-methyl epimer in a ratio of (88:12); IR(KBr) 1775 cm$^{-1}$; (M+H)$^+$=362.

The following additional compounds of formula III were also prepared

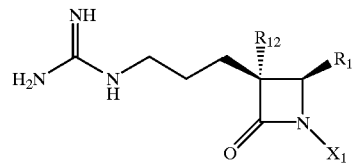

| Ex | $X_1$ | $R_1$ | $R_{12}$ | salt | stereochemistry | (M + H)$^+$ |
|---|---|---|---|---|---|---|
| 169 | —C(O)—NH—C₆H₅ | —C(O)—N(piperidine) | CH₃ | 1.0 HCl | racemate | 415 |
| 170 | —C(O)—NH—C₆H₅ | —CO₂H | CH₃ | — | racemate | 348 |

EXAMPLE 171

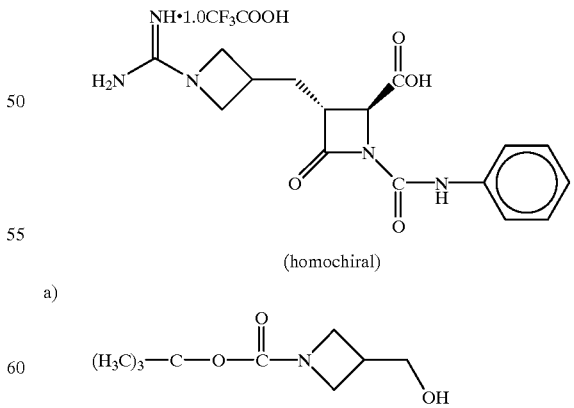

(homochiral)

a)

(H₃C)₃—C—O—C(O)—N⟨azetidine⟩—CH₂OH

The azetidine carboxylic acid

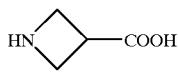

was prepared from epichlorohydrin according to the procedure of A. G. Anderson Jr. and R. Lok, J. Org. Chem., Vol. 37, p. 3953, (1972). This azetidine carboxylic acid was then converted to the desired product according to the procedure of T. L. Hansen et al., WO97/23508.

b)

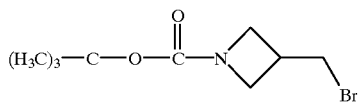

A solution of triphenylphosphine (1.57 g, 6 mmol) in methylene chloride (6 ml) was added dropwise to a stirred solution of the product from part (a) (936 mg, 5 mmol) and carbon tetrabromide (2.32 g, 7 mmol) in methylene chloride 910 ml) at 0° C. under argon. The reaction was then stirred at room temperature for 16 hours. The reaction was concentrated in vacuo and the residue was triturated with ethyl ether. Filtration and evaporation of the filtrate gave 3.34 g of an oily residue which was chromatographed over silica gel by eluting with methylene chloride and then methylene chloride:ethyl acetate (19:1) to give 1.02 g of the desired product as an oily residue.

c)

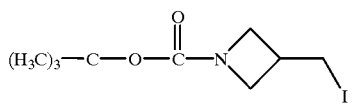

A mixture of the product from part (b) (1.00 g, 4 mmol) and sodium iodide (1.80 g, 12 mmol) in dry acetonitrile (10 ml) under argon was stirred at 65° C. for 2.5 hours, cooled to room temperature and concentrated in vacuo. The residue was taken up in ethyl acetate and water and the ethyl acetate layer was washed with water (twice), dilute sodium thiosulfate, and water (twice), dried over sodium sulfate, and concentrated to give 1.18 g of the desired product as an oily residue.

d)

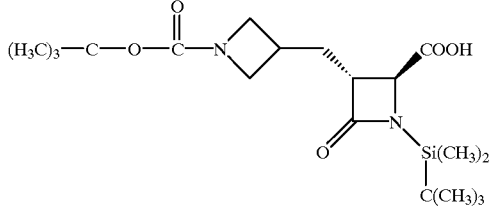

To diisopropylamine (0.63 ml, 4.5 mmol) in tetrahydrofuran (3.5 ml) at −20° C. under argon was added 1.6 ml of 2.5 M n-butyl lithium in hexane (4 mmol). The mixture was stirred for 15 minutes and cooled to −70° C. A solution of (4S)-N-(t-butyldimethylsilyl) azetidine-2-one-4-carboxylic acid (459 mg, 2.0 mmol) [Baldwin et al, Tetrahedron, Vol. 46, p. 4733–4748, 1990] in tetrahydrofuran (2.5 ml) was added over 3 minutes and the reaction was warmed to −20° C. over 15 minutes. A solution of the product from part (c) (1.19 g, 4 mmol) in tetrahydrofuran (3 ml) was added and the reaction was stirred between −20° C. and −30° C. for 1.5 hours and then at −20° C. for 16 hours. The reaction was warmed to 0° C. and quenched by the addition of 5% potassium bisulfate and then ethyl acetate. After extraction with ethyl acetate (three times), the ethyl acetate extracts were combined, washed with brine, dried over sodium sulfate, and concentrated to an oily residue. The residue was dissolved in ethyl ether and washed with saturated sodium bicarbonate (twice). The combined sodium bicarbonate extract was washed with ethyl ether and then layered with ethyl acetate. The pH was adjusted to 2.2 (10% potassium bisulfate) and after extraction with ethyl acetate (three times), the acidic ethyl acetate extract was washed with brine, dried over sodium sulfate, and concentrated to give 624 mg of the desired product as a crude oil.

e)

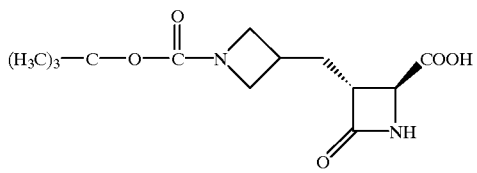

To the crude product from part (d) in tetrahydrofuran (3 ml) at 0–5° C. under nitrogen was added 2.7 ml of 1M tetrabutylammonium fluoride in tetrahydrofuran. The reaction was stirred for 1.5 hours at room temperature and then the solvent was removed in vacuo and the residue was taken up in ethyl acetate, water and 10% potassium bisulfate (11 ml). After extraction with ethyl acetate (three times), the extracts were combined, washed with small amounts of water (twice), and brine, dried over sodium sulfate, and concentrated to give 470 mg of crude desired product as an amorphous residue.

f)

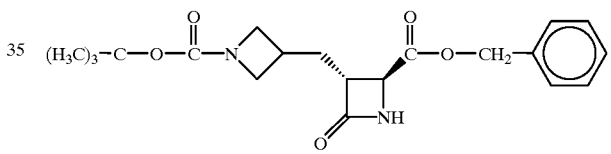

A solution of the product from part (e) (466 mg), benzyl bromide (0.84 ml, 7.1 mmol) and sodium bicarbonate (239 mg, 2.84 mmol) in dry dimethylformamide (4 ml) was stirred at room temperature under nitrogen for 16 hours. The reaction was diluted with ethyl acetate and water, and the aqueous layer was extracted with ethyl acetate (twice). The ethyl acetate extracts were combined, and washed with dilute potassium bisulfate, water (twice) and brine, dried over sodium sulfate, and concentrated to give 563 mg of an oil. This oil was chromatographed over silica gel by eluting with methylene chloride and then methylene chloride:ethyl acetate (1:1) to give 407 mg of the desired product as an amorphous residue.

g)

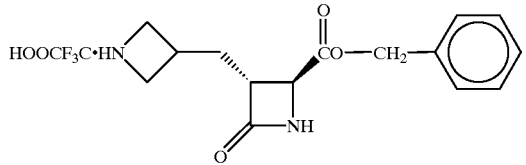

Trifluoroacetic acid (1 ml) was added to a stirred solution of the product from step (f) (300 mg, 0.80 mmol) in methylene chloride (3 ml) at 0–5° C. After 5 minutes, the reaction was stirred at room temperature for 1 hour and then h)

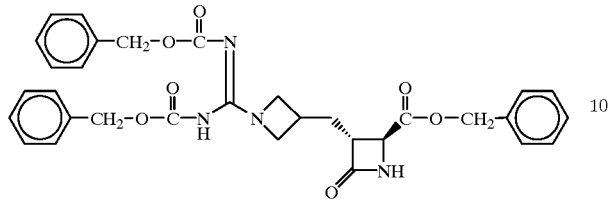

To a solution of the product from part (g) (0.80 mmol) in dry dimethylformamide (3 ml) under argon was added sequentially N,N'-dicarbobenzyloxy-S-methylisothiourea (430 mg, 1.20 mmol), triethylamine (0.45 ml, 3.23 mmol), and mercuric chloride (326 mg, 1.20 mmol). The reaction was stirred at room temperature for 2.5 hours and then filtered through Celite® using ethyl acetate. The filtrate was washed with dilute aqueous potassium bisulfate (twice) and brine, dried over sodium sulfate, and concentrated to an oily residue (767 mg). Purification by chromatography over silica gel eluting with methylene chloride:ethyl acetate (6:4) and methylene chloride: ethyl acetate (3:7) gave 342 mg of the desired product as an oily residue.

i)

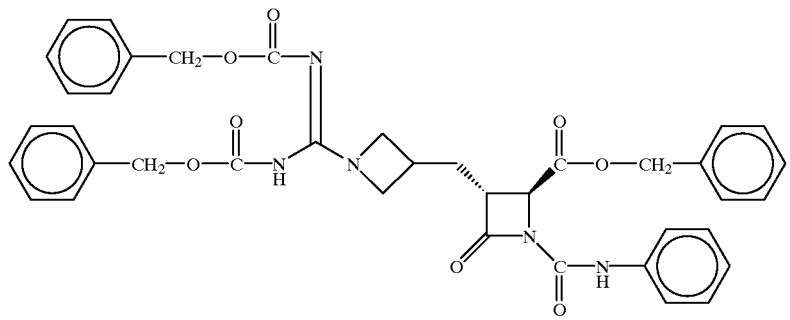

To the product from part (h) (136 mg, 0.23 mmol), previously dried by azetroping from tetrahydrofuran and toluene, in tetrahydrofuran (2 ml) at −78° C. under argon was added 0.30 ml of 1.0M sodium bis(trimethylsilyl)amide (0.30 mmol). The mixture was stirred for 10 minutes and then phenylisocyanate (31 µl, 0.28 mmol) was added. The reaction was warmed to 0° C. over 40 minutes and poured into 2 ml of 10% potassium bisulfate and water. After extraction with ethyl acetate (three times), the ethyl acetate extracts were combined, washed with water (three times), dried over sodium sulfate, and concentrated to give 193 mg of an oil. Purification by chromatography over silica gel eluting with methylene chloride:ethyl acetate (98:2) and then methylene chloride:ethyl acetate (95:5) gave 121 mg of the desired product as an oily residue.

j)

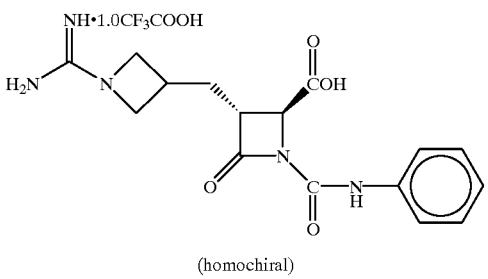

(homochiral)

The product from part (i) (115 mg, 0.163 mmol) was hydrogenated in dioxane (4 ml) and 1.00N HCl (163 µl, 0.163 mmol) in the presence of 10% palladium on carbon catalyst (35 mg) at 1 atmosphere for 1 hour. After filtration using aqueous dioxane, the filtrate was concentrated to a residue. This residue was lyophilized from aqueous dioxane to give 89 mg of crude product. Purification by preparative HPLC [YMC S5 ODS 30×250 mm, 25 ml/min, using a gradient (10–40%) of solvent A (10% methanol+90% water+0.1% trifluoroacetic acid) and solvent B (90% methanol+10% water+0.1% trifluoroacetic acid)] gave after lyophilization 31 mg of desired product as a white hydroscopic solid, IR (KBr) 1780 cm$^{-1}$; (M+H)+=346.

EXAMPLE 172

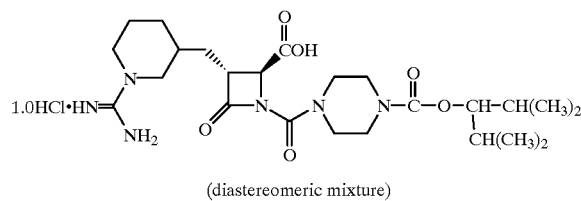

(diastereomeric mixture)

a)

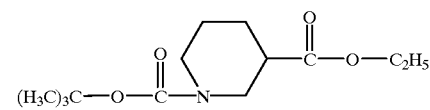

Di-tert-butyl dicarbonate (10.9 g, 50 mmol) was slowly added to a stirred solution of ethyl nipecotate (6.2 ml, 40 mmol) and N,N-diisopropylethylamine (7.0 ml, 40 mmol) in methylene chloride (80 ml) at 0° C. under argon. The cooling bath was removed, dimethylaminopyridine (0.49 g, 4 mmol) was added, and the reaction was stirred overnight at room temperature. The reaction was concentrated in vacuo and the residue was taken up in ethyl acetate. The ethyl acetate was washed with dilute HCl(2×) and brine (2×), dried over magnesium sulfate and concentrated to an oil, which was pased through a column of silica gel using hexanes-ethyl acetate (8:2) to provide 10.2 g of the desired product as a colorless oil.

b)

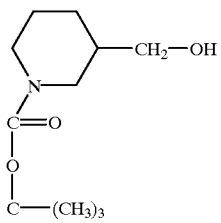

A solution of 1M lithium aluminum hydride in tetrahydrofuran (40.4 ml, 40.4 mmol) was added over 10 minutes to a stirred solution of the product from part (a) (9.92 g, 38.5 mmol) in tetrahydrofuran (120 ml) at 0° C. under argon. After 45 minutes, the ice water cooled reaction was decomposed by the cautious dropwise addition of 5N sodium hydroxide (10 ml). The mixture was stirred for 10 minutes and the semigranular mixture was filtered. The filtrate was concentrated to an oil, which was taken up in ether. The ether was washed with brine, dried over sodium sulfate and concentrated to an oil, which solidified in vacuo to give 7.73 g of the desired product.

c)

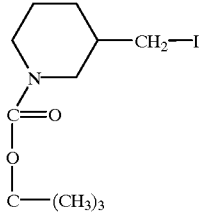

A solution of the product from part (b) (4.1 g, 20 mmol) in 30 ml of methylene chloride was added over 10 minutes to a stirred solution of triphenylphosphine (7.34 g, 28 mmol), imidazole (1.91 g, 28 mmol) and iodine (7.1 g, 28 mmol) in 70 ml of methylene chloride at 0° C. under argon. The cooling bath was removed and the reaction was stirred at room at room temperature for 1 hour and filtered. Concentration of the filtrate gave an oil which was stirred with ethyl acetate for 15 minutes. After filtration, the filtrate was washed with 5% sodium thiosulfate (3×) and then brine, dried over magnesium sulfate, and concentrated to give 11.4 g of crude product, which was chromatographed over silica gel using methylene chloride to afford 6.1 g of the desired product as a colorless oil.

d)

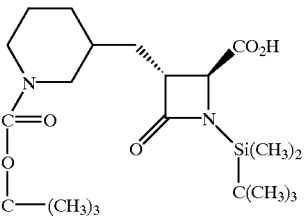

Reaction of (4S)-N-(t-butyldimethylsilyl)azetidine-2-one-4-carboxylic acid (1.15 g, 5 mmol) and the product from part (c) (3.25 g, 10 mmol) according to the procedure of Example 171 step (d) gave 1.98 g of the crude desired product as a foam.

e)

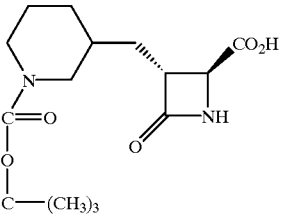

Treatment of the product from part (d) (1.98 g) with tetra-butylammonium fluoride in tetrahydrofuran according to the procedure of Example 171 step (e) gave 1.64 of the crude desired product as an oil.

f)

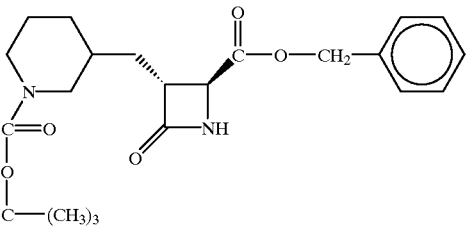

Treatment of the product from part (e) (1.64 g) with benzyl bromide according to the procedure of Example 171 step (f) gave 1.23 g of the desired product as an oil after silica gel chromatography by eluting with methylene chloride and then methylene chloride/ethyl acetate (6:4).

g)

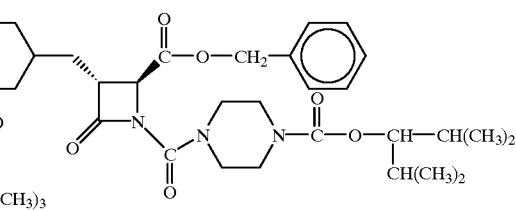

A solution of the product from part (f) (402 mg, 1 mmol), triethylamine (0.28 ml, 2.0 mmol), 1-diisopropylmethoxycarbonyl-piperazine-4-carbonylchloride (436 mg, 1.50 mmol) and dimethylaminopyridine (31 mg, 0.25 mmol) in methylene chloride (4.5 ml) was stirred at room temperature under argon for 8 hours and stored at 0° C. overnight. The reaction was concentrated in vacuo and the residue was taken up in ethyl acetate, 10% potassium bisulfate (4 ml) and water. The ethyl acetate layer was washed again with dilute potassium bisulfate, water (2×), and brine, dried over sodium sulfate and concentrated to a viscous oil (779 mg). Chromatography of the oil over silica gel using 10% and then 20% ethyl acetate in methylene chloride provided 618 mg of the desired product as an oil.

h)

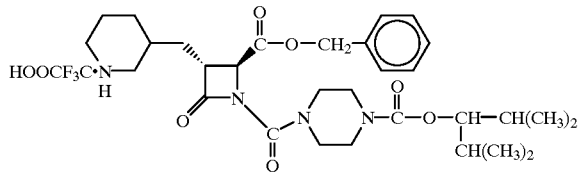

i)

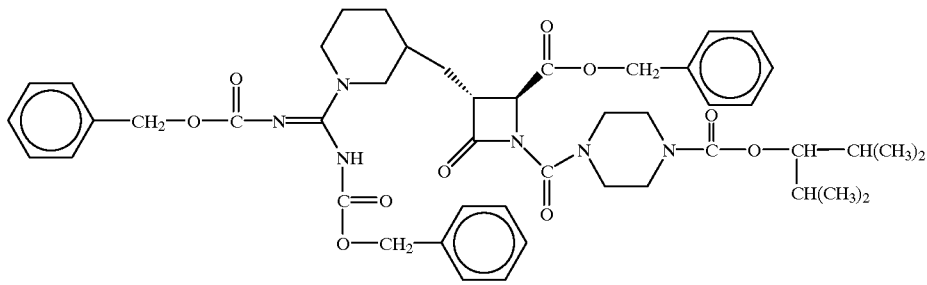

Trifluoroacetic acid (0.75 ml) was added to a stirred solution of the product from part (g) (436 mg, 0.66 mmol) in methylene chloride (3 ml) at 0–5° C. After 5 minutes, the reaction was stirred at room temperature for 2 hours and concentrated in vacuo to a residue, which was further concentrated from methylene chloride (5x) and then chloroform (2x) to give 648 mg of compound of the desired product as an oil.

To a solution of the product from part (h) (0.25 ml) in dimethylformamide (1.5 ml) under argon were added sequentially N,N'-dicarbobenzyloxy-S-methylisothiourea (136 mg, 0.38 mmol), triethylamine (0.21 ml, 1.5 mmol) and mercuric chloride (103 mg, 0.38 mmol). The reaction was stirred at room temperature for 3 hours, diluted with ethyl acetate and filtered through Celite. The filtrate was washed with dilute aqueous potassium bisulfate (2x) and brine (2x), dried over sodium sulfate and concentrated to an oil (280 mg), which was purified by chromatography over silica gel by eluting with 15% and then 20% ethyl acetate in methylene chloride to give 146 mg of the desired product as an oily residue.

j)

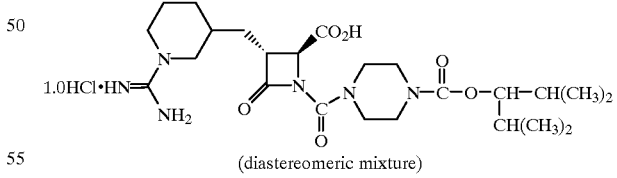

(diastereomeric mixture)

The product from part (i) (141 mg, 0.163 mmol) was hydrogenated in dioxane (5 ml) and 1.0 N HCl (0.163 mmol) in the presence of 10% palladium on carbon catalyst (42 mg) at 1 atmosphere for 1 hour. After filtration using aqueous dioxane, the filtrate was concentrated to remove dioxane, filtered, and lyophilized to give 47 mg of the desired product as a white solid; IR(KBr) 1787 cm⁻, consisting of a mixture (52:48) of diastereomers as determined by HPLC.

The following additional compounds of formula I were also prepared

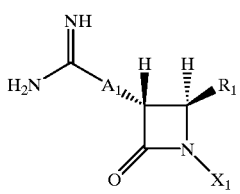

| Ex | —A₁— | X₁ | R₁ | salt | stereo-chemistry | (M + H)⁺ |
|---|---|---|---|---|---|---|
| 173 | azetidinyl-CH₂ | -C(O)-N(piperazine)-C(O)-O-CH(CH(CH₃)₂)-CH(CH₃)₂ | —CO₂H | — | homochiral | 481 |
| 174 | piperidinyl-CH₂ | -C(O)-NH-CH(CH₃)-(1-naphthyl) | —CO₂H | 1.0 HCl | homochiral | 452 |
| 175 | piperidinyl-CH₂ | -C(O)-NH-phenyl | —CO₂H | 1.0 HCl | homochiral | 374 |
| 176 | piperidinyl-CH₂ | -C(O)-NH-phenyl | —(CH₂)₂-phenyl | 1.0 HCl | racemate | 434 |
| 177 | pyrrolidinyl-CH₂ | -C(O)-N(piperazine)-C(O)-O-CH(CH(CH₃)₂)-CH(CH₃)₂ | —CO₂H | 1.0 HCl | diastereomeric mixture | 495 |

EXAMPLE 178

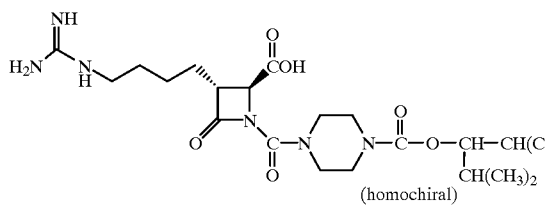
(homochiral)

a)

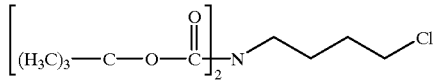

To a solution of di(tert-butoxycarbonyl)amine (2.17 g, 10 mmol) in dimethylformamide (40 ml) at 0° C. was added 6.8 g of a solution of potassium tert-butylamylate in toluene. The addition was carried out very slowly over 30 minutes. After stirring for one hour at 0° C., 1-chloro-4-iodobutane (2.18 g, 10 mmol) was added dropwise and stirring was continued for 2 more hours. Water (20 ml) and hexane (20 ml) were added for the work-up. The aqueous layer was extracted with additional hexane (3×20 ml). The combined organic layer was washed with 1.0 N ice cold sodium hydroxide, saturated sodium phosphate, monobasic solution, and finally brine. After drying over sodium sulfate and evaporation, 2.76 g of the desired product was obtained as a light yellow oil.

b)

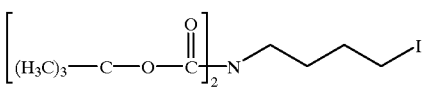

To a solution of the product from part (a) (4.5 g, 15 mmol) in acetone (60 ml) were added sodium iodide (7.3 g, 49 mmol) and sodium bicarbonate (12 mmol). The reaction was refluxed at 60° C. for 12 hours.

At that time, additional sodium iodide (2 g) and acetone (30 ml) were added and refluxing was continued for another 8 hours. Evaporation and extraction of the residue (oil and solid) with hexane (5×30 ml) and washing of the combined extraction solutions with 2.0 N sodium sulfite and brine, and drying over sodium sulfate yielded after concentration 5.02 g of the desired product as a yellow oil.

c)

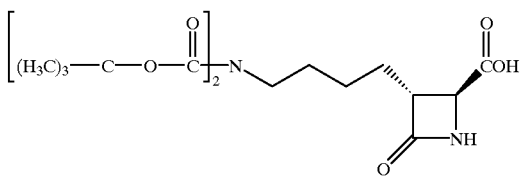

(4S)-N-(tert-Butyldimethylsilyl)azetidine-2-one-4-carboxylic acid (2.30 g, 10 mmol) [Baldwin et al., Tetrahedron, Vol. 46, p. 4733–4748, 1990] dissolved in tetrahydrofuran (10 ml) was added dropwise over 20 minutes to a solution of lithium diisopropylamide (21 mmol) in tetrahydrofuran (60 ml) at −50° C. After the addition was completed, the temperature was allowed to rise to −20° C. at which time a solution of the product from part (b) (4.80 g, 12 mmol) dissolved in tetrahydrofuran (10 ml) was added dropwise. Stirring was continued for 2 hours at −20° C. after the addition was completed. After warminig to 0° C., water (100 ml) was added and the pH was adjusted to 12.5 by the addition of 1.0 N sodium sulfate solution. After stirring for 1 hour at 0° C. the reaction solution was extracted with hexane (50 ml). The aqueous layer was adjusted to pH 3 with 6.0 N HCl and extracted with ethyl acetate (150 ml). The organic phase was washed with brine and dried to give 4.13 g of the desired product as a colorless oil.

d)

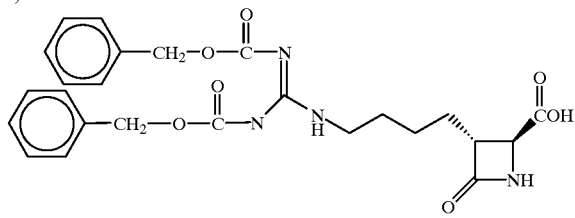

Trifluoroacetic acid (25 ml) was slowly added to the product from part (c) (2.5 g, 5 mmol) dissolved in methyle chloride (50 ml) at 0° C. After stirring for 30 minutes and evaporation, toluene (20 ml) was added to the oily residue. The toluene was evaporated again to remove excess trifluoroacetic acid and give 1.6 g of

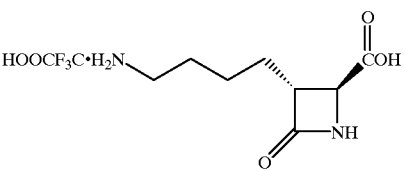

which was used for the next step without purification.

The above trifluoroacetic acid salt (1.6 g) was dissolved in methanol (30 ml) and after cooling to −5° C. the pH was adjusted to 8.5 by adding triethylamine (0.7 ml) followed by N,N'-dicarbobenzyloxy-S-methylisothiourea (2 g, 5.5 mmol). The reaction was stirred for 12 hours at room temperature. The methanol was stripped off in vacuo an the oily residue was taken up in ethyl acetate (20 ml) and water (10 ml). After cooling to 0° C., the pH was adjusted to 3.0 with 2.0 N sodium bisulfate solution. The layers were separated, and the aqueous layer was extracted with ethyl acetate (2×20 ml). The combined organic layer was washed with brine and extracted with an ice cold saturated sodium bicarbonate solution (3×20 ml). After cooling to 0° C., the aqueous phase was acidified with concentrated HCl to a pH of 3.2 and reextracted with ethyl acetate (3×20 ml). The combined organic layers were washed with brine, dried over sodium sulfate, and concentrated to give 1.95 g of the desired product as a colorless oil.

e)

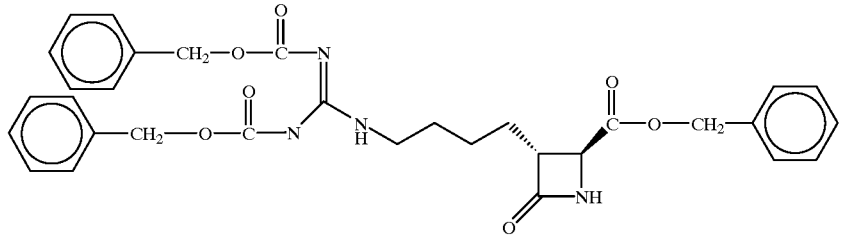

The product from part (d) (497 mg, 1.0 mmol) was dissolved in tetrahydrofuran (5 ml) and butanol (155 μl, 1.5 mmol), dicyclohexylcarbodiimide (210 mg, 1.0 mmol), 4-dimethylaminopyridine (10 mg) and hydroxybenzotriazole (20 mg) were added with stirring. After stirring for 6 hours at room temperature, methylene chloride (5 ml) was added. After filtration, the filtrate was concentrated in vacuo to give 570 mg of crude product as a colorless oil. Purification by flash chromatography on silica gel eluting with ethyl acetate/hexane gave 495 mg of the desired product; IR (KBr) 1745 cm$^{-1}$.

f)
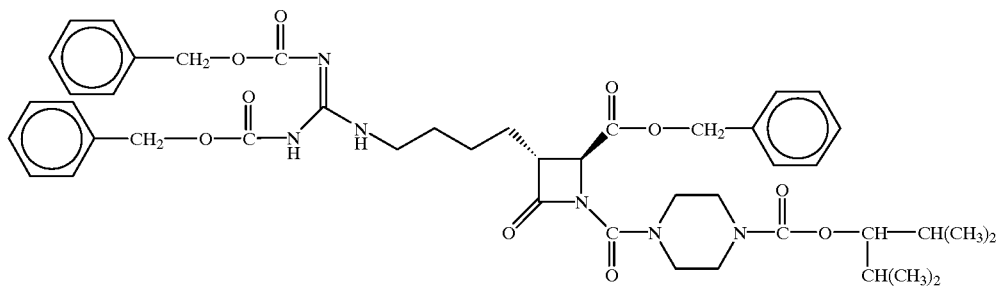

The product from part (e) (295 mg, 0.5 mmol) was dissolved in methylene chloride (7 ml). After the addition of diisopropylamine (194 mg, 1.5 mmol), 1-diisopropylmethoxycarbonylpiperazine-4-carbonylchloride (218 mg, 0.75 mmol) and dimethylaminopyridine (10 mg), the reaction solution was stirred overnight at room temperature. Additional 1-diisopropylmethoxycarbonylpiperazine-4-carbonylchloride (20 mg) was added and stirring was continued for 4 hours. The reaction was quenched with 10 ml of ice water (pH was adjusted to 4 with potassium sulfate solution) and ethyl acetate. The aqueous layer was extracted with ethyl acetate (2×10 ml) and the combined organic layer was washed with brine, dried over magnesium sulfate, and concentrated in vacuo. The resulting colorless oily residue was purified by flash chromatography over silica gel eluting with ethyl acetate:hexanes (4:6) to give 392 mg of the desired product; IR(KBr) 1790 cm$^{-1}$.

g)
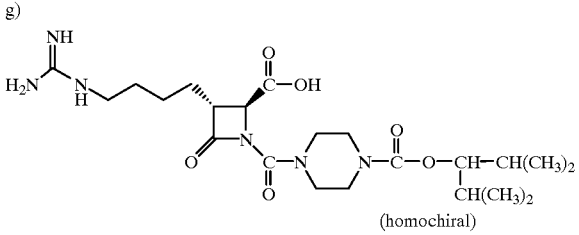
(homochiral)

A mixture of the product from part (f) (96 mg, 0.11 mmol, 1N HCl (110 µl, 0.11 mmol), 10% palladium on carbon catalyst (37 mg) in dioxane (2.5 ml) was stirred under a hydrogen atmosphere (hydrogen balloon) at room temperature for 1 hour. The reaction was filtered through a Celite® cake, passed through a polyvinylpyrrolidone resin column, and lyophilized to give 44 mg of the desired product as a white fluffy powder; IR (KBr) 1780 cm$^{-1}$, 1669 cm$^{-1}$; (M+H)+=483.3, (M−H)−=481.

In addition to the compounds prepared by Han in U.S. Pat. No. 5,037,819, the following compounds of formula VI were prepared

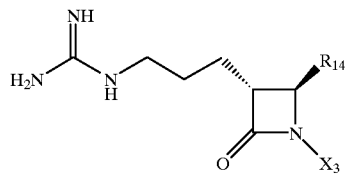

| Ex | X$_3$ | R$_{14}$ | salt | stereochemistry | (M + H)$^+$ |
|---|---|---|---|---|---|
| 179 | —C(O)—C$_6$H$_5$ | —CO$_2$H | 1.0 CF$_3$CO$_2$H | homochiral | 319 |
| 180 | —C(O)—NH—C$_6$H$_5$ | —CO$_2$H | 1.0 HCl | homochiral | 334 |
| 181 | —C(O)—NH—C$_6$H$_5$ | —CO$_2$CH$_3$ | 1.0 HCl | homochiral | 348 |

-continued

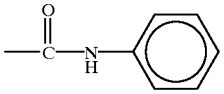

| Ex | X₃ | R₁₄ | salt | stereochemistry | (M + H)⁺ |
|---|---|---|---|---|---|
| 182 | —C(O)—NH—Ph | —CO₂H | 1.0 CF₃CO₂H | racemate | 334 |
| 183 | —C(O)—NH—Ph | —C(O)—N(piperidine) | 1.0 HCl | racemate | 401 |
| 184 | —C(O)—CH₃ | —(CH₂)₂—Ph | 1.0 HCl | homochiral | 317 |
| 185 | —C(O)—NH—Ph | —(CH₂)₂—Ph | 1.0 HCl | racemate | 394 |

The following additional compounds of formula VI were also prepared

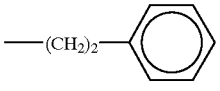

| Ex | X₃ | R₁₄ | salt | stereochemistry | (M + H)⁺ |
|---|---|---|---|---|---|
| 186 | —C(O)—NH—Ph | —(CH₂)₂—Ph | 1.0 HCl | racemate | 394 |
| 187 | —C(O)—CH₃ | —(CH₂)₂—Ph | 1.0 HCl | racemate | 317 |

The following additional compounds of formula VI were also prepared

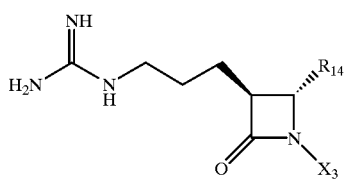

| Ex | $X_3$ | $R_{14}$ | salt | stereochemistry | $(M + H)^+$ |
|---|---|---|---|---|---|
| 188 | —C(O)—NH—Ph | —$CO_2CH_3$ | 1.0 $CF_3CO_2H$ | homochiral | 348 |
| 189 | —C(O)—NH—Ph | —$CO_2H$ | — | homochiral | 332 |

The following additional compounds of formula VI were also prepared

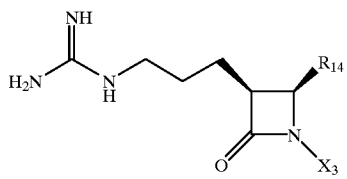

| Ex | $X_3$ | $R_{14}$ | salt | stereochemistry | $(M + H)^+$ |
|---|---|---|---|---|---|
| 190 | —C(O)—NH—Ph | —$CO_2CH_3$ | 1.0 HCl | racemate | 348 |
| 191 | —C(O)—NH—Ph | —$CO_2H$ | 1.0 $CF_3CO_2H$ | racemate | 334 |

EXAMPLE 192

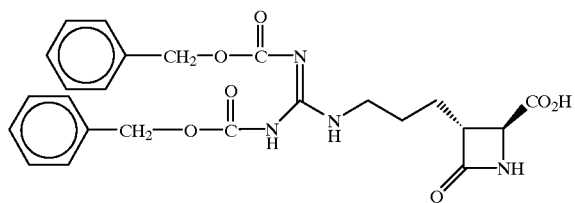

The intermediate of Example 1(b) was also prepared as follows:

a)

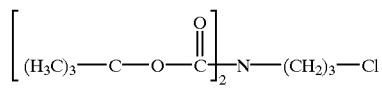

Potassium t-amylate (25% wt in toluene, 164.0 g, 322.6 mmol) was added to a solution of di-t-butyl iminodicarboxylate (70.1 g, 322.6 mmol) in dimethylformamide (500 ml) over a 15 minute period under nitrogen. The resulting white creamy solution was stirred at 0° C. for 40 minutes. 1-Chloro-3-iodopropane (60.0 g, 31. ml, 293.3 mmol) was added and the mixture was stirred at 0° for 3 hours. Hexane (500 ml) and water (300 ml) were added to the mixture. The aqueous layer was separated and extracted with hexane (300 ml). The combined hexane extracts were washed with 1N sodium hydroxide (3×300 ml), saturated sodium hydrogen phosphate (300 ml), half-saturated brine (300 ml), and brine (500 ml) and dried over sodium sulfate. Removal of the sodium sulfate by filtration followed by concentration gave 84.2 g of the desired product as a light yellow oil which was dried under vacuum overnight.

b)

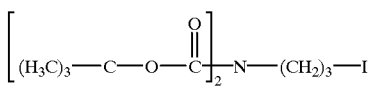

The product from part (a) (55.0 g, 187.2 mmol) was dissolved in acetone (550 ml). Sodium iodide (84.2 g, 561.6 mmol) and sodium bicarbonate (7.9 g, 93.6 mmol) were added. The mixture was stirred at 58° C. (oil bath) under nitrogen for 6 hours and additional sodium iodide (14 g, 93.4 mmol) was added). The reaction mixture was stirred for 12 hours and the acetone was evaporated. Hexane (400 ml) and water (300 ml) were added to the resulting solid. The hexane layer was separated, washed with 5% sodium thiosulfate (300 ml), half-saturated brine (300 ml) and brine (300 ml), dried over sodium sulfate, and filtered through 20 g of a silica gel pad. The silica gel pad was washed with hexane (400 ml). Concentration of the filtrate gave 68.2 g of the desired product as a light yellow oil which was dried under vacuum overnight.

c)

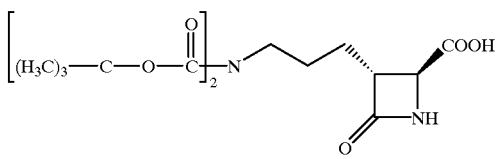

n-Butyl lithium (2.5 M in hexane, 46 ml, 115.0 mmol) was added to a solution of diisopropylamine (11.7 g, 16.2 ml, 115.3 mmol) in tetrahydrofuran (150 ml) at 0° C. under nitrogen. The resulting solution was stirred at 0° C. for 30 minutes then cooled to −30° C. A solution of (4S)-N-(t-butyldimethylsilyl)-azetidine-2-one-4-carboxylic acid (12.0 g, 52.4 mmol) [Baldwin et al, Tetrahedron, Vol. 46, p. 4733–4748, 1990] in tetrahydrofuran (60 ml) was added and the mixture was stirred at −20° C. for 30 minutes. A solution of the iodo product from part (b) (24.0 g, 62.3 mmol) in tetrahydrofuran (30 ml) was added dropwise over a 20 minute period and the resulting mixture was stirred at −20° C. for 2 hours. The reaction mixture was allowed to warm to 0° C. and water (300 ml) was added. The mixture, adjusted to pH 12.5 with 10% sodium bisulfate, was stirred at 0° C. for 30 minutes and then washed with hexane (2×100 ml). The aqueous layer was cooled in an ice-bath and acidified to pH 3.0 by the dropwise addition of 6N HCl. This solution was saturated with sodium chloride and extracted with ethyl acetate (3×150 ml). The combined ethyl acetate extracts were washed with brine (200 ml), dried over sodium sulfate, filtered and concentrated to give a yellow oil. This oil was dissolved in acetonitrile (20 ml) and evaporation of the acetonitrile gave 16.4 g of the desired product as a yellow foam.

d)

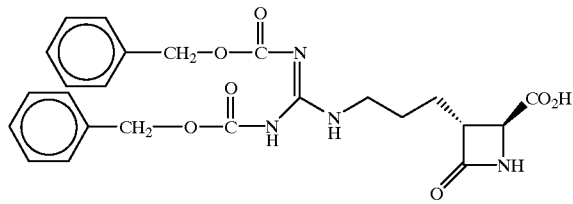

The product from part (c) (4.25 g, 11.4 mmol) was added to a 1:2 mixture of trifluroacetic acid/methylene chloride (42 ml). The resulting mixture was stirred at room temperature for 30 minutes under a nitrogen atmosphere. Toluene was added (80 ml) and the mixture was concentrated to a small volume (approximately 15 ml). Additional toluene (80 ml) was added and the mixture was concentrated to dryness to afford a yellow oil.

A mixture of triethylamine (3.97 ml, 28.5 mmol) and methanol (42 ml) was added into the above oil at 0° C. Additional triethylamine (0.85 ml, 5.7 mmol) and N,N'-bis(benzyloxycarbonyl)-1-guanylpyrazole (4.31 g, 11.4 mmol) [Wu et al, Synthetic Communications, 23(21), p. 3055–3060 (1993)] were added. The mixture was stirred at room temperature for 11 hours and then concentrated in vacuo at 25° C. to afford a yellow oil.

Ethyl acetate (30 ml) and water (10 ml) were added to this oil followed by acidification to pH 3.2 at 0° C. by the addition of 2M potassium bisulfate which was saturated with sodium chloride. The acidic mixture was poured into a separatory funnel. The layers were separated, and the aqueous layer was washed with ethyl acetate (2×25 ml) while ensuring that the pH of the aqueous solution was in the range of 2.9 to 3.2. The combined ethyl acetate solutions were washed with saturated sodium chloride solution (25 ml)and the product was extracted with saturated sodium bicarbonate (3×25 ml). The combined sodium bicarbonate solutions were washed with ethyl acetate (2×25 ml), acidified to pH 3.2 with concentrated HCl at 0° C., treated with saturated sodium chloride (solid), and finally extracted with ethyl acetate (3×25 ml). The combined ethyl acetate solution was dried over anhydrous magnesium sulfate, filtered, and concentrated in vacuo to afford 4.61 (9.55 mmol) of the desired product as a pale yellow foam.

EXAMPLE 193

The product of Examples 21 and 32 was also prepared as follows:

a)

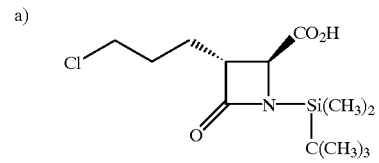

Diisopropylamine (14.05 ml, 0.10 mmol) was added to a dry, three-necked flask equipped with mechanical stirrer and maintained under an argon atmosphere. Tetrahydrofuran (anhydrous, 33 ml) was charged to the flask and while the mixture was stirred and cooled to −20° C., a solution of n-butyl lithium (38.3 ml of a 2.5 M solution in hexanes, 0.096 mol) was added dropwise and the solution was stirred at −20° C. for 10 minutes. A solution of (4S)-N-(t-butyldimethylsilyl)-azetidine-2-one-4-carboxylic acid (10.0 g, 43.6 mmol) [Baldwin et al, Tetrahedron, Vol. 46, p. 4733–4748, 1990] was added slowly while maintaining the temperature at −20° C. and allowed to stir for 30 minutes. A solution of 1-chloro-3-iodopropane (5.6 ml, 52 mmol, 1.2 eq.) in tetrahydrofuran (30 ml) was added over approximately 10 minutes. After stirring at −20° C. for approximately 2 hours, 2.6M potassium bisulfate (75 ml), water (100 ml) and ethyl acetate (100 ml) were added and the mixture was transferred to a separatory funnel. The aqueous layer (pH 2–3 ) was drawn off and back extracted with ethyl acetate (2×50 ml). The organic solutions were combined and washed sequentially with water (2×50 ml), 10% sodium thiosulfate (1×50 ml) and then with saturated sodium chloride to neutral pH. The organic solution was dried over sodium sulfate (15 g), filtered and concentrated to an oil. The oil was seeded with a few crystals of the desired product and placed under high vacuum overnight to dry. The resultant crystalline solid was slurried with hexane (100 ml), filtered, washed with hexane (100 ml) and dried under high vacuum to give 11.5 g of the desired product.

b)

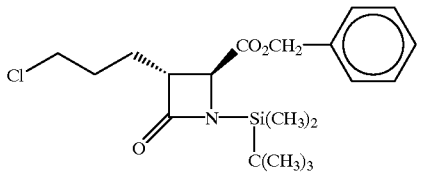

The product from part (a) (7.02 g, 22.9 mmol) was dissolved in methylene chloride (anhydrous, 40 ml) under an argon atmosphere. The solution was stirred and cooled to 0° C., and triethylamine (3.5 ml, 25.2 mmol) was added slowly while maintaining approximately 0° C. Benzylchloroformate (3.6 ml, 25.2 mmol) was added along with an additional 10 ml of methylene chloride to aid stirring. 4-Dimethyl-aminopyridine (2.8 g, 22.9 mmol) was added as a solid in one portion with considerable gas evolution. The solution was allowed to stir at 0° C. for 30 minutes. Additional benzylchloroformate (0.3 ml, 2.5 mmol) was added and the reaction was stirred for an additional 20 minutes. The reaction was quenched with 1M potassium bisulfate (30 ml). The mixture was transferred to a separatory funnel and the layers were separated. The organic layer was washed with 2N potassium bisulfate (20 ml), and the aqueous washes were combined and back extracted with methylene chloride (25 ml). The organic solutions were combined, washed sequentially with water (25 ml), saturated sodium bicarbonate (25 ml), and saturated sodium chloride (2×25 ml), and dried over sodium sulfate (15 g). The methylene chloride solution was filtered through silica (15 g) and the silica was washed with 200 ml 3:1 (volume:volume) hexane/ethyl acetate. The filtrate was concentrated to an oil, evaporated under reduced pressure from toluene (2×25 ml) and dried under vacuum overnight to give 8.12 of the desired product.

c)

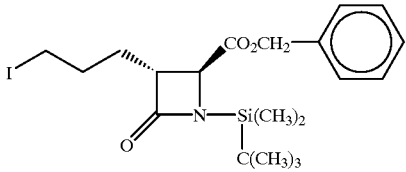

A solution of the product from part (b) (10.55 g, 26.6 mmol) in 4-methyl-2-pentanone (40 ml) was stirred under an argon atmosphere. Sodium iodide (20 g, 133 mmol) was added and the mixture was heated at approximately 110° C., protected from light, for 7 hours. The mixture was cooled to ambient temperature, diluted with hexane (100 ml) and filtered through a plug of Celite®. The Celite® was washed with hexane (2×50 ml). The filtrates were combined, washed with sodium thiosulfate (50 ml) and then with water (50 ml). The aqueous washes were back extracted with ethyl acetate (100 ml). The organic solutions were combined and concentrated to an oil, dissolved in hexane (50 ml) and filtered through a plug of silica. The silica was washed with hexane (200 ml) and then with 4:1 (volume:volume) hexane/ethyl acetate (500 ml). The hexane/ethyl acetate solution was concentrated to give 11.84 g of the desired product as an oil.

d)

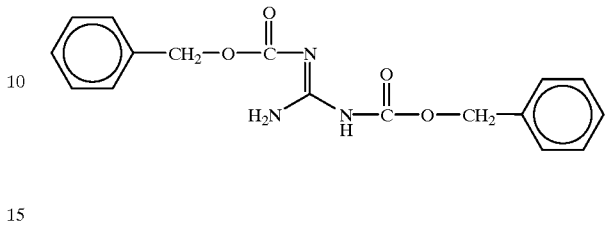

The compound of the formula:

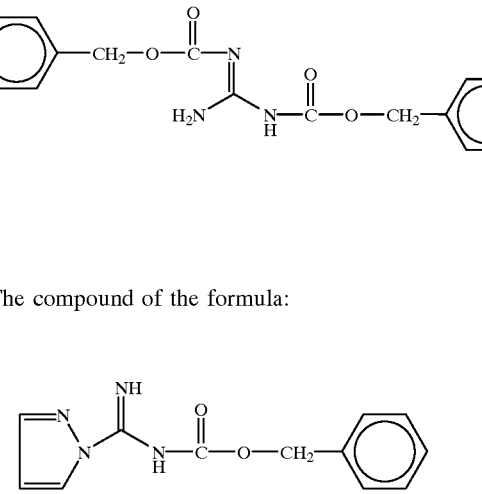

(5 g, 20.5 mmol) and tetrahydrofuran (27 ml, anhydrous) were charged to a dry flask under nitrogen. The solution was stirred and cooled to 0° C. Sodium hydride (2.62 g, 65.5 mmol, 3.2 equivalents of a 60% dispersion in mineral oil) was charged to the flask slowly (exotherm). The suspension was stirred at 0° C. N-(Benzyloxycarbonyloxy)succinimde (8.2 g, 32.8 mmol, 1.6 eq.) was added portionwise maintaining a temperature of approximately 0° C. The cooling was removed and the reaction was allowed to warm to room temperature. After 1 hour, an additional amount of N-(benzyloxycarbonyloxy)succinimide (1 g, 0.2 eq) was added and the reaction was stirred at room temperature overnight. The reaction was worked up by cooling to approximately 0° C. and quenched slowly by the addition of 13% aqueous ammonium chloride. The layers were separated, and the aqueous layer was back extracted with ethyl acetate (3×20 ml). The combined organic solution was washed sequentially with 13% aqueous ammonium chloride (5 ml), water (15 ml) and saturated sodium chloride (2×15 ml). The organic solution was dried over sodium sulfate, filtered and concentrated. The resulting crude oil was charged to a flask with a 2M solution of ammonia in methanol (51 ml, 101 mmol, 5 eq) and allowed to stir at ambient temperature overnight. The reaction was worked up by concentration under reduced pressure, followed by coevaporation with hexanes (2×25 ml). The resultant material was dissolved in methylene chloride (50 ml) and washed with water (50 ml). The aqueous layer was back extracted with methylene chloride (2×50 ml). The organic extracts were combined and washed with water (25 ml) and saturated sodium chloride (25 ml), dried over sodium sulfate, filtered and concentrated to a solid. The solid was crystallized from ethyl acetate to give 4.65 g of the desired product as white crystals.

e)

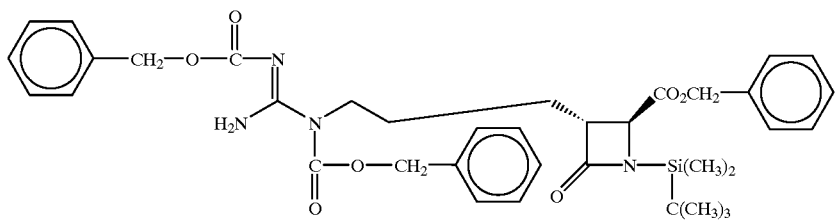

The product from part (d) (6.01 g, 18.37 mmol) was dissolved in 1-methyl-2-pyrrolidinone (anhydrous, 10 ml) and warmed to 35–40° C. under an argon atmosphere. Potassium carbonate (finely ground and dried, 12.7 g, 92 mmol) was added and the mixture was allowed to stir for 25 minutes. A solution of the product from part (c) (9.5 g, 18.37 mmol) in 1-methyl-2-pyrrolidone (10 ml) was added and the reaction mixture was allowed to stir for 8 hours at 35–40° C. The reaction mixture was cooled to ambient temperature, diluted with ethyl acetate (100 ml) and filtered into a separatory funnel. The mixture was washed with 1M potassium bisulfate (84 ml) and the layers were separated. The aqueous layer was back extracted with ethyl acetate (50 ml). The organic solutions were combined, washed sequentially with water (50 ml), 10% sodium thiosulfate (50 ml) and saturated sodium chloride (50 ml), dried over sodium sulfate, filtered and concentrated to an oil. The oil was dissolved in 50 ml. 1:1 (volume:volume) hexane/ethyl acetate and filtered through silica. The filtrate was concentrated to give 12.88 g of the desired product as a crude oil that was used without further purification.

f)

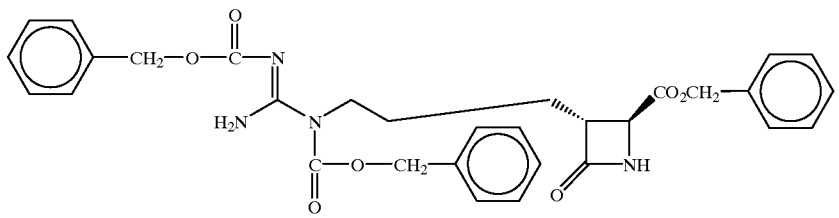

The crude oil product from step (e) was dissolved in acetonitrile (50 ml) and water (5 ml). Ammonium fluoride (3.4 g, 92 mmol) and glacial acetic acid (5.25 ml, 92 mmol) were added and the mixture was stirred for 30 minutes. The reaction was diluted with ethyl acetate (150 ml), transferred to a separatory funnel and washed with saturated sodium bicarbonate (30 ml). The layers were separated and the aqueous layer was back extracted with ethyl acetate. The organic solutions were combined, washed with saturated sodium chloride, dried over sodium sulfate, filtered and concentrated to an oil. The oil was dissolved in ethyl acetate (30 ml) and warmed to 60° C. Hexane (25 ml) was added and the mixture was allowed to cool slowly with stirring and seeding. As crystallization occurred, hexane (75 ml) was added portionwise. The resultant solid was filtered, washed with hexane, and dried to give 8.91 g of the desired product.

g)

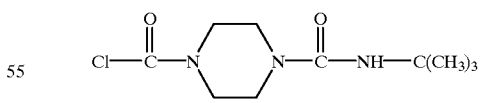

A 2 liter dried flask equipped with a mechanical stirrer and argon inlet was charged with 1-benzylpiperazine (40 ml, 230 mmol) and toluene (250 ml). With vigorous stirring t-butyl isocyanate (27 ml, 236 mmol) was added in rapid dropwise fashion over 15 minutes. The product precipitated to form a thick slurry. The slurry was stirred over an hour to reach 25° C. Heptane (570 ml) was added to the slurry over 30 minutes. The flask was stoppered and placed in a cold room (5° C.) for 4 hours. The product was collected by filtration, rinsed with heptane (1×200 ml) and air dried to give 61.0 g of the piperazine of the formula:

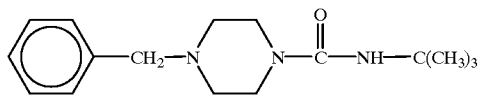

as a white solid.

A 500 ml flask equipped with a magnetic stir bar and a sparging tube was charged with methanol (200 ml). The flask was cooled to 1° C. and with stirring acetyl chloride (5.7 ml, 79.9 mmol) was added over 10 minutes. The solution was allowed to reach room temperature and the above piperazine (20.0 g, 72.6 mmol) was added. Palladium hydroxide on carbon (8.0 g, moisture content less than or equal to 50%) was added and the mixture was then sparged with argon for 10 minutes. The reaction mixture was then sparged with hydrogen. After 3.5 hours, HPLC indicated the starting material was consumed completely. The mixture was filtered through Celite® and the Celite® rinsed with methanol (60 ml). The filtrate was concentrated until solid started to crystallize (175 ml methanol collected). Isopropyl alcohol (200 ml) was added slowly with manual stirring. The mixture was concentrated to a solid/liquid mixture (153 g weight). The mixture was allowed to stand for 2 hours. The product was collected by filtration, washed with isopropyl alcohol (1×30 ml) and air dried to yield 14.0 g of the hydrochloride salt of the formula:

h)

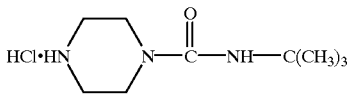

as a light yellow solid.

A 100 ml, three-necked flask with a magnetic stir bar and a sparging tube was charged with this hydrochloride salt (5.0 g, 22.6 mmol) and anhydrous methylene chloride (50 ml). 1,8-Diazabicyclo[5.4.0]undec-7-ene (6.7 ml, 45.1 mmol) and pyridine (1.8 ml, 22.6 mmol) were added to the mixture. The mixture became homogeneous. The mixture was sparged with dry carbon dioxide gas at room temperature for 1 hour.

A dry 500 ml flask with a magnetic stir bar was charged with thionyl chloride (4.9 ml, 67.7 mmol) and anhydrous methylene chloride (25 ml). The solution was cooled to −10° C. and dimethylformamide (0.17 ml, 2.26 mmol) was added. The above carbon dioxide sparged mixture was added via cannula under carbon dioxide pressure over 35 minutes. The flask was rinsed with methylene chloride (5 ml) and the rinse was added to the reaction. The reaction was stirred at −10° C. for 30 minutes. The reaction mixture was poured into 0.5 M HCl (75 ml) and shaken vigorously. The organic layer was collected, dried over magnesium sulfate, filtered and concentrated in vacuo to give 4.95 g of the desired product as a light yellow solid.

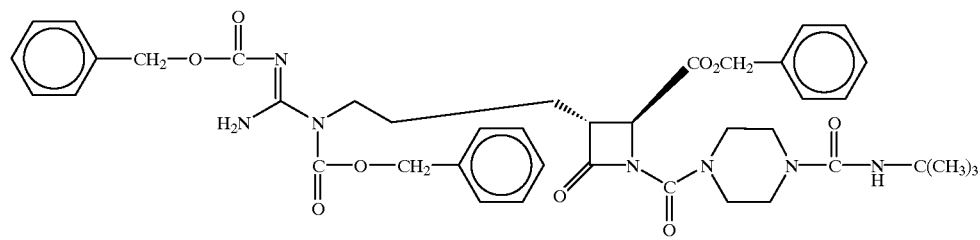

The product from step (f) (11.84 g, 20.7 mmol) was dissolved in anhydrous methylene chloride (100 ml) under argon with stirring. The carbamoyl chloride product from step (g) (7.47 g, 26.9 mmol, 1.3 eq.), triethylamine (4.6 ml, 33.1 mmol, 1.6 eq.), and 4-dimethylaminopyridine (0.76 g, 6.2 mmol, 0.3 eq) were added, and the reaction was allowed to stir at ambient temperature overnight. The reaction was poured into 0.5 N HCl (110 ml), the layers were separated, and the organic layer was washed with a second portion of 0.5 N HCl. The acidic aqueous layers were back extracted with methylene chloride (50 ml) and combined with the main organic portion. The combined organic layers were washed with saturated sodium bicarbonate (100 ml) and saturated sodium chloride, and dried over sodium sulfate. The solution was filtered and concentrated to give 17.0 g of the desired product as a crude white solid.

i)

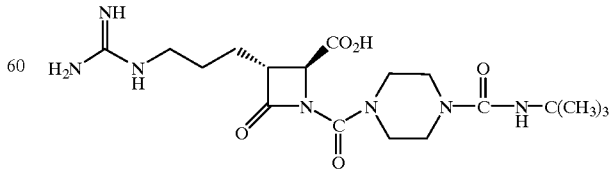

The crude product from part (h) (17.0 g) was dissolved in absolute ethanol (350 ml) with stirring. The solution was sparged with argon and 10% palladium on carbon catalyst (1.7 g, 50% by weight water) was added in one portion followed by additional argon sparging. The solution was sparged with hydrogen for 2 minutes, and then placed under atmospheric hydrogen pressure (balloon). Two additional charges of palladium on carbon catalyst (1.7 g each) were added to the reaction, along with a repeat of the sparging procedure. The reaction was judged complete in approximately 4 hours (HPLC analysis). The reaction was sparged with argon for 5 minutes and filtered through a packed pad of Celite®. The Celite® was washed with ethanol (2×125 ml). The combined ethanol filtrates were concentrated to approximately 50 g and allowed to stir for 4 days. Crystals formed in the flask. The crystals were filtered, washed with absolute ethanol (25 ml) and dried to give 7.74 g of the desired product as white crystalline material. This material was further purified by warming in 95% ethanol to approximately 40° C. for 30 minutes, followed by cooling, filtration and drying.

EXAMPLE 194

The product of Examples 21, 32 and 193 was also prepared as a zwitterion or inner salt as follows:

a)

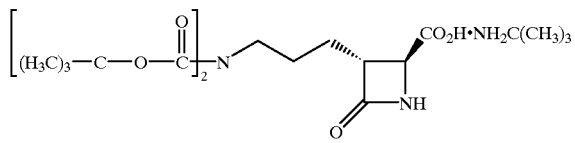

A dry, 3-necked, 12-L flask (flask A) was charged with 769.4 g of (4S)-N-(t-butyldimethylsilyl)azetidinone carboxylic acid followed by 6 L of dry tetrahydrofuran. A separate 3-necked, 5-L flask (flask B) was charged with 1537.8 g of the iodo product from Example 192 step (b) followed by 2 L of dry tetrahydrofuran. Under a nitrogen atmosphere, 4 L of dry tetrahydrofuran was charged into a 22-L flask (flask C) followed by 3.69 L of lithium diisopropylamide. The solution of lithium diisopropylamide was cooled to −30 to −35° C. While maintaining the temperature at less than −20° C., the contents of flask A were added to flask C. The mixture was stirred at −20 to −25° C. for 30 to 60 minutes and cooled to −35° C. to −40° C. The contents of flask B were then added portionwise over 25 to 45 minutes while maintaining the internal temperature of flask C at less than about −20° C. The resulting mixture was stirred for 2 to 3 hours between −20° C. and −23° C. The reaction was quenched by the addition of 6 L of cold water while maintaining the internal batch temperature at −20° C. to +5° C. After stirring for an additional 15 to 30 minutes to ensure removal of the silyl protecting group, the pH was adjusted to 8.0 by the addition of cold 6N HCl(1.69 L). The reaction mixture was transferred to a phase splitter and the top organic layer was discarded. The aqueous layer was washed twice with 4L portions of hexane. The aqueous phase was cooled to about 0° C. and treated with 6N HCl (about 400 ml) until the pH was 3.0. The batch temperature was maintained at less than 50 during this operation. The cloudy aqueous phase was extracted three times with 4 L portions of ethyl acetate. The combined organic extracts were washed with brine (3×3L) and concentrated to an oil. The oil was redissolved in 8 L of fresh ethyl acetate, transferred to a 22-L flask, and cooled under nitrogen. While maintaining the batch temperature at less than 8° C., tert-butylamine was added and the resulting mixture was stirred overnight at room temperature. The mixture was concentrated to a yellow slurry, treated with 6L of methyl tert-butyl ether and stirred for 3 hours at room temperature. The mixture was filtered and the filter cake was washed with methyl tert-butyl ether (1.5 L) and dried to a constant weight of 805.9 g of the desired product.

b)

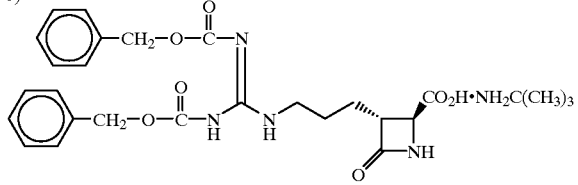

Trifluroacetic acid (31.1 ml, 403.9 mmol, 18 equivalents) was added dropwise to a suspension of the product from part (a) (10.0 g, 22.44 mmol) in methylene chloride (40 ml) at between −5° C. to +5° C. under nitrogen. The resulting light yellow clear solution was stirred at 0° C. until less than 1% of the mono tert-butoxycarbonyl intermediate was detected by HPLC (about 4 to 7 hours). The methylene chloride and trifluoroacetic acid were removed in vacuo at room temperature. Toluene (30 ml) was added to the residue and then removed in vacuo. The residue was treated with isopropyl alcohol (10 ml) followed by toluene (20 ml) and the resulting solution was concentrated in vacuo to an oil. This step was repeated one time.

Isopropyl alcohol (50 ml) was added to the above oil (about 23 g) and the resulting solution was cooled to 0° C. The pH was adjusted to 8.5 to 9.0 by the dropwise addition of triethylamine between −5° C. to 5° C. (18 ml of triethylamine was used in this procedure). N,N'-Bis (benzyloxycarbonyl)-1-guanylpyrazole (8.07 g, 21.32 mmol, 0.95 equivalents) was added in one portion and the cooling bath was removed. The mixture was stirred under nitrogen at room temperature for approximately 30 hours until the ratio of product/pyrazole was greater than 25:1 as determined by HPLC. The solvent was removed in vacuo at room temperature to afford approximately 42 g of yellow oil. This oil was diluted with ethyl acetate (70 ml) and water (70 ml), and cooled to 0° C. The pH of the solution was adjusted to 3.0 with 2M potassium bisulfate and treated with sodium chloride until saturated. The organic layer was separated and the aqueous layer was extracted with ethyl acetate (2×60 ml). The combined ethyl acetate layers were washed with saturated sodium chloride solution (2×60 ml), dried over sodium sulfate and filtered. The solvent was evaporated to give a yellow oil (14.4 g) which was redissolved in ethyl acetate (40 ml). The resulting clear yellow solution was warmed to 36–40° C. and treated dropwise with tert-butylamine (3.3 ml). After crystallization of the salts, the slurry was cooled to room temperature, stirred for 12 hours, then cooled to 4° C., and stirred for an additional 12 hours. The product was filtered, washed with cold ethyl acetate/hexane (2×5 ml) and cold hexane (2×5 ml), and dried in vacuo to give 8 g of the desired product.

c)

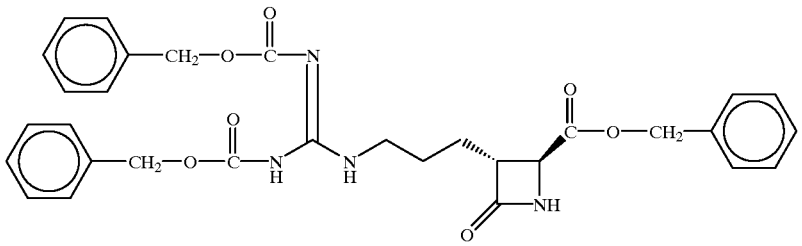

A dry, argon atmosphere 50 ml flask was charged with the product from part (b) (5.0 g). N,N'-Dimethylpropyleneurea (15 ml) was added, and the mixture was stirred for 5 minutes. The system was not homogeneous at this time. A 22° C. water bath was applied to the flask, and benzyl bromide (2.1 ml, 1.96 equivalents) was added rapidly (no exotherm was observed). tert-Butylamine (0.90 ml, 0.95 equivalents) was added dropwise (the temperature rose to 27.5° C. during the addition, held there for approximately 1 minute after the addition was complete, and then began to fall). When the temperature dropped to 25° C., the water bath was removed and the reaction was stirred overnight (16 hours). Completion of the reaction was confirmed by HPLC analysis. The reaction was diluted with ethyl acetate (30 ml) and tert-butyl methyl ether (30 ml). This solution was washed three times with 5% citric acid (1×30 ml, 2×15 ml) and then washed with saturated sodium chloride (1×15 ml). The resulting solution was dried over magnesium sulfate, filtered and concentrated in vacuo to give 5.85 g of the desired product as an orange oil.

d)

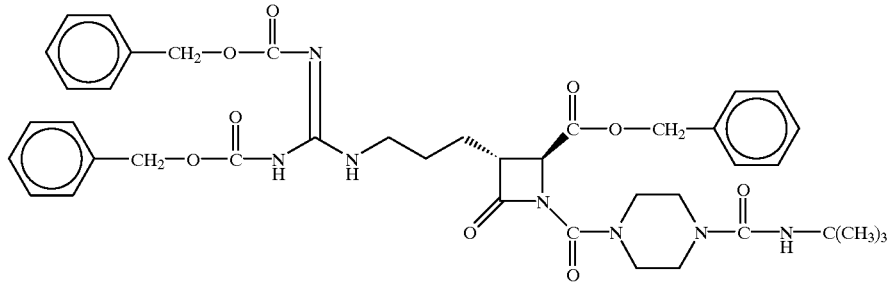

A dry, argon atmopsphere 50 ml flask was charged with the product from part (c) (2.5 g), anhydrous methylene chloride (25 ml), the carbamoyl chloride product from Example 32(c) or 193 (g) (1.3 g, 1.2 equivalents), triethylamine (0.98 ml, 1.6 equivalents), and 4-dimethylaminopyridine (0.16 g, 0.3 equivalents). The reaction was stirred for 5 hours. HPLC analysis confirmed that the reaction was 99.4% complete. The reaction mixture was shaken with 10% citric acid (aqueous, 25 ml). The aqueous layer was separated and extracted with methylene chloride (10 ml). The combined organic layers were washed with saturated sodium bicarbonate (aqueous, 25 ml) and with saturated sodium chloride (aqueous, 25 ml). The organic layer was separated, dried with magnesium sulfate, filtered and concentrated in vacuo to afford 3.46 g of the desired product as a tan foam.

e)

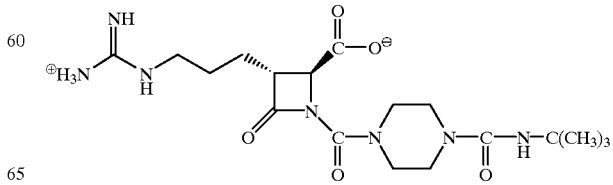

A 12 L three necked round bottom flask was charged with 10% palladium on carbon catalyst (50.34 g, 47.31 mmol), water (362 ml), ethanol (6883 ml), and the product from part (d) (345 g). The mixture was agitated and sparged with nitrogen for approximately 20 to 30 minutes, then continuously sparged with hydrogen gas at 15° to 25° C. until HPLC analysis confirmed completion of the reaction. The reaction mixture was sparged with nitrogen for approximately 20–30 minutes, filtered, and the filter was washed 2L ethanol/water (95/5). The ethanol/water was partially concentrated in vacuo at room temperature to a solution of 8 to 10 ml per gram of product. Concentration gave a cloudy to white solution.

The above solution was allowed to crystallize overnight at room temperature with agitation (120–200 revolutions per minute). The product was filtered and the filter cake was washed three times with 300 ml of cold ethanol/water (95/5, 0° to 5° C.). The filter cake was dried in vacuo for 10 to 20 minutes. The resulting solid was dried to constant weight in a vacuum oven at room temperature to give 155 g of the desired final product as a white solid.

EXAMPLE 195 a)

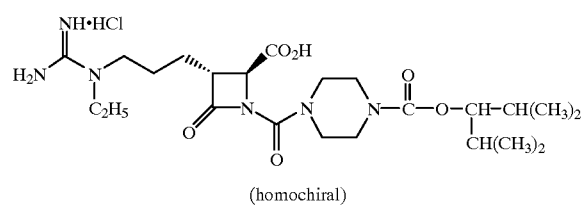

(homochiral)

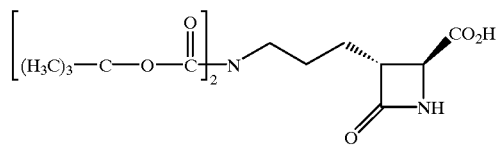

A. 2.5 M hexane solution of n-butyl lithium (5.75 ml, 14.39 mmol) was added dropwise to a stirred solution of diisopropylamine (2.02 ml, 14.39 mmol) in tetrahydrofuran (18ml) at 0° C. After 30 minutes of stirring the solution was cooled to −300C and a solution of (4S)-N-(t-butyldimethylsilyl)azetidinone carboxylic acid (1.50 g, 6.54 mmol) in tetrahydrofuran (8.0 ml) was added dropwise. The reaction mixture was stirred between −20° C. and −25° C. for 30 minutes. A solution of the iodo product from Example 192 step (b) (3.02 g, 7.85 mmol) in tetrahydrofuran (4.0 ml) was then added over 10 minutes. After 2 hours, the reaction mixture was warmed to 0° C. and quenched by the addition of ice cold water (35 ml). The pH was adjusted to 12.5 using 10% potassium bisulfate. After 30 minutes stirring, the solution was washed with hexanes, cooled to 0° C., and acidified to pH of 3.0 using 5N HCl. The aqueous solution was saturated with sodium chloride and extracted with ethyl acetate (twice). The organic extracts were combined, washed with brine, dried over magnesium sulfate, and concentrated to give 1.10 g of the desired product.

b)

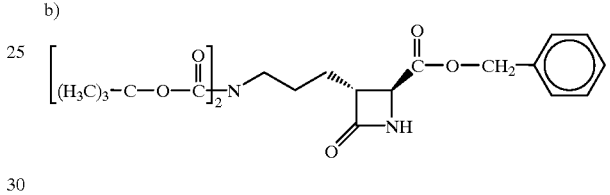

Sodium bicarbonate (0.62 g, 7.40 mmol) was added to a stirred solution of the product from step (a) (1.10 g, 2.96 mmol) in dimethylformamide (10 ml). Benzyl bromide (1.76 ml, 14.78 mmol) was then added. After 48 hours the reaction mixture was partitioned between ethyl acetate and water. The organic phase was isolated, washed with brine, dried over magnesium sulfate, and concentrated. The crude product was purified by silica gel chromatography to give 1.26 g of the desired product.

c)

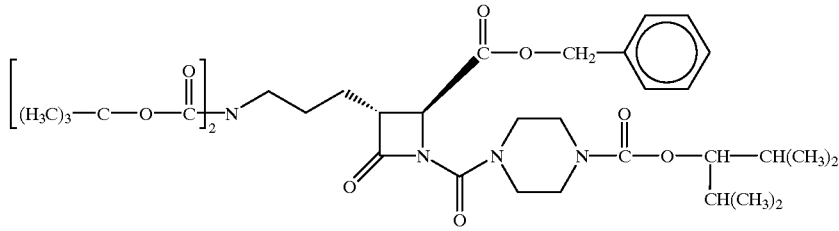

The benzyl ester product from step (b) (227 mg, 0.491 mmol) and 1-diisopropylmethoxycarbonylpiperazine-4-carbonylchloride (178 mg, 0.614 mmol) were dissolved in methylene chloride (2.0 ml). Triethylamine (103 μl, 0.737 mmol) was added followed by dimethylaminopyridine (6.0 mg, 0.049 mmol). After 48 hours the reaction mixture was concentrated and the residue was partitioned between ethyl acetate and water. The organic phase was isolated, washed with 5% potassium bisulfate and saturated sodium chloride, dried over magnesium sulfate, and concentrated. The residue was purified by silica gel chromatography to afford 300 mg of the desired product.

d)

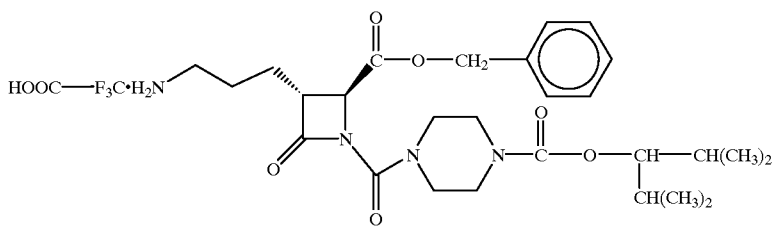

Trifluoroacetic acid was added dropwise to a stirred solution of the product from part (c) (300 mg, 0.418 mmol) in methylene chloride (1.8 ml) at 0° C. The reaction mixture was then stirred at room temperature. After one hour, the reaction mixture was concentrated and dried in vacuo. The crude product was dissolved in chloroform and concentrated. The procedure was repeated 3 times. The crude product was then dried in vacuo to give 297 mg of the desired product.

e)

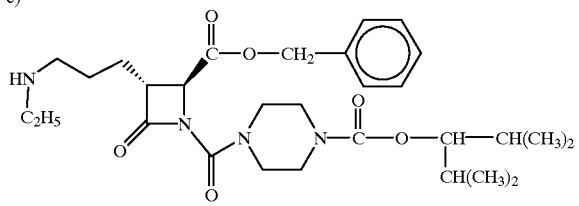

Acetaldehyde (15.0 mg, 0.330 mmol) was added to a stirred solution of the product from part (d) (198 mg, 0.314 mmol) in methylene chloride (1.50 ml). Acetic acid (36 μl, 0.628 mmol) was added. After 20 minutes of stirring, triacetoxy sodium borohydride (100 mg, 0.471 mmol) was added. After 24 hours the reaction mixture was diluted with ethyl acetate. One drop of acetic acid was added and the reaction was quenched by the addition of water. The organic phase was isolated, washed with saturated sodium chloride, dried over magnesium sulfate, and concentrated to give 175 mg of the desired product.

f)

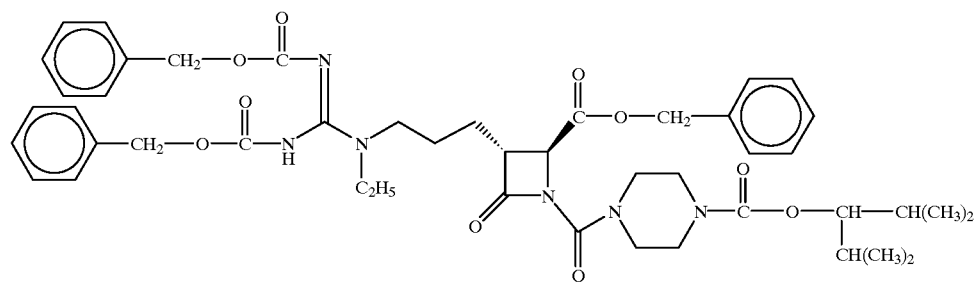

The product from part (e) (174 mg, 0.264 mmol) and N,N'-dicarbobenzyloxy—S-methyisothiourea (95 mg, 0.264 mmol) were dissolved in dimethylformamide (1.5 ml). Mercuric chloride (72.0 mg, 0.264 mmol) was added followed by triethylamine (110 μl, 0.792 mmol). After 3 hours, the reaction was diluted with ethyl acetate and filtered to remove mercury salts. The filtrate was washed with saturated sodium chloride, dried over magnesium sulfate, and concentrated. The crude product was purified by silica gel chromatography to afford 45 mg of the desired product.

g)

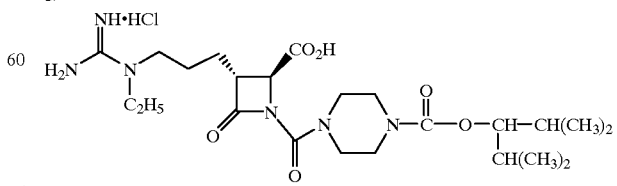

(homochiral)

The product from part (f) (45 mg, 0.053 mmol) was dissolved in 1,4-dioxane (0.5 ml). 1N HCl (53 μl, 0.053 mmol) was added followed by 10% palladium on carbon catalyst (15 mg). A hydrogen atmosphere was introduced via balloon. After 3 hours of stirring at room temperature the reaction mixture was diluted with water: 1,4-dioxane (1:1) and filtered. The filtrate was lyophilized to afford 25 mg of the desired product; (M+H)$^+$=497.

EXAMPLE 196

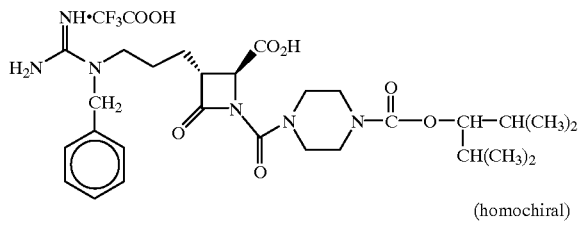

(homochiral)

Following the procedure of Example 195 but employing benzaldehyde in place of acetaldehyde in step (e) the above compound was obtained and isolated as the trifluoroacetic acid salt; (M+H)$^+$=559.

EXAMPLE 197

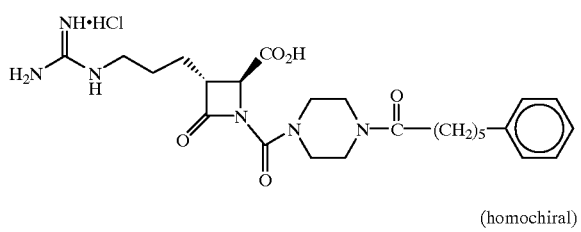

(homochiral)

a)

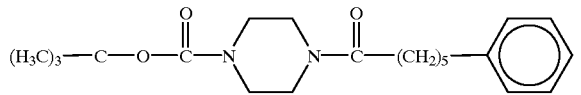

To a solution of 6-phenylhexanoic acid (4.0 g, 20.81 mmol) and hydroxybenztriazole (3.50 g, 22.89 mmol) in anhydrous methylene chloride (100 ml) was added ethyl-3—(dimethylamino)propyl carbodiimide, hydrochloride salt (4.39 g, 22.89 mmol) at 0° C. The mixture was stirred for 30 minutes. 1-tert-Butoxycarbonylpiperazine (3.88 g, 20.81 mmol) and diisopropylethylamine (4.35 ml, 24.97 mmol) were added and the mixture became a homogeneous solution. The solution was slowly warmed to room temperature over 3 hours and stirred overnight. The solvent was replaced with ethyl acetate (300 ml). The resulting solution was washed with 0.25 M potassium bisulfate (pH of 3 to 4), saturated sodium bicarbonate (pH of 9 to 10), and brine, dried over magnesium sulfate, and concentrated to give the desired product in crude form as a colorless oil.

b)

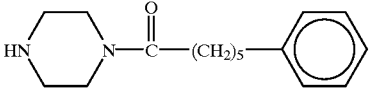

The crude product from part (a) was dissolved in methylene chloride (160 ml). The solution was cooled to 0° C. and trifluoroacetic acid (40 ml) was added dropwise. The ice-bath was removed. The mixture was stirred at room temperature for one hour. The solvents were removed under vacuum. The residue was diluted with ethyl acetate (200 ml). The solution was neutralized with saturated sodium bicarbonate (pH of 10). The aqueous layer was extracted with ethyl acetate (2×100 ml). The combined ethyl acetate solution was washed with brine, dried over magnesium sulfate and concentrated to give the desired product as a colorless oil.

c)

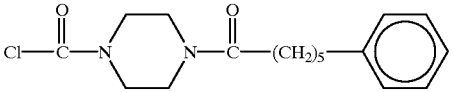

A solution of phosgene (20% in toluene, 50 mmol, 26.3 ml) was dissolved in methylene chloride (30 ml) and cooled to 0° C. A solution of the crude product from part (1)) and triethylamine in methylene chloride (30 ml) was slowly added to the above solution over 20 minutes. The resulting solution was stirred at 0° C. for 1.5 hours. The precipitate was removed by filtration. The filtrate was concentrated and the residue was purified with silica gel chromatography (hexane:ethyl acetate, 2:1, R$_f$=0.15) to afford 5.00 g of the desired product as a white solid; (M+H)$^+$=323.3; IR (KBr) 1731 cm$^{-1}$.

d)

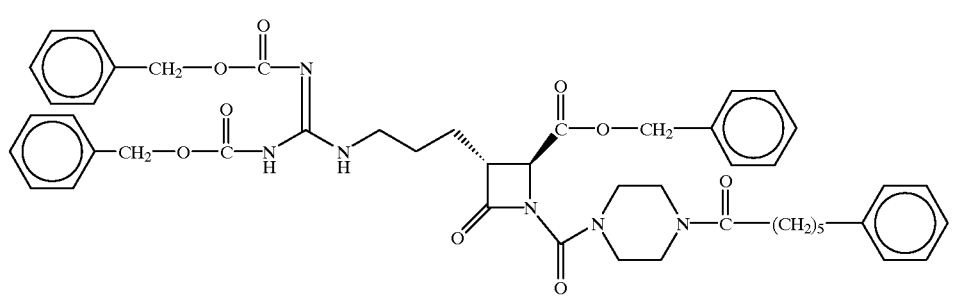

To a solution of the benzyl ester product from Example 1(c) (150 mg, 0.26 mmol) in methylene chloride (3 ml) was added triethylamine (0.043 ml, 0.31 mmol), the product from part (c) (102 mg, 0.31 mmol), and 4-dimethylaminopyridine (1.6 mg, 0.015 mmol). The solution was stirred for 3 hours and the solvent was removed. The residue was purified with silica gel chromatography (hexane:ethyl acetate, 1:1, $R_f$=0.22) to afford 210 mg of the desired product as a colorless oil. (M+H)+=859.5; (M–H)−= 857.5.

A mixture of the product from part (d) (100 mg, 0.115 mmol), palladium on carbon catalyst (10%, 30 mg), and 1N HCl (115 μl, 0.115 mmol) was stirred under a hydrogen atmosphere (balloon) at room temperature for 45 minutes. Analytical HPLC indicated the reaction was completed. The reaction mixture was diluted with water (6 ml), filtered, and lyophilized to give 53 mg of the desired product as a white powder. (M+H)+=501.3;; (M–H)−=499.2; IR (KBr) 1785 cm$^{-1}$.

e)

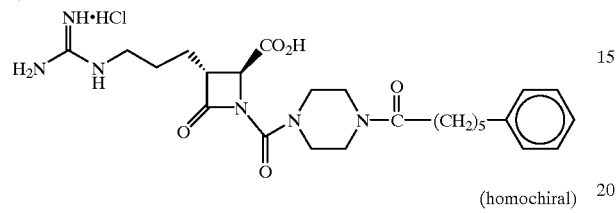

(homochiral)

EXAMPLE 198 a)

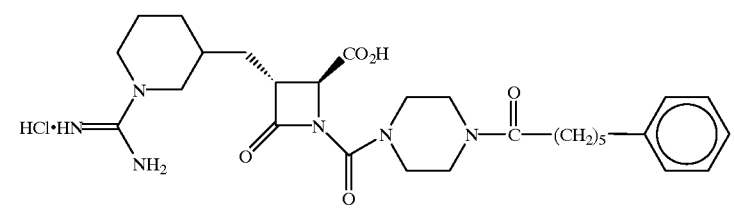

(diastereomeric mixture)

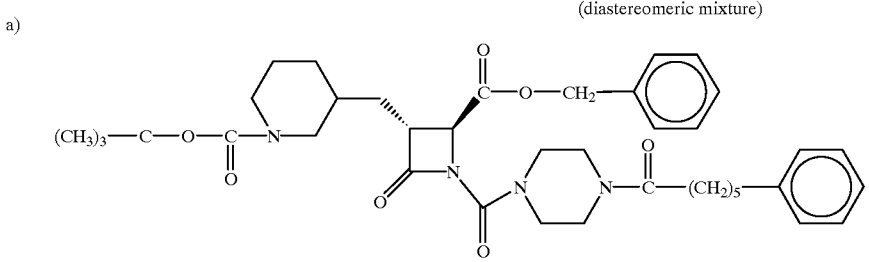

A solution of the product from Example 172(f) (80.5 mg, 0.20 mmol), triethylamine (0.056 ml, 0.40 mmol), the product of Example 197 (c) (97 mg, 0.30 mmol) and dimethylaminopyridine (6 mg, 0.05 mmol) in methylene chloride (1 ml) was stirred at room temperature under argon for 21 hours. The reaction was concentrated in vacuo and the residue was taken up in ethyl acetate, 10% potassium bisulfate, and water. The ethyl aceate layer was washed again with dilute potassium bisulfate, water (2×) and brine, dried over sodium sulfate and concentrated to an oil (179 mg). Chromatography of the oil over silica gel using 15% and then 25% ethyl acetate in methylene chloride provided 122 mg of the desired product as an oil.

b)

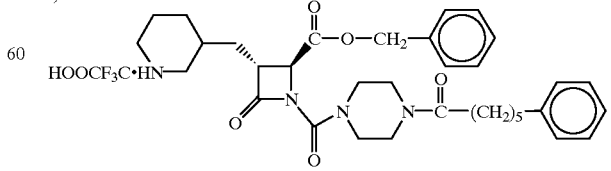

Treatment of the product from part (a) (120 mg, 0.174 mmol) with trifluoroacetic acid in methylene chloride according to the procedure described in Example 172 step (h) afforded 174 mg of the crude desired product.

c)

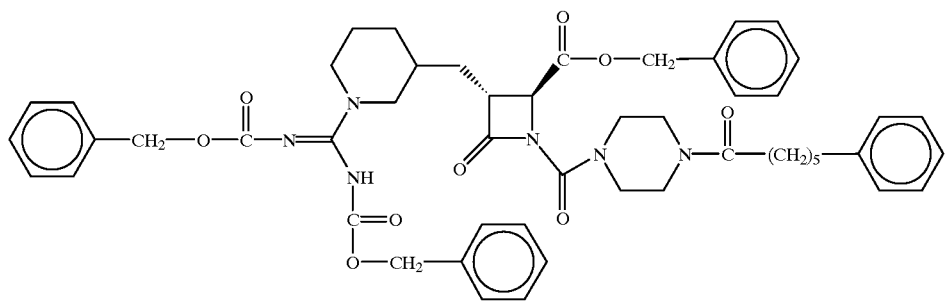

Treatment of the crude product from part (b) with N,N'-dicarbobenzyloxy-S-methylisothiourea according to the procedure in Example 172 step (i) gave 204 mg of crude product. Purification by chromatography over silica gel using methylene chloride: ethyl acetate (3:1) gave 79 mg of the desired product as an oily residue.

d)

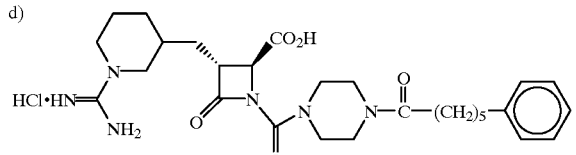

(diastereomeric mixture)

The product from step (c) (76 mg, 0.085 mmol) was hydrogenated in dioxane (3 ml) and 1.0N HCl (0.085 ml, 0.085 mmol) in the presence of 10% palladium on carbon catalyst (24 mg) at 1 atmosphere of hydrogen for 1 hour. After filtration using aqueous dioxane, the filtrate was concentrated to remove dioxane, filtered and lyophilized to give 42 mg of the desired proudct as a white solid; (IR (KBr) 1784 cm$^{-1}$, consisting of a mixture (62.38) of diastereomers as determined by HPLC.

EXAMPLE 199

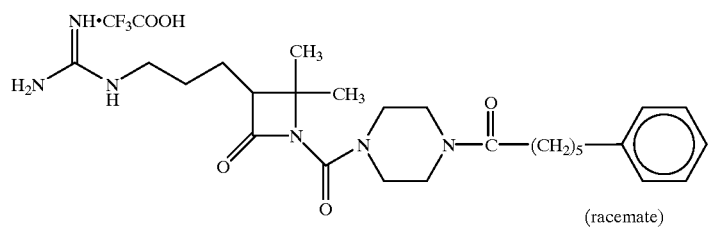

(racemate)

a)

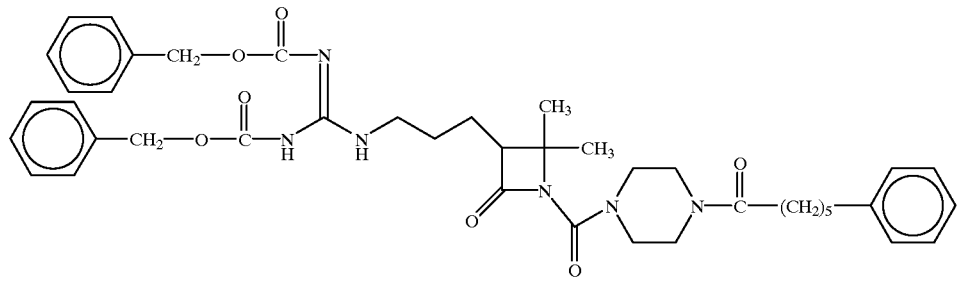

To a stirred solution of the protected dimethyl azetidinone from Example 135(f) (55 mg, 0.12 mmol) in tetrahydrofuran (3 ml) at −78° C. was added sodium bis(trimethylsilyl)amide (1N in hexanes, 0.13 mmol) and the solution was kept at this temperature for 30 minutes. A solution of the product from Example 197(c) (43 mg, 0.13 mmol) in tetrahydrofuran (1 ml) was added dropwise and the resulting mixture was warmed to −20° C. After 1 hour, the reaction was quenched with aqueous saturated ammonium chloride (5 ml) and extracted with ethyl acetate (2×5 ml). The combined organic layers were washed with brine and dried over magnesium sulfate. Filtration, concentration and purification by column chromatography (silica gel, 50% ethyl acetate in hexanes) afforded 79 mg of the desired product as a colorless oil.

b)

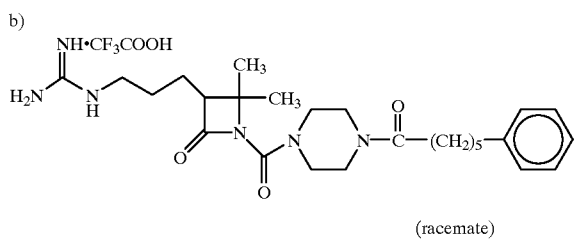

(racemate)

To a stirred solution of the product from part (a) (79 mg, 0.11 mmol) in a mixture of ethanol (1.5 ml), water (0.5 ml and ethyl acetate (1.5 ml) at room temperature was added palladium on carbon catalyst (10% wet, 15 mg). The resulting suspension was bubbled with hydrogen for 3 hours and the reaction mixture was then filtered. Concentration and purification by preparative HPLC (YMC ODS A 20×250 mm, 5 μ, 0 to 100% B over 35 minutes, hold time 15 minutes, A=10% methanol in water and 0.1% trifluoroacetic acid, B=90% methanol in water and 0.1% trifluoroacetic acid) afforded 42 mg of the desired product as a white solid; $(M+H)^+=485$.

EXAMPLE 200

(2S, 3R)-3-[[(3R)-1-(Aminoiminomethyl)-3-piperidinyl]methyl]-4-oxo-1-[[4-(1-oxo-6-phenylhexyl)-1-piperazinyl]carbonyl]-2-azetidinecarboxylic acid

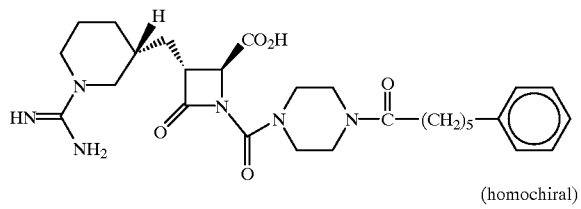

(homochiral)

a)

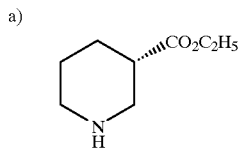

(±) Ethylnipeconate (100 g) and D-(−)tartaric acid (96 g) were dissolved in ethanol (500 ml, 95%) and heated to give a solution, which was filtered to remove minor insoluble material. The flask containing the solution was placed in a hot water bath to allow a very slow cooling and crystallization. After 4 hours, the formed crystals were filtered off and washed with ice cold ethanol (50 ml, 100%) yielding 70 g of the S(−) tartaric acid salt of ethylnipeconate. The mother liquor was concentrated and set aside. The crystallization was repeated twice to give 58 g of the S(−) tartaric acid salt. $[\alpha]_D=-10.56°$ (c=5% in water). See. R. Gollamudi et al., Med. Chem. Res., Vol 4, p. 597–603 (1994); $[\alpha]_D=-10.50°$ (c=5% in water).

The free base was liberated from an ice cold aqueous solution of the 32 g of the S(−) tartrate salt at pH 11.5 (3.0 N sodium hydroxide solution) by extraction with chloroform. Concentration of the dried chloroform solution gave 12.9 g of the desired product as a colorless mobile oil. $[\alpha]_D=+1.69$ (c=5% in water).

b)

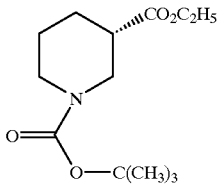

The product from part (a) (10 g, 63.61 mmol) was dissolved in dry ether (400 ml) at 0° C. with stirring and a solution of di-t-butyldicarbonate (13.9 g) in ether (20 ml) was added over 10 minutes. After stirring overnight at room temperature, the reaction mixture was cooled to 0° C., placed in an ice bath, and citric acid solution (50 ml, 35%) was slowly added with stirring. After phase separation, the ether layer was washed with brine (3×300 ml) and dried over sodium sulfate. Concentration gave 13.8 g of the desired product as a colorless oil.

c)

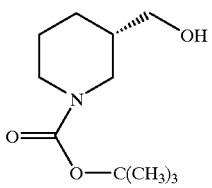

A solution of 1.0 N lithium aluminum hydride in tetrahydrofuran (52.4 ml) was added to the product from part (b) (13.5 g, 52.4 mmol) dissolved in tetrahydrofuran (100 ml) at 0° C. over a period of 15 minutes. The reaction was completed after 1.5 hours with stirring. The slow addition of 5.0 N sodium hydroxide (6.8 ml) with stirring, filtration, and concentration of the filtrate yielded an oil. This oil was dissolved in ether (80 ml). The ether solution was washed with brine and concentrated to a colorless oil, which on standing crystallized to give 10.18 g of the desired product as white crystals.

d)

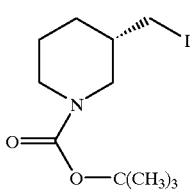

A solution of the product from part (c) (9.0 g, 41.8 mmol) in methylene chloride (50 ml) was added dropwise to a solution triphenylphosphine (16.13 g, 61.5 mmol), imidazole (4.19 g, 61.5 mmol) and iodine (15.6 g, 61.5 mmol) in methylene chloride (120 ml) at 0° C. (addition takes approximately 15 minutes). After stirring for 1.5 hours at room temperature, the reaction mixture was filtered and the filtrate was concentrated and taken up in ethyl acetate (100 ml). The resulting solution was washed with 5% sodium thiosulfate solution until the yellow color disappeared, washed with brine, dried over magnesium sulfate, and concentrated to an oil which crystallized slowly on standing. The material was purified by column chromatography on 300 g silica gel (methylene chloride/hexane, 4:1) and a second column chromatography on 200 g silica gel (ethyl acetate/hexane, 2:3) to give 11.1 g of desired product as white crystals. $[\alpha]_D$=+8.38° (c=5% in chloroform).

e)

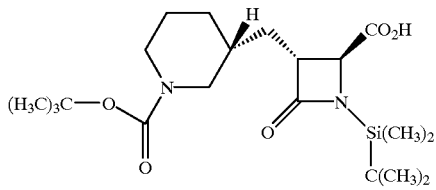

To a solution of diisopropylamine (7.83 ml, 52.7 mmol) in dry tetrahydrofuran (50 ml) was added at −20° C. a solution of 2.5 N butyl lithium in hexane (18.64 ml, 46.6 mmol). After stirring at −20° C. for 30 minutes, the solution was cooled to −70° C. and a solution of (4S)-N-(t-butyldimethylsilyl)azetidine-2-one-4-carboxylic acid (5.36 g, 46.6 mmol) in tetrahydrofuran (15 ml) was slowly added. After the addition was completed, the temperature was allowed to rise to −20° C. and a solution of the product from step (d) (10.5 g, 32.3 mmol) was added and the reaction mixture was stirred at −20° C. for 30 hours. The resulting suspension was poured into 200 ml ice/water and the pH was adjusted to 2.0. After extraction with ethyl acetate (five times), the ethyl acetate extracts were combined, washed with brine, and concentrated to an oil. This oil was dissolved in ether (100 ml) and the ether was extracted (five times) with 30 ml of sodium bicarbonate solution (5%). The combined aqueous layer at 0° C. was acidified with potassium bisulfate solution to pH 2.0 and extracted with ethyl acetate (3×30 ml). The organic layer was washed with brine, dried, and concentrated to give 7.82 of the desired product as an off-white foam.

f)

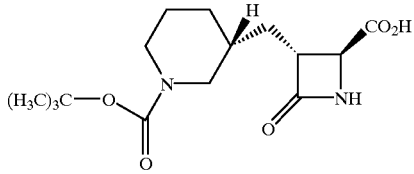

A solution of the product from step (e) (7.8 g) and 22.8 ml of tetrabutyl ammonium fluoride (1.0 N in tetrahydrofuran) was stirred for 30 hours at 0° C. and for one hour at room temperature. After concentration, the residue was dissolved in ethyl acetate (50 ml) and poured into 100 ml ice/water. The pH was then adjusted to 2.0 with potassium bisulfate solution, the phases were separated, and the aqueous layer was extracted with ethyl acetate (4×30 ml). The organic layers were combined, concentrated, and dried to yield 5.32 g of the desired product.

g)

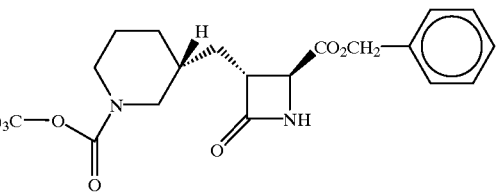

The product from part (f) (5.3 g, 12.88 mmol), benzyl bromide (6.3 ml, 53.0 mmol), and sodium bicarbonate (4.45 g, 53.0 mmol) were stirred at room temperature for 24 hours in dimethylformamide (60 ml). After 60 ml of ice/water was added, the mixture was extracted with ethyl acetate (4×30 ml). The combined organic layer was washed with brine and dried over sodium sulfate. Concentration gave a crude colorless oil which was purified by flash column chromatography on 300 g of silica gel (ethyl acetate/hexane, 1:1). The resulting colorless oil crystallized by scratching with a small amount of ether to give 5.8 g of the desired product as white crystals. MS (M+H)$^+$=403.

h)

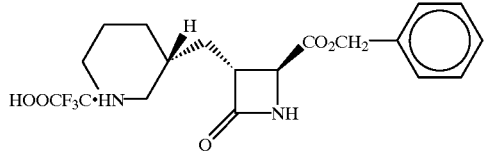

The product from part (g) (5.7 g, 14.18 mmol) was dissolved in methylene chloride (25 ml) and trifluoroacetic acid (10 ml) was added dropwise with stirring. The reaction was completed in one hour. The reaction mixture was concentrated and evaporated (3 times) from toluene (10 ml) to remove excess trifluoroacetic acid and give 7.96 g of the desired product as a white foam.

i)

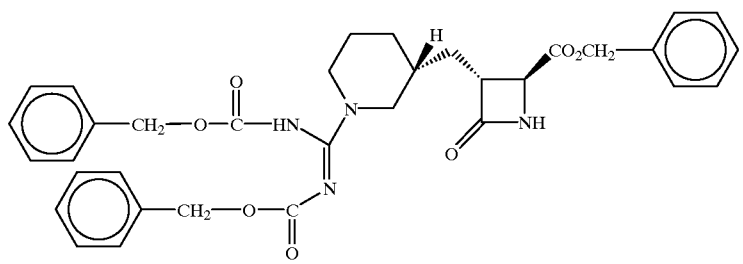

The product from part (h) (7.95 g), N,N'-bis (benzyloxycarbonyl)-1-guanylpyrazole (7.8 g, 21.4 mmol) and triethylamine (12.9 ml, 92.5 mmol) were stirred in dimethylformamide (50 ml) at 0° C. for one hour and for an additional 24 hours at room temperature. Ice water (50 ml) was added and the pH was adjusted to 3.0 with potassium bisulfate solution. The aqueous layer was extracted with ethyl acetate (5×30 ml). The organic layers were combined and washed with 5% potassium bisulfate solution, which was saturated with sodium chloride, half saturated brine, and brine. After drying and concentration, 12.05 g of crude product was obtained as a yellow-brown oil. Purification by column chromatography on silica gel (methylene chloride/ ethyl acetate, 8:2 and 7.3) gave 6.9 g of product as a colorless oil. This oil crystallized when stirred with ether and seed crystals (obtained from a small amount of oil in diisopropyl ether/pentane) to give 5.6 g of the desired product as white crytals. IR(KBr) 1749 cm$^{-1}$; MS (M+H)$^+$= 613.

j)

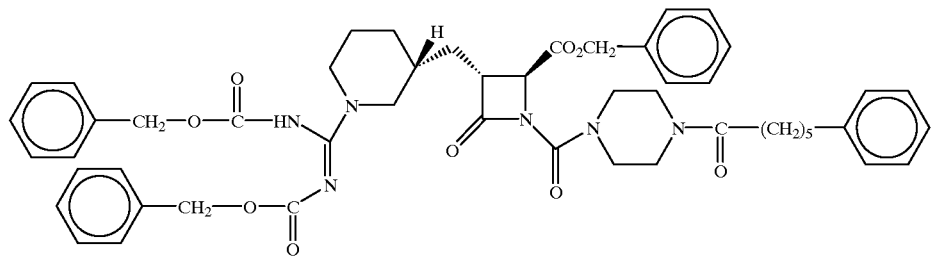

The product from part (i) (800 mg, 1.30 mmol), the product from Example 197(c) (421 mg, 1.31 mmol), diisopropylethylamine (343 µl) and 10 mg of catalytic dimethylaminopyridine were dissolved in 8 ml of methylene chloride and stirred for 24 hours at room temperature. After concentration, the reaction mixture was taken up with ethyl acetate (20 ml), extracted with potassium bisulfate/ice water solution at pH 3.0, washed with brine, and dried over sodium sulfate to yield from the organic phase 1.08 g of crude product. Purification by flash chromtography on 200 g silica gel (ethyl acetate/hexane, 3:2) gave 746 mg of desired product as a white foam. IR (film) 1786 cm$^{-1}$; MS (M+H)$^+$= 899.

k)

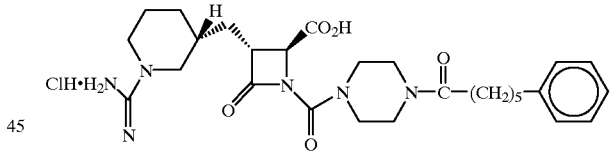

The product from part (j) (740 mg, 0.82 mmol) was dissolved in dioxane (10 ml). Palladium on carbon catalyst (400 mg, 10%) and 1.0 N HCl (823 µl) were added and the mixture was hydrogenated (balloon) for 2.5 hours. Filtration, concentration of the filtrate, and lyophilization yielded 465 mg of the desired product as a white powder. IR (KBr) 1785 cm$^{-1}$; MS(M+H)$^+$=541.

l)

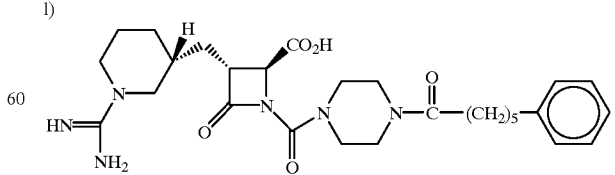

The product from part (j) (455 mg, 0.79 mmol) was dissolved in aqueous dioxane and passed through a column of 5 g of polyvinylpyridine packed in water-dioxane (70:30).

Product containing fractions were combined, concentrated, and lyophilized to give 375 mg of the desired product as a white solid. IR (KBr) 1775 cm$^{-1}$; MS (M+H)$^+$=541.

Anal. calc'd for $C_{28}H_{40}N_6O_5 \cdot 1.60\ H_2O$: C, 59.05; H, 7.65; N,14.76; $H_2O$, 5.06. Found: C,58.81; H, 7.60; N. 14.12; $H_2O$, 4.61.

EXAMPLE 201

(2S,3R)-3-[[(3S)-(Aminoiminomethyl)-3-piperidinyl]methyl]-4-oxo-1-[[4-(1-oxo-6-phenylhexyl)-1-piperazinyl]carbonyl]-2-azetidinecarboxylic acid

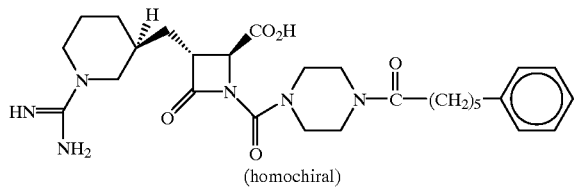
(homochiral)

a)

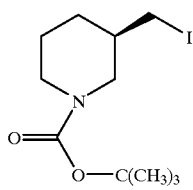

Following the procedure of Example 200 step (a) but employing L-(+) tartaric acid for the resolution, the R(+) tartaric acid salt of ethylnipeconate was obtained. $[\alpha]_D$=+10.68° (c=5% in water). See R. Gollamudi et al, Med. Chem. Res., Vol. 4, p. 597–603; $[\alpha]_D$=10.60° (c=5% in water).

The free base was liberated from the R(+) tartaric acid salt as a colorless liquid; $[\alpha]_D$=−1.68° (c=5% in water).

b)

The product from part (a) was reacted with di-t-butyldicarbonate according to the procedure of Example 200(b) to give the desired product as a colorless oil that crystallized after standing.

c)

The product from part (b) was reacted with lithium aluminum hydride according to the procedure of Example 200(c) to give the desired product as white crystals.

d)

The product from part (c) was reacted with triphenylphosphine, imidazole and iodine according to the procedure of Example 200 (d) to give the desired product as white crystals. $[\alpha]_D$=−8.42° (c=5% in chloroform).

e)

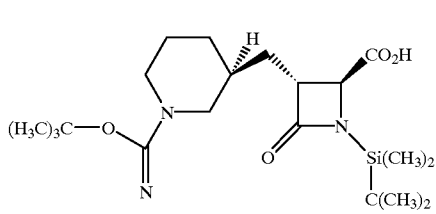

The product from part (d) was reacted with (4S)-N-(t-butyldimethylsilyl)azetidine-2-one-4-carboxylic acid according to the procedure of Example 200(e) to give the desired product as a yellow foam.

f)

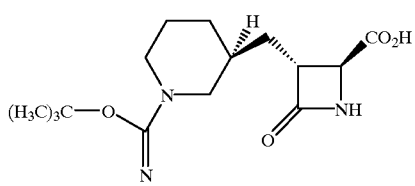

The product from part (e) was reacted with tetrabutyl ammonium fluoride according to the procedure of Example 200(f) to give the desired product as a somewhat yellow foam.

g)

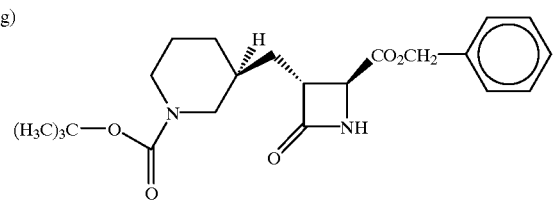

The product from part (f) was reacted with benzyl bromide according to the procedure of Example 200(g) to give the desired product as white crystals from ethyl acetate (the product did not crystallize directly from the concentrated work-up solution). IR (KBr) 1770 cm$^{-1}$; MS (M+H)$^+$=403.

h)

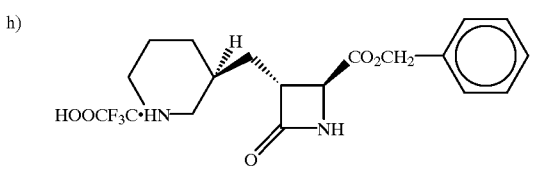

The product from part (g) was reacted with trifluoroacetic acid according to the procedure of Example 200(h), to give the desired product as an off-white foam.

i)

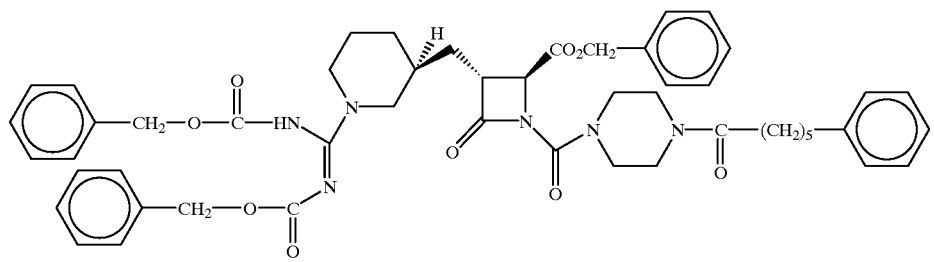

The product from part (h) was reacted with N,N'-bis (benzyloxycarbonyl)-1-guanylpyrazole according to the procedure of Example 200(i) to give 4.8 g of crude product that crystallized directly from the work-up concentrated ethyl acette solution. Recrystallization from methylene chloride/hexane gave the desired product as off-white crystals. IR (KBr) 1753 cm$^{-1}$; MS (M+H)$^+$=613.

j)

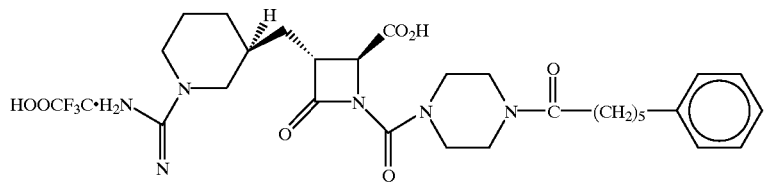

The product from part (i) was reacted with the product from Example 197(c) according to the procedure of Example 200(j) to give the desired product as a white foam. IR (film) 1785 cm$^{-1}$; MS (M+H)$^+$=899.

k)

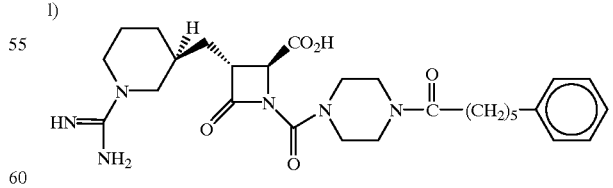

The product from part (j) was hydrogenated according to the procedure of Example 200(k) to give the product as an HCl salt. IR (KBr) 1784 cm$^{-1}$; MS (M+H)$^+$=514.

The above trifluoroacetic acid salt was obtained by preparative HPLC (reverse phase methanol, water, trifluoroacetic acid) to give the desired product as a white lyophilate.

l)

The product from part (k) was dissolved in aqueous dioxane and passed through a column of 5 g of polyvinylpyridine packed in water-dioxane (70:30). Product containing fractions were combined, concentrated and lyophilized to give the desired product as a white solid. IR (KBr) 1776 cm$^{-1}$; MS (M+H)$^+$=541.

EXAMPLE 202

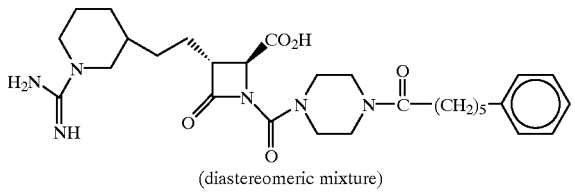

(diastereomeric mixture)

a)

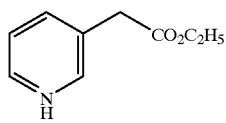

Ethyl 3-pyridylacetate (13.2 g, 80 mmol) was hydrogenated in 40 ml of absolute ethanol and 40 ml of acetic acid with 0.8 g of platinum oxide at 3 atmospheres for 20 hours. After filtration and removal of solvents in vacuo, the yellow residual oil was dissolved in chloroform and treated with a solution of 45 g of potassium carbonate in 200 ml of water. After extraction with chloroform (3×), the chloroform extract was dried over sodium sulfate and concentrated to an oil. The oil was taken up in ether and then concentrated to give 11.73 g of the desired product as an oil.

b)

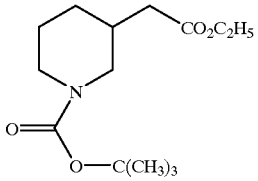

A solution of di-t-butyldicarbonate (15.0 g, 68.7 mmol) in ether (15 ml) was added over several minutes to a stirred solution of the product from part (a) (11.73 g, 68.5 mmol) in ether (100 ml) under nitrogen and stirred overnight at room temperature. Aqueous citric acid solution (50 ml of a solution of 350 g/1000 ml water) was added slowly to the reaction cooled in an ice water bath. The layers were separated and the aqueous layer was extracted with ether. The combined ether layers were washed with water, brine, and water, dried over sodium sulfate, and concentrated to give 17.95 g of the desired product as a yellow oil.

c)

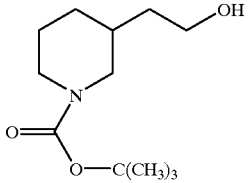

The product from part (b) was treated with lithium aluminum hydride according to the procedure of Example 200(c) to give the desired product as a colorless oil.

d)

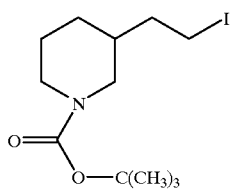

The product from part (c) was treated with triphenylphosphine, imidazole and iodine according to the procedure of Example 200(d) to give the desired product as an amorphous solid.

e)

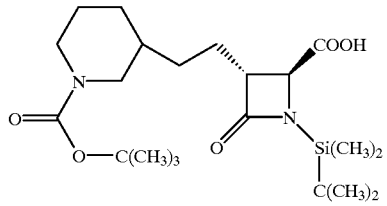

The product from part (d) was reacted with (4S)-N-(t-butyldimethylsilyl)azetidine-2-one-4-carboxylic acid according to the procedure of Example 200(e) to give the desired product.

f)

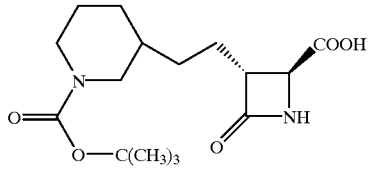

The product from part (e) was reacted with tetrabutyl ammonium fluoride according to the procedure of Example 200(f) to give the desired product as an oil.

g)

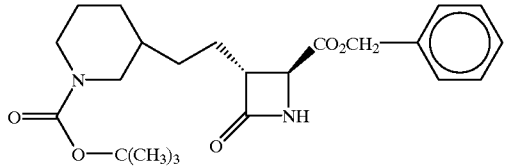

The product from part (f) was reacted with benzyl bromide according to the procedure of Example 200(g) to give the desired product as an amorphous white solid.

h)

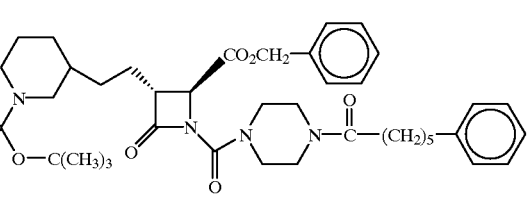

A solution of the product from part (g) (167 mg, 0.40 mmol), triethylamine (0.116 ml, 0.80 mmol), the product from Example 197(c) (194 mg, 0.60 mmol) and dimethylaminopyridine (12 mg, 0.10 mmol) in methylene chloride (2 ml) was stirred at room temperature under argon for 20 hours. The reaction was concentrated in vacuo and the residue was taken up in ethyl acetate, 10% potassium bisulfate and water. The ethyl acetate layer was washed again with dilute potassium bisulfate, water (2×), and brine, dried over sodium sulfate, and concentrated to give 362 mg of an oil. Chromatography of the oil over silica gel using 10%, 20% and the 35% ethyl acetate in methylene chloride gave 247 mg of the desired product as an oil.

catalyst (25 mg). A hydrogen atmosphere was introduced via balloon. After 2 hours of stirring at room temperature, the mixture was diluted with water (1.0 ml) and filtered. The solution was then put on a one inch column of polyvinylpyridine resin which had been cleaned by rinsing with methylene chloride, methanol and water. The column was eluted with water. Product containing fractions were combined and lyophilized to give 36.6 mg of the desired product. MS(M+H)$^+$ 555.

i)

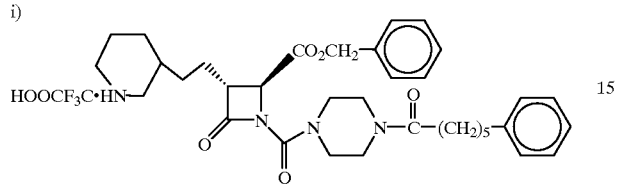

Trifluoroacetic acid (0.50 ml) was added dropwise to a stirred solution of the product from part (h) (170 mg, 0.242 mmol) in methylene chloride (1.50 ml) at 0° C. The reaction mixture was then stirred at room temperature. After one hour, the reaction mixture was concentrated and dried in vacuo. The crude product was dissolved in chloroform and concentrated. This procedure was repeated three times. The crude product was then dried in vacuo to give 173 mg of the desired product.

EXAMPLE 203

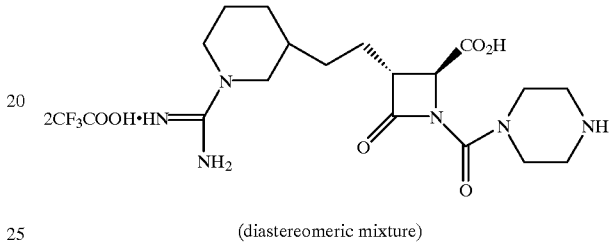

(diastereomeric mixture)

j)

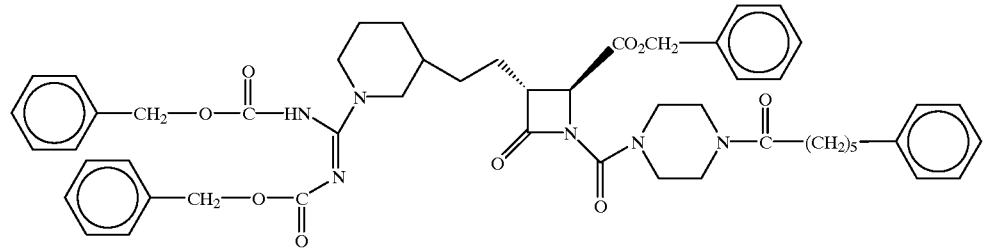

The product from part (i) (173 mg, 0.241 mmol) and N,N'-dicarbobenzyloxy-S-methylisothiourea (260 mg, 0.362 mmol) were dissolved in dimethylformamide (2.0 ml). Mercuric chloride (98.0 mg. 0.362 mmol) was added followed by triethylamine (134 μl, 0.964 mmol). After 2 hours the reaction mixture was diluted with ethyl acetate and filtered to remove mercury salts. The filtrate was washed with saturated sodium chloride, dried over magnesium sulfate, and concentrated. The crude product was purified by silica gel chromatography to give 101 mg of the desired product.

k)

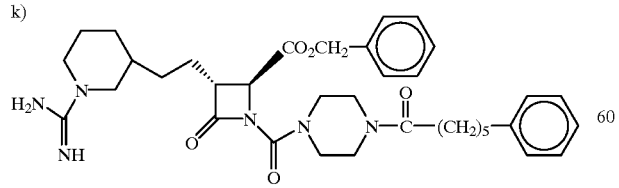

The product from part (j) (94 mg, 0.103 mmol) was dissolved in 1,4-dioxane (1.0 ml). 1N HCl (103 μl, 0.103 mmol) was added followed by 10% palladium on carbon -continued a)

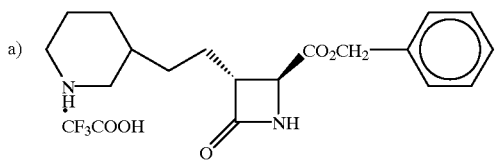

Treatment of the product of Example 172(f) (12.6 g, 31.3 mmol) with trifluoroacetic acid (25 ml) in methylene chloride (100 ml) according to the procedure of Example 172(h) afforded the desired product (crude) as a viscous oil.

b)

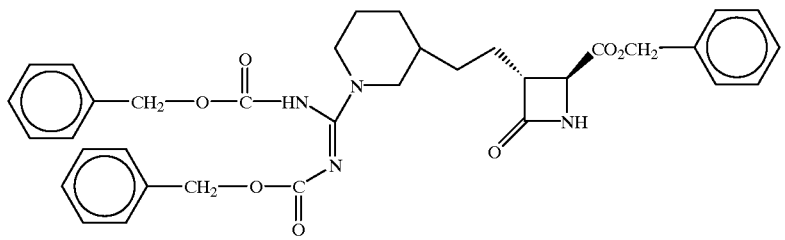

Triethylamine (22 ml, 158 mmol) was slowly added to a solution of the crude product from part (a) (31.3 mmol) and N,N'dicarbobenzyloxy-S-methylisothiourea (13.0 g) in dimethylformamide (31 ml) under argon cooled in an ice-water bath. The reaction was stirred at room temperature for 20 hours and concentrated to a residue. The residue was taken up in ethyl acetate (500 ml). The ethyl acetate was washed with water (500 ml) and the aqueous layer was extracted with ethyl acetate (200 ml). The combined ethyl acetate layer was washed with dilute potassium bisulfate plus brine (2×) and brine (2×), dried over sodium sulfate, and concentrated to a viscous oil (23 g). Chromatography of the oil over silica gel using methylene chloride-ethyl acetate (8:2) and then (1:1), followed by concentration of the combined fractions from ethyl acetate gave 14.1 g of the desired product as a white solid consisting of a mixture (60:40) of diastereomers.

c)

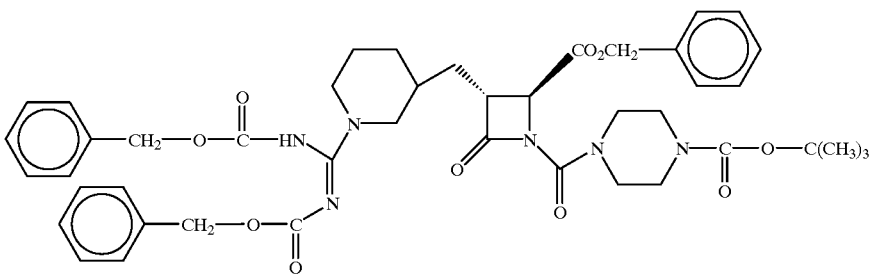

Triethylamine (90 μl, 0.66 mmol) and 4-dimethylaminopyridine (5 mg, 0.04 mmol) were added to a stirred solution of the product from part (b) (132 mg, 0.22 mmol) and the carbamoyl chloride from Example 20(a) (59 mg, 0.24 mmol) in methylene chloride (5 ml) at room temperature. After 2 hours, the reaction mixture was concentrated and purified by silica gel chromatography (50% ethyl acetate in hexanes) to give 177 mg of the desired product as a white solid.

d)

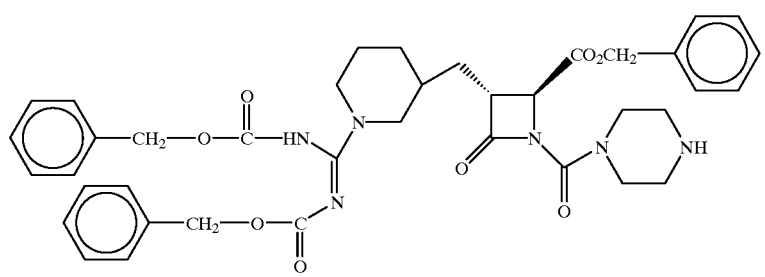

Trifluoroacetic acid (0.2 ml, 2.46 mmol) was added to a stirred solution of the product from part (c) (177 mg, 0.22 mmol) in methylene chloride (5 ml) at room temperature. After 30 minutes, the reaction was first concentrated under reduced pressure and then diluted with ethyl acetate. Aqueous sodium bicarbonate was added to the resulting organic solution until the pH of the aqueous layer reached 10. The aqueous layer was extracted with ethyl acetate and the combined organic layers were dried over magnesium sulfate. Filtration and concentration under reduced pressure gave 125 mg of the desired product as a colorless oil.

e)

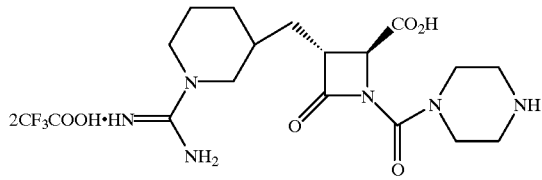

f)

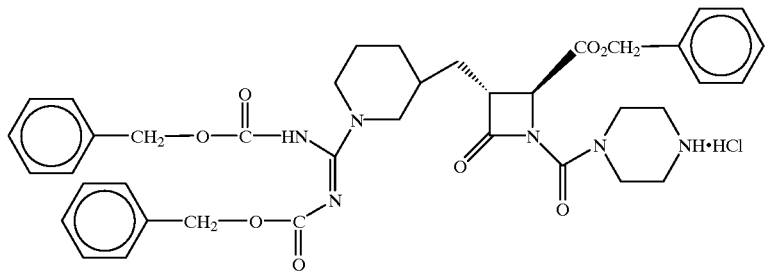

The above intermediate was prepared as follows.

Trifluoroacetic acid (0.2 ml, 2.46 mmol) was added to a stirred solution of the product from part (c) (177 mg, 0.22 mmol) in methylene chloride (5 ml) at room temperature. After 30 minutes, the reaction was concentrated under reduced pressure. The resulting oil was diluted with methylene chloride followed by the addition of HCl in diethyl ether (1N, 0.30 ml, 0.30 mmol). Additional diethyl ether (3.0 ml) induced formation of a white precipitate which was filtered to give the desired HCl salt as a white solid.

Palladium on carbon catalyst (10%, 20 mg) was added to a stirred solution of the product from part (d) (40 mg, 0.06 mmol) in a mixture of ethyl acetate (2 ml), ethanol (2 ml) and water (1 ml) at room temperature. Hydrogen gas was bubbled through the resulting suspension for 3 hours. After filtration through a plug of Celite® and concentration, the mixture was purified by preparative HPLC (YMC ODS A 20×250 mm, 5 µl, 0 to 100% B over 30 minutes, hold time 15 minutes, A=10% methanol in water and 0.1% trifluoroacetic acid, B=90% methanol in water and 0.1% trifluoroacetic acid) to afford 8 mg of the desired trifluoroacetic acid salt product as a white solid. MS $(M+H)^+=367$.

EXAMPLE 204

(diastereomeric mixture)

a)

Ethyl succinylchloride (1.92 g, 11.65 mmol) was added to a solution of 2-aminoacetophenone (2.00 g, 11.65 mmol) in pyridine (12 ml) at 0° C. The mixture was stirred at room temperature for 20 hours and then diluted with chloroform (75 ml) and water (10 ml). The organic layer was then separated and washed with 5% sodium bicarbonate (20 ml), dried over magnesium sulfate, and concentrated to give 3.14 g of the desired product as an orange solid.

b)

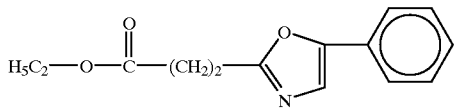

A mixture of the product from part (a) (2.1 g) and phosphorus pentoxide (4.53 g, 31.9 mmol) in chloroform (20 ml) under nitrogen was heated at reflux for 16 hours. The solution was cooled to room temperature and ice was added followed by neutralization with 5% sodium bicarbonate. The mixture was extracted with chloroform (3×30 ml), dried over magnesium sulfate, and concentrated to give a crude product. Silica gel chromatography (ethyl acetate/hexanes, 4:6) afforded 0.75 g of the desired product as a faint yellow oil.

c)

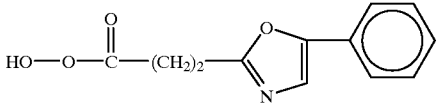

To a solution of the product from part (b) (0.70 g, 2.85 mmol) in dioxane/water (15.0/7.5 ml) was added 1N sodium hydroxide (7.1 ml, 7.1 mmol). The mixture was stirred until disappearance of the starting material. It was then concentrated, water (10 ml) was added, the mixture was cooled in an ice bath, and the pH was adjusted to 5.0 with the addition of 1N HCl to give a precipitate. The precipitate was collected and dried to give 0.26 g of the desired product as a white solid.

d)

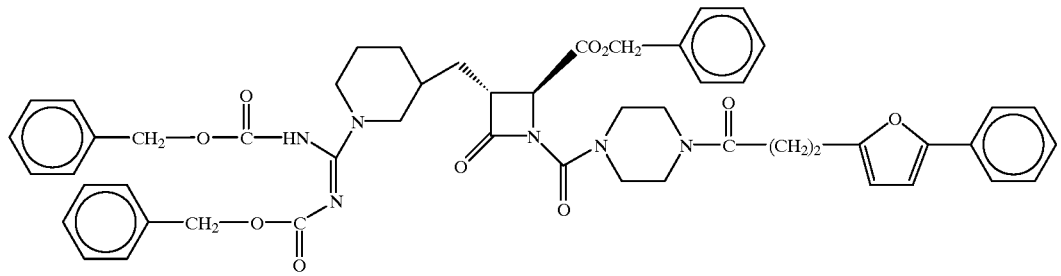

To a solution of the product from part (c) (0.026 g, 0.12 mmol) and hydroxybenzotriazole (0.016 g, 0.016 mmol) in methylene chloride (3 ml) was added 1-(3-dimethylaminopropyl)-3-ethylcarbodiimide hydrochloride (0.023 g, 0.12 mmol) at 0° C. and stirred for 30 minutes. The HCl salt product from Example 203 (f) (0.075 g, 0.11 mmol) and diisopropylethylamine (0.034 g, 0.27 mmol) were added and the reaction mixture was stirred at room temperature for 18 hours. The reaction mixture was diluted with methylene chloride and washed with 5% sodium bicarbonate, dried over magnesium sulfate, and concentrated to give a crude product. Silica gel chromatography (3% methanol/chloroform) afforded 0.053 g of the desired product as a colorless oil.

e)

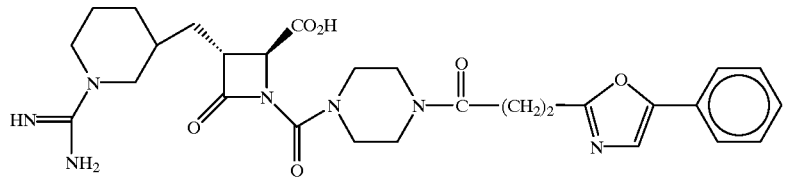

A mixture of the product from part (d) (20 mg, 0.02 mmol), palladium on carbon catalyst (10%, 5 mg) in dioxane (1 ml) and 1N HCl (0.02 ml) was stirred under hydrogen atmosphere (hydrogen balloon) at room temperature for one hour. The reaction mixture was filtered through a Celite® pad and purified by preparative HPLC and lyophilized to give the desired product as a trifluroacetic acid salt.

This salt was passed through a polyvinylpyridine column and lyophilized to afford 10 mg of the desired product (zwitterion) as a white lyophilate. IR (KBr) 1775 cm$^{-1}$; MS (M+H)$^+$=566.

EXAMPLE 205

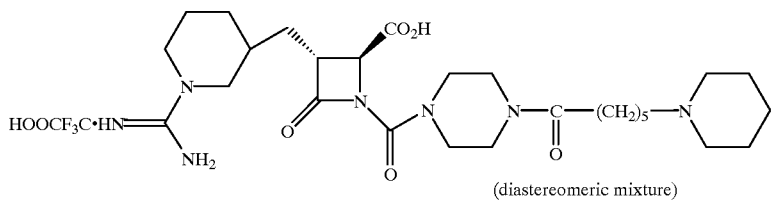

(diastereomeric mixture)

a)

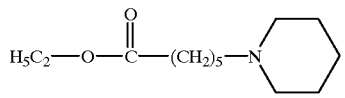

Ethyl 6-bromohexanote (8.00 ml, 44.82 mmol) was added to a solution of piperidine (11.98 ml, 121.01 mmol) in toluene (20 ml). The mixture was heated at 90° C., stirred for 2 hours, and then cooled to room temperature. The white precipitate was filtered out. The filtrate was diluted with ethyl acetate (60 ml), washed with water (2×30 ml) and brine (20 ml), and then acidified to pH 3.0 with 1N HCl. The aqueous layer was basified to pH 9.0 with solid potassium carbonate and extracted with ethyl acetate (3×30 ml). The combined ethyl acetate solution was washed with brine, dried over magnesium sulfate, and concentrated to give 10.0 g of the desired product as a colorless oil.

b)

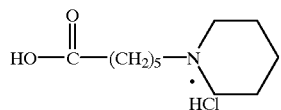

A solution of the product from part (a) (5.0 g, 0.022 mmol) in 5% sodium hydroxide ethanolic solution (100 ml) was stirred overnight and quenched with acetic acid (7.5 ml). The solvent was removed and the residue was dissolved in methylene chloride: methanol:acetic acid (2:1:1), flashed on a silica gel column (eluted with methylene chloride:methanol:acetic acid, 2:1:1) to give after concentration a colorless oil. This oil was dissolved in water (20 ml) and treated with concentrated HCl (25 ml). The extra HCl was removed under vacuum. The solution was lyophilized to provide 5.05 g of the desired product as a gray yellow solid.

c)

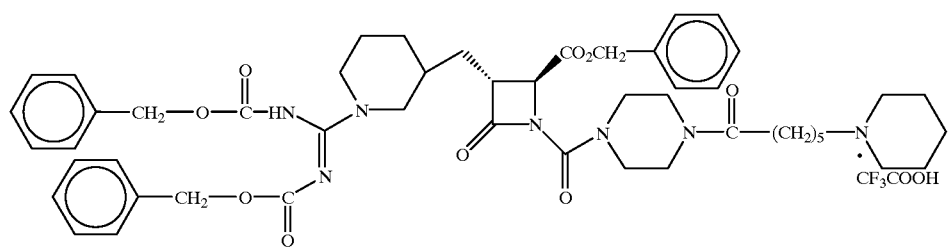

To a solution of the product from part (b) (25 mg, 0.11 mmol) and hydroxybenzotriazole (18 mg, 0.12 mmol) in methylene chloride (2 ml) was added 1-(3-dimethylaminopropyl)-3-ethylcarbodiimide hydrochloride (22 mg, 0.12 mmol) at 0° C. The mixture was stirred for 30 minutes and the HCl salt product from Example 203 (f) (72 mg, 0.11 mmol) and diisopropylethylamine (66 μl, 0.38 mmol) were added and the mixture was changed into a homogeneous solution. The solution was slowly warmed to room temperature within 3 hours, stirred overnight and concentrated. The residue was purified with preparative HPLC (reverse phase, methanol, water, trifluoroacetic acid), and lyophilized to give 40 mg of the desired product as a white solid. MS $(M+H)^+$=906.

d)
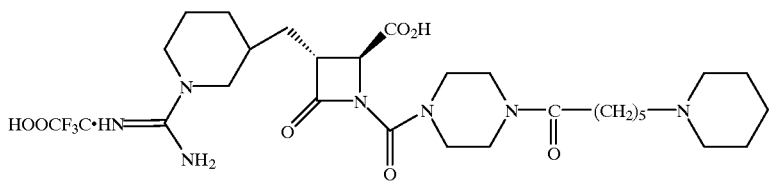

A mixture of the product from part (c) (45 mg, 0.050 mmol), palladium on carbon catalyst (10%, 15 mg) and 1N HCl (100 μl, 0.10 mmol) in 1,4-dioxane (1.0 ml) was stirred under a hydrogen atmosphere (hydrogen balloon) at room temperature for 45 minutes. The reaction mixture was filtered through Celite® pad. The filtrate was concentrated.

The residue was taken up with methanol:water (1:1), purified with preparative HPLC (reverse phase, methanol, water, trifluoroacetic acid), and lyophilized to give a white lyophilate. The lyophilate was dissolved in methanol: water (1:1) and passed through a polyvinylpyridine pad (eluted with methanol:water, 1:1). After methanol was removed, the solution was lyophilized to provide 8.3 mg of the desired product as a white powder (lyophilate). IR (KBr) 1776 cm$^{-1}$; MS (M+H)$^+$548.

EXAMPLE 206

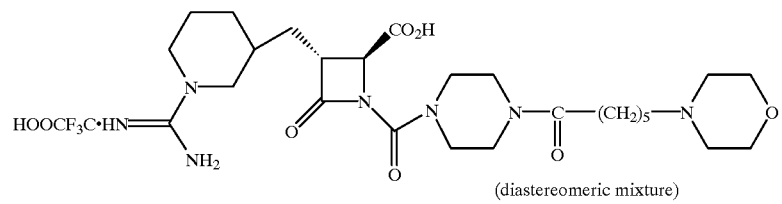
(diastereomeric mixture)

a)
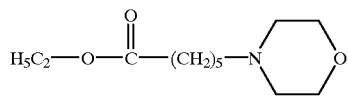

Following the procedure of Example 205(a) but employing morpholine in place of the piperidine, the desired product was obtained as a colorless oil.

b)
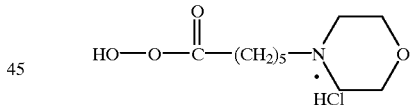

The product from part (a) was treated with a 5% sodium hydroxide ethanolic solution and concentrated HCl according to the procedure of Example 205(b) to give the desired product as a white solid following lyophilization.

c)
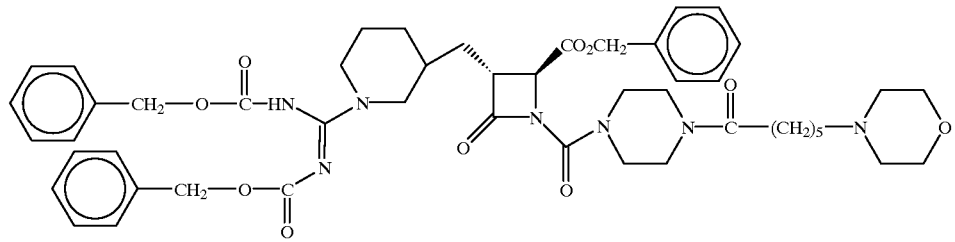

The product from part (b) was coupled to the HCl salt product from Example 203(f) according to the procedure of Example 205(c) to give the desired product as a white solid following lyophilization. MS(M+H)+ 908.

d)
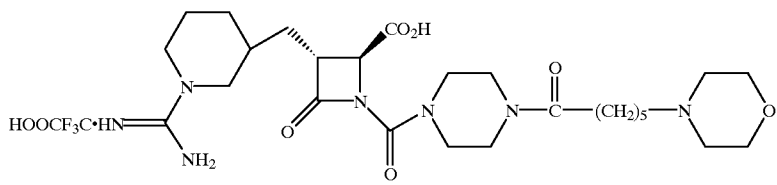

The product from part (c) was hydrogenated and purified according to the procedure of Example 205(d) to give the desired product as a white powder following lyophilization. IR(KBr) 1775 cm$^{-1}$; MS(M+H)$^+$=550.

The following procedure of Examples 204 to 206, the following compounds were also prepared:

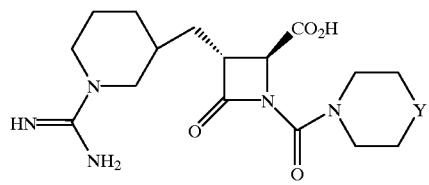

| Ex | Y | salt | stereochemistry | (M + H)+ |
|---|---|---|---|---|
| 207 | N—C(O)—CH₂—NH—C(O)—NH—phenyl | — | diastereomeric mixture | 557 |
| 208 | N—C(O)—(CH₂)₃—indole | — | diastereomeric mixture | 552 |
| 209 | N—C(O)—(CH₂)₅—cyclohexyl | — | diastereomeric mixture | 547 |
| 210 | N—C(O)—N(piperazine)N—(CH₂)₂—pyridyl | 1.0 HCl | diastereomeric mixture | 583 |

EXAMPLE 211 a)
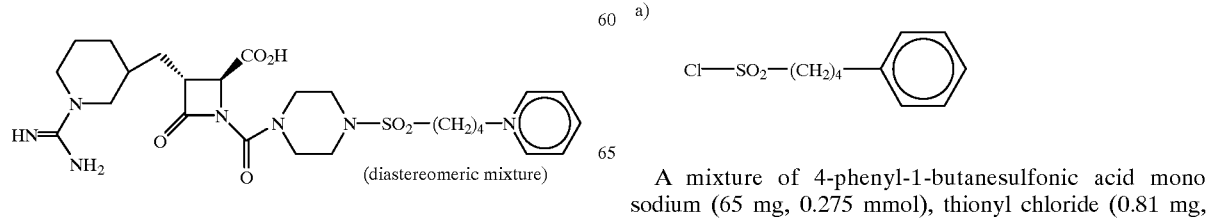
(diastereomeric mixture)

A mixture of 4-phenyl-1-butanesulfonic acid mono sodium (65 mg, 0.275 mmol), thionyl chloride (0.81 mg, 6.85 mmol), and dimethylformamide (a few drops) was heated at 65° C. for 3 hours. The mixture was cooled in an ice-bath and ice water was added to give a greenish residue. This residue was extracted with methylene chloride, dried over magnesium sulfate, and concentrated to give the desired product as a colorless oil.

b)

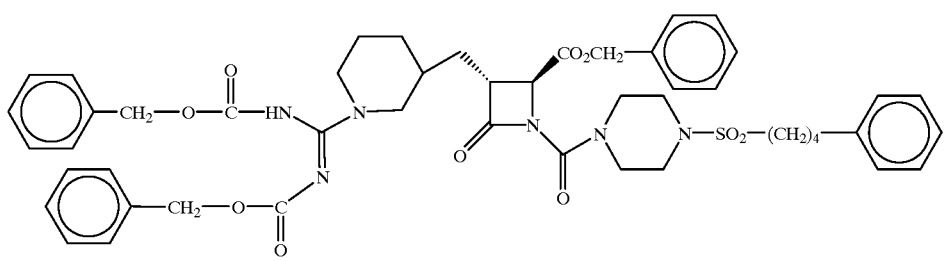

The product from part (a) (24.0 mg, 0.1 mmol) was added to a mixture of the product from Example 203 (d) (78.5 mg, 0.1 mmol) and potassium carbonate (41.5 mg, 0.3 mmol) in acetonitrile (1.0 ml) under argon at 0° C. and stirred at room temperature for 15 hours. The reaction mixture was then heated at 45° C. for 2 hours and triethylamine (30 mg, 0.3 mmol) and methylene chloride (0.5 ml) were added. The reaction mixture was then heated at 45° C. for 2 hours and concentrated in vacuo. Silica gel chromatography (methanol/chloroform, 1%) afforded 34 mg of the desired product as a clear oil.

c)

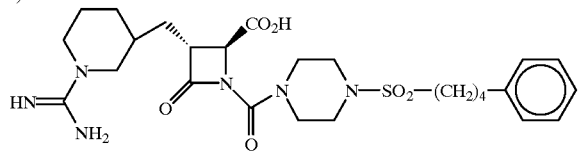

A mixture of the product from part (b) (34 mg, 0.037 mmol) and palladium on carbon catalyst (10%, 8 mg) in isopropanol (1 ml) and 1N HCl (0.11 ml) was stirred under hydrogen atmosphere (hydrogen balloon) at room temperature for 1 hour. Additional palladium on carbon catalyst (5 mg) was added and the mixture was stirred under hydrogen atmosphere for 1 hour. The reaction mixture was filtered through a Celite® pad, and purified by preparative HPLC and lyophilized to give the trifluoroacetic acid salt of the desired product. This salt was passed through a polyvinylpyridine column and lyophilized to afford 10.4 mg of the desired product (zwitterion) as a white lyophilate. IR(KBr) 1778 cm$^{-1}$; MS (M+H)$^+$=563.

EXAMPLE 212

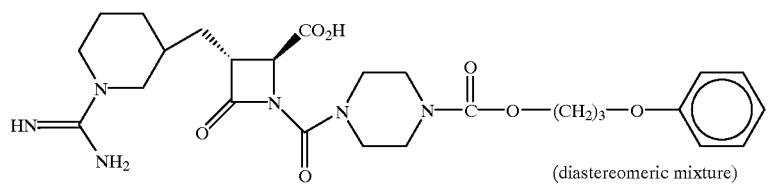

(diastereomeric mixture)

a)

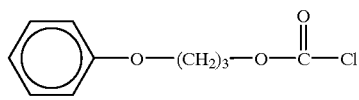

Sodium bicarbonate (1.0 g, 11.9 mmol) was added to a stirred solution of phenoxy-3-propanol (200 mg, 1.32 mmol) in methylene chloride (4 ml) at room temperature followed by phosgene (4.0 ml, 20% in toluene). An exothermic reaction occurred and the evolution of $CO_2$ gas was observed. After 30 minutes, the reaction mixture was filtered through a plug of silica gel to remove solids. The organic solution was concentrated to afford 265 mg of the desired product as a white solid.

b)

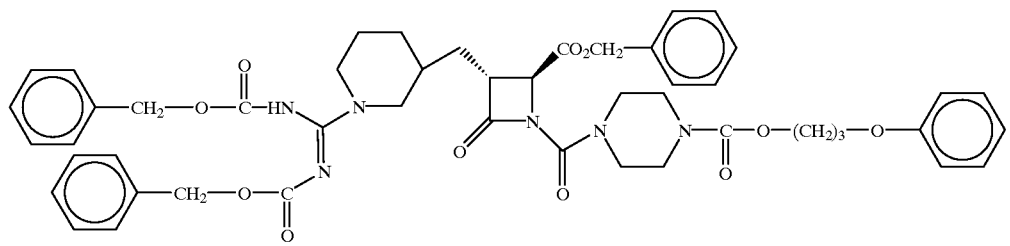

Triethylamine (35 µl, 0.25 mmol) and dimethylaminopyridine (1.5 mg, 0.01 mmol) were added to a stirred solution of the product from Example 203(d) (37 mg, 0.05 mmol) and the product from part (a) (15 mg, 0.07 mmol) in methylene chloride (3 ml) at room temperature. After 3 hours, the reaction mixture was directly purified by silica gel chromatography (50% ethyl acetate in hexanes) to give 42 mg of the desired product as a colorless oil.

c)

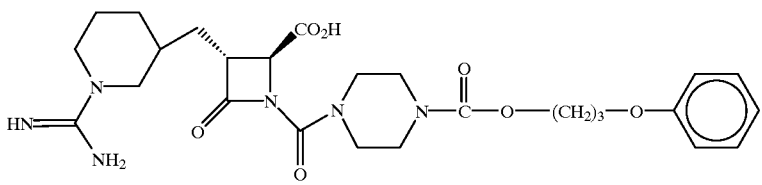

Palladium on carbon catalyst (10%, 20 mg) was added to a stirred solution of the product from part (b) (40 mg, 0.04 mmol) in a mixture of ethyl acetate (2 ml), ethanol (2 ml), and water (1 ml) at room temperature. Hydrogen gas was bubbled through the resulting suspension for 5 hours. After filtration through a plug of Celite® and concentration, the mixture was purified by preparative HPLC to afford the triluoroacetic acid salt of the desired product as a white solid. This trifluoroacetic acid salt was filtered through a column of polyvinylpyridine resin followed by lyophilization to give 18 mg of the desired product (zwitterion). IR(KBr) 1778 cm$^{-1}$; MS (M+H)$^{+}$=543.

EXAMPLE 213

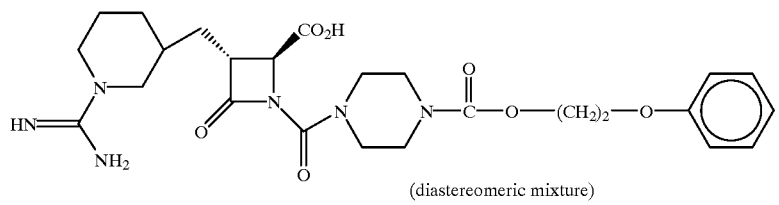

(diastereomeric mixture)

a)

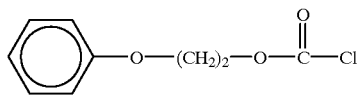

Following the procedure of Example 212(a) but employing phenoxy-2-ethanol, the desired compound was obtained as a white solid.

b)

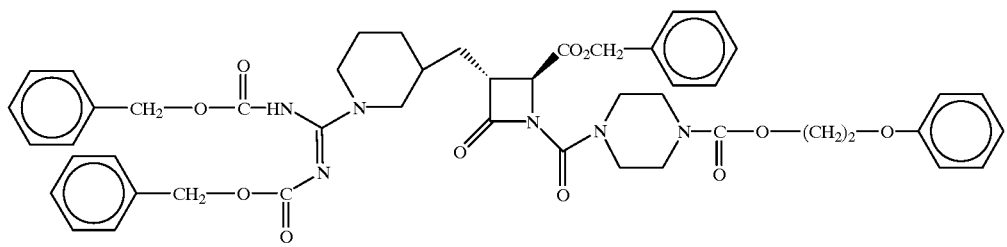

The product from part (a) was reacted with the product from Example 203(d) according the the procedure of Example 212(b) to give the desired product as a colorless oil.

c)

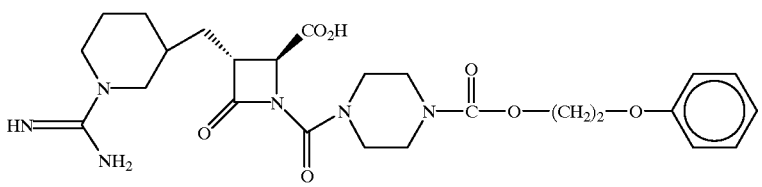

The product from part (b) was hydrogenated and worked-up according to the procedure of Example 212(c) to give the desired zwitterion product as a lyophilate. IR(KBr) 1776 cm$^{-1}$; MS (M+H)$^+$=543.

EXAMPLE 214

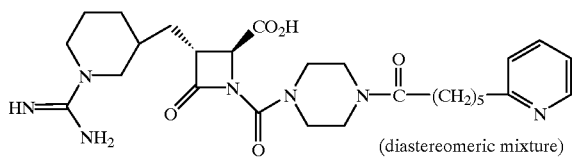
(diastereomeric mixture)

a)

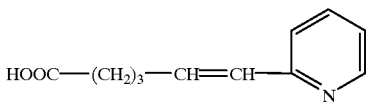

A suspsension of (4-carboxybutyl)triphenylphosphonium bromide (4.44 g, 10 mmol) in dry tetrahydrofuran (150 ml) was stirred at room temperature under an argon atmosphere and 2.5 equivalents of a 0.5 M solution of potassium bis(trimethylsilyl)amide (50 ml) in toluene was added. The resulting mixture was stirred overnight at room temperature and became a deep orange color. Pyridine-2-carboxaldehyde (1.18 g, 11 mmol) was added and the mixture was stirred for 3 hours. The reaction mixture was evaporated yielding a dark residue which was triturated with ether removing most of the triphenylphosphene oxide and giving 1.0 g of the desired product as a mixture of cis and trans isomers.

b)

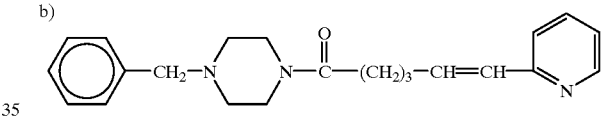

A mixture of the product from part (a) (900 mg), 1-benzylpiperazine (916 mg, 5.2 mmol), ethyl-3-(dimethylamino)propyl carbodiimide, hydrochloride salt (996 mg, 5.2 mmol), 1-hydroxybenzotriazole (700 mg, 5.2 mmol), and N-methylmorpholine (1.05 g, 10.4 mmol, 1.04 ml) in dimethylformamide (10 ml) was stirred at room temperature overnight under an argon atmosphere. The reaction was diluted with water and extracted with ethyl acetate, washed with water, 5% lithium chloride, and brine, and dried over anhydrous sodium sulfate. Evaporation yielded the crude product as a yellow oil. Purification by column chromatrography on silica, eluting with ethyl acetate/hexane (3:1) yielded 400 mg of the desired product.

c)

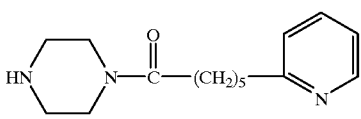

Platinum (IV) oxide (75 mg) was added to a solution of the product from part (b) (350 mg, 1.0 mmol) in ethanol (10 ml) and the resulting mixture was stirred under a hydrogen atmosphere overnight. The catalyst was removed by filtering through Celite® and the solvent was evaporated yielding 260 mg of the desired product as a colorless oil.

d)

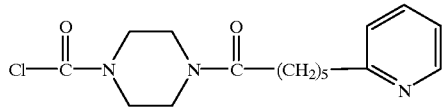

A solution of 3.5 equivalents of 20% phosgene in toluene (1.9 ml) and methylene chloride (15 ml) was cooled to 0° C. under an argon atmosphere and a solution of the product from part (c) (250 mg, 0.95 mmol) and triethylamine (135 mg, 1.33 mmol) in methylene chloride (15 ml) was added over 30 minutes. The reaction was stirred for 1 hour and was filtered, the solvents evaporated, and the crude product purified by column chromatography on silica eluting with 20% ethyl acetate/hexane yielding 150 mg of the desired product as a colorless solid.

e)

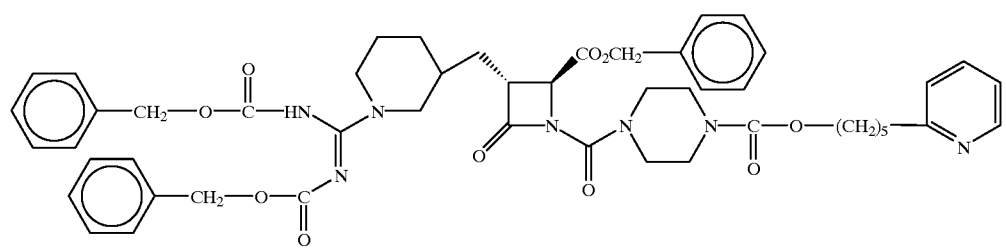

A mixture of the product from Example 203 (b) (245 mg, 0.4 mmol), the product from part (d) (130 mg, 0.4 mmol), diisopropylethylamine (51.7 mg, 0.4 mmol) and N,N-dimethylaminopyridine (5 mg) was stirred together in dry methylene chloride (1 ml). After stirring overnight at room temperature the mixture was evaporated and the crude product was purified by column chromatography eluting with 15% ethyl acetate/hexane yielding 142 mg of the desired product as a colorless glass-like residue. MS $(M+H)^+=901$.

f)

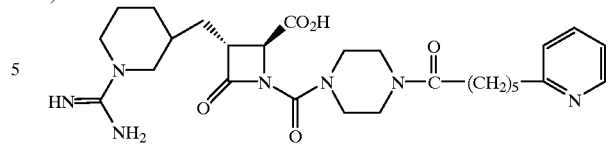

A solution of the product from part (e) (140 mg, 0.14 mmol) in dioxane (2 ml) containing 2.5 equivalents of 0.1N HCl and 10% palladium on carbon catalyst (20 mg) was stirred under a hydrogen atmosphere for 1.5 hours at room temperature. The reaction was filtered and passed through approximately 5 equivalents of polyvinylpyridine resin with water/dioxane (1:1). The solvents were removed by lyophilization yielding 56 mg of crude product as a colorless solid. Purification by preparative HPLC yielded 18 mg of colorless material, which was passed through a polyvinylpyridine resin yielding 9 mg of the desired product. MS $(M+H)^+=542$.

Examples 215–221

Following the procedure of Example 214, the following compounds were also prepared:

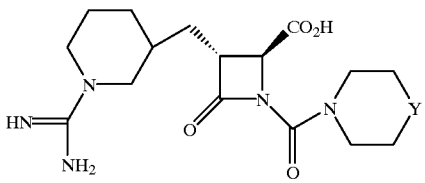

| Ex | Y | salt | stereochemistry | $(M+H)^+$ |
|---|---|---|---|---|
| 215 | N—C(=O)—N(H)—(CH$_2$)$_4$—Ph | — | diastereomeric mixture | 542 |
| 216 | N—C(=O)—C(=O)—N(H)—(CH$_2$)$_4$—Ph | — | diastereomeric mixture | 570 |

-continued

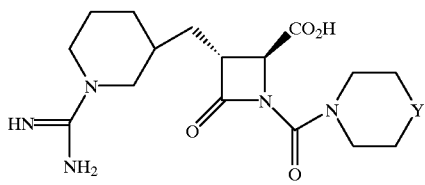

| Ex | Y | salt | stereochemistry | (M + H)+ |
|---|---|---|---|---|
| 217 | N—C(O)—C(O)—NH—(CH₂)₃—Ph | — | diastereomeric mixture | 556 |
| 218 | N—(CH₂)₆—Ph | HCl | diastereomeric mixture | 527 |
| 219 | N—C(O)—CH₂—C₆H₄—(CH₂)₂—Ph | — | diastereomeric mixture | 589 |
| 220 | N—C(O)—(CH₂)₃—C₆H₄—Ph | — | diastereomeric mixture | 587 |
| 221 | N—C(O)—O—(CH₂)₄—Ph | — | diastereomeric mixture | 543 |
| 222 | N—C(O)—(CH₂)₄—N(benzimidazolone) | — | diastereomeric mixture | 583 |

EXAMPLE 223

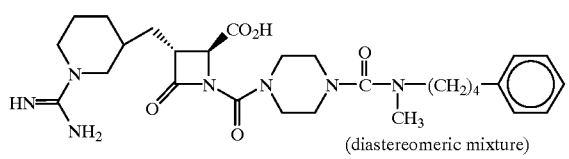

(diastereomeric mixture)

a)

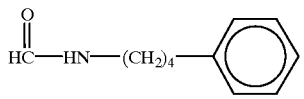

Formic acid (1.50 ml, 42.88 mmol) was added dropwise to acetic anhydride (3.29 ml, 34.84 mmol) at 0° C., then the solution was gently heated (50–60° C., 2 hours). The mixture was cooled to room temperature. Tetrahydrofuran (5 ml) was added followed by the addition of a solution of 4-phenylbutylamine (2.0 g, 13.40 mmol) in tetrahydrofuran (10 ml). The solution was stirred for 3 hours. The volatiles were removed in vacuo to give 2.5 g of the crude desired product.

b)

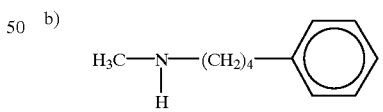

The crude product from part (a) was dissolved in tetrahydrofuran (15 ml) and cooled to 0° C. Borane dimethylsulfide complex (3.35 ml, 33.50 mmol) was added dropwise. After vigorous reaction ceased, the resulting mixture was brought to a gentle reflux and maintained at that temperature until completion (about 3 hours). The reaction was cooled to 0° C. Methanol (10 ml) was added and the mixture was stirred for 1 hour. Anhydrous HCL was bubbled through the mixture to attain a pH less than or equal to 2.0. The mixture was gently refluxed for 1 hour and then cooled to room temperature. Methanol (20 ml) was added and the solvents were removed. The residue was made basic by adding aqueous sodium hydroxide and then extracted with ether (3×20 ml).

The combined ether layers were dried over magnesium sulfate and concentrated to give 2.2 of the desired product as a colorless oil. MS $(M+H)^+=164$.

c)

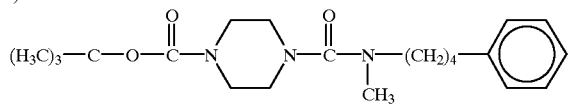

The carbamoyl chloride from Example 20(a) (19.43 mmol) was added to a solution of the product from part (b) (2.2 g, 13.50 mmol) and triethylamine (2.71 ml, 19.43 mmol) in methylene chloride (100 ml). The solution was stirred for 3 hours. The solvent was removed and the residue was purified by silica gel chromatography (hexane:ethyl acetate, 7:1 to 2:1) to give 3.90 g of the desired product as a colorless oil. MS $(M+H)^+=376$.

d)

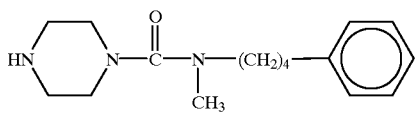

The product from part (c) was dissolved in methylene chloride (40 ml). The solution was cooled to 0° C. and trifluoroacetic acid (10 ml) was added dropwise. The ice-bath was removed. The mixture was stirred at room temperature for 1 hour. The solvents were removed under vacuum. The residue was diluted with ethyl acetate (50 ml). The solution was neutralized with saturated sodium bicarbonate (pH 10). The aqueous layer was extracted with ethyl acetate (2×30 ml). The combined ethyl acetate solution was washed with brine, dried over magnesium sulfate and concentrated to give the crude desired product as a colorless oil.

e)

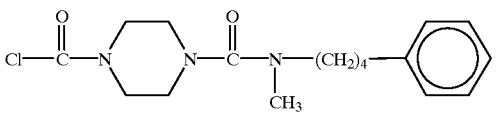

A solution of 20% phosgene in toluene (26.3 ml, 50 mmol) was dissolved in methylene chloride (15 ml) and cooled to 0° C. A solution of the crude product from part (d) and triethylamine in methylene chloride (15 ml) was added to the above solution over 10 minutes. The resulting solution was stirred at 0° C. for 1.5 hours. The precipitate was removed by filtration. The filtrate was concentrated. The residue was purified by silica gel chromatography (hexane:ethyl acetate, 3:1 to 2:1) to give 1.9 g of the desired product as a white solid.

f)

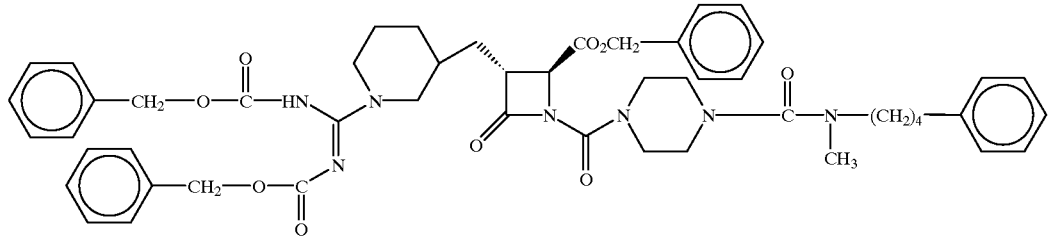

Triethylamine (0.018 ml, 0.13 mmol), the carbamoyl chloride product of part (e) (42.4 mg, 0.13 mmol) and 4-dimethylaminopyridine (1.0 mg, 0.007 mmol) were added to a solution of the product from Example 203(b) (60 mg, 0.10 mmol) in methylene chloride (2 ml). The solution was stirred for 3 hours. The solvent was removed and the residue was purified by silica gel chromatography (hexane:ethyl acetate, 4:3 to 1:1) to give 94 mg of the desired product as a colorless oil. MS $(M+H)^+=914$.

g)

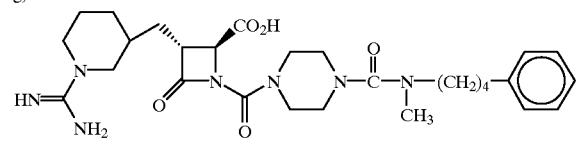

A mixture of the product from part (f) (94 mg, 0.10 mmol), palladium on carbon catalyst (10%, 25 mg) and 1N HCl (100 μl, 0.10 mmol) in dioxane (2.0 ml) was stirred under a hydrogen atmosphere (hydrogen balloon) at room temperature for 45 minutes. HPLC indicated completion of the reaction. The reaction mixture was filtered through a Celite® pad and the filtrate was concentrated. The residue was taken up with methanol-water (1:1) and passed through a polyvinylpyridine pad (eluted with 1:1 methanol-water). After the methanol was removed, the solution was lyophilized to provide 46 mg of the desired product as a white lyophilate. IR(KBr) 1775 cm$^{-1}$; MS $(M+H)^+=556$.

EXAMPLE 224

(2S,3R)-3-[[(3S)-1-(Aminoiminomethyl)-3-piperidinyl]methyl-1-[[4-[[methyl(4-phenylbutyl)amino]carbonyl-1-piperazinyl]carbonyl]-4-oxo-2-azetidinecarboxylic acid

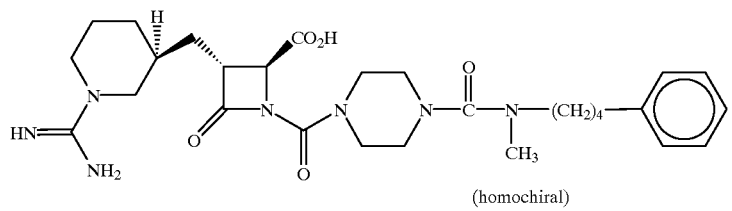

(homochiral)

a)

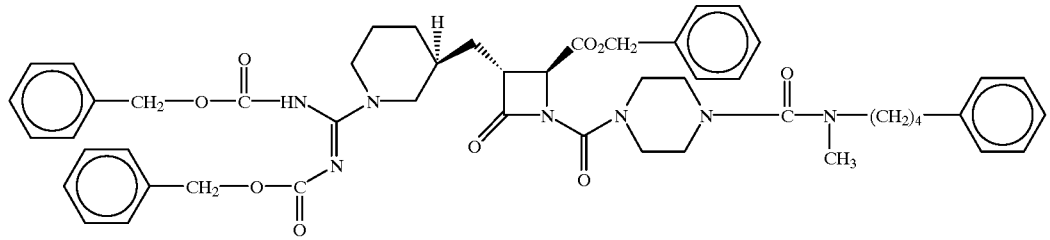

A solution of the product from Example 201(i) (613 mg, 1.0 mmol), triethylamine (0.30 ml, 2.15 mmol), the product of Example 223 (e) (422 mg, 1.25 mmol) and 4-dimethylaminopyridine (30.5 mg, 0.25 mmol) in methylene chloride (4 ml) was stirred under argon for 23 hours. The reaction was concentrated in vacuo and the residue was taken up in ethyl acetate, 10% potassium bisulfate, and water. The ethyl acetate layer was washed again with dilute potassium bisulfate, water (2×) and brine, dried over sodium sulfate, and concentrated to a foamy residue (1.03 g). Chromatography of the residue over silica gel using 60% and then 70% ethyl acetate in hexanes provided 803 mg of the desired product as an oily residue.

b)

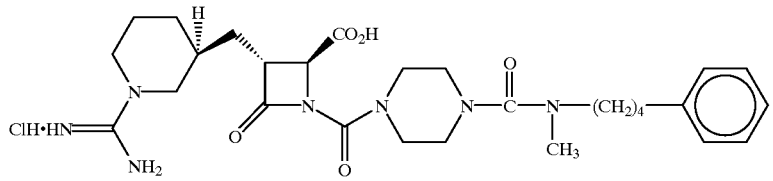

The product from part (a) (777 mg, 0.85 mmol) was hydrogenated in dioxane (10 ml) and 1.0 N HCl (0.87 mmol) in the presence of 10% palladium on carbon catalyst (230 mg) at 1 atmosphere for 1.3 hours. After filtration using aqueous dioxane, the filtrate was concentrated to remove dioxane, filtered and lyophilized to give 492 mg of the desired product as a white solid.

c)

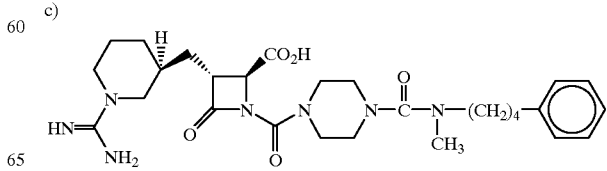

The product from part (b) (490 mg, 0.83 mmol) was passed through a column of 8 g of polyvinylpyridine resin packed in dioxane-water (30:70), and the product containing fractions were concentrated in vacuo and lyophilized to give 315 mg of the desired product as a white solid. IR(KBr) 1776 cm$^{-1}$; MS(M+H)$^+$=556.

Anal. calc'd for $C_{28}H_{41}N_7O_5$.1.9 $H_2O$.0.30 dioxane: C, 56.90; H, 7.72; N, 15.91; $H_2O$, 5.55. Found: C, 56.49; H, 7.43; N, 15.92, $H_2O$, 4.77.

EXAMPLE 225

(2S,3R)-3-[[(3R)-1-(Aminoiminomethyl)-3-piperidinyl]methyl-1-[[4-[[methyl(4-phenylbutyl)amino]carbonyl-1-piperazinyl]carbonyl]-4-oxo-2-azetidinecarboxylic acid a)

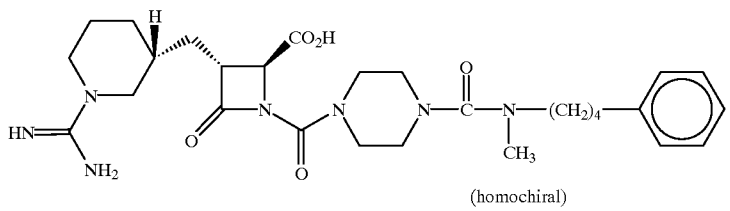

(homochiral)

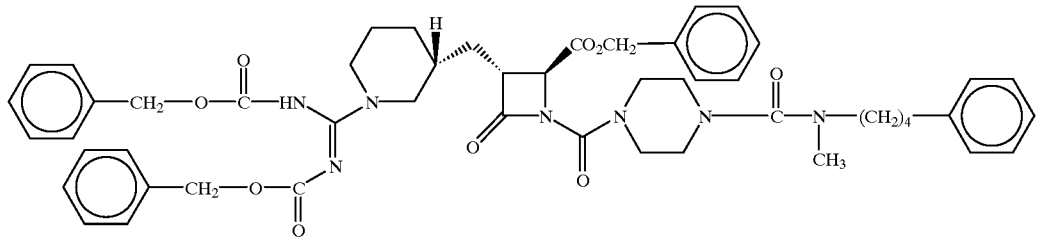

A solution of the product from Example 200 (i) (613 mg, 1.0 mmol) is Example 200(i) (613 mg, 1.0 mmol) is reacted with the product of Example 223(e) (422 mg, 1.25 mol) in the presence of triethylamine and 4-dimethylaminopyridine according to the procedure of Example 224 (a) to give 805 mg of the desired product as a foamy residue after chromatography over silica gel using 20% and then 30% ethyl acetate in methylene chloride.

b)

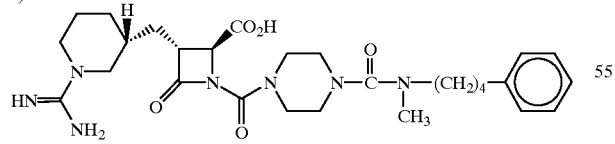

Hydrogenation of the product from part (a) according to the procedure of Example 224 (b) provided 460 mg of the desired product as a white solid after lyophilization.

c)

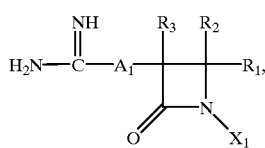

Passage of the product from part (b) (460 mg, 0.78 mmol) through a column of 8 g of polyvinylpyridine resin according to the procedure of Example 224(c) afforded after lyophilization 402 mg of the desired product as a white solid. IR(KBr) 1775 cm$^{-1}$; MS(M+H)$^+$=556.

Anal. calc'd for $C_{28}H_{41}N_7O_5$.1.50 $H_2O$.0.30 dioxane: C, 57.58; H, 7.68; N, 16.10; $H_2O$, 4.44. Found: C, 57.24; H, 7.30; N, 16.37, $H_2O$, 3.99.

What is claimed is:
1. A compound of the formulas:

(I)

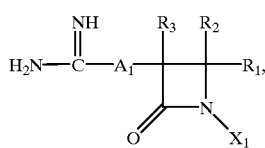

(IV)

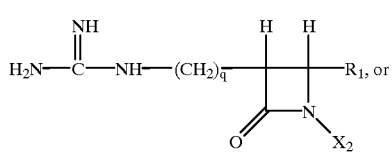

(V)

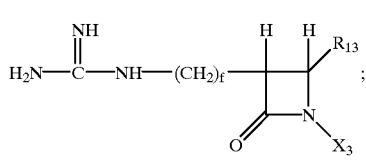

including an inner salt thereof, or a pharmaceutically acceptable salt thereof, or a hydrolyzable ester thereof, or a solvate thereof wherein:

$R_1$ is hydrogen, carboxy, alkoxycarbonyl, $A_2$-aryl,

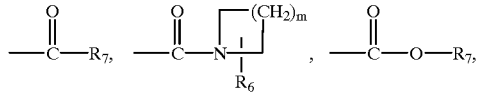

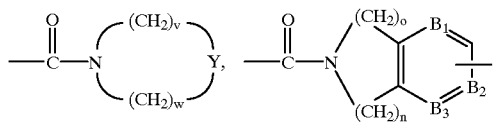

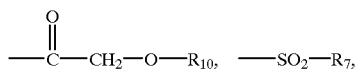

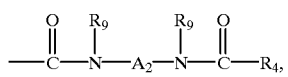

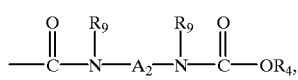

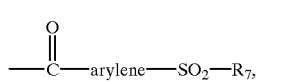

or $R_1$ is alkyl provided that $R_2$ is alkyl and $R_3$ is hydrogen;

$R_1'$ is carboxy, alkoxycarbonyl, $A_2$-aryl,

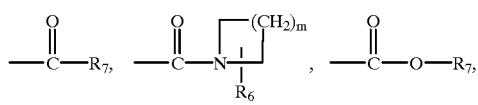

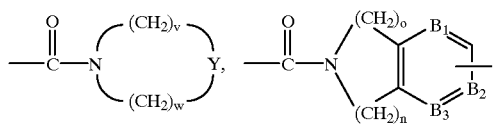

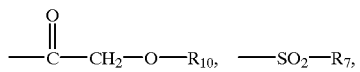

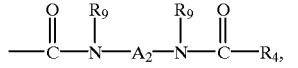

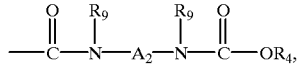

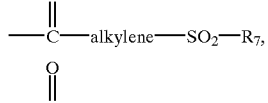

$R_2$ and $R_3$ are both hydrogen, or $R_2$ is alkyl provided that $R_3$ is hydrogen, or $R_3$ is alkyl provided that $R_2$ is hydrogen;

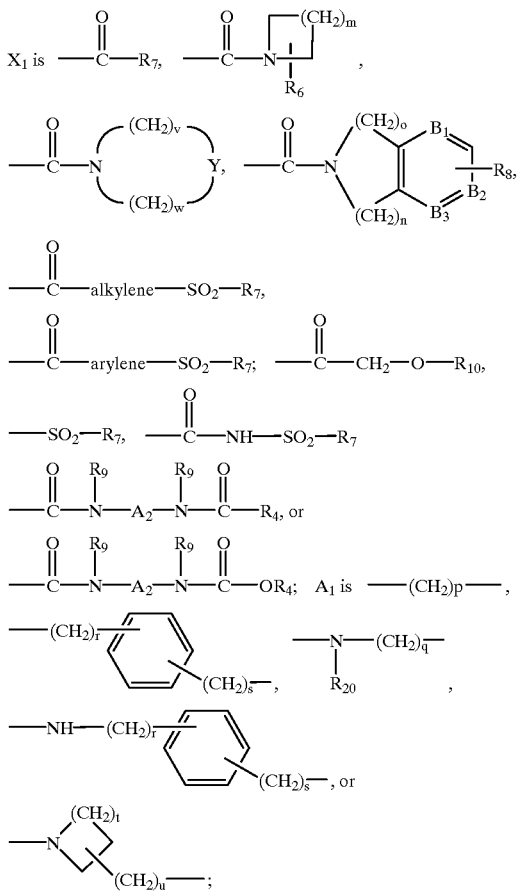

$R_4$ and $R_5$ are independently selected from hydrogen, alkyl, substituted alkyl, cycloalkyl, substituted cycloalkyl $A_2$-cycloalkyl, $A_2$-substituted cycloalkyl, aryl, substituted aryl, $A_2$-aryl, $A_2$-substituted aryl, heteroaryl, $A_2$-heteroaryl, heterocycloalkyl, $A_2$-heterocycloalkyl, arylene-$A_3$-aryl, $A_2$-arylene-$A_3$-aryl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, $A_2$-arylene-$A_3$-heterocycloalkyl, arylene-$A_3$-substituted aryl, $A_2$-arylene-$A_3$-substitued aryl, arylene-$A_3$-substituted cycloalkyl, $A_2$-arylene-$A_3$-substituted cycloalkyl, cycloalkylene-$A_3$-cycloalkyl, $A_2$-cycloalkylene-$A_3$-cycloalkyl, cycloalkylene-$A_3$-aryl, $A_2$-cycloalkylene-$A_3$-aryl, cycloalkylene-$A_3$-heteroaryl, $A_2$-cycloalkylene-$A_3$-heteroaryl, cycloalkylene-$A_3$-heterocycloalkyl, $A_2$-cycloalkylene-$A_3$-heterocycloalkyl, cycloalkylene-$A_3$-substituted cycloalkyl, $A_2$-cycloalkylene-$A_3$-substituted cycloalkyl, cycloalkylene-$A_3$-substituted aryl, $A_2$-cycloalkylene-$A_3$-substituted aryl, substituted cycloalkylene-$A_3$-cycloalkyl, $A_2$-substituted cycloalkylene-$A_3$-cycloalkyl, substituted cycloalkylene-$A_3$-substituted cycloalkyl, $A_2$-substituted cycloalkylene-$A_3$-substituted cycloalkyl, substituted cycloalkylene-$A_3$-aryl, $A_2$-substituted cycloalkylene-$A_3$-aryl, substituted cycloalkylene-$A_3$-heteroaryl, $A_2$-substituted cycloalkylene-$A_3$-heteroaryl, substituted cycloalkylene-$A_3$-heterocycloalkyl, $A_2$-substituted cycloalkylene-$A_3$-heterocycloalkyl, substituted cycloalkylene-A₃-substituted aryl, A₂-substituted cycloalkylene-A₃-substituted aryl, heteroarylene-A₃-heteroaryl, A₂-heteroarylene-A₃-heteroaryl, heteroarylene-A₃-cycloalkyl, A₂-heteroarylene-A₃-cycloalkyl, heteroarylene-A₃-substituted cycloalkyl, A₂-heteroarylene-A₃-substituted cycloalkyl, heteroarylene-A₃-aryl, A₂-heteroarylene-A₃-aryl, heteroarylene-A₃-heterocycloalkyl, A₂-heteroarylene-A₃-heterocycloalkyl, heteroarylene-A₃-substituted aryl, A₂-heteroarylene-A₃-substituted aryl, heterocycloalkylene-A₃-heterocycloalkyl, A₂-heterocycloalkylene-A₃-heterocycloalkyl, heterocycloalkylene-A₃-cycloalkyl, A₂-heterocycloalkylene-A₃-cycloalkyl, heterocycloalkylene-A₃-substituted cycloalkyl, A₂-heterocycloalkylene-A₃-substituted cycloalkyl, heterocycloalkylene-A₃-aryl, A₂-heterocycloalkylene-A₃-aryl, heterocycloalkylene-A₃-substituted aryl, A₂-heterocycloalkylene-A₃-substituted aryl, heterocycloalkylene-A₃-heteroaryl, A₂-heterocycloalkylene-A₃-heteroaryl, substituted arylene-A₃-substituted aryl, A₂-substituted arylene-A₃-substituted aryl, substituted arylene-A₃-cycloalkyl, A₂-substituted arylene-A₃-cycloalkyl, substituted arylene-A₃-substituted cycloalkyl, A₂-substituted arylene-A₃-substituted cycloalkyl, substituted arylene-A₃-aryl, A₂-substituted arylene-A₃-aryl, substituted arylene-A₃-heteroaryl, A₂-substituted arylene-A₃-heteroaryl, substituted arylene-A₃-heterocycloalkyl, and A₂-substituted arylene-A₃-heterocycloalkyl;

$R_6$ is hydrogen, alkyl, substituted alkyl, cycloalkyl, substituted cycloalkyl, A₂-cycloalkyl, A₂-substituted cycloalkyl, aryl, substituted aryl, A₂-aryl, A₂-substituted aryl, arylene-A₃-aryl, A₂-arylene-A₃-aryl, heteroaryl, A₂-heteroaryl, heterocycloalkyl, A₂-heterocycloalkyl, arylene-A₃-cycloalkyl, A₂-arylene-A₃-cycloalkyl, arylene-A₃-heteroaryl, A₂-arylene-A₃-heteroaryl, arylene-A₃-heterocycloalkyl, A₂-arylene-A₃-heterocycloalkyl, carboxy, alkoxycarbonyl, arloxycarbonyl,

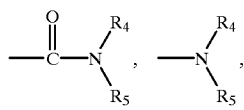

alkoxycarbonylamino, aryloxycarbonylamino, arylcarbonylamino, —N(alkyl)(alkoxycarbonyl), —N(alkyl)(aryloxycarbonyl), alkylcarbonylamino, —N(alkyl)(alkylcarbonyl), or —N(alkyl)(arylcarbonyl);

m is an integer from 1 to 5;

Y is O, S, N—R₄, N—SO₂—R₇,

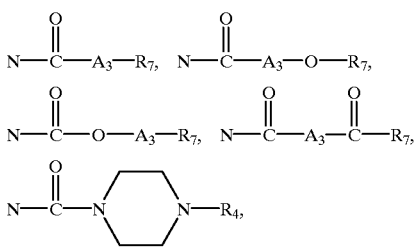

$R_7$ is alkyl, substituted alkyl, cycloalkyl, substituted cycloalkyl, A₂-cycloalkyl, A₂-substituted cycloalkyl, aryl, substituted aryl, A₂-aryl, A₂-substituted aryl, heteroaryl, A₂-heteroaryl, heterocycloalkyl, A₂-heterocycloalkyl, arylene-A₃-aryl, A₂-arylene-A₃-aryl, arylene-A₃-cycloalkyl, A₂-arylene-A₃-cycloalkyl, arylene-A₃-heteroaryl, A₂-arylene-A₃-heteroaryl, arylene-A₃-heterocycloalkyl, A₂-arylene-A₃-heterocycloalkyl, arylene-A₃-substituted aryl, A₂-arylene-A₃-substitued aryl, arylene-A₃-substituted cycloalkyl, A₂-arylene-A₃-substituted cycloalkyl, cycloalkylene-A₃-cycloalkyl, A₂-cycloalkylene-A₃-cycloalkyl, cycloalkylene-A₃-aryl, A₂-cycloalkylene-A₃-aryl, cycloalkylene-A₃-heteroaryl, A₂-cycloalkylene-A₃-heteroaryl, cycloalkylene-A₃-heterocycloalkyl, A₂-cycloalkylene-A₃-heterocycloalkyl, cycloalkylene-A₃-substituted cycloalkyl, A₂-cycloalkylene-A₃-substituted cycloalkyl, cycloalkylene-A₃-substituted aryl, A₂-cycloalkylene-A₃-substituted aryl, substituted cycloalkylene-A₃-cycloalkyl, A₂-substituted cycloalkylene-A₃-cycloalkyl, substituted cycloalkylene-A₃-substituted cycloalkyl, A₂-substituted cycloalkylene-A₃-substituted cycloalkyl, substituted cycloalkylene-A₃-aryl, A₂-substituted cycloalkylene-A₃-aryl, substituted cycloalkylene-A₃-heteroaryl, A₂-substituted cycloalkylene-A₃-heteroaryl, substituted cycloalkylene-A₃-heterocycloalkyl, A₂-substituted cycloalkylene-A₃-heterocycloalkyl, substituted cycloalkylene-A₃-substituted aryl, A₂-substituted cycloalkylene-A₃-substituted aryl, heteroarylene-A₃-heteroaryl, A₂-heteroarylene-A₃-heteroaryl, heteroarylene-A₃-cycloalkyl, A₂-heteroarylene-A₃-cycloalkyl, heteroarylene-A₃-substituted cycloalkyl, A₂-heteroarylene-A₃-substituted cycloalkyl, heteroarylene-A₃-aryl, A₂-heteroarylene-A₃-aryl, heteroarylene-A₃-heterocycloalkyl, A₂-heteroarylene-A₃-heterocycloalkyl, heteroarylene-A₃-substituted aryl, A₂-heteroarylene-A₃-substituted aryl, heterocycloalkylene-A₃-heterocycloalkyl, A₂-heterocycloalkylene-A₃-heterocycloalkyl, heterocycloalkylene-A₃-cycloalkyl, A₂-heterocycloalkylene-A₃-cycloalkyl, heterocycloalkylene-A₃-substituted cycloalkyl, A₂-heterocycloalkylene-A₃-substituted cycloalkyl, heterocycloalkylene-A₃-aryl, A₂-heterocycloalkylene-A₃-aryl, heterocycloalkylene-A₃-substituted aryl, A₂-heterocycloalkylene-A₃-substituted aryl, heterocycloalkylene-A₃-heteroaryl, A₂- heterocycloalkylene-$A_3$-heteroaryl, substituted arylene-$A_3$-substituted aryl, $A_2$-substituted arylene-$A_3$-substituted aryl, substituted arylene-$A_3$-cycloalkyl, $A_2$-substituted arylene-$A_3$-cycloalkyl, substituted arylene-$A_3$-substituted cycloalkyl, $A_2$-substituted arylene-$A_3$-substituted cycloalkyl, substituted arylene-$A_3$-aryl, $A_2$-substituted arylene-$A_3$-aryl, substituted arylene-$A_3$-heteroaryl, $A_2$-substituted arylene-$A_3$-heteroaryl, substituted arylene-$A_3$-heterocycloalkyl, $A_2$-substituted arylene-$A_3$-heterocycloalkyl,

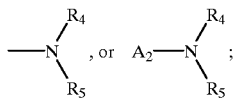

n and o are one or two provided that the sum of n plus o is two or three;

v and w are one, two, or three provided that the sum of v plus w is three, four, or five;

$R_8$ is hydrogen, halo, amino, —NH(lower alkyl), —N(lower alkyl)$_2$, nitro, alkyl, substituted alkyl, alkoxy, hydroxy, aryl, substituted aryl, $A_2$-aryl, $A_2$-substituted aryl, arylene-$A_3$-aryl, $A_2$-arylene-$A_3$-aryl, cycloalkyl, substituted cycloalkyl, $A_2$-cycloalkyl, $A_2$-substituted cycloalkyl, heteroaryl, $A_2$-heteroaryl, heterocycloalkyl, $A_2$-heterocycloalkyl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, or $A_2$-arylene-$A_3$-heterocycloalkyl;

$B_1$, $B_2$ and $B_3$ are each CH, or two of $B_1$, $B_2$ and $B_3$ are CH and the other is N, or one of $B_1$, $B_2$ and $B_3$ is CH and the other two are N;

$R_9$ is hydrogen or lower alkyl;

$R_{10}$ is alkyl, substituted alkyl, alkylene-O-alkyl, alkylene-O-alkylene-O-alkyl, cycloalkyl, substituted cycloalkyl, $A_2$-cycloalkyl, $A_2$-substituted cycloalkyl, aryl, substituted aryl, $A_2$-aryl, $A_2$-substituted aryl, arylene-$A_3$-aryl, $A_2$-arylene-$A_3$-aryl, heteroaryl, $A_2$-heteroaryl, heterocycloalkyl, $A_2$-heterocycloalkyl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl or $A_2$-arylene-$A_3$-heterocyloalkyl;

$R_{20}$ is alkyl, substituted alkyl, cycloalkyl, substituted cycloalkyl, $A_2$-cycloalkyl, $A_2$-substituted cycloalkyl, $A_2$-aryl, or $A_2$-substituted aryl;

$R_{21}$, and $R_{22}$ are independently selected from hydrogen, alkyl, substituted alkyl, cycloalkyl, substituted cycloalkyl, $A_2$-cycloalkyl, $A_2$-substituted cycloalkyl, $A_2$-aryl, and $A_2$-substituted aryl;

p is an integer from 2 to 6;
q is an integer from 1 to 6;
f is an integer from 3 to 5;
r is zero, one or two;
s is one or two;
t is one, two, three or four;
u is one, two or three;

$A_2$ is an alkylene or a substituted alkylene bridge of 1 to 10 carbons, an alkenylene or substituted alkenylene bridge of 2 to 10 carbons having one or more double bonds, or an alkynylene or substituted alkynylene bridge of 2 to 10 carbons having one or more triple bonds;

$A_3$ is a bond, an alkylene or a substituted alkylene bridge of 1 to 10 carbons, an alkenylene or substituted alkenylene bridge of 2 to 10 carbons having one or more double bonds, an alkynylene or substituted alkynylene bridge of 2 to 10 carbons having one or more triple bonds,

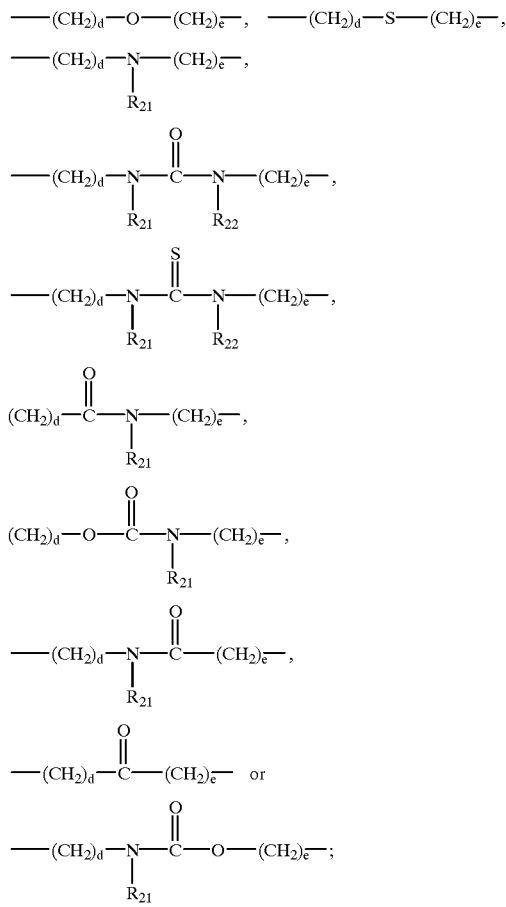

d and e are independently selected from zero and an integer from 1 to 10 provided that the sum of d plus e is no greater then 10;

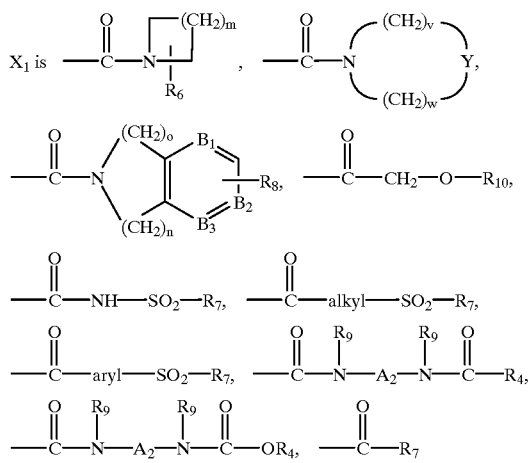

provided that

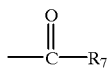

is other then alkylcarbonyl, phenylcarbonyl, substituted phenylcarbonyl, naphthylcarbonyl, substituted naphthylcarbonyl, phenylaminocarbonyl, substituted phenylaminocarbonyl, napththylaminocarbonyl, or substituted naphthylaminocarbonyl, or —SO$_2$—R$_7$ provided that —SO$_2$R$_7$ is other then alkylsulfonyl, phenylsulfonyl, substituted phenylsulfonyl, naphthylsulfonyl or substituted naphthylsulfonyl;

X$_3$ is phenylaminocarbonyl, substituted phenylaminocarbonyl, naphthylaminocarbonyl, substituted naphthylaminocarbonyl, alkylcarbonyl, phenylcarbonyl, substituted phenylcarbonyl, naphthylcarbonyl, substituted napthylcarbonyl, alkylsulfonyl, phenylsulfonyl, substituted phenylsulfonyl, naphthylsulfonyl, or substituted naphthylsulfonyl; and R$_{13}$ is

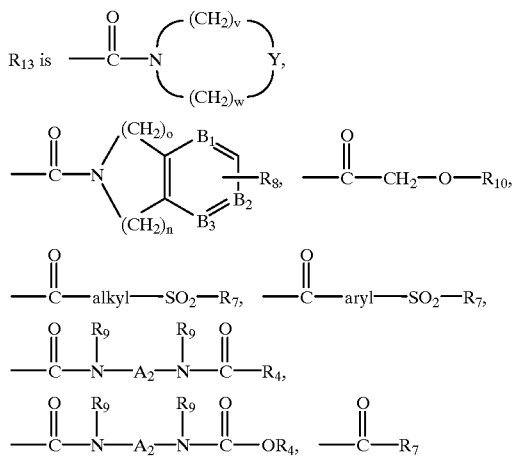

provided that

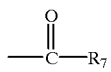

is other then phenylaminocarbonyl, substituted phenylaminocarbonyl, naphthylaminocarbonyl, substituted naphthylaminocarbonyl, carboxymethylaminocarbonyl, or alkoxycarbonylmethylaminocarbonyl, —SO$_2$—R$_7$ provided that —SO$_2$R$_7$ is other then alkylsulfonyl, phenylsulfonyl, substituted phenylsulfonyl, naphthylsulfonyl or substituted naphthylsulfonyl, or

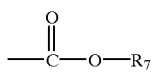

provided that

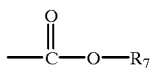

is other then alkoxycarbonyl, or

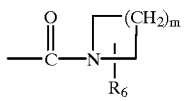

provided that if m is 1, 2 or 3 then R$_6$ is other then hydrogen, carboxy, alkoxycarbonyl or aryloxycarbonyl.

2. A compound of claim 1

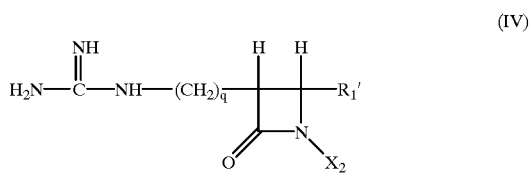

(IV)

including an inner salt or a pharmaceutically acceptable salt thereof wherein:

q is 3;

R$_1$' is carboxy,

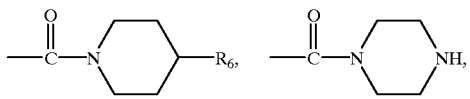

R$_1$' is carboxy,

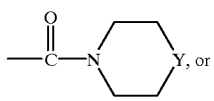

X$_2$ is

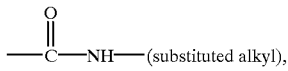

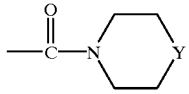

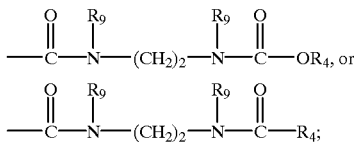

R$_6$ is aminocarbonyl,

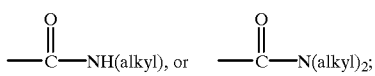

Y is

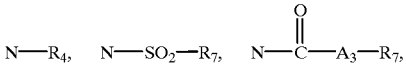

-continued

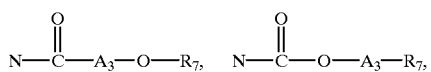

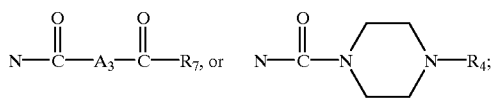

$R_4$ in the definition of Y and $X_2$ is alkyl, cycloalkyl, substituted alkyl, substituted cycloalkyl, —$(CH_2)_{1\ to\ 6}$-aryl, or heteroaryl;

$R_7$ is alkyl, cycloalkyl, substituted alkyl, substituted cycloalkyl, —$(CH_2)_{0\ to\ 4}$-aryl, —$(CH_2)_{0\ to\ 4}$-arylene-$A_3$-aryl, —$(CH_2)_{0\ to\ 4}$-heteroaryl, —$(CH_2)_{0\ to\ 4}$-heterocycloalkyl, —$(CH_2)_{0\ to\ 4}$-heteroarylene-$A_3$-aryl,

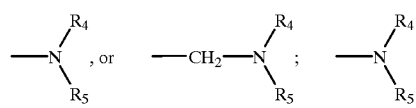

is amino —NH(alkyl), —N(alkyl)$_2$ or —NH—$(CH_2)_{1\ to\ 4}$-aryl;

$R_9$ is lower alkyl;

$A_3$ is a bond, an alkylene bridge of 1 to 6 carbons,

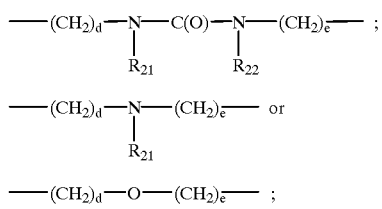

d and e are independently selected from zero and an integer from 1 to 6 provided that the sum of d plus e is no greater then 10; and $R_{21}$ and $R_{22}$ are independently selected from hydrogen and lower alkyl.

3. A compound of claim 2 including an inner salt or a pharmaceutically acceptable salt thereof selected from the group consisting of

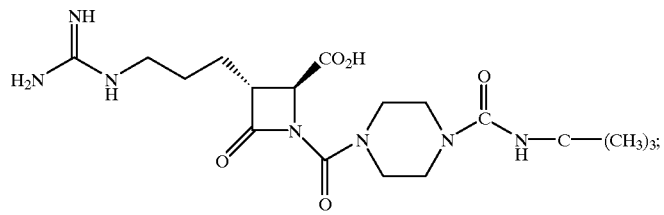

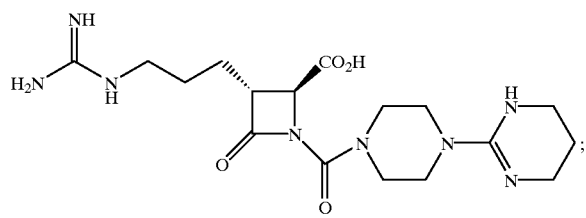

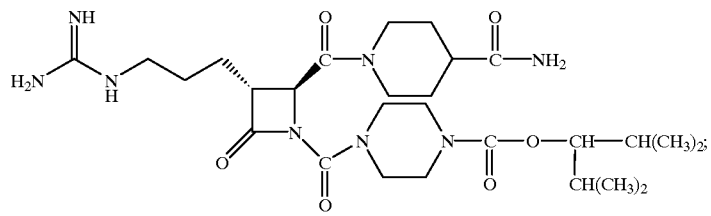

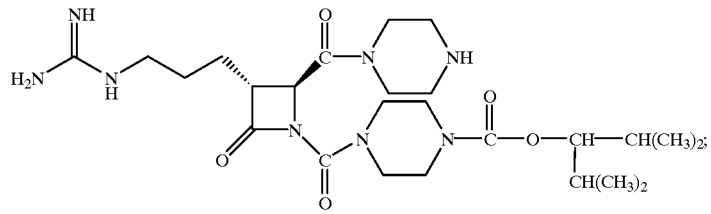

-continued
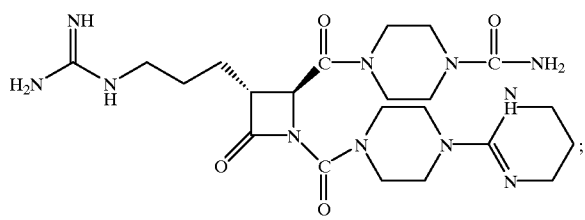
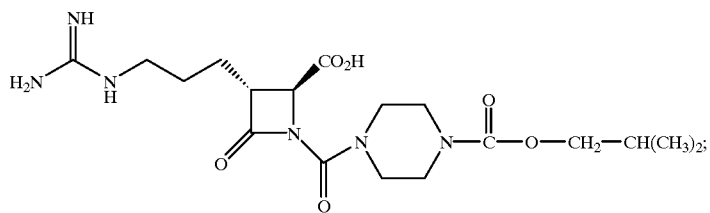
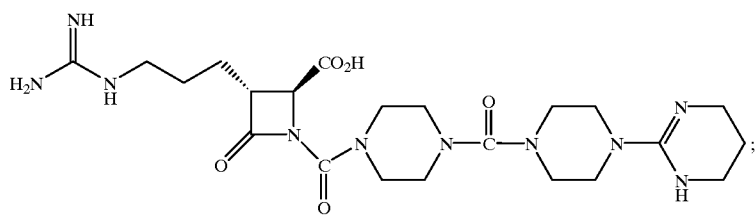
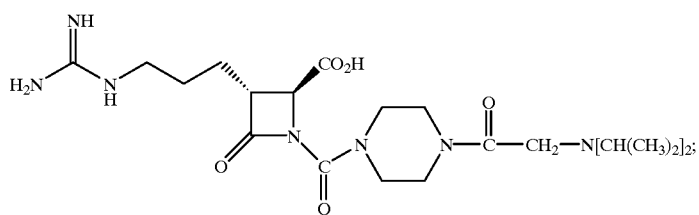
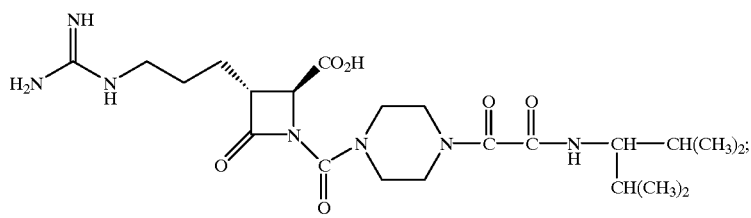
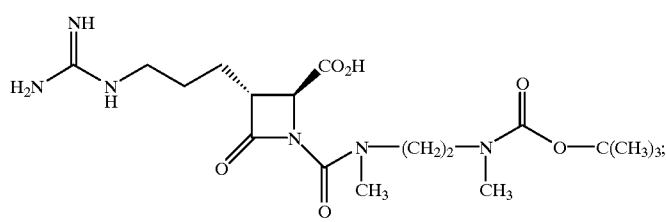
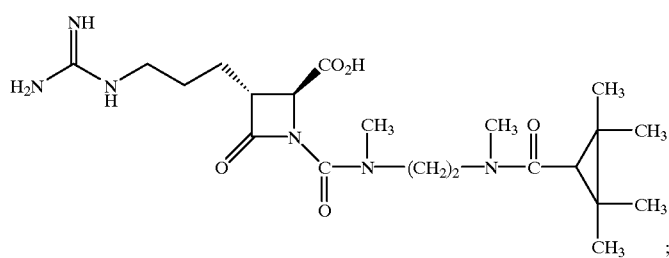

-continued
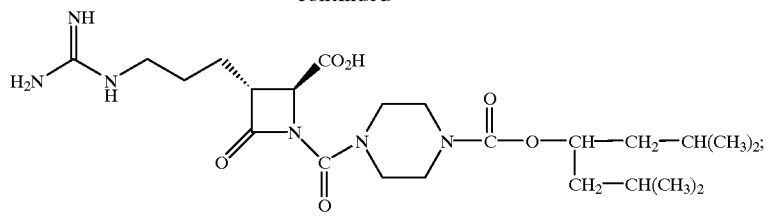
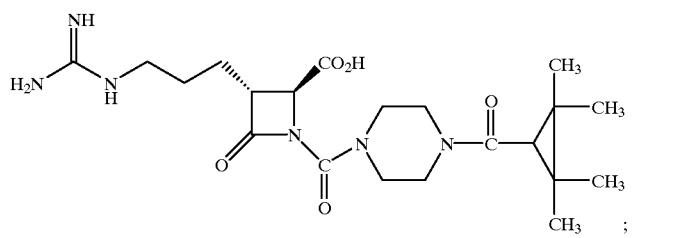
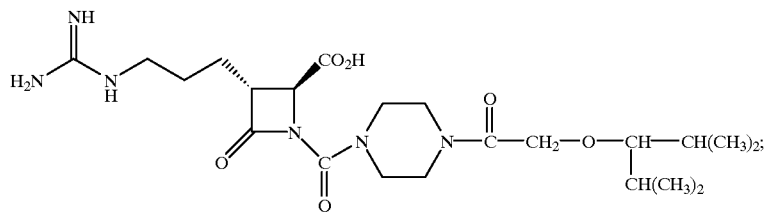
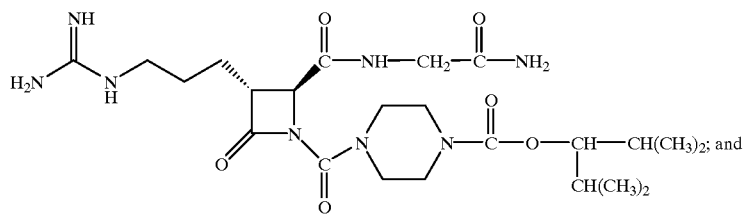
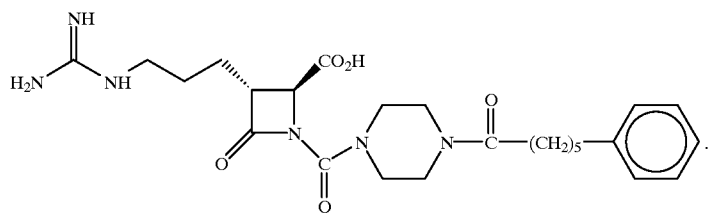
4. The compound of claim 3
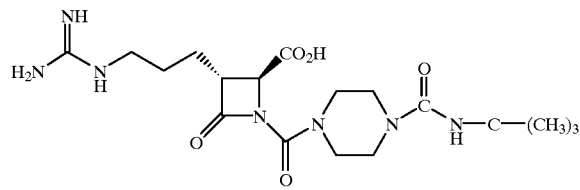
including an inner salt or a pharmaceutically acceptable salt thereof.
5. A compound of claim 1
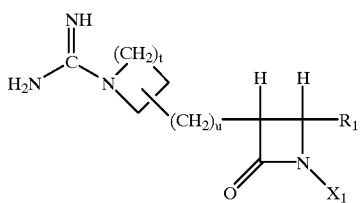

including an inner salt or pharmaceutically acceptable salt thereof wherein:

$R_1$ is carboxy,

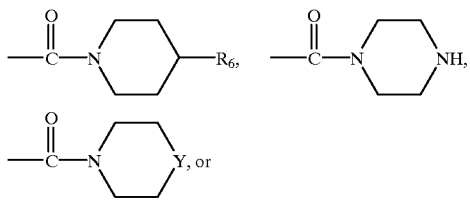

$R_1'$ is carboxy,

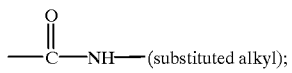

$X_1$ is

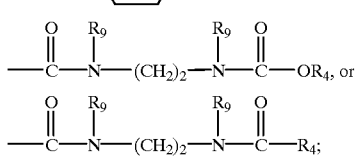

t is two or three;
u is one;
$R_6$ is aminocarbonyl,

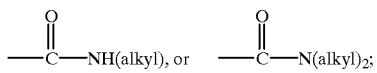

Y is

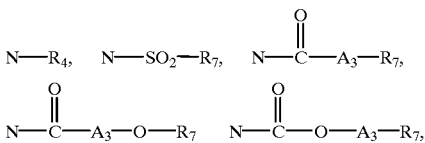

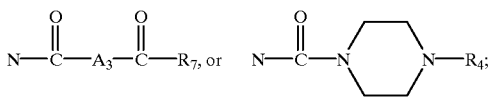

$R_4$ in the definition of Y and $X_2$ is alkyl, cycloalkyl, substituted alkyl, substituted cycloalkyl, $-(CH_2)_{1\ to\ 6}$-aryl, or heteroaryl;

$R_7$ is alkyl, cycloalkyl, substituted alkyl, substituted cycloalkyl, $-(CH_2)_{0\ to\ 4}$-aryl, $-(CH_2)_{0\ to\ 4}$-arylene-$A_3$-aryl, $-(CH_2)_{0\ to\ 4}$-heteroaryl, $-(CH_2)_{0\ to\ 4}$-heterocycloalkyl, $-(CH_2)_{0\ to\ 4}$-heteroarylene-$A_3$-aryl,

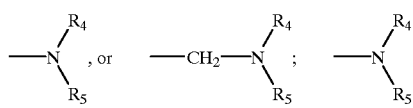

is amino $-NH(alkyl)$, $-N(alkyl)_2$, or $-NH-(CH_2)_{1\ to\ 4}$-aryl;

$R_9$ is lower alkyl;

$A_3$ is a bond, an alkylene bridge of 1 to 6 carbons,

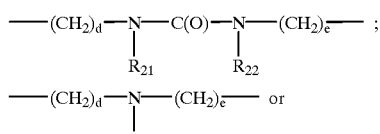

d and e are independently selected from zero and an integer from 1 to 6 provided that the sum of d plus e is no greater then 10; and $R_{21}$ and $R_{22}$ are independently selected from hydrogen and lower alkyl.

6. A compound of claim 5 including an inner salt or a pharmaceutically acceptable salt thereof selected from the group consisting of:

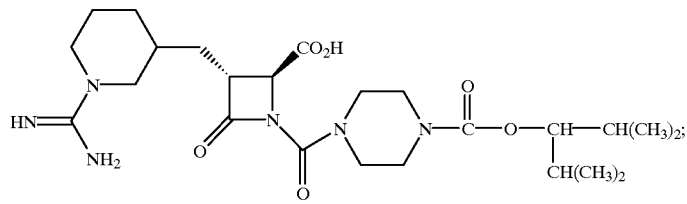

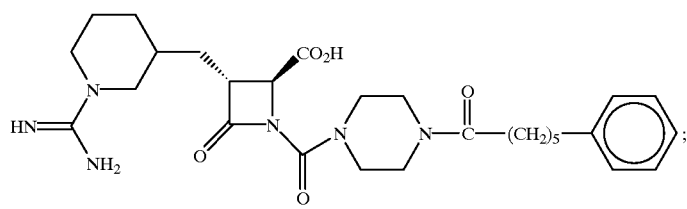

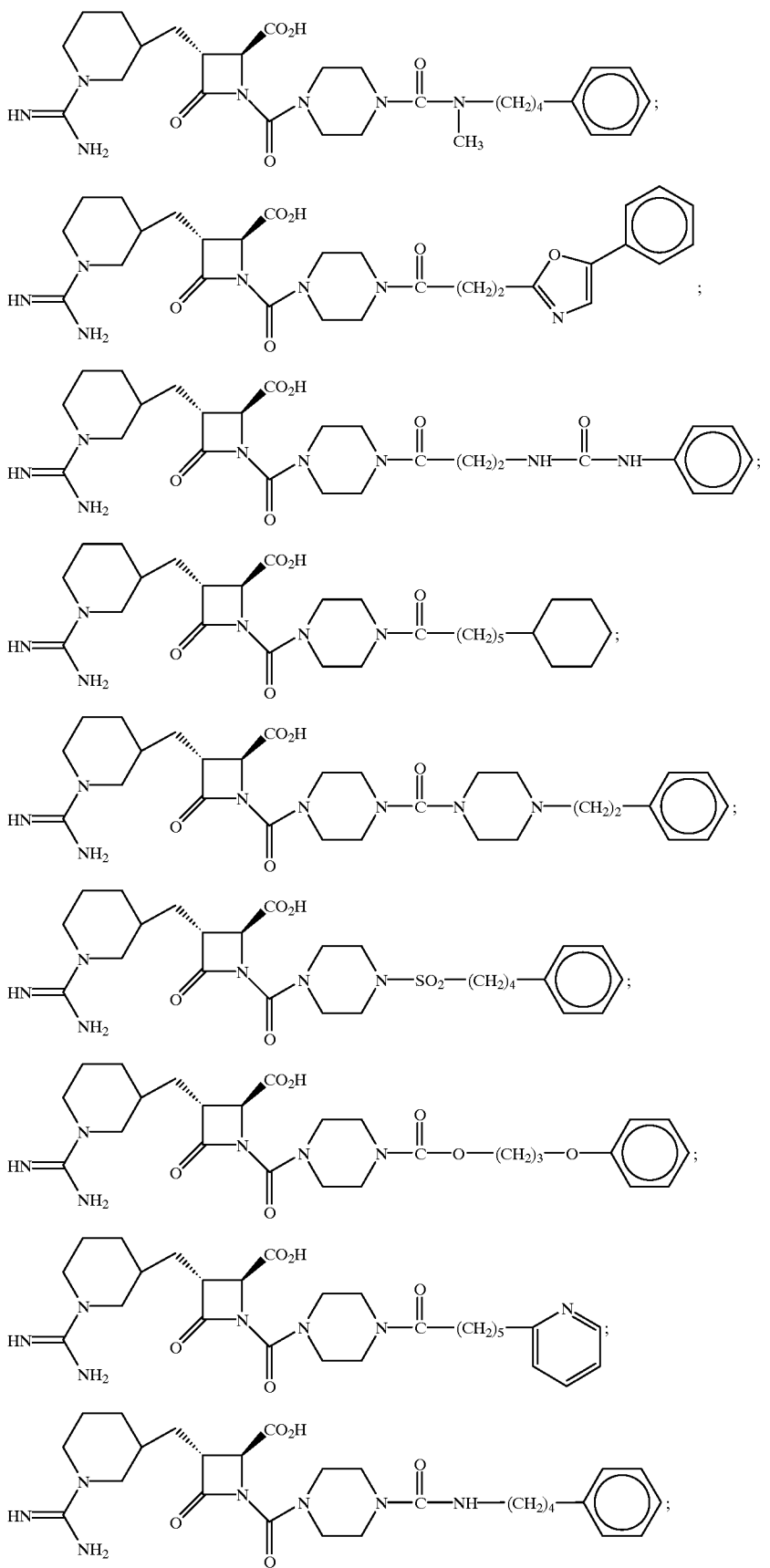

-continued

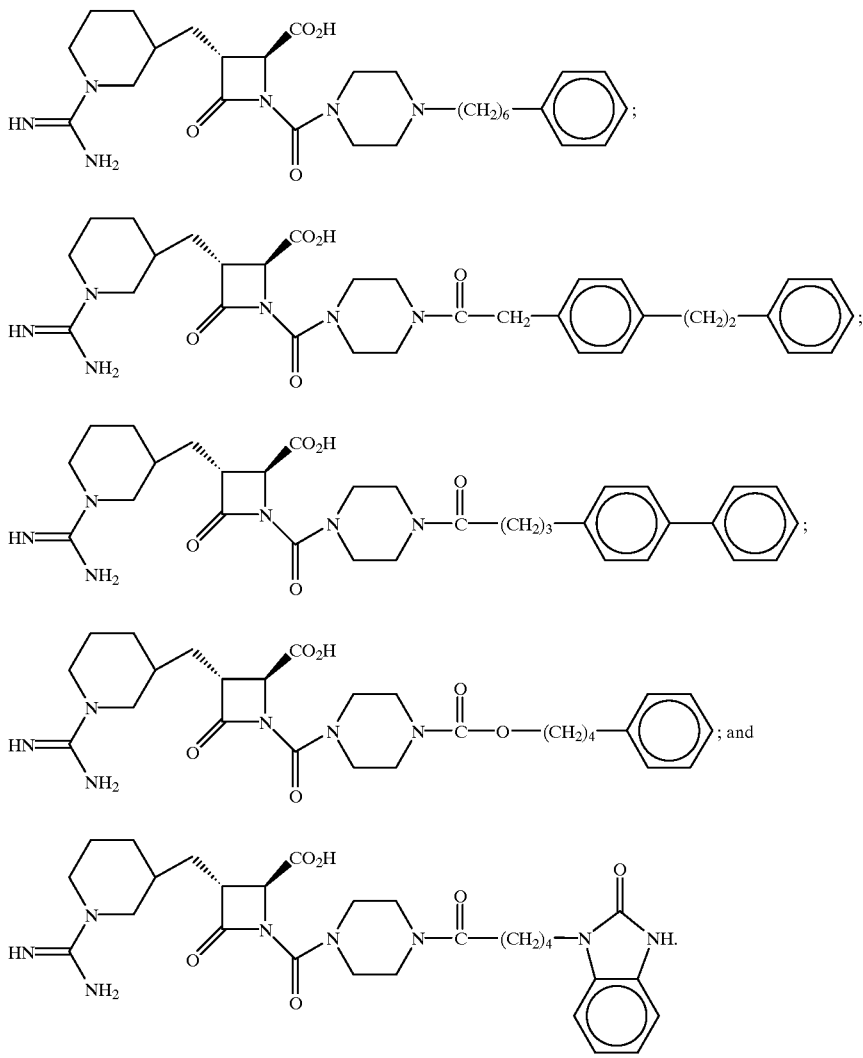

7. The compound of claim 6 including an inner salt or a pharmaceutically acceptable salt thereof of the formula:

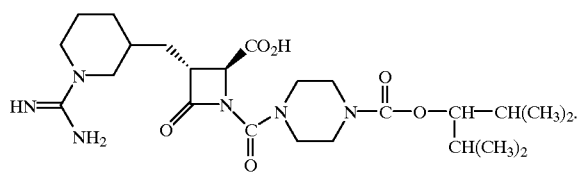

8. The compound of claim 6 including an inner salt or a pharmaceutically acceptable salt thereof of the formula:

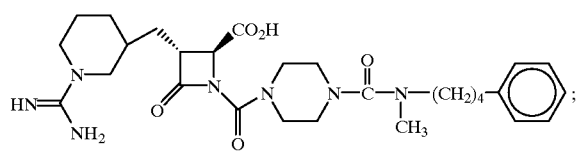

9. The compound of claim 6 including an inner salt or a pharmaceutically acceptable salt thereof of the formula:

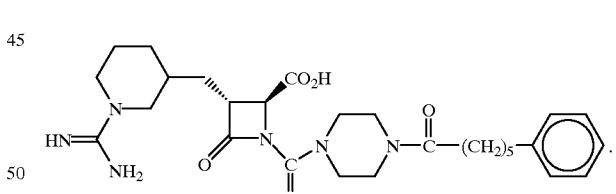

10. The compound of claim 9 (2S,3R)-3-[[(3R)-1-(aminoiminomethyl)-3-piperidinyl]methyl]-4-oxo-1-[[4-(1-oxo-6-phenylhexyl)-1-piperazinyl]carbonyl]-2-azetidinecarboxylic acid.

11. A compound of the formulas:

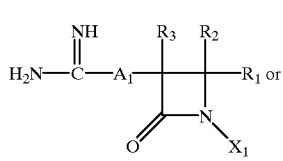

(I)

309
-continued

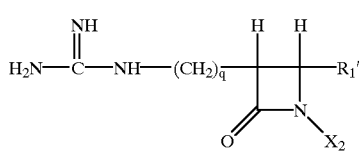
(IV)

including an inner salt thereof, or a pharmaceutically acceptable salt thereof, or a hydrolyzable ester thereof, or a solvate thereof wherein:

$A_1$, $R_1$, $R_2$, $R_3$, q and $R_1'$ are as defined in claim 1;
$X_1$ and $X_2$ are

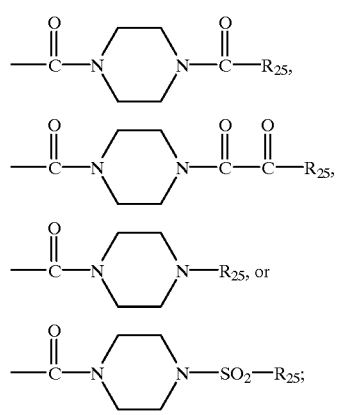

and $R_{25}$ is a spacer terminating in a lipophilic group wherein, said spacer comprises groups of 3 or more atoms or groups of 2 or more atoms and a phenylene, substituted phenylene, cycloalklene, heteroarylene, or heterocycloalkylene ring and said lipophilic terminating group is aryl, substituted aryl, cycloalkyl, heteroaryl, or heterocycloalkyl.

12. A compound of claim 11 wherein $R_{25}$ is selected from the group consisting of

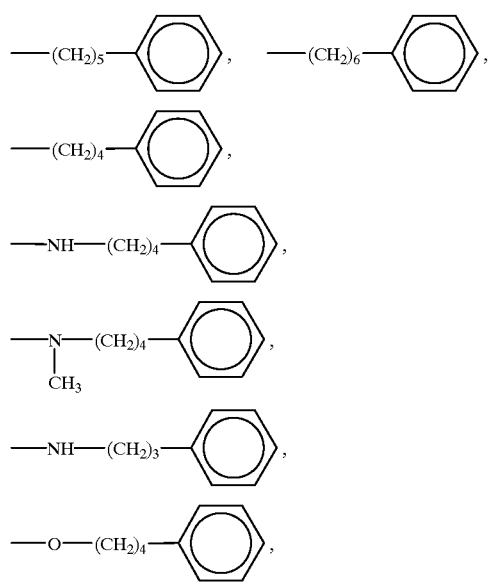

310
-continued

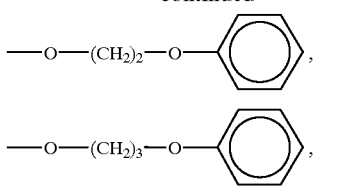

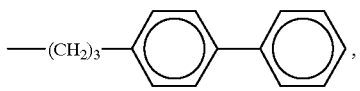

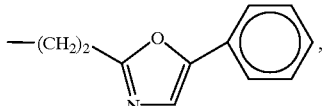

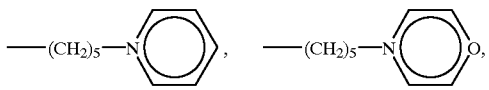

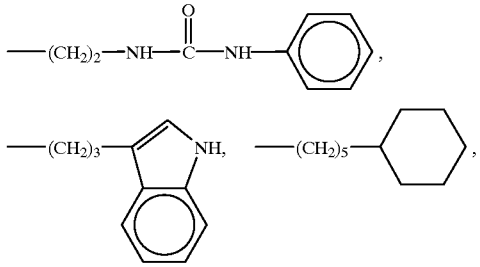

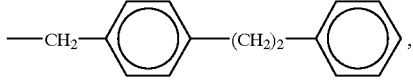

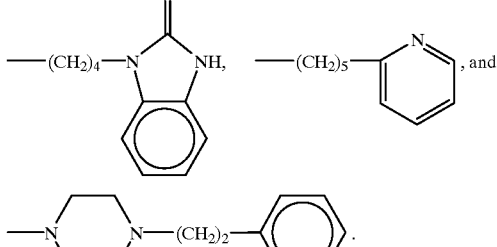

13. A compound of claim 12 wherein $R_{25}$ is

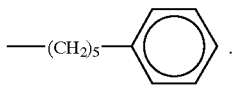.

14. A pharmaceutical composition comprising an effective amount of a compound of claim 1 including an inner salt or a pharmaceutically acceptable salt thereof, a hydrolyzable ester thereof, or a solvate thereof and one or more pharmaceutically acceptable carriers.

15. A pharmaceutical composition useful for treating asthma or allergic rhinitis comprising an effective amount of a compound of claim 1 including an inner salt or a pharmaceutically acceptable salt thereof, a hydrolyzable ester thereof, or a solvate thereof and one or more pharmaceutically acceptable carriers.

16. A pharmaceutical composition useful for treating chronic asthma comprising an effective amount of a compound of claim 5 including an inner salt or a pharmaceutically acceptable salt thereof and one or more pharmaceutically acceptable carriers, said composition being adapted for inhalation administration to the bronchioles.

17. The composition of claim 16 wherein the active agent is of the formula:

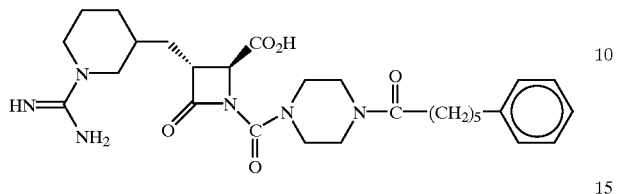

including an inner salt or a pharmaceutically acceptable salt thereof.

18. The composition of claim 17 wherein the active agent is (2S,3R)-3-[[(3R)-1-(aminoiminomethyl)-3-piperidinyl]methyl]-4-oxo-1-[[4-(1-oxo-6-phenylhexyl)-1-piperazinyl]carbonyl]-2-azetidinecarboxylic acid.

19. A method for treating asthma or allergic rhinitis in a mammalian species comprising administering an effective amount of the composition of claim 15.

20. A method for treating chronic asthma in a mammalian species comprising administering by inhalation to the bronchioles an effective amount of the composition of claim 16.

21. A method for treating chronic asthma in a mammalian species comprising administering by inhalation to the bronchioles an effective amount of the composition of claim 17.

22. The method of claim 21 wherein the active agent is (2S,3R)-3-[[(3R)-1-(aminoiminomethyl)-3-piperidinyl]methyl]-4-oxo-1-[[4-(1-oxo-6-phenylhexyl)-1-piperazinyl]carbonyl]-2-azetidinecarboxylic acid.

23. A compound of the formula:

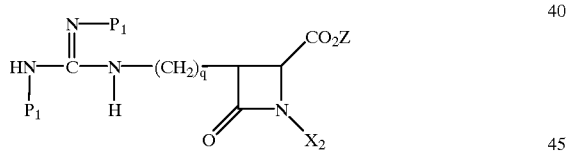

wherein $X_2$ is

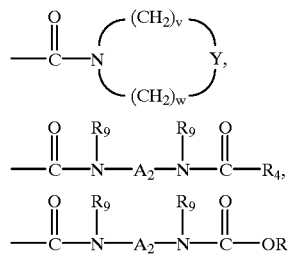

Y is

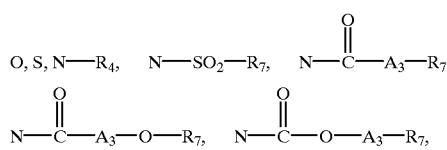

-continued

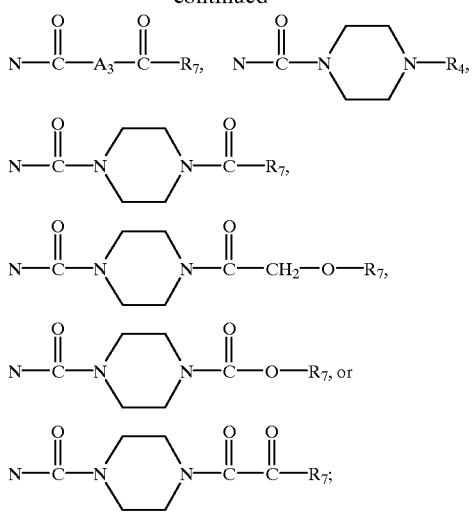

$R_4$ and $R_5$ are independently selected from hydrogen, alkyl, substituted alkyl, cycloalkyl, substituted cycloalkyl $A_2$-cycloalkyl, $A_2$-substituted cycloalkyl, aryl, substituted aryl, $A_2$-aryl, $A_2$-substituted aryl, heteroaryl, $A_2$-heteroaryl, heterocycloalkyl, $A_2$-heterocycloalkyl, arylene-$A_3$-aryl, $A_2$-arylene-$A_3$-aryl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, $A_2$-arylene-$A_3$-heterocycloalkyl, arylene-$A_3$-substituted aryl, $A_2$-arylene-$A_3$-substitued aryl, arylene-$A_3$-substituted cycloalkyl, $A_2$-arylene-$A_3$-substituted cycloalkyl, cycloalkylene-$A_3$-cycloalkyl, $A_2$-cycloalkylene-$A_3$-cycloalkyl, cycloalkylene-$A_3$-aryl, $A_2$-cycloalkylene-$A_3$-aryl, cycloalkylene-$A_3$-heteroaryl, $A_2$-cycloalkylene-$A_3$-heteroaryl, cycloalkylene-$A_3$-heterocycloalkyl, $A_2$-cycloalkylene-$A_3$-heterocycloalkyl, cycloalkylene-$A_3$-substituted cycloalkyl, $A_2$-cycloalkylene-$A_3$-substituted cycloalkyl, cycloalkylene-$A_3$-substituted aryl, $A_2$-cycloalkylene-$A_3$-substituted aryl, substituted cycloalkylene-$A_3$-cycloalkyl, $A_2$-substituted cycloalkylene-$A_3$-cycloalkyl, substituted cycloalkylene-$A_3$-substituted cycloalkyl, $A_2$-substituted cycloalkylene-$A_3$-substituted cycloalkyl, substituted cycloalkylene-$A_3$-aryl, $A_2$-substituted cycloalkylene-$A_3$-aryl, substituted cycloalkylene-$A_3$-heteroaryl, $A_2$-substituted cycloalkylene-$A_3$-heteroaryl, substituted cycloalkylene-$A_3$-heterocycloalkyl, $A_2$-substituted cycloalkylene-$A_3$-heterocycloalkyl, substituted cycloalkylene-$A_3$-substituted aryl, $A_2$-substituted cycloalkylene-$A_3$-substituted aryl, heteroarylene-$A_3$-heteroaryl, $A_2$-heteroarylene-$A_3$-heteroaryl, heteroarylene-$A_3$-cycloalkyl, $A_2$-heteroarylene-$A_3$-cycloalkyl, heteroarylene-$A_3$-substituted cycloalkyl, $A_2$-heteroarylene-$A_3$-substituted cycloalkyl, heteroarylene-$A_3$-aryl, $A_2$-heteroarylene-$A_3$-aryl, heteroarylene-$A_3$-heterocycloalkyl, $A_2$-heteroarylene-$A_3$-heterocycloalkyl, heteroarylene-$A_3$-substituted aryl, $A_2$-heteroarylene-$A_3$-substituted aryl, heterocycloalkylene-$A_3$-heterocycloalkyl, $A_2$-heterocycloalkylene-$A_3$-heterocycloalkyl, heterocycloalkylene-$A_3$-cycloalkyl, $A_2$-heterocycloalkylene-$A_3$-cycloalkyl, heterocycloalkylene-$A_3$- substituted cycloalkyl, A$_2$-heterocycloalkylene-A$_3$-substituted cycloalkyl, heterocycloalkylene-A$_3$-aryl, A$_2$-heterocycloalkylene-A$_3$-aryl, heterocycloalkylene-A$_3$-substituted aryl, A$_2$-heterocycloalkylene-A$_3$-substituted aryl, heterocycloalkylene-A$_3$-heteroaryl, A$_2$-heterocycloalkylene-A$_3$-heteroaryl, substituted arylene-A$_3$-substituted aryl, A$_2$-substituted arylene-A$_3$-substituted aryl, substituted arylene-A$_3$-cycloalkyl, A$_2$-substituted arylene-A$_3$-cycloalkyl, substituted arylene-A$_3$-substituted cycloalkyl, A$_2$-substituted arylene-A$_3$-substituted cycloalkyl, substituted arylene-A$_3$-aryl, A$_2$-substituted arylene-A$_3$-aryl, substituted arylene-A$_3$-heteroaryl, A$_2$-substituted arylene-A$_3$-heteroaryl, substituted arylene-A$_3$-heterocycloalkyl, and A$_2$-substituted arylene-A$_3$-heterocycloalkyl;

R$_7$ is alkyl, substituted alkyl, cycloalkyl, substituted cycloalkyl, A$_2$-cycloalkyl, A$_2$-substituted cycloalkyl, aryl, substituted aryl, A$_2$-aryl, A$_2$-substituted aryl, heteroaryl, A$_2$-heteroaryl, heterocycloalkyl, A$_2$-heterocycloalkyl, arylene-A$_3$-aryl, A$_2$-arylene-A$_3$-aryl, arylene-A$_3$-cycloalkyl, A$_2$-arylene-A$_3$-cycloalkyl, arylene-A$_3$-heteroaryl, A$_2$-arylene-A$_3$-heteroaryl, arylene-A$_3$-heterocycloalkyl, A$_2$-arylene-A$_3$-heterocycloalkyl, arylene-A$_3$-substituted aryl, A$_2$-arylene-A$_3$-substitued aryl, arylene-A$_3$-substituted cycloalkyl, A$_2$-arylene-A$_3$-substituted cycloalkyl, cycloalkylene-A$_3$-cycloalkyl, A$_2$-cycloalkylene-A$_3$-cycloalkyl, cycloalkylene-A$_3$-aryl, A$_2$-cycloalkylene-A$_3$-aryl, cycloalkylene-A$_3$-heteroaryl, A$_2$-cycloalkylene-A$_3$-heteroaryl, cycloalkylene-A$_3$-heterocycloalkyl, A$_2$-cycloalkylene-A$_3$-heterocycloalkyl, cycloalkylene-A$_3$-substituted cycloalkyl, A$_2$-cycloalkylene-A$_3$-substituted cycloalkyl, cycloalkylene-A$_3$-substituted aryl, A$_2$-cycloalkylene-A$_3$-substituted aryl, substituted cycloalkylene-A$_3$-cycloalkyl, A$_2$-substituted cycloalkylene-A$_3$-cycloalkyl, substituted cycloalkylene-A$_3$-substituted cycloalkyl, A$_2$-substituted cycloalkylene-A$_3$-substituted cycloalkyl, substituted cycloalkylene-A$_3$-aryl, A$_2$-substituted cycloalkylene-A$_3$-aryl, substituted cycloalkylene-A$_3$-heteroaryl, A$_2$-substituted cycloalkylene-A$_3$-heteroaryl, substituted cycloalkylene-A$_3$-heterocycloalkyl, A$_2$-substituted cycloalkylene-A$_3$-heterocycloalkyl, substituted cycloalkylene-A$_3$-substituted aryl, A$_2$-substituted cycloalkylene-A$_3$-substituted aryl, heteroarylene-A$_3$-heteroaryl, A$_2$-heteroarylene-A$_3$-heteroaryl, heteroarylene-A$_3$-cycloalkyl, A$_2$-heteroarylene-A$_3$-cycloalkyl, heteroarylene-A$_3$-substituted cycloalkyl, A$_2$-heteroarylene-A$_3$-substituted cycloalkyl, heteroarylene-A$_3$-aryl, A$_2$-heteroarylene-A$_3$-aryl, heteroarylene-A$_3$-heterocycloalkyl, A$_2$-heteroarylene-A$_3$-heterocycloalkyl, heteroarylene-A$_3$-substituted aryl, A$_2$-heteroarylene-A$_3$-substituted aryl, heterocycloalkylene-A$_3$-heterocycloalkyl, A$_2$-heterocycloalkylene-A$_3$-heterocycloalkyl, heterocycloalkylene-A$_3$-cycloalkyl, A$_2$-heterocycloalkylene-A$_3$-cycloalkyl, heterocycloalkylene-A$_3$-substituted cycloalkyl, A$_2$-heterocycloalkylene-A$_3$-substituted cycloalkyl, heterocycloalkylene-A$_3$-aryl, A$_2$-heterocycloalkylene-A$_3$-aryl, heterocycloalkylene-A$_3$-substituted aryl, A$_2$-heterocycloalkylene-A$_3$-substituted aryl, heterocycloalkylene-A$_3$-heteroaryl, A$_2$-heterocycloalkylene-A$_3$-heteroaryl, substituted arylene-A$_3$-substituted aryl, A$_2$-substituted arylene-A$_3$-substituted aryl, substituted arylene-A$_3$-cycloalkyl, A$_2$-substituted arylene-A$_3$-cycloalkyl, substituted arylene-A$_3$-substituted cycloalkyl, A$_2$-substituted arylene-A$_3$-substituted cycloalkyl, substituted arylene-A$_3$-aryl, A$_2$-substituted arylene-A$_3$-aryl, substituted arylene-A$_3$-heteroaryl, A$_2$-substituted arylene-A$_3$-heteroaryl, substituted arylene-A$_3$-heterocycloalkyl, A$_2$-substituted arylene-A$_3$-heterocycloalkyl,

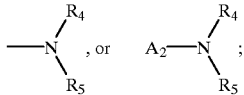

R$_9$ is hydrogen or lower alkyl;

A$_2$ is an alkylene or a substituted alkylene bridge of 1 to 10 carbons, an alkenylene or substituted alkenylene bridge of 2 to 10 carbons having one or more double bonds, or an alkynylene or substituted alkynylene bridge of 2 to 10 carbons having one or more triple bonds;

A$_3$ is a bond, an alkylene or a substituted alkylene bridge of 1 to 10 carbons, an alkenylene or substituted alkenylene bridge of 2 to 10 carbons having one or more double bonds, an alkynylene or substituted alkynylene bridge of 2 to 10 carbons having one or more triple bonds,

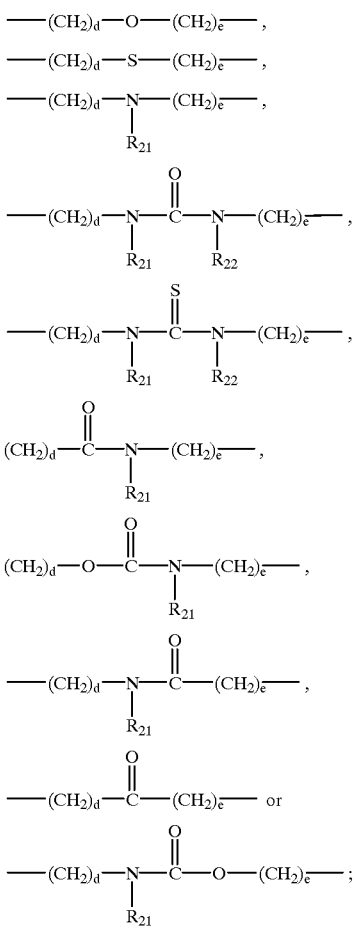

R$_{21}$ and R$_{22}$ are independently selected from hydrogen, alkyl, substituted alkyl, cycloalkyl, substituted cycloalkyl, A$_2$-cycloalkyl, A$_2$-substituted cycloalkyl, A$_2$-aryl, and A$_2$-substituted aryl;

d and e are independently selected from zero and an integer from 1 to 10 provided that the sum of d plus e is no greater then 10;

v and w are one, two, or three provided that the sum of v plus w is three, four, or five;

$R_8$ is hydrogen, halo, amino, —NH(lower alkyl), —N(lower alkyl)$_2$, nitro, alkyl, substituted alkyl, alkoxy, hydroxy, aryl, substituted aryl, $A_2$-aryl, $A_2$-substituted aryl, arylene-$A_3$-aryl, $A_2$-arylene-$A_3$-aryl, cycloalkyl, substituted cycloalkyl, $A_2$-cycloalkyl, $A_2$-substituted cycloalkyl, heteroaryl, $A_2$-heteroaryl, heterocycloalkyl, $A_2$-heterocycloalkyl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, or $A_2$-arylene-$A_3$-heterocycloalkyl;

$P_1$ is an N-protecting group; and

Z is benzyl or benzhydryl.

24. A process for preparing the compounds of the formula:

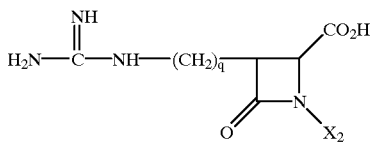

including an inner salt or pharmaceutically acceptable salt thereof wherein $X_2$ is

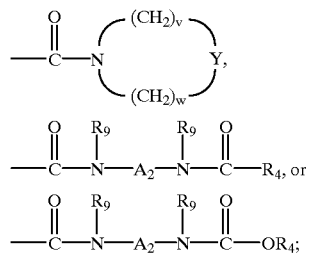

and Y, $R_4$, $R_9$, $R_7$, $A_2$, $A_3$, v, w, $R_{21}$, $R_{22}$, d, e and q are as defined in claim 1 which comprises:

a) reacting the compound of the formula:

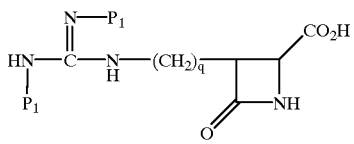

wherein $P_1$ is an N-protecting group with an alcohol of the formula:

or with a bromide or iodide of the formula:

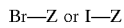

wherein Z is a protecting group selected from benzyl or benzhydryl to give the compound of the formula:

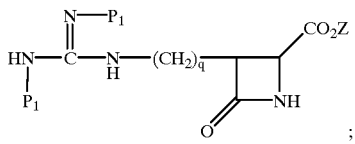

b) reacting the product from step (a) with a chloro compound selected from:

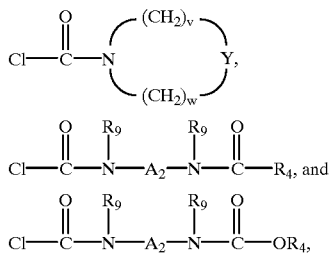

to give the compound of the formula:

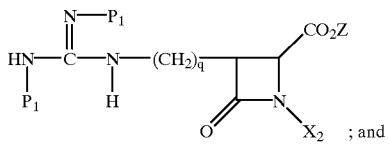

c) treating the product from step (b) to remove the Z protecting group and the $P_1$ N-protecting groups to give the desired compounds.

25. The process of claim 24 for preparing the compound of the formula:

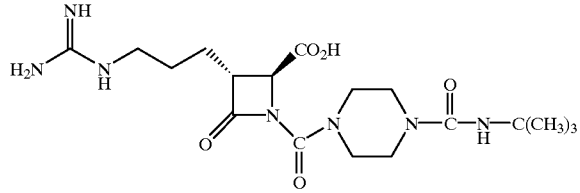

or an inner salt or pharmaceutically acceptable salt thereof which comprises:

a) reacting the compound of the formula:

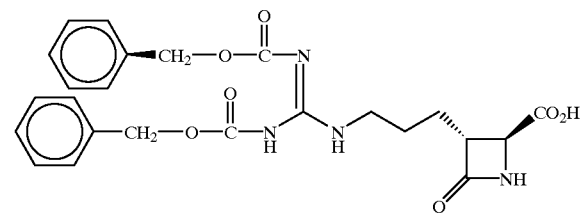

with benzyl bromide in the presence of sodium bicarbonate and tetrabutylammonium iodide to give the benzyl ester of the formula:

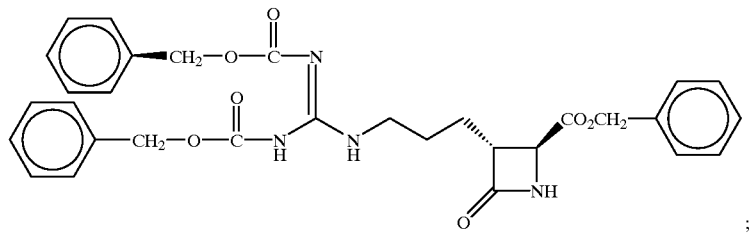

b) reacting the benzyl ester product from step (a) with the carbamoyl chloride of the formula:

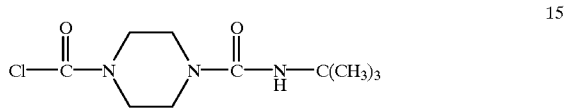

to give the azetidinone of the formula:

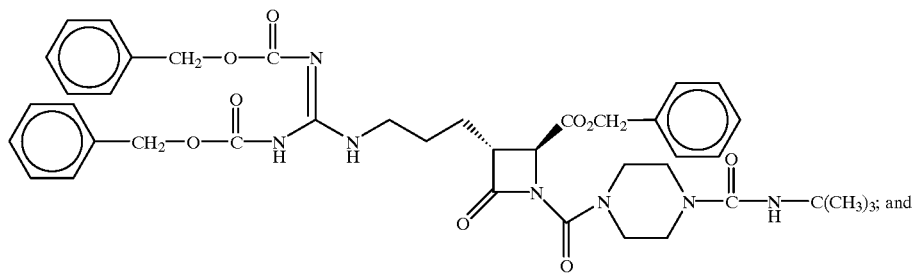

c) treating the product from step (b) with hydrogen in the presence of palladium on carbon catalyst to remove the benzyl ester and benzyloxycarbonyl N-protecting groups and give the desired compound.

26. A compound of the formula:

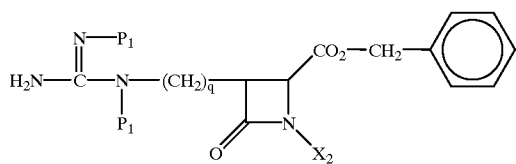

wherein:

$X_2$ is

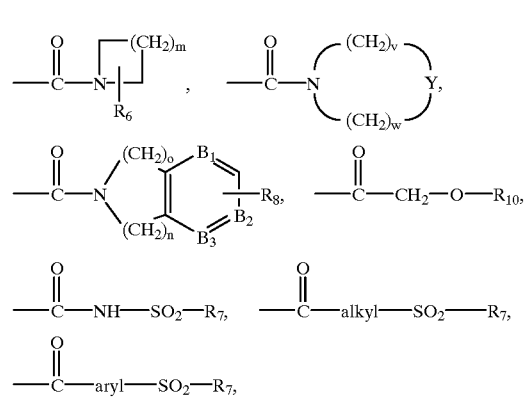

-continued

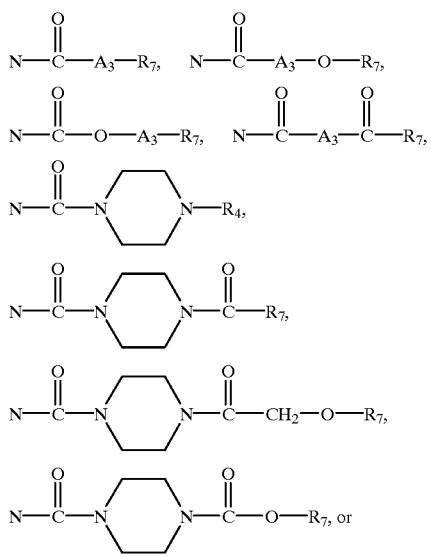

provided that

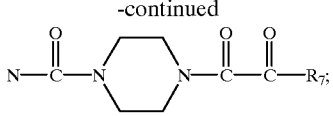

is other then alkylcarbonyl, phenylcarbonyl, substituted phenylcarbonyl, naphthylcarbonyl, substituted naphthylcarbonyl, phenylaminocarbonyl, substituted phenylaminocarbonyl, napththylaminocarbonyl, or substituted naphthylaminocarbonyl, or —SO$_2$—R$_7$ provided that —SO$_2$R$_7$ is other then alkylsulfonyl, phenylsulfonyl, substituted phenylsulfonyl, naphthylsulfonyl or substituted naphthylsulfonyl;

Y is O, S, N—R$_4$, N—SO$_2$—R$_7$,

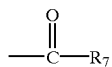

B$_1$, B$_2$ and B$_3$ are each CH, or two of B$_1$, B$_2$ and B$_3$ are CH and the other is N, or one of B$_1$, B$_2$ and B$_3$ is CH and the other two are N;

R$_4$ and R$_5$ are independently selected from hydrogen, alkyl, substituted alkyl, cycloalkyl, substituted cycloalkyl, A$_2$-cycloalkyl, A$_2$-substituted cycloalkyl, aryl, substituted aryl, A$_2$-aryl, A$_2$-substituted aryl, heteroaryl, A$_2$-heteroaryl, heterocycloalkyl, A$_2$-heterocycloalkyl, arylene-A$_3$-aryl, A$_2$-arylene-A$_3$-aryl, arylene-A$_3$-cycloalkyl, A$_2$-arylene-A$_3$-cycloalkyl, arylene-A$_3$-heteroaryl, A$_2$-arylene-A$_3$-heteroaryl, arylene-A$_3$-heterocycloalkyl, A$_2$-arylene-A$_3$-heterocycloalkyl, arylene-A$_3$-substituted aryl, A$_2$-arylene-A$_3$-substitued aryl, arylene-A$_3$-substituted cycloalkyl, A$_2$-arylene-A$_3$-substituted cycloalkyl, cycloalkylene-A$_3$-cycloalkyl, A$_2$-cycloalkylene-A$_3$-cycloalkyl, cycloalkylene-A$_3$-aryl, A$_2$-cycloalkylene-A$_3$-aryl, cycloalkylene-A$_3$-heteroaryl, A$_2$-cycloalkylene-A$_3$-heteroaryl, cycloalkylene-A$_3$-heterocycloalkyl, A$_2$-cycloalkylene-A$_3$-heterocycloalkyl, cycloalkylene-A$_3$-substituted cycloalkyl, A$_2$-cycloalkylene-A$_3$-substituted cycloalkyl, cycloalkylene-A$_3$-substituted aryl, A$_2$-cycloalkylene-A$_3$-substituted aryl, substituted cycloalkylene-A$_3$-cycloalkyl, A$_2$-substituted cycloalkylene-A$_3$-cycloalkyl, substituted cycloalkylene-A$_3$-substituted cycloalkyl, A$_2$-substituted cycloalkylene-A$_3$-substituted cycloalkyl, substituted cycloalkylene-A$_3$-aryl, A$_2$-substituted cycloalkylene-A$_3$-aryl, substituted cycloalkylene-A$_3$-heteroaryl, A$_2$-substituted cycloalkylene-A$_3$-heteroaryl, substituted cycloalkylene-A$_3$-heterocycloalkyl, A$_2$-substituted cycloalkylene-A$_3$-heterocycloalkyl, substituted cycloalkylene-A$_3$-substituted aryl, A$_2$-substituted cycloalkylene-A$_3$-substituted aryl, heteroarylene-A$_3$-heteroaryl, A$_2$-heteroarylene-A$_3$-heteroaryl, heteroarylene-A$_3$-cycloalkyl, A$_2$-heteroarylene-A$_3$-cycloalkyl, heteroarylene-A$_3$-substituted cycloalkyl, A$_2$-heteroarylene-A$_3$-substituted cycloalkyl, heteroarylene-A$_3$-aryl, A$_2$-heteroarylene-A$_3$-aryl, heteroarylene-A$_3$-heterocycloalkyl, A$_2$-heteroarylene-A$_3$-heterocycloalkyl, heteroarylene-A$_3$-substituted aryl, A$_2$-heteroarylene-A$_3$-substituted aryl, heterocycloalkylene-A$_3$-heterocycloalkyl, A$_2$-heterocycloalkylene-A$_3$-heterocycloalkyl, heterocycloalkylene-A$_3$-cycloalkyl, A$_2$-heterocycloalkylene-A$_3$-cycloalkyl, heterocycloalkylene-A$_3$-substituted cycloalkyl, A$_2$-heterocycloalkylene-A$_3$-substituted cycloalkyl, heterocycloalkylene-A$_3$-aryl, A$_2$-heterocycloalkylene-A$_3$-aryl, heterocycloalkylene-A$_3$-substituted aryl, A$_2$-heterocycloalkylene-A$_3$-substituted aryl, heterocycloalkylene-A$_3$-heteroaryl, A$_2$-heterocycloalkylene-A$_3$-heteroaryl, substituted arylene-A$_3$-substituted aryl, A$_2$-substituted arylene-A$_3$-substituted aryl, substituted arylene-A$_3$-cycloalkyl, A$_2$-substituted arylene-A$_3$-cycloalkyl, substituted arylene-A$_3$-substituted cycloalkyl, A$_2$-substituted arylene-A$_3$-substituted cycloalkyl, substituted arylene-A$_3$-aryl, A$_2$-substituted arylene-A$_3$-aryl, substituted arylene-A$_3$-heteroaryl, A$_2$-substituted arylene-A$_3$-heteroaryl, substituted arylene-A$_3$-heterocycloalkyl, and A$_2$-substituted arylene-A$_3$-heterocycloalkyl;

R$_6$ is hydrogen, alkyl, substituted alkyl, cycloalkyl, substituted cycloalkyl, A$_2$-cycloalkyl, A$_2$-substituted cycloalkyl, aryl, substituted aryl, A$_2$-aryl, A$_2$-substituted aryl, arylene-A$_3$-aryl, A$_2$-arylene-A$_3$-aryl, heteroaryl, A$_2$-heteroaryl, heterocycloalkyl, A$_2$-heterocycloalkyl, arylene-A$_3$-cycloalkyl, A$_2$-arylene-A$_3$-cycloalkyl, arylene-A$_3$-heteroaryl, A$_2$-arylene-A$_3$-heteroaryl, arylene-A$_3$-heterocycloalkyl, A$_2$-arylene-A$_3$-heterocycloalkyl, carboxy, alkoxycarbonyl, aryloxycarbonyl,

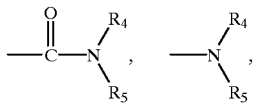

alkoxycarbonylamino, aryloxycarbonylamino, arylcarbonylamino, —N(alkyl)(alkoxycarbonyl), —N(alkyl)(aryloxycarbonyl), alkylcarbonylamino, —N(alkyl)(alkylcarbonyl), or —N(alkyl)(arylcarbonyl);

R$_7$ is alkyl, substituted alkyl, cycloalkyl, substituted cycloalkyl, A$_2$-cycloalkyl, A$_2$-substituted cycloalkyl, aryl, substituted aryl, A$_2$-aryl, A$_2$-substituted aryl, heteroaryl, A$_2$-heteroaryl, heterocycloalkyl, A$_2$-heterocycloalkyl, arylene-A$_3$-aryl, A$_2$-arylene-A$_3$-aryl, arylene-A$_3$-cycloalkyl, A$_2$-arylene-A$_3$-cycloalkyl, arylene-A$_3$-heteroaryl, A$_2$-arylene-A$_3$-heteroaryl, arylene-A$_3$-heterocycloalkyl, A$_2$-arylene-A$_3$-heterocycloalkyl, arylene-A$_3$-substituted aryl, A$_2$-arylene-A$_3$-substitued aryl, arylene-A$_3$-substituted cycloalkyl, A$_2$-arylene-A$_3$-substituted cycloalkyl, cycloalkylene-A$_3$-cycloalkyl, A$_2$-cycloalkylene-A$_3$-cycloalkyl, cycloalkylene-A$_3$-aryl, A$_2$-cycloalkylene-A$_3$-aryl, cycloalkylene-A$_3$-heteroaryl, A$_2$-cycloalkylene-A$_3$-heteroaryl, cycloalkylene-A$_3$-heterocycloalkyl, A$_2$-cycloalkylene-A$_3$-heterocycloalkyl, cycloalkylene-A$_3$-substituted cycloalkyl, A$_2$-cycloalkylene-A$_3$-substituted cycloalkyl, cycloalkylene-A$_3$-substituted aryl, A$_2$-cycloalkylene-A$_3$-substituted aryl, substituted cycloalkylene-A$_3$-cycloalkyl, A$_2$-substituted cycloalkylene-A$_3$-cycloalkyl, substituted cycloalkylene-A$_3$-substituted cycloalkyl, A$_2$-substituted cycloalkylene-A$_3$-substituted cycloalkyl, substituted cycloalkylene-A$_3$-aryl, A$_2$-substituted cycloalkylene-A$_3$-aryl, substituted cycloalkylene-A$_3$-heteroaryl, A$_2$-substituted cycloalkylene-A$_3$-heteroaryl, substituted cycloalkylene-A$_3$-heteroaryl, substituted cycloalkylene-$A_3$-heterocycloalkyl, $A_2$-substituted cycloalkylene-$A_3$-heterocycloalkyl, substituted cycloalkylene-$A_3$-substituted aryl, $A_2$-substituted cycloalkylene-$A_3$-substituted aryl, heteroarylene-$A_3$-heteroaryl, $A_2$-heteroarylene-$A_3$-heteroaryl, heteroarylene-$A_3$-cycloalkyl, $A_2$-heteroarylene-$A_3$-cycloalkyl, heteroarylene-$A_3$-substituted cycloalkyl, $A_2$-heteroarylene-$A_3$-substituted cycloalkyl, heteroarylene-$A_3$-aryl, $A_2$-heteroarylene-$A_3$-aryl, heteroarylene-$A_3$-heterocycloalkyl, $A_2$-heteroarylene-$A_3$-heterocycloalkyl, heteroarylene-$A_3$-substituted aryl, $A_2$-heteroarylene-$A_3$-substituted aryl, heterocycloalkylene-$A_3$-heterocycloalkyl, $A_2$-heterocycloalkylene-$A_3$-heterocycloalkyl, heterocycloalkylene-$A_3$-cycloalkyl, $A_2$-heterocycloalkylene-$A_3$-cycloalkyl, heterocycloalkylene-$A_3$-substituted cycloalkyl, $A_2$-heterocycloalkylene-$A_3$-substituted cycloalkyl, heterocycloalkylene-$A_3$-aryl, $A_2$-heterocycloalkylene-$A_3$-aryl, heterocycloalkylene-$A_3$-substituted aryl, $A_2$-heterocycloalkylene-$A_3$-substituted aryl, heterocycloalkylene-$A_3$-heteroaryl, $A_2$-heterocycloalkylene-$A_3$-heteroaryl, substituted arylene-$A_3$-substituted aryl, $A_2$-substituted arylene-$A_3$-substituted aryl, substituted arylene-$A_3$-cycloalkyl, $A_2$-substituted arylene-$A_3$-cycloalkyl, substituted arylene-$A_3$-substituted cycloalkyl, $A_2$-substituted arylene-$A_3$-substituted cycloalkyl, substituted arylene-$A_3$-aryl, $A_2$-substituted arylene-$A_3$-aryl, substituted arylene-$A_3$-heteroaryl, $A_2$-substituted arylene-$A_3$-heteroaryl, substituted arylene-$A_3$-heterocycloalkyl, $A_2$-substituted arylene-$A_3$-heterocycloalkyl,

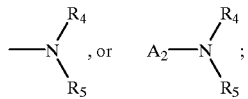

$R_8$ is hydrogen, halo, amino, —NH(lower alkyl), —N(lower alkyl)$_2$, nitro, alkyl, substituted alkyl, alkoxy, hydroxy, aryl, substituted aryl, $A_2$-aryl, $A_2$-substituted aryl, arylene-$A_3$-aryl, $A_2$-arylene-$A_3$-aryl, cycloalkyl, substituted cycloalkyl, $A_2$-cycloalkyl, $A_2$-substituted cycloalkyl, heteroaryl, $A_2$-heteroaryl, heterocycloalkyl, $A_2$-heterocycloalkyl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, or $A_2$-arylene-$A_3$-heterocycloalkyl;

$R_9$ is hydrogen or lower alkyl;

$R_{10}$ is alkyl, substituted alkyl, alkylene-O-alkyl, alkylene-O-alkylene-O-alkyl, cycloalkyl, substituted cycloalkyl, $A_2$-cycloalkyl, $A_2$-substituted cycloalkyl, aryl, substituted aryl, $A_2$-aryl, $A_2$-substituted aryl, arylene-$A_3$-aryl, $A_2$-arylene-$A_3$-aryl, heteroaryl, $A_2$-heteroaryl, heterocycloalkyl, $A_2$-heterocycloalkyl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl or $A_2$-arylene-$A_3$-heterocyloalkyl;

$A_2$ is an alkylene or a substituted alkylene bridge of 1 to 10 carbons, an alkenylene or substituted alkenylene bridge of 2 to 10 carbons having one or more double bonds, or an alkynylene or substituted alkynylene bridge of 2 to 10 carbons having one or more triple bonds;

$A_3$ is a bond, an alkylene or a substituted alkylene bridge of 1 to 10 carbons, an alkenylene or substituted alkenylene bridge of 2 to 10 carbons having one or more double bonds, an alkynylene or substituted alkynylene bridge of 2 to 10 carbons having one or more triple bonds,

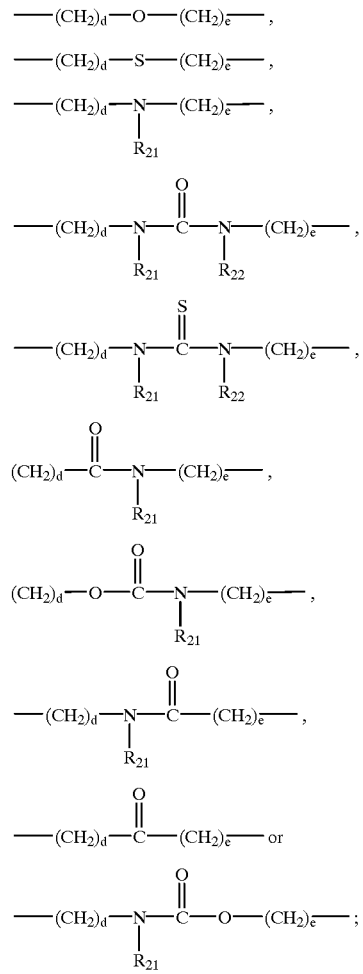

$R_{21}$ and $R_{22}$ are independently selected from hydrogen, alkyl, substituted alkyl, cycloalkyl, substituted cycloalkyl, $A_2$-cycloalkyl, $A_2$-substituted cycloalkyl, $A_2$-aryl, and $A_2$-substituted aryl;

n and o are one or two provided that the sum of n plus o is two or three;

v and w are one, two, or three provided that the sum of v plus w is three, four, or five;

m is an integer from 1 to 5;

q is an integer from 1 to 6; and $P_1$ is an N-protecting group.

27. The compound of claim 26 wherein:

q is 3;

$X_2$ is

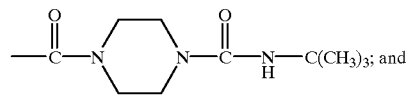

P₁ is

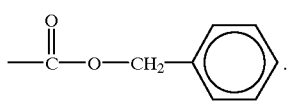

28. A process for preparing the compounds of the formula:

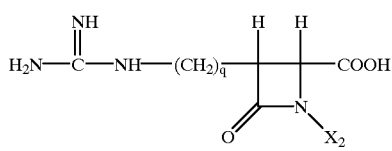

or an inner salt or pharmaceutically acceptable salt thereof wherein:

X₂ is

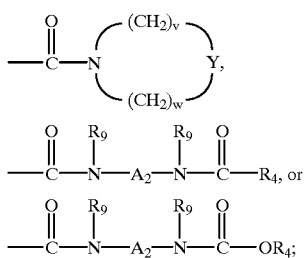

Y, $R_4$, $R_9$, $R_7$, $A_2$, $A_3$, $R_{21}$, $R_{22}$, v, w, d, e and q are as defined in claim 1 which comprises:

a) reacting the azetidinone of the formula:

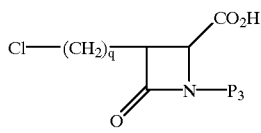

wherein P₃ is a silyl protecting group with benzylchloroformate in the presence of triethylamine and dimethylaminopyridine to give the compound of the formula:

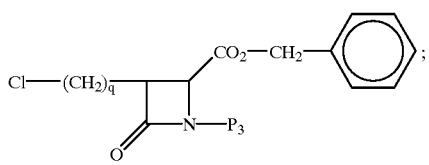

b) treating the benzyl ester product from step (a) with sodium iodide to give the compound of the formula:

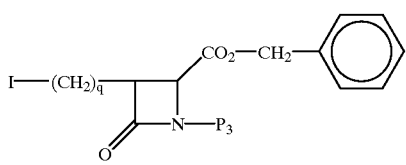

c) reacting the iodo product from step (b) with the diprotected guanidine of the formula:

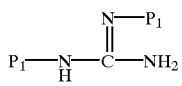

to give the azetidinone compound of the formula:

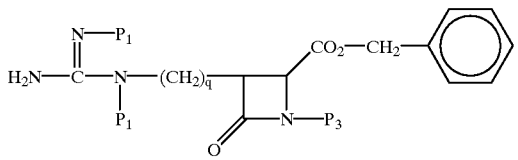

wherein P₁ is an N-protecting group;

d) reacting the aztetidinone product from step (c) with ammonium fluoride to give the azetidinone of the formula:

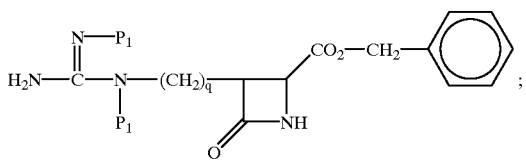

e) reacting the azetidinone product of (d) with a chloro compound selected from:

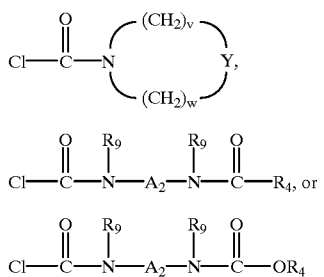

to give the compound of the formula:

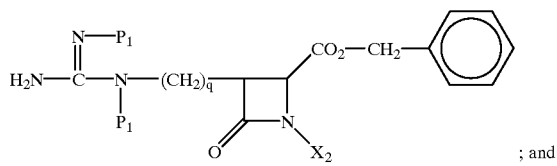

; and f) treating the benzyl ester product from step (e) to remove the benzyl and P₁ protecting groups and give the desired product.

29. The process of claim 28 for preparing the compound of the formula:

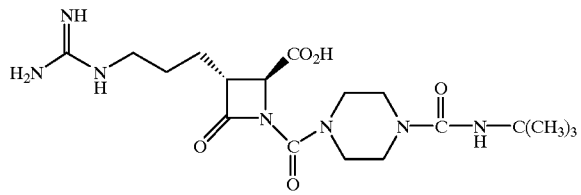

or an inner salt or pharmaceutically acceptable salt thereof which comprises a) reacting the azetidinone of the formula:

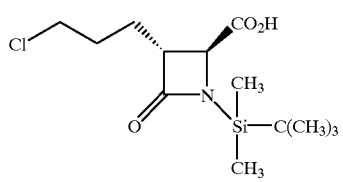

with benzylchloroformate in the presence of triethylamine and dimethylaminopyridine to give the compound of the formula:

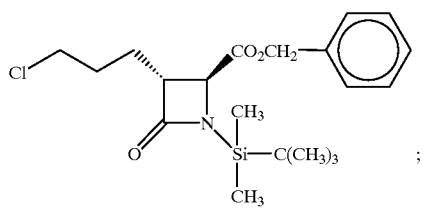

b) treating the benzyl ester product from step (a) with sodium iodide to give the compound of the formula:

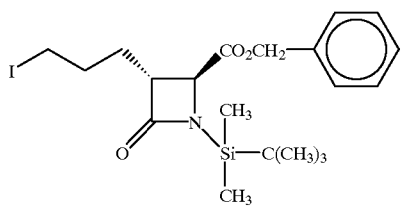

c) reacting the iodo product from step (b) with the diprotected guanidine of the formula:

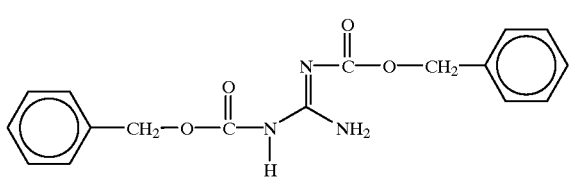

to give the azetidinone of the formula:

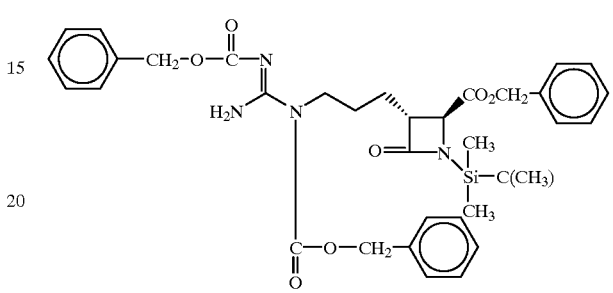

d) reacting the azetidinone product from step (c) with ammonium fluoride to give the azetidinone of the formula:

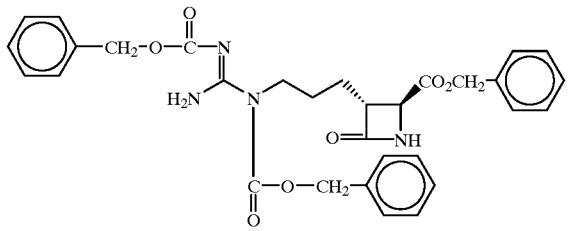

e) treating the azetidinone product of step (d) with the carbamoyl chloride;

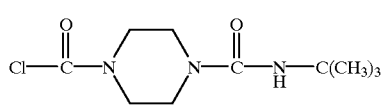

to give the azetidinone of the formula:

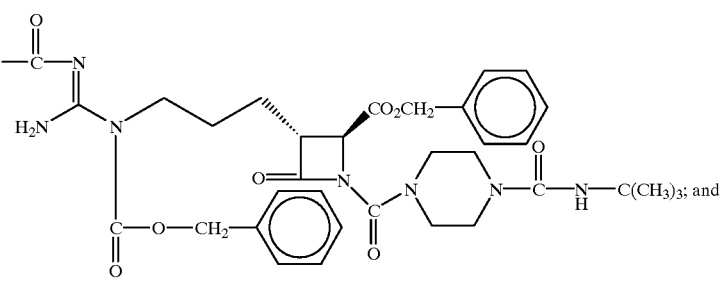

f) treating the azetidinone product of step (e) with hydrogen in the presence of palladium on carbon catalyst to remove the benzyl and benzyloxycarbonyl protecting groups and give the desired product.

30. A process for preparing the azetidinone compounds of the formula:

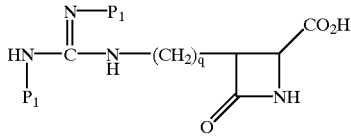

or an amine salt thereof wherein $P_1$ is an N-protecting group and q is an integer from 1 to 6 which comprises:

a) reacting the diprotected amine of the formula:

with the alkyldihalide of the formula:

to give the chloro compound of the formula:

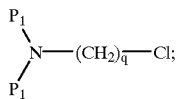

b) treating the chloro product from step (a) with sodium iodide in the optional presence of base to give the iodo compound of the formula:

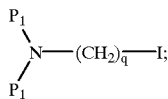

c) reacting the iodo product from step (b) with the silyl protected azetidinone of the formula:

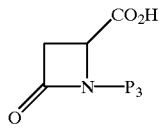

wherein $P_3$ is a silyl protecting group to give after removal of the $P_3$ protecting group the azetidinone of the formula:

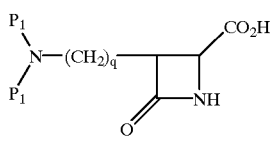

which may optionally be isolated as an inner salt; and d) treating the azetidinone product from step (c) to remove the $P_1$ protecting groups and reacting the resulting compound with the diprotected guanylating agent of the formula:

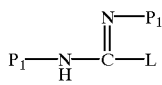

wherein L is a leaving group selected from methylthio or pyrazolyl to give the desired compound which may optionally be isolated as an amine salt.

31. The process of claim 30 for preparing the azetidinone compound of the formula:

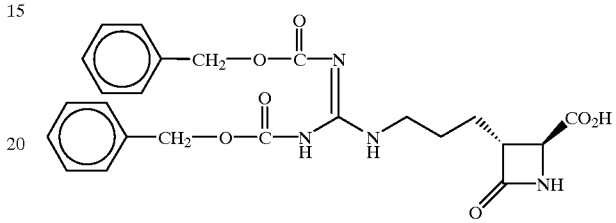

or an amine salt thereof which comprises:

a) reacting the diprotected amine of the formula:

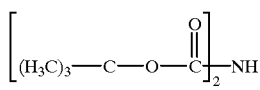

with the alkydihalide of the formula:

to give the chloro compound of the formula:

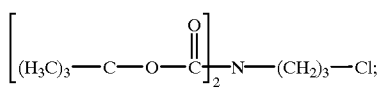

b) treating the chloro product from step (a) with sodium iodide in the presence of base to give the iodo compound of the formula:

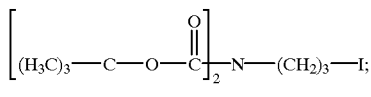

c) reacting the iodo product from step (b) with the silyl protected azetidinone of the formula:

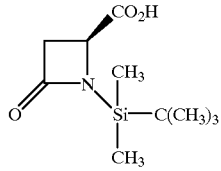

to give after removal of the tert-butyidimethylsilyl protecting group the azetidinone of the formula:

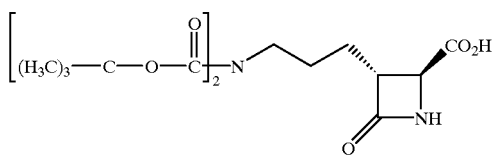

which may optionally be isolated as an amine salt; and d) treating the azetidinone product from step (c) with trifluoroacetic acid to remove the tert-butoxycarbonyl protecting groups and reacting the resulting amine with the diprotected guanylating agent of the formula:

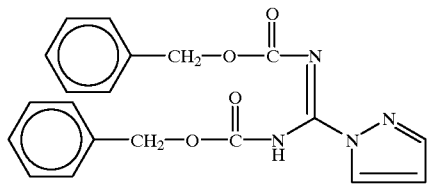

to give the desired compound which may optionally be isolated as an amine salt.

32. A compound of the formula:

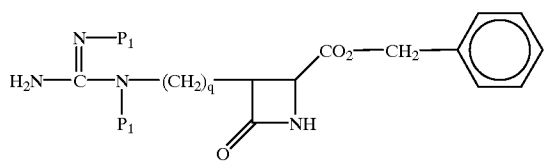

wherein q is an integer from 1 to 6; and $P_1$ is an N-protecting group.

33. The compound of claim 32 wherein:

q is 3; and $P_1$ is

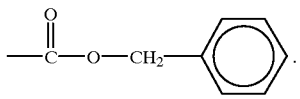

34. The process of claim 24 for preparing the compound of the formula:

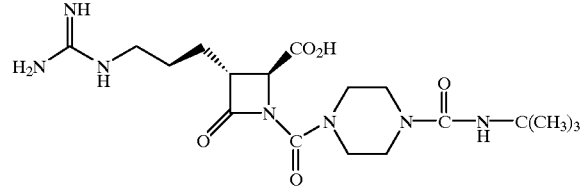

or an inner salt or pharmaceutically acceptable salt thereof which comprises:

a) reacting the compound of the formula:

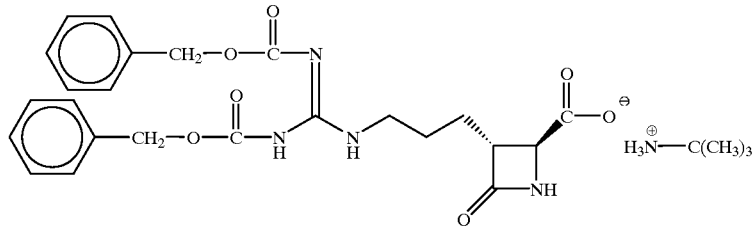

with benzyl bromide in the presence of tert-butylamine and N,N'-dimethylpropyleneurea to give the benzyl ester of the formula:

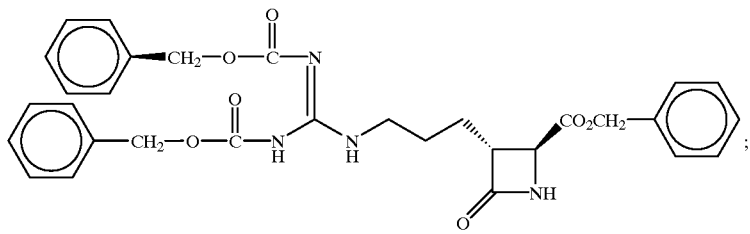

b) reacting the benzyl ester product from step (a) with the carbamoyl chloride of the formula:

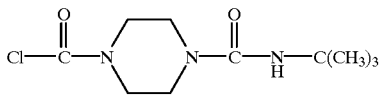

to give the azetidinone of the formula:

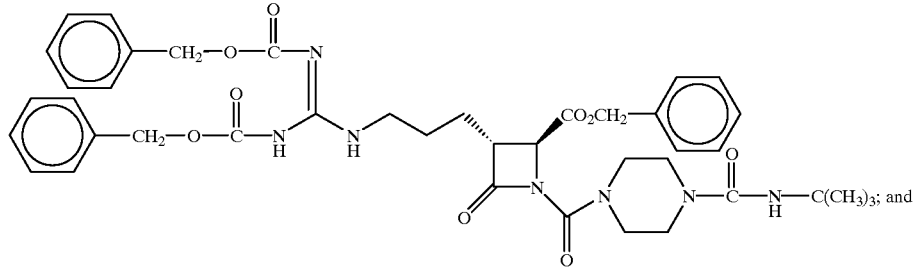

c) treating the product from step (b) with hydrogen in the presence of palladium on carbon catalyst to remove the benzyl ester and benzyloxycarbonyl N-protecting groups and give the desired compound.

35. A compound of the formula:

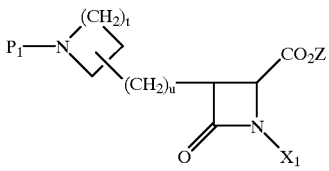

wherein:

$X_1$ is

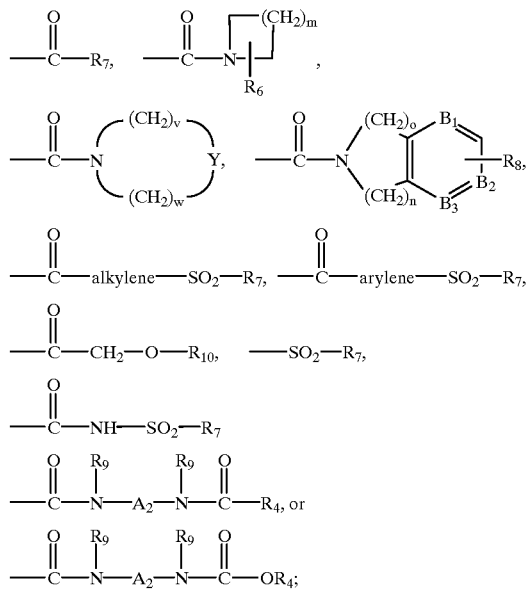

Y is O, S, $N-R_4$, $N-SO_2-R_7$,

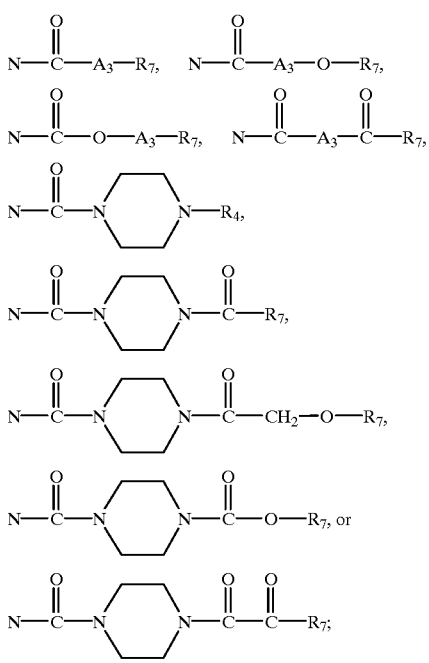

$B_1$, $B_2$ and $B_3$ are each CH, or two of $B_1$, $B_2$ and $B_3$ are CH and the other is N, or one of $B_1$, $B_2$ and $B_3$ is CH and the other two are N;

$R_4$ and $R_5$ are independently selected from hydrogen, alkyl, substituted alkyl, cycloalkyl, substituted cycloalkyl, $A_2$-cycloalkyl, $A_2$-substituted cycloalkyl, aryl, substituted aryl, $A_2$-aryl, $A_2$-substituted aryl, heteroaryl, $A_2$-heteroaryl, heterocycloalkyl, $A_2$-heterocycloalkyl, arylene-$A_3$-aryl, $A_2$-arylene-$A_3$-aryl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, $A_2$-arylene-$A_3$-heterocycloalkyl, arylene-$A_3$-substituted aryl, $A_2$-arylene-$A_3$-substitued aryl, arylene-$A_3$-substituted cycloalkyl, $A_2$-arylene-$A_3$-substituted cycloalkyl, cycloalkylene-$A_3$-cycloalkyl, $A_2$-cycloalkylene-$A_3$-cycloalkyl, cycloalkylene-$A_3$-aryl, $A_2$-cycloalkylene- $A_3$-aryl, cycloalkylene-$A_3$-heteroaryl, $A_2$-cycloalkylene-$A_3$-heteroaryl, cycloalkylene-$A_3$-heterocycloalkyl, $A_2$-cycloalkylene-$A_3$-heterocycloalkyl, cycloalkylene-$A_3$-substituted cycloalkyl, $A_2$-cycloalkylene-$A_3$-substituted cycloalkyl, cycloalkylene-$A_3$-substituted aryl, $A_2$-cycloalkylene-$A_3$-substituted aryl, substituted cycloalkylene-$A_3$-cycloalkyl, $A_2$-substituted cycloalkylene-$A_3$-cycloalkyl, substituted cycloalkylene-$A_3$-substituted cycloalkyl, $A_2$-substituted cycloalkylene-$A_3$-substituted cycloalkyl, substituted cycloalkylene-$A_3$-aryl, $A_2$-substituted cycloalkylene-$A_3$-aryl, substituted cycloalkylene-$A_3$-heteroaryl, $A_2$-substituted cycloalkylene-$A_3$-heteroaryl, substituted cycloalkylene-$A_3$-heterocycloalkyl, $A_2$-substituted cycloalkylene-$A_3$-heterocycloalkyl, substituted cycloalkylene-$A_3$-substituted aryl, $A_2$-substituted cycloalkylene-$A_3$-substituted aryl, heteroarylene-$A_3$-heteroaryl, $A_2$-heteroarylene-$A_3$-heteroaryl, heteroarylene-$A_3$-cycloalkyl, $A_2$-heteroarylene-$A_3$-cycloalkyl, heteroarylene-$A_3$-substituted cycloalkyl, $A_2$-heteroarylene-$A_3$-substituted cycloalkyl, heteroarylene-$A_3$-aryl, $A_2$-heteroarylene-$A_3$-aryl, heteroarylene-$A_3$-heterocycloalkyl, $A_2$-heteroarylene-$A_3$-heterocycloalkyl, heteroarylene-$A_3$-substituted aryl, $A_2$-heteroarylene-$A_3$-substituted aryl, heterocycloalkylene-$A_3$-heterocycloalkyl, $A_2$-heterocycloalkylene-$A_3$-heterocycloalkyl, heterocycloalkylene-$A_3$-cycloalkyl, $A_2$-heterocycloalkylene-$A_3$-cycloalkyl, heterocycloalkylene-$A_3$-substituted cycloalkyl, $A_2$-heterocycloalkylene-$A_3$-substituted cycloalkyl, heterocycloalkylene-$A_3$-aryl, $A_2$-heterocycloalkylene-$A_3$-aryl, heterocycloalkylene-$A_3$-substituted aryl, $A_2$-heterocycloalkylene-$A_3$-substituted aryl, heterocycloalkylene-$A_3$-heteroaryl, $A_2$-heterocycloalkylene-$A_3$-heteroaryl, substituted arylene-$A_3$-substituted aryl, $A_2$-substituted arylene-$A_3$-substituted aryl, substituted arylene-$A_3$-cycloalkyl, $A_2$-substituted arylene-$A_3$-cycloalkyl, substituted arylene-$A_3$-substituted cycloalkyl, $A_2$-substituted arylene-$A_3$-substituted cycloalkyl, substituted arylene-$A_3$-substituted cycloalkyl, substituted arylene-$A_3$-aryl, $A_2$-substituted arylene-$A_3$-aryl, substituted arylene-$A_3$-heteroaryl, $A_2$-substituted arylene-$A_3$-heteroaryl, substituted arylene-$A_3$-heterocycloalkyl, and $A_2$-substituted arylene-$A_3$-heterocycloalkyl;

$R_6$ is hydrogen, alkyl, substituted alkyl, cycloalkyl, substituted cycloalkyl, $A_2$-cycloalkyl, $A_2$-substituted cycloalkyl, aryl, substituted aryl, $A_2$-aryl, $A_2$-substituted aryl, arylene-$A_3$-aryl, $A_2$-arylene-$A_3$-aryl, heteroaryl, $A_2$-heteroaryl, heterocycloalkyl, $A_2$-heterocycloalkyl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, $A_2$-arylene-$A_3$-heterocycloalkyl, carboxy, alkoxycarbonyl, aryloxycarbonyl, $$-\overset{O}{\underset{}{C}}-N\genfrac{}{}{0pt}{}{R_4}{R_5},\quad -N\genfrac{}{}{0pt}{}{R_4}{R_5},$$

alkoxycarbonylamino, aryloxycarbonylamino, arylcarbonylamino, —N(alkyl)(alkoxycarbonyl), —N(alkyl)(aryloxycarbonyl), alkylcarbonylamino, —N(alkyl)(alkylcarbonyl), or —N(alkyl)(arylcarbonyl);

$R_7$ is alkyl, substituted alkyl, cycloalkyl, substituted cycloalkyl, $A_2$-cycloalkyl, $A_2$-substituted cycloalkyl, aryl, substituted aryl, $A_2$-aryl, $A_2$-substituted aryl, heteroaryl, $A_2$-heteroaryl, heterocycloalkyl, $A_2$-heterocycloalkyl, arylene-$A_3$-aryl, $A_2$-arylene-$A_3$-aryl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, $A_2$-arylene-$A_3$-heterocycloalkyl, arylene-$A_3$-substituted aryl, $A_2$-arylene-$A_3$-substitued aryl, arylene-$A_3$-substituted cycloalkyl, $A_2$-arylene-$A_3$-substituted cycloalkyl, cycloalkylene-$A_3$-cycloalkyl, $A_2$-cycloalkylene-$A_3$-cycloalkyl, cycloalkylene-$A_3$-aryl, $A_2$-cycloalkylene-$A_3$-aryl, cycloalkylene-$A_3$-heteroaryl, $A_2$-cycloalkylene-$A_3$-heteroaryl, cycloalkylene-$A_3$-heterocycloalkyl, $A_2$-cycloalkylene-$A_3$-heterocycloalkyl, cycloalkylene-$A_3$-substituted cycloalkyl, $A_2$-cycloalkylene-$A_3$-substituted cycloalkyl, cycloalkylene-$A_3$-substituted aryl, $A_2$-cycloalkylene-$A_3$-substituted aryl, substituted cycloalkylene-$A_3$-cycloalkyl, $A_2$-substituted cycloalkylene-$A_3$-cycloalkyl, substituted cycloalkylene-$A_3$-substituted cycloalkyl, $A_2$-substituted cycloalkylene-$A_3$-substituted cycloalkyl, substituted cycloalkylene-$A_3$-aryl, $A_2$-substituted cycloalkylene-$A_3$-aryl, substituted cycloalkylene-$A_3$-heteroaryl, $A_2$-substituted cycloalkylene-$A_3$-heteroaryl, substituted cycloalkylene-$A_3$-heterocycloalkyl, $A_2$-substituted cycloalkylene-$A_3$-heterocycloalkyl, substituted cycloalkylene-$A_3$-substituted aryl, $A_2$-substituted cycloalkylene-$A_3$-substituted aryl, heteroarylene-$A_3$-heteroaryl, $A_2$-heteroarylene-$A_3$-heteroaryl, heteroarylene-$A_3$-cycloalkyl, $A_2$-heteroarylene-$A_3$-cycloalkyl, heteroarylene-$A_3$-substituted cycloalkyl, $A_2$-heteroarylene-$A_3$-substituted cycloalkyl, heteroarylene-$A_3$-aryl, $A_2$-heteroarylene-$A_3$-aryl, heteroarylene-$A_3$-heterocycloalkyl, $A_2$-heteroarylene-$A_3$-heterocycloalkyl, heteroarylene-$A_3$-substituted aryl, $A_2$-heteroarylene-$A_3$-substituted aryl, heterocycloalkylene-$A_3$-heterocycloalkyl, $A_2$-heterocycloalkylene-$A_3$-heterocycloalkyl, heterocycloalkylene-$A_3$-cycloalkyl, $A_2$-heterocycloalkylene-$A_3$-cycloalkyl, heterocycloalkylene-$A_3$-substituted cycloalkyl, $A_2$-heterocycloalkylene-$A_3$-substituted cycloalkyl, heterocycloalkylene-$A_3$-aryl, $A_2$-heterocycloalkylene-$A_3$-aryl, heterocycloalkylene-$A_3$-substituted aryl, $A_2$-heterocycloalkylene-$A_3$-substituted aryl, heterocycloalkylene-$A_3$-heteroaryl, $A_2$-heterocycloalkylene-$A_3$-heteroaryl, substituted arylene-$A_3$-substituted aryl, $A_2$-substituted arylene-$A_3$-substituted aryl, substituted arylene-$A_3$-cycloalkyl, $A_2$-substituted arylene-$A_3$-cycloalkyl, substituted arylene-$A_3$-substituted cycloalkyl, $A_2$-substituted arylene-$A_3$-substituted cycloalkyl, substituted arylene-$A_3$-aryl, $A_2$-substituted arylene-$A_3$-aryl, substituted arylene-$A_3$-heteroaryl, $A_2$-substituted arylene-$A_3$-heteroaryl, substituted arylene-$A_3$-heterocycloalkyl, $A_2$-substituted arylene-$A_3$-heterocycloalkyl, $$-N\genfrac{}{}{0pt}{}{R_4}{R_5},\text{ or }A_2-N\genfrac{}{}{0pt}{}{R_4}{R_5};$$

$R_8$ is hydrogen, halo, amino, —NH(lower alkyl), —N(lower alkyl)$_2$, nitro, alkyl, substituted alkyl, alkoxy, hydroxy, aryl, substituted aryl, $A_2$-aryl, $A_2$-substituted aryl, arylene-$A_3$-aryl, $A_2$-arylene-$A_3$-arylene, cycloalkyl, substituted cycloalkyl, $A_2$-cycloalkyl, $A_2$-substituted cycloalkyl, heteroaryl, $A_2$-heteroaryl, heterocycloalkyl, $A_2$-heterocycloalkyl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl, or $A_2$-arylene-$A_3$-heterocycloalkyl;

$R_9$ is hydrogen or lower alkyl;

$R_{10}$ is alkyl, substituted alkyl, alkylene-O-alkyl, alkylene-O-alkylene-O-alkyl, cycloalkyl, substituted cycloalkyl, $A_2$-cycloalkyl, $A_2$-substituted cycloalkyl, aryl, substituted aryl, $A_2$-aryl, $A_2$-substituted aryl, arylene-$A_3$-aryl, $A_2$-arylene-$A_3$-aryl, heteroaryl, $A_2$-heteroaryl, heterocycloalkyl, $A_2$-heterocycloalkyl, arylene-$A_3$-cycloalkyl, $A_2$-arylene-$A_3$-cycloalkyl, arylene-$A_3$-heteroaryl, $A_2$-arylene-$A_3$-heteroaryl, arylene-$A_3$-heterocycloalkyl or $A_2$-arylene-$A_3$-heterocyloalkyl;

$A_2$ is an alkylene or a substituted alkylene bridge of 1 to 10 carbons, an alkenylene or substituted alkenylene bridge of 2 to 10 carbons having one or more double bonds, or an alkynylene or substituted alkynylene bridge of 2 to 10 carbons having one or more triple bonds;

$A_3$ is a bond, an alkylene or a substituted alkylene bridge of 1 to 10 carbons, an alkenylene or substituted alkenylene bridge of 2 to 10 carbons having one or more double bonds, an alkynylene or substituted alkynylene bridge of 2 to 10 carbons having one or more triple bonds,

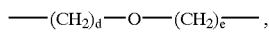

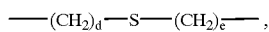

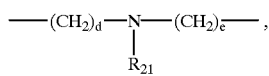

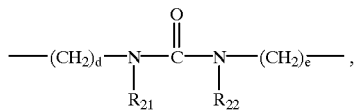

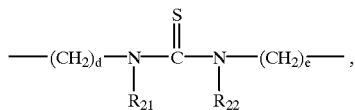

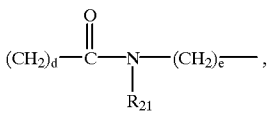

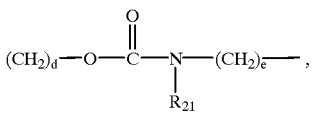

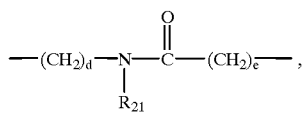

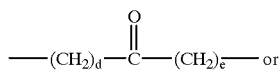 or

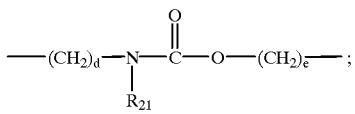

o and n are one or two provided that the sum of n plus o is two or three;

v and w are one, two, or three provided that the sum of v plus w is three, four, or five;

$R_{21}$ and $R_{22}$ are independently selected from hydrogen, alkyl, substituted alkyl, cycloalkyl, substituted cycloalkyl, $A_2$-cycloalkyl, $A_2$-substituted cycloalkyl, $A_2$-aryl, and $A_2$-substituted aryl;

d and e are independently selected from zero and an integer from 1 to 10 provided that the sum of d plus e is no greater then 10;

t is one, two, three or four;

u is one, two or three;

$P_1$ is an N-protecting group; and

Z is benzyl or benzhydryl.

36. A compound of the formula:

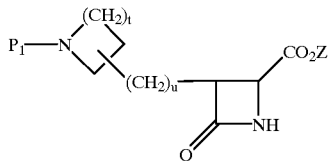

wherein:

t is one, two, three or four;

u is one, two or three;

$P_1$ is an N-protecting group; and

Z is benzyl or benzhydryl.

37. A process for preparing compounds of claim 1 having the formula:

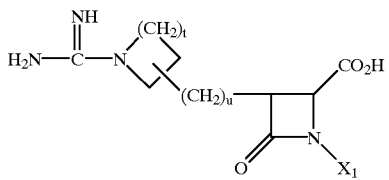

including an inner salt or pharmaceutically acceptable salt thereof which comprises:

a) reacting the compound of the formula:

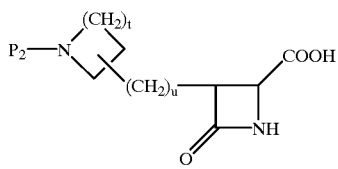

wherein $P_2$ is the N-protecting group t-butoxycarbonyl with an alcohol of the formula:

HO—Z or with a bromide or iodide of the formula:

Br—Z or I—Z wherein Z is the protecting group benzyl to give the compound of the formula:

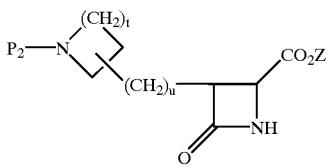

wherein t and u are as defined in claim 1;

b) reacting the product from step (a) with a chloro compound selected from

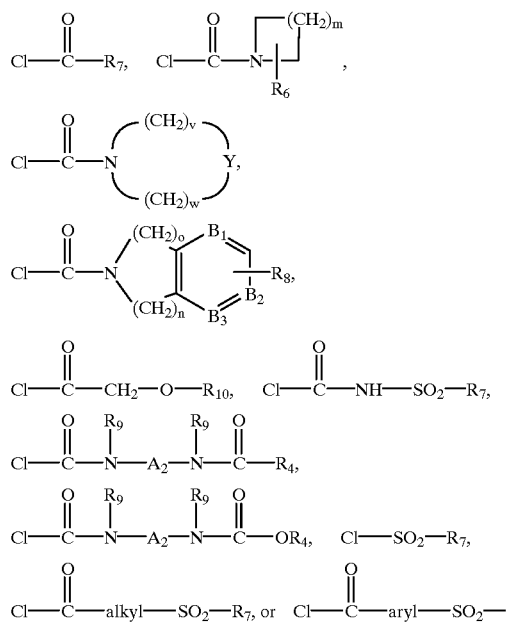

or reacting with OCN—SO—$R_7$ to give the compound of the formula:

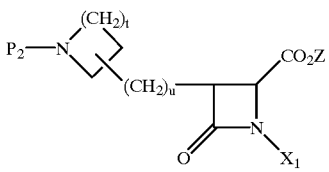

wherein $R_4$, $R_6$, $R_7$, $R_8$, $R_9$, $R_{10}$, v, w, o, n, m, $B_1$, $B_2$, $B_6$, and $A_2$ are as defined in claim 1;

c) treating the product from step (b) to remove the $P_2$ protecting group;

d) reacting the product from step (c) with the diprotected guanylating agent of the formula:

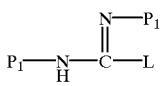

wherein L is a leaving group selected from methylthio or pyrazolyl to give the compound of the formula:

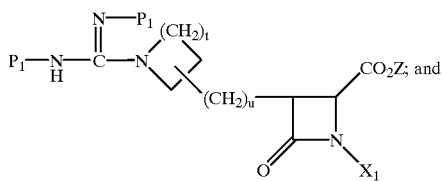

e) treating the product from step (d) to remove the $P_1$ and Z protecting groups and give the desired final product.

38. A process for preparing compounds of claim 1 having the formula:

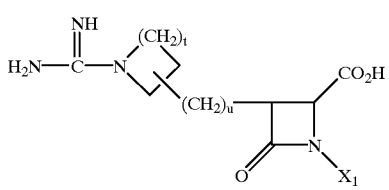

including an inner salt or pharmaceutically acceptable salt thereof which comprises:

a) reacting the compound of the formula:

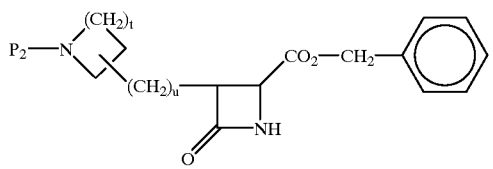

wherein $P_2$ is the N-protecting group t-butoxycarbonyl with trifluoroacetic acid to give the compound of the formula:

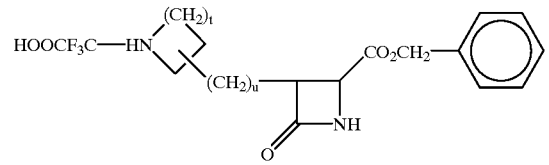

wherein t and u are as defined in claim 1;

b) reacting the product from step (a) with the diprotected guanylating agent of the formula:

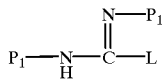

wherein L is a leaving group selected from methylthio or pyrazolyl to give the compound of the formula:

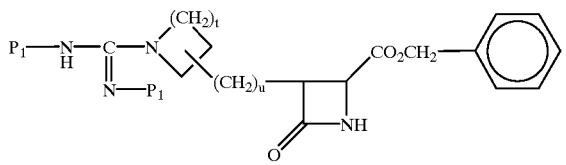

wherein $P_1$ is an N-protecting group;

c) reacting the product from step (b) with a chloro compound selected from

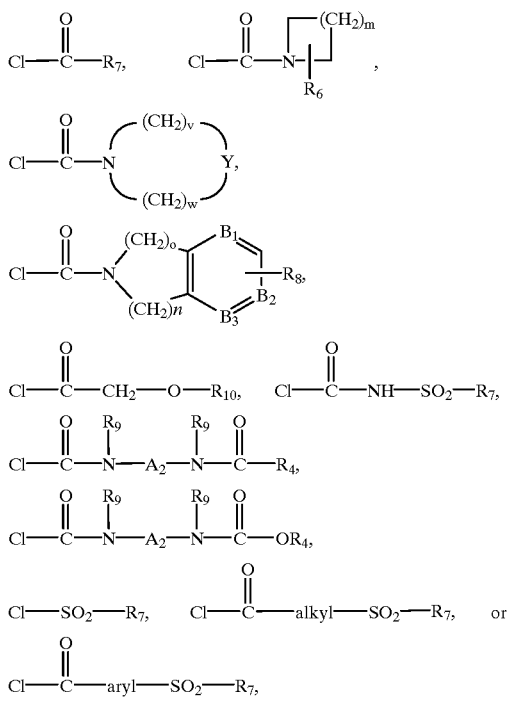

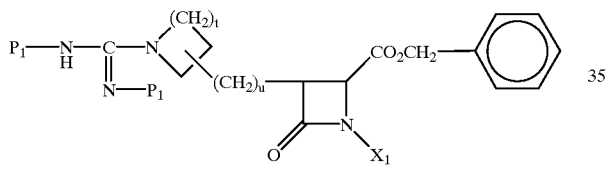

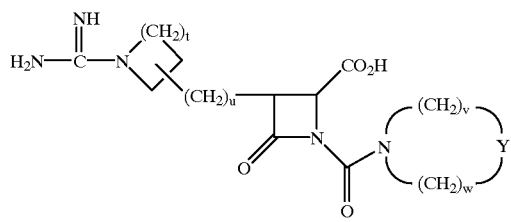

or reacting with OCN—SO$_2$—R$_7$ to give the compound of the formula:

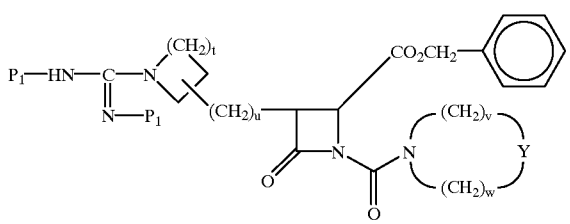

wherein R$_4$, R$_6$, R$_7$, R$_8$, R$_9$, R$_{10}$, v, w, o, n, m, B$_1$, B$_2$, B$_6$, and A$_2$ are as defined in claim 1; and d) treating the product from step (c) to remove the P$_1$ and benzyl protecting groups and give the desired final product.

39. A process for preparing compounds of claim 1 having the formula:

including an inner salt or pharmaceutically acceptable salt thereof wherein Y is

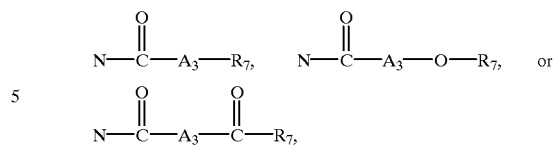

and A$_3$, R$_7$, v and w are as defined in claim 1 which comprises:

a) reacting a compound of the formula:

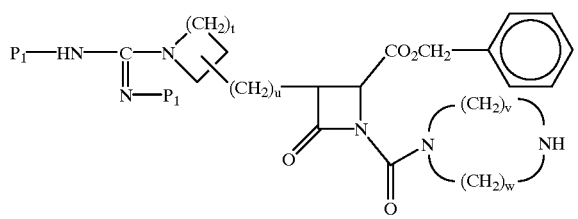

with a compound of the formula:

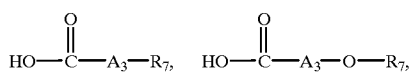

or 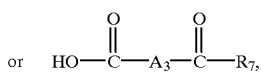

in the presence of a coupling reagent to give the compound of the formula:

wherein Y is defined above and t and u are as defined in claim 1; and b) treating the product from step (a) to remove the P$_1$ and benzyl protecting groups and give the desired product.

* * * * *